US010689458B2

(12) United States Patent
Ma et al.

(10) Patent No.: US 10,689,458 B2

(45) Date of Patent: Jun. 23, 2020

(54) SITE SPECIFIC HER2 ANTIBODY DRUG CONJUGATES

(71) Applicant: Pfizer Inc., New York, NY (US)

(72) Inventors: Dangshe Ma, Millwood, NY (US); Frank Loganzo, Jr., New City, NY (US); Kimberly Ann Marquette, Somerville, MA (US); Edmund Idris Graziani, Chestnut Ridge, NY (US); Puja Sapra, River Edge, NJ (US); Pavel Strop, San Mateo, CA (US)

(73) Assignee: Pfizer Inc., New York, NY (US)

( * ) Notice: Subject to any disclaimer, the term of this patent is extended or adjusted under 35 U.S.C. 154(b) by 145 days.

(21) Appl. No.: 15/356,750

(22) Filed: Nov. 21, 2016

(65) Prior Publication Data

US 2017/0151341 A1 Jun. 1, 2017

Related U.S. Application Data

(60) Provisional application No. 62/409,105, filed on Oct. 17, 2016, provisional application No. 62/289,744, filed on Feb. 1, 2016, provisional application No. 62/289,727, filed on Feb. 1, 2016, provisional application No. 62/260,854, filed on Nov. 30, 2015.

(51) Int. Cl.

| | |
|---|---|
| *C07K 16/32* | (2006.01) |
| *A61K 47/68* | (2017.01) |
| *C07K 16/30* | (2006.01) |
| *A61K 39/00* | (2006.01) |

(52) U.S. Cl.

CPC .......... *C07K 16/32* (2013.01); *A61K 47/6803* (2017.08); *A61K 47/6811* (2017.08); *A61K 47/6855* (2017.08); *A61K 47/6857* (2017.08); *A61K 47/6863* (2017.08); *C07K 16/30* (2013.01); *C07K 16/303* (2013.01); *C07K 16/3015* (2013.01); *C07K 16/3023* (2013.01); *C07K 16/3053* (2013.01); *C07K 16/3069* (2013.01); *A61K 2039/505* (2013.01); *C07K 2317/52* (2013.01); *C07K 2317/565* (2013.01); *C07K 2317/73* (2013.01); *C07K 2317/732* (2013.01); *C07K 2317/92* (2013.01); *C07K 2317/94* (2013.01)

(58) Field of Classification Search

CPC . C07K 16/32; A61K 47/6801; A61K 47/6803

USPC .................................... 424/133.1; 530/388.1

See application file for complete search history.

(56) References Cited

U.S. PATENT DOCUMENTS

| | | | | |
|---|---|---|---|---|
| 3,773,919 | A | 11/1973 | Boswell et al. | |
| 4,485,045 | A | 11/1984 | Regen | |
| 4,544,545 | A | 10/1985 | Ryan et al. | |
| 5,013,556 | A | 5/1991 | Woodle et al. | |
| 5,208,020 | A | 5/1993 | Chari et al. | |
| 5,648,095 | A | 7/1997 | Illum et al. | |
| 5,821,337 | A | 10/1998 | Carter et al. | |
| 5,981,568 | A | 11/1999 | Kunz et al. | |
| 6,309,633 | B1 | 10/2001 | Ekwuribe et al. | |
| 6,461,603 | B2 | 10/2002 | Bentley et al. | |
| 8,337,856 | B2 | 12/2012 | Blättler et al. | |
| 2006/0205670 | A1 | 9/2006 | Bradshaw et al. | |
| 2011/0033378 | A1 | 2/2011 | Dimasi et al. | |
| 2012/0213705 | A1 | 8/2012 | Dimasi et al. | |
| 2013/0122020 | A1 | 5/2013 | Liu et al. | |
| 2014/0288280 | A1 | 9/2014 | Bhakta et al. | |
| 2015/0017188 | A1 | 1/2015 | Eigenbrot et al. | |
| 2015/0160192 | A1 | 6/2015 | Chen et al. | |
| 2015/0273077 | A1 | 10/2015 | Van Berkel et al. | |
| 2015/0352225 | A1* | 12/2015 | Rabuka .................. | C07K 16/32 424/178.1 |
| 2016/0215060 | A1 | 7/2016 | Chung et al. | |
| 2016/0346402 | A1 | 12/2016 | Lerchen et al. | |

FOREIGN PATENT DOCUMENTS

| | | | |
|---|---|---|---|
| EP | 2083017 | A1 | 7/2009 |
| EP | 2478912 | A1 | 8/2016 |
| HK | 1173382 | | 5/2013 |
| RU | 2 404 810 | C9 | 6/2015 |
| RU | 2 553 566 | C2 | 6/2015 |
| WO | 00/53211 | A2 | 9/2000 |
| WO | 2005/117986 | A2 | 12/2005 |
| WO | 2006/033700 | A2 | 3/2006 |
| WO | 2007/038658 | A2 | 4/2007 |
| WO | 2009/052249 | A1 | 4/2009 |
| WO | 2009/099728 | A1 | 8/2009 |
| WO | 2012/022814 | A1 | 2/2012 |
| WO | 2012/031198 | A2 | 3/2012 |
| WO | 2012/059882 | A2 | 5/2012 |
| WO | 2012/075581 | A1 | 6/2012 |
| WO | 2012/162482 | A1 | 11/2012 |
| WO | 2013/072813 | A2 | 5/2013 |
| WO | 2013/093809 | A1 | 6/2013 |
| WO | 2013/165690 | A1 | 11/2013 |

(Continued)

OTHER PUBLICATIONS

Alley et al, "Contribution of Linker Stability to the Activities of Anticancer Immunoconjugates", Bioconjugate Chemistry 19:759-765 (2008).

Anbazhagan et al, "Association of c-erbB-2 expression and S-phase fraction in the prognosis of node positive breast cancer", Annals of Oncology 2:47-53 (1991).

Andrulis et al, "neu/erbB-2 Amplification Identities a Poor-Prognosis Group of Women With Node-Negative Breast Cancer", Journal of Clinical Oncology 16(4):1340-1349 (1998).

Badescu et al, "A New Reagent for Stable Thiol-Specific Conjugation", Bioconjugate Chemistry 25:460-469 (2014).

Badescu et al, "Bridging Disulfides for Stable and Defined Antibody Drug Conjugates", Bioconjugate Chemistry 25:1124-1136 (2014).

Bastian et al, "Caveolae at a glance", Journal of Cell Science 123:3831-3836 (2010).

(Continued)

*Primary Examiner* — Yan Xiao

(74) *Attorney, Agent, or Firm* — Maria V. Marucci

(57) ABSTRACT

The present invention provides site specific HER2 antibody drug conjugates and methods for preparing and using the same.

6 Claims, 62 Drawing Sheets

Specification includes a Sequence Listing.

(56) References Cited

FOREIGN PATENT DOCUMENTS

| WO | 2013/173337 A2 | 11/2013 |
|---|---|---|
| WO | 2014/022592 A1 | 2/2014 |
| WO | 2014/022846 A1 | 2/2014 |
| WO | 2014/057073 A1 | 4/2014 |
| WO | 2014/072888 A1 | 5/2014 |
| WO | 2014/124316 A2 | 8/2014 |
| WO | 2014/159981 A2 | 10/2014 |
| WO | 2015/002486 A1 | 1/2015 |
| WO | 2015/023355 A1 | 2/2015 |
| WO | 2015/038426 A1 | 3/2015 |
| WO | 2015/096982 A1 | 7/2015 |
| WO | 2015/110935 A1 | 7/2015 |
| WO | 2015/157592 A1 | 10/2015 |
| WO | 2016/151432 A1 | 9/2016 |
| WO | 2017/093845 A1 | 6/2017 |

OTHER PUBLICATIONS

Béranger et al; "IMGT Scientific chart: Correspondence between the IMGT unique numbering for C-Domain, the IMGT exon numbering, the Eu and Kabat numberings: Human IGHG" (May 17, 2001), Retrieved from the Internet: URL:http://www.imgt.org/IMGTScientificChart/Numbering/Hu_IGHGnber.html.
Bird et al, "Single-Chain Antigen-Binding Proteins", Science 242:423-426 (1988).
Boghaert et al, "Determination of pharmacokinetic values of calicheamicin-antibody conjugates in mice by plasmon resonance analysis of small (5 µl) blood samples", Cancer Chemother Pharmacol 61:1027-1035 (2008).
Boswell et al, "Effects of Charge on Antibody Tissue Distribution and Pharmacokinetics", Bioconjugate Chemistry 21:2153-2163 (2010).
Bumbaca et al, "Physiochemical and Biochemical Factors Influencing the Pharmacokinetics of Antibody Therapeutics", The AAPS Journal 14(3):554-558 (2012).
Burke et al, "Development and pharmacological properties of PEGylated glucuronide-auristatin linkers", Presentation Abstract #1786, AACR Annual Meeting, San Diego, CA, Apr. 5-9, 2014.
Burris et al, "Phase II Study of the Antibody Drug Conjugate Trastuzumab-DM1 for the Treatment of Human Epidermal Growth Factor Receptor 2 (HER2)-Positive Breast Cancer After Prior HER2-Directed Therapy", Journal of Clinical Oncology 29(4):398-405 (2010).
Burton, "Immunoglobulin G: Functional Sites", Molecular Immunology 22(3):161-206 (1985).
Caceci et al, "Fitting Curves to Data: The Simplex algorithm is the answer", BYTE 9:340-342, 344, 346, 348,350, 354-358, 360, 362 (1984).
Carter et al, "Humanization of an anti-p185HER2 antibody for human cancer therapy", Proc. Natl. Acad. Sci. USA 89:4285-4289 (1992).
Chari et al, "Immunoconjugates Containing Novel Maytansinoids: Promising Anticancer Drugs", Cancer Research 52:127-131 (1992).
Chazin et al, "Transformation mediated by the human HER-2 gene independent of the epidermal growth factor receptor", Oncogene 7:1859-1866 (1992).
Christie et al, "Stabilization of cysteine-linked antibody drug conjugates with N-aryl maleimides", Journal of Controlled Release 220:660-670 (2015).
Database Genbank [online] (Mar. 30, 1995), "Human c-erb-B-2 mRNA [*Homo sapiens*]", retrieved from www.NCBI.NLM.NIH.GOV Database Accession No. X03363.1.
Di Fiore et al, "erbB-2 Is a Potent Oncogene When Overexpressed in NIH/3T3 Cells", Science 237(4811):178-182 (1987).
Di Joseph et al, "CMC-544 (inotuzamab ozogamicin): A CD22-targeted immunoconjugate of calicheamicin", Hematology Meeting Reports 5(6):74-77 (2008).
Dokter et al, "Impressive efficacy and safety profile of a novel generation duocarmycin-based HER2-targeting ADC", Presentation Abstract #2651, AACR Annual Meeting, San Diego, CA, Apr. 5-9, 2014.
Doronina et al, "Development of potent monoclonal antibody auristatin conjugates for cancer therapy", Nature Biotechnology 21(7):778-784 (2003).
Doronina et al, "Elucidating the role of drug-linker hydrophobicity in the disposition of antibody-drug conjugates", Presentation Abstract #4470, AACR Annual Meeting, San Diego, CA, Apr. 5-9, 2014.
Dorywalska et al, "Effect of Attachment Site on Stability of Cleavable Antibody Drug Conjugates", Bioconjugate Chemistry 26:650-659 (2015).
Edelman et al, "The Covalent Structure of an Entire gammaG Immunoglobulin Molecule", Biochemistry 63:78-85 (1969).
Eppstein et al, "Biological activity of liposome-encapsulated murine interferon gamma is mediated by a cell membrane receptor", Proc. Natl. Acad. Sci. USA 82:3688-3692 (1985).
Erickson et al, "The Effect of Different Linkers on Target Cell Catabolism and Pharmacokinetics/Pharmacodynamics of Trastuzamab Maytansinoid Conjugates", Molecular Cancer Therapeutics 11(5):1133-1142 (2012).
Eustáquio et al, "Spliceostatin hemiketal biosynthesis in Burkholderia spp. is catalyzed by an iron/α-ketoglutarate-dependent dioxygenase", PNAS 111(33):E3376-E3385 (2014).
Fujimoto-Ouchi et al, "Antitumor activity of trastuzumab in combination with chemotherapy in human gastric cancer xenograft models", Cancer Chemother Pharmacol 59:795-805 (2007).
Gancberg et al, "Evaluation of HER-2/NEU protein expression in breast cancer by immunohistochemistry: an interlaboratory study assessing the reproducibility of HER-2/neu testing", Breast Cancer Research and Treatment 74:113-120 (2002).
Guy et al, "Expression of the neu protooncogene in the mammary epithelium of transgenic mice induces metastatic disease", Proc. Natl. Acad. Sci. USA 89:10578-10582 (1992).
Hamblett et al, "Effects of Drug Loading on the Antitumor Activity of a Monoclonal Antibody Drug Conjugate", Clinical Cancer Research 10:7063-7070 (2004).
He et al, "Cytotoxic Spliceostatins from Burkholderia sp. and Their Semisynthetic Analogues", Journal of Natural Products 77:1864-1870 (2014).
Holliger et al, "'Diabodies': Small bivalent and bispecific antibody fragments', Proc. Natl. Acad. Sci. USA 90:6444-6448 (1993).
Hu et al, "Minibody: A Novel Engineered Anti-Carcinoembryonic Antigen Antibody Fragment (Single-Chain Fv-CH3) Which Exhibits Rapid, High-Level Targeting of Xenografts", Cancer Research 56:3055-3061 (1996).
Hudziak et al, "Increased expression of the putative growth factor receptor p185HER2 causes transformation and tumorigenesis of NIH 3T3 cells", Proc. Natl. Acad. Sci. USA 84:7159-7163 (1987).
Huston et al, "Protein engineering of antibody binding sites: Recovery of specific activity in an anti-digoxin single-chain Fv analogue produced in *Escherichia coli*", Proc. Natl. Acad. Sci. USA 85:5879-5883 (1988).
Hwang et al, "Hepatic uptake and degradation of unilmellar sphingomyelin/cholesterol liposomes: A kinetic study", Proc. Natl. Acad. Sci. USA 77(7):4030-4034 (1980).
Jackson et al, "In Vitro and In Vivo Evaluation of Cysteine and Site Specific Conjugated Herceptin Antibody-Drug Conjugates", PLOS ONE 9(1):E83865 (2014).
Jacobs et al, "Comparison of Fluorescence in Situ Hybridization and Immunohistochemistry for the Evaluation of HER-2/neu in Breast Cancer", Journal of Clinical Oncology 17(7):1974-1982 (1999).
Jeffrey et al, "Development and Properties of β-Glucuronide Linkers for Monoclonal Antibody-Drug Conjugates", Bioconjugate Chemistry 17:831-840 (2006).
Junutula et al, "Site-specific conjugation of a cytotoxic drug to an antibody improves the therapeutic index", Nature Biotechnology 26(8):925-932 (2008).
Kellogg et al, "Disulfide-Linked Antibody-Maytansinoid Conjugates: Optimization of In Vivo Activity by Varying the Steric Hindrance at Carbon Atoms Adjacent to the Disulfide Linkage", Bioconjugate Chemistry 22:717-727 (2011).
Kern et al, "Discovery of Pyrophosphate Diesters as Tunable, Soluble, and Bioorthogonal Linkers for Site-Specific Antibody-Drug Conjugates", Journal of the American Chemical Society 138:1430-1445 (2016).

(56) References Cited

OTHER PUBLICATIONS

Kim et al, "Statistical Modeling of the Drug Load Distribution on Trastuzumab Emtansine (Kadcyla), a Lysine-Linked Antibody Drug Conjugate", Bioconjugate Chemistry 25:1223-1232 (2014).
Kim et al, "Strategies and Advancement in Antibody-Drug Conjugate Optimization for Targeted Cancer Therapeutics", Biomolecules & Therapeutics 23(6):493-509 (2015).
Kovtun et al, "Antibody-Drug Conjugates Designed to Eradicate Tumors with Homogeneous and Heterogeneous Expression of the Target Antigen", Cancer Research 66(6):3214-3221 (2006).
Krop et al, "Phase I Study of Trastuzumab-DM1, an HER2 Antibody-Drug Conjugate, Given Every 3 Weeks to Patients With HER2-Positive Metastatic Breast Cancer", Journal of Clinical Oncology 28(16)2698-2704 (2010).
Tumey et al.; "Optimization of Tubulysin Antibody-Drug Conjugates: A Study in Addressing ADC Metabolism", ACS Medicinal Chemistry Letters, vol. 7, No. 11, pp. 977-982, 2016.
Kunkel, "Rapid and efficient site-specific mutagenesis without phenotypic selection", Proc. Natl. Acad. Sci. USA 82:488-492 (1985).
Lin et al, "Pharmacokinetic Considerations for Antibody Drug Conjugates", Pharm Res 29:2354-2366 (2012).
Lyon et al, "Self-hydrolyzing maleimides improve the stability and pharmacological properties of antibody-drug conjugates", Nature Biotechnology 32(10):1059-1062 (2014).
Lyon et al, "Self-stabilizing ADCs: antibody-drug conjugates prepared with maleimido drug-linkers that catalyze their own thiosuccinimide ring hydrolysis", Presentation Abstract #4333, AACR Annual Meeting, Washington, DC, Apr. 6-10, 2013.
Lyon et al, "Reducing hydrophobicity of homogeneous antibody-drug conjugates improves pharmacokinetics and therapeutic index", Nature Biotechnology 33:733-735 (2015).
Lyons et al, "Site-specific attachment to recombinant antibodies via introduced surface cystein residues", Protein Engineering 3(8):703-708 (1990).
Martin et al, "HER2 in solid tumors: more than 10 years under the microscope; where are they now?", Future Oncology 10(8):1469-1486 (2014).
Ménard et al, "HER2 overexpression in various tumor types, focussing on its relationship to the development of invasive breast cancer", Annals of Oncology 12(Suppl. 1):S15-S19 (2001).
Olafsen et al, "Characterization of engineered anti-p185HER-2 (scFv-CH3)2 antibody fragments (minibodies) for tumor targeting", Protein Engineering, Design & Selection 17(4):315-323 (2004).
Owens et al, "HER2 Amplification Ratios by Fluorescence In Situ Hybridization and Correlation with Immunohistochemistry in a Cohort of 6556 Breast Cancer Tissues", Clinical Breast Cancer 5(1):63-69 (2004).
PCT International Search Report and Written Opinion for International Patent Application No. PCT/IB2016/057017 dated Apr. 25, 2017.
Phillips et al, "Targeting HER2-Positive Breast Cancer with Trastuzumab-DM1, an Antibody-Cytotoxic Drug Conjugate", Cancer Research 68(22):9280-9290 (2008).
Poljak, "Production and structure of diabodies", Structure 2:1121-1123 (1994).
Polson et al, "Antibody-Drug Conjugates for the Treatment of Non-Hodgkin's Lymphoma: Target and Linker-Drug Selection", Cancer Research 69(6):2358-2364 (2009).
Press et al, "Diagnostic Evaluation of HER-2 as a Molecular Target: An Assessment of Accuracy and Reproducibility of Laboratory Testing in Large, Prospective, Randomized Clinical Trials", Clinical Cancer Research 11(18):6598-6607 (2005).
Remillard et al, "Antimitotic Activity of the Potent Tumor Inhibitor Maytansine", Science 189(4207):1002-1005 (1975).
Sapra, "A Novel Site-Specific HER2-ADC for Treatment of HER2+ Solid Tumors", Presentation #868, 2016 AACR Annual Meeting, New Orleans, LA, Apr. 17, 2016 (15 pages).
Sapra, "A Novel Site-Specific HER2-ADC for Treatment of HER2+ Solid Tumors", Bioconjugates: From Targets to Therapeutics, San Francisco, CA, Jun. 14, 2016 (18 pages).
Sauter et al, "Guidelines for Human Epidermal Growth Factor Receptor 2 Testing: Biologic and Methodologic Considerations", Journal of Clinical Oncology 27(8):1323-1333 (2009).
Scholl et al, "Targeting HER2 in other tumor types", Annals of Oncology 12(Suppl. 1):S81-S87 (2001).
Semba et al, "A v-erbB-related protooncogene, c-erbB-2, is distinct from the c-erbB-1/epidermal growth factor-receptor gene and is amplified in a human salivary gland adenocarcinoma", Proc. Natl. Acad. Sci. USA 82:6497-6501 (1985).
Senter et al, "The discovery and development of brentuximab vedotin for use in relapsed Hodgkin lymphoma and systemic anaplasitc large cell lymphoma", Nature Biotechnology 30(7):631-637 (2012).
Shen et al, "Conjugation site modulates the in vivo stability and therapeutic activity of antibody-drug conjugates", Nature Biotechnology 30(2):184-189 (2012).
Slamon et al, "Human Breast Cancer: Correlation of Relapse and Survival with Amplification of the HER-2/neu Oncogene", Science 235(4785):177-182 (1987).
Slamon et al, "Studies of the HER-2/neu Proto-oncogene in Human Breast and Ovarian Cancer", Science 244 (4905):707-712 (1989).
Strop et al, "Location Matters: Site of Conjugation Modulates Stability and Pharmacokinetics of Antibody Drug Conjugates", Chemistry & Biology 20:161-167 (2013).
Sung et al, "Caveolae-mediated endocytosis as a novel mechanism of resistance to T-DM1 ADC", Presentation Abstract #2113, AACR Annual Meeting, New Orleans, LA, Apr. 16-20, 2016.
Thomas et al, "Overcoming Multidrug Resistance in Cancer: An Update on the Clinical Strategy of Inhibiting P-Glycoprotein", Cancer Control 10(2):159-165 (2003).
Tian et al, "A general approach to site-specific antibody drug conjugates", PNAS 111(5):1766-1771 (2014).
Toda et al, "Rapid, Stable, Chemoselective Labeling of Thiols with Julia-Kocieński-like Reagents: A Serum-Stable Alternative to Maleimide-Based Protein Conjugation", Angew. Chem. Int. Ed. 52:12592-12596 (2013).
Tumey, "In Vivo ADC Stability", Hanson-Wade webinar, Jun. 3, 2014 (36 pages).
Tumey, "Metabolism of ADC Linkers & Payloads—How In Vivo & In Vitro Stability Data is Used to Advance Decision Making", ADC World Summit, San Diego, CA, Oct. 26-19, 2014 (29 pages).
Tumey et al, "Mild Method for Succinimide Hydrolysis on ADCs: Impact on ADC Potency, Stability, Exposure, and Efficacy", Bioconjugate Chemistry 25:1871-1880 (2014).
Tumey, "ADC Biotransformation: Metabolism of ADC Linkers & Payloads in vitro and in vivo", WRIB, Miami, FL, Mar. 2015 (25 pages).
Tumey, "Dreaming Big and Thinking Small: Applying Medicinal Chemistry Strategy to Antibody-Drug-Conjugates", ACS Webinar, Jun. 2016 (33 pages).
Tumey, "Site-specific Conjugation for the Advancement of New Linker-Payloads", ADC World Summit, Berlin, Germany, Feb. 2016 (30 pages).
Vogel et al, "Efficacy and Safety of Trastuzumab as a Single Agent in First-Line Treatment of HER2-Overexpressing Metastatic Breast Cancer", Journal of Clinical Oncology 20(3):719-726 (2002).
Von Pawel-Rammingen et al, "IdeS, a novel streptococcal cysteine proteinase with unique specificity for Immunoglobulin G", The EMBO Journal 21(7):1607-1615 (2002).
Voynov et al, "Design and Application of Antibody Cysteine Variants", Bioconjugate Chemistry 21(2):385-392 (2010).
Ward et al, "Binding activities of a repertoire of single immunoglobulin variable domains secreted from *Escherichia coli*", Nature 341:544-546 (1989).
Wolff et al, "American Society of Clinical Oncology/College of American Pathologists Guideline Recommendations for Human Epidermal Growth Factor Receptor 2 Testing in Breast Cancer", Journal of Clinical Oncology 25(1):118-145 (2007).

(56) References Cited

OTHER PUBLICATIONS

Wolff et al, "Recommendations for Human Epidermal Growth Factor Receptor 2 Testing in Breast Cancer: American Society of Clinical Oncology/College of American Pathologists Clinical Practice Guideline Update", Journal of Clinical Oncology 31(31):3997-4013 (2013).
Wong et al, "A double-filter method for nitrocellulose-filter binding: Application to protein-nucleic acid interactions", Proc. Natl. Acad. Sci. USA 90:5428-5432 (1993).
Xie et al, "Pharmacokinetics and Biodistribution of the Antitimor Immunoconjugate, Cantuzumab Mertansine (huC242-DM1), and Its Two Components in Mice", The Journal of Pharmacology and Experimental Therapeutics 308 (3):1073-1082 (2004).
Yamamoto et al, "Similarity of protein encoded by the human c-erb-B-2 gene to epidermal growth factor receptor", Nature 319:230-234 (1986).
Yu et al, "Engineering Hydrophobic Protein—Carbohydrate Interactions to Fine-Tune Monoclonal Antibodies", Journal of the American Chemical Society 135:9723-9732 (2013).
Zoller et al, "Oligonucleotide-directed mutagenesis using M13-derived vectors: an efficient and general procedure for the production of point mutations in any fragment of DNA", Nucleic Acids Research 10:6487-6500 (1982).
Laguzza et al, "New Antitumor Monoclonal Antibody-Vinca Conjugates LY203725 and Related Compounds: Design, Preparation, and Representative in Vivo Activity", J. Med. Chem. 32:548-555 (1989).
Langer, "New Methods of Drug Delivery", Science 249(4976):1527-1533).
Lillo et al, "A Human Single-Chain Antibody Specific for Integrin alpha 3 beta 1 Capable of Cell Internalization and Delivery of Antitumor Agents", Chemistry & Biology 11:897-906 (2004).
Wu et al, "Arming antibodies: prospects and challenges for immunoconjugates", Nature Biotechnology 23:1137-1146 (2005).

* cited by examiner

T(kK183+290)-vc0101

T(K334C+K392C)-vc0101

T(LCQ05+K222R)-AcLysvc0101

T-vc0101

T-DM1

BT474(NK92)
E:T ratio=10:1

FIG. 5

| ADC | Cell Line (with HER2 expression level) | | | | | | | | | |
|---|---|---|---|---|---|---|---|---|---|---|
| | 3+ | 3+ | 3+ | 3+ | 2+ | 2+ | 2+ | 1+ | - | - |
| | N87 | BT474 | HCC 1954 | SKBR3 | MDA-MB-361-DYT2 | JIMT1 | MDA-MB-453 | MDA-MB-175-VII | MDA-MB-468 | HT29 |
| T-DM1 | 1.66 +/- 1.53 (37) | 4.82 +/- 3.74 (26) | 0.4 +/- 0.28 (11) | 0.16 +/- 0.06 (8) | 0.99 +/- 1.33 (37) | 29 +/- 12 (16) | 1.02 +/- 0.47 (6) | 87 +/- 67 (10) | 80 +/- 36 (25) | 152 +/- 70 (17) |
| T-vc0101 | 0.44 +/- 0.15 (79) | 0.31 +/- 0.12 (47) | 0.27 +/- 0.08 (28) | 0.13 +/- 0.04 (4) | 0.28 +/- 0.09 (75) | 8 +/- 9 (40) | 0.66 +/- 0.13 (7) | 19 +/- 8 (10) | 460 +/- 141 (47) | 325 +/- 160 (37) |
| T(LCQ05+K222R)-AcLysvc0101 | 0.67 +/- 0.29 (14) | 0.25 +/- 0.07 (8) | 0.24 +/- 0.1 (2) | 0.13 +/- 0.01 (2) | 0.97 +/- 1.3 (17) | 72 +/- 79 (7) | 3.1 +/- 3 (5) | 75 +/- 23 (5) | 434 +/- 226 (8) | 318 +/- 159 (14) |
| T(N297Q+K222R)-AcLysvc0101 | 0.49 +/- 0.08 (8) | 0.21 +/- 0.06 (4) | 0.23 +/- 0.04 (3) | 0.13 +/- 0.02 (2) | 0.29 +/- 0.08 (6) | 19 +/- 14 (3) | 0.38 +/- 0.04 (4) | 4.9 +/- 1.7 (3) | 526 +/- 157 (4) | 637 +/- 240 (3) |
| T(N297A+K222R+LCQ05)-AcLysvc0101 | 0.51 +/- 0.03 (2) | 0.29 +/- 0.08 (3) | 0.24 +/- 0.07 (2) | 0.15 +/- 0 (2) | 0.31 +/- 0.09 (2) | 61 +/- 76 (2) | 0.42 +/- 0.03 (3) | 7.8 +/- 0.2 (2) | 493 +/- 94 (3) | 827 (1) |
| T(N297Q)-AcLysvc0101 | 0.46 +/- 0.07 (4) | 0.27 +/- 0.11 (6) | 0.25 +/- 0.07 (3) | 0.14 +/- 0 (2) | 0.23 +/- 0.09 (5) | 21 +/- 37 (6) | 0.39 +/- 0.04 (4) | 9.1 +/- 7.3 (5) | 542 +/- 93 (5) | 716 +/- 137 (5) |
| T(kK183C+K290C)-vc0101 | 0.43 +/- 0.01 (2) | 0.37 +/- 0.11 (3) | 0.21 +/- 0.03 (2) | 0.14 +/- 0.01 (2) | 0.33 +/- 0.09 (2) | 16 +/- 9 (2) | 0.54 +/- 0.1 (3) | 9.6 +/- 2.8 (2) | 385 +/- 22 (3) | 382 +/- 24 (2) |
| T(kK183C+K334C)-vc0101 | 0.71 +/- 0.29 (3) | 0.29 +/- 0.19 (2) | 0.22 (1) | 0.15 +/- 0.01 (2) | 0.45 +/- 0.21 (3) | 18 (1) | 0.44 +/- 0.03 (2) | 16 (1) | 455 +/- 39 (2) | 564 +/- 357 (2) | continued

FIG. 5 continued

| | | | | | | | | | | |
|---|---|---|---|---|---|---|---|---|---|---|
| T(kK183C+K392C)-vc0101 | 0.57 +/- 0.14 (2) | 0.27 +/- 0.09 (2) | 0.22 +/- 0.01 (2) | 0.15 +/- 0.01 (2) | 0.35 +/- 0.03 (2) | 8.1 +/- 3.9 (2) | 0.41 +/- 0.04 (2) | 9.5 +/- 3.4 (2) | 483 +/- 168 (2) | 528 +/- 245 (2) |
| T(kK183C+L443C)-vc0101 | 0.42 +/- 0.22 (4) | 0.28 +/- 0.05 (4) | 0.37 +/- 0.07 (4) | (0) | 0.33 +/- 0.23 (8) | 5.2 +/- 2.7 (8) | 0.62 (1) | 10.7 +/- 1.9 (2) | 461 +/- 94 (7) | 240 +/- 35 (3) |
| T(K290C+K334C)-vc0101 | 0.61 +/- 0.13 (6) | 0.34 +/- 0.11 (3) | 0.21 +/- 0.01 (2) | 0.16 +/- 0.01 (2) | 0.32 +/- 0.08 (6) | 8.8 +/- 6.8 (2) | 0.46 +/- 0.02 (3) | 18 (1) | 662 +/- 383 (3) | 658 +/- 169 (3) |
| T(K290C+K392C)-vc0101 | 0.53 +/- 0.01 (2) | 0.35 +/- 0.14 (3) | 0.22 +/- 0.03 (2) | 0.14 +/- 0.03 (2) | 0.36 +/- 0.08 (2) | 9.7 +/- 4.9 (2) | 0.47 +/- 0.08 (3) | 9.5 +/- 2.2 (2) | 774 +/- 85 (3) | (0) |
| T(K334C+K392C)-vc0101 | 0.59 +/- 0.15 (5) | 0.36 +/- 0.25 (2) | 0.21 +/- 0.02 (2) | 0.16 +/- 0.02 (2) | 0.25 +/- 0.06 (5) | 6.4 +/- 1.4 (2) | 0.45 +/- 0.06 (2) | 11 +/- 8 (2) | 884 (1) | 885 +/- 111 (3) |
| T(kK183C)-vc0101 | 0.34 +/- 0.12 (4) | 0.31 +/- 0.07 (3) | 0.29 +/- 0.08 (2) | (0) | 0.64 +/- 0.47 (4) | 133 +/- 174 (3) | 1.26 (1) | 115 (1) | 414 +/- 226 (3) | 459 +/- 114 (3) |
| T(K290C)-vc0101 | 0.57 +/- 0.28 (5) | 0.28 +/- 0.16 (2) | 0.23 (1) | 0.14 +/- 0.05 (2) | 0.68 +/- 0.58 (6) | 235 (1) | 1.45 +/- 0.05 (2) | 147 (1) | 499 +/- 151 (2) | 575 +/- 199 (4) |
| T(K334C)-vc0101 | 0.47 +/- 0.13 (5) | 0.28 +/- 0.16 (2) | 0.17 (1) | 0.11 +/- 0.02 (2) | 3.57 +/- 7.91 (6) | 289 (1) | 1.14 +/- 0.24 (2) | 123 (1) | 588 +/- 73 (2) | 775 +/- 49 (2) |
| T(K392C)-vc0101 | 0.41 +/- 0.09 (5) | 0.29 +/- 0.11 (3) | 0.19 (1) | 0.13 +/- 0.03 (2) | 1 +/- 1.43 (5) | 172 +/- 180 (2) | 1.24 +/- 0.13 (2) | 164 (1) | 645 +/- 229 (3) | 423 +/- 9 (2) |
| T(L443C)-vc0101 | 0.4 +/- 0.27 (5) | 0.23 +/- 0.08 (3) | 0.32 +/- 0.06 (3) | (0) | 0.48 +/- 0.28 (5) | 41 +/- 34 (3) | 4.4 (1) | 118 (1) | 457 +/- 207 (4) | 88 (1) |

FIG. 6

| ADC | Cell Line (with HER2 expression level) | | | | | | | | | |
|---|---|---|---|---|---|---|---|---|---|---|
| | 3+ | 3+ | 3+ | 3+ | 2+ | 2+ | 2+ | 1+ | - | - |
| | N87 | BT474 | HCC 1954 | SKBR 3 | MDA-MB-361-DYT2 | JIMT1 | MDA-MB-453 | MDA-MB-175-VII | MDA-MB-468 | HT29 |
| T-DM1 | 62 +/- 54 (37) | 190 +/- 143 (26) | 16 +/- 12 (11) | 6 +/- 2 (8) | 40 +/- 59 (37) | 1073 +/- 484 (16) | 38 +/- 15 (6) | 3626 +/- 2750 (10) | 3140 +/- 1211 (25) | 5488 +/- 2415 (17) |
| T-vc0101 | 17 +/- 6 (79) | 12 +/- 4 (47) | 10 +/- 3 (28) | 5 +/- 2 (4) | 10 +/- 4 (75) | 294 +/- 308 (40) | 24 +/- 5 (7) | 718 +/- 295 (10) | 17141 +/- 5658 (47) | 11908 +/- 6136 (37) |
| T(LCQ05+K222R)-AcLysvc0101 | 50 +/- 21 (14) | 19 +/- 6 (8) | 18 +/- 7 (2) | 10 +/- 1 (2) | 73 +/- 97 (17) | 5379 +/- 5938 (7) | 233 +/- 225 (5) | 5644 +/- 1743 (5) | 32560 +/- 16978 (8) | 23766 +/- 11898 (14) |
| T(N297Q+K222R)-AcLysvc0101 | 18 +/- 3 (8) | 8 +/- 2 (4) | 9 +/- 2 (3) | 5 +/- 1 (2) | 11 +/- 3 (6) | 700 +/- 515 (3) | 14 +/- 2 (4) | 185 +/- 63 (3) | 19737 +/- 5885 (4) | 23886 +/- 8990 (3) |
| T(N297A+K222R +LCQ05)-AcLysvc0101 | 19 +/- 1 (2) | 11 +/- 3 (3) | 9 +/- 3 (2) | 6 +/- 0 (2) | 12 +/- 4 (2) | 2280 +/- 2851 (2) | 16 +/- 1 (3) | 291 +/- 9 (2) | 18489 +/- 3511 (3) | 31002 (1) |
| T(N297Q)-AcLysvc0101 | 17 +/- 3 (4) | 10 +/- 4 (6) | 9 +/- 2 (3) | 5 +/- 0 (2) | 9 +/- 3 (5) | 770 +/- 1362 (6) | 15 +/- 1 (4) | 333 +/- 262 (5) | 20532 +/- 3846 (5) | 26609 +/- 5265 (5) |
| T(kK183C+K290C)-vc0101 | 16 +/- 0 (2) | 14 +/- 4 (3) | 8 +/- 1 (2) | 5 +/- 0 (2) | 12 +/- 3 (2) | 603 +/- 327 (2) | 20 +/- 4 (3) | 351 +/- 94 (2) | 14134 +/- 1027 (3) | 14305 +/- 912 (2) |
| T(kK183C+K334C)-vc0101 | 29 +/- 11 (3) | 12 +/- 8 (2) | 9 (1) | 6 +/- 0 (2) | 18 +/- 8 (3) | 717 (1) | 18 +/- 1 (2) | 660 (1) | 18375 +/- 1564 (2) | 23284 +/- 15156 (2) |
| T(kK183C+K392C)-vc0101 | 20 +/- 5 (2) | 9 +/- 3 (2) | 8 +/- 0 (2) | 5 +/- 0 (2) | 12 +/- 1 (2) | 280 +/- 133 (2) | 14 +/- 1 (2) | 328 +/- 118 (2) | 16685 +/- 5787 (2) | 18645 +/- 9043 (2) |
| T(kK183C+L443C)-vc0101 | 16 +/- 8 (4) | 11 +/- 2 (4) | 15 +/- 3 (4) | (0) | 13 +/- 9 (8) | 204 +/- 109 (8) | 23 (1) | 255 +/- 128 (2) | 18005 +/- 3005 (7) | 8900 +/- 1269 (3) | continued

FIG. 6 continued

| | | | | | | | | | | |
|---|---|---|---|---|---|---|---|---|---|---|
| T(K290C+K334C)-vc0101 | 22 +/- 5 (6) | 13 +/- 4 (3) | 8 +/- 1 (2) | 6 +/- 0 (2) | 12 +/- 3 (6) | 317 +/- 246 (2) | 17 +/- 1 (3) | 640 (1) | 24104 +/- 13727 (3) | 23859 +/- 6116 (3) |
| T(K290C+K392C)-vc0101 | 20 +/- 0 (2) | 13 +/- 5 (3) | 8 +/- 1 (2) | 5 +/- 1 (2) | 13 +/- 3 (2) | 354 +/- 178 (2) | 17 +/- 3 (3) | 345 +/- 78 (2) | 28372 +/- 2664 (3) | (0) |
| T(K334C+K392C)-vc0101 | 22 +/- 5 (5) | 13 +/- 9 (2) | 8 +/- 1 (2) | 6 +/- 1 (2) | 9 +/- 2 (5) | 231 +/- 51 (2) | 16 +/- 2 (2) | 417 +/- 274 (2) | 32063 (1) | 32519 +/- 4670 (3) |
| T(kK183C)-vc0101 | 26 +/- 8 (4) | 23 +/- 5 (3) | 22 +/- 7 (2) | (0) | 49 +/- 37 (4) | 9743 +/- 12536 (3) | 91 (1) | 8364 (1) | 31205 +/- 16416 (3) | 34516 +/- 7772 (3) |
| T(K290C)-vc0101 | 47 +/- 18 (5) | 20 +/- 12 (2) | 17 (1) | 10 +/- 4 (2) | 71 +/- 94 (6) | 17052 (1) | 105 +/- 4 (2) | 10682 (1) | 36261 +/- 10973 (2) | 42511 +/- 15090 (4) |
| T(K334C)-vc0101 | 41 +/- 5 (5) | 20 +/- 12 (2) | 13 (1) | 8 +/- 1 (2) | 552 +/- 1290 (6) | 21025 (1) | 83 +/- 17 (2) | 8956 (1) | 42743 +/- 5313 (2) | 57272 +/- 4844 (2) |
| T(K392C)-vc0101 | 36 +/- 9 (5) | 21 +/- 9 (3) | 14 (1) | 10 +/- 2 (2) | 129 +/- 226 (5) | 12847 +/- 13493 (2) | 93 +/- 9 (2) | 12330 (1) | 48108 +/- 16750 (3) | 31531 +/- 931 (2) |
| T(L443C)-vc0101 | 30 +/- 20 (5) | 17 +/- 6 (3) | 24 +/- 5 (3) | (0) | 36 +/- 21 (5) | 3015 +/- 2485 (3) | 326 (1) | 8744 (1) | 34157 +/- 15675 (4) | 6520 (1) |

T(kK183C+K290C)-vc0101

T(kK183C)-vc0101

T(K334C+K392C)-vc0101

T(N297Q+K222R)-AcLysvc0101

T(kK183C+K290C)-vc0101

T(LCQ05+K222R)-AcLysvc0101

T(N297Q+K222R)-AcLysvc0101

T-vc0101

T(kK183C+K290C)-vc0101

T(N297Q+K222R)-AcLysvc0101

FIG. 14

| In vitro resistance profile of N87 parental vs. N87-TM resistant cell lines. | | | | | | | | | | | | Relative Resistance | |
|---|---|---|---|---|---|---|---|---|---|---|---|---|---|
| | | N87 | | | N87-TM-1 | | | N87-TM-2 | | | | Avg IC50 (nM) Payload Fold Change compared to N87 | |
| ADC | Linker Type | Avg ± SD IC50 (nM) Payload | Avg ± SD IC50 (ng/mL) Antibody | n | Avg ± SD IC50 (nM) Payload | Avg ± SD IC50 (ng/mL) Antibody | n | Avg ± SD IC50 (nM) Payload | Avg ± SD IC50 (ng/mL) Antibody | n | | N87-TM-1 | N87-TM-2 |
| T-DM1 | N | 1.3 ± 0.6 | 51.9 ± 32.6 | 25 | 150 ± 58 | 5335 ± 1815 | 12 | 191 ± 109 | 6806 ± 3835 | 24 | | 114 | 146 |
| T-mc8261 | N | 3.0 ± 1.8 | 107 ± 61 | 9 | >1000 ± ND | >35247 ± ND | 9 | >1000 ± ND | >35247 ± ND | 9 | | >330 | >330 |
| T-m(H20)c8261 | N | 39.9 ± 75.9 | 1639 ± 3123 | 4 | >1000 ± ND | >41127 ± ND | 5 | >1000 ± ND | 20781 ± ND | 4 | | >25.1 | >25.1 |
| T-MalPeg8261 | N | 3.7 ± 2.6 | 176 ± 123 | 3 | >1000 ± ND | >47767 ± ND | 4 | >1000 ± ND | >47767 ± ND | 2 | | >272 | >272 |
| T-mc6121 | N | 0.41 ± ND | 17.4 ± ND | 1 | 3.9 ± 2.2 | 166 ± 93 | 2 | 1.5 ± ND | 64.8 ± ND | 1 | | 9.5 | 3.70 |
| T-MalPeg6121 | N | 0.45 ± ND | 18.8 ± ND | 1 | ND ± ND | ND ± ND | ND | >1000 ± ND | >42133 ± ND | 1 | | ND | >2242 |
| T-MalPegMMAD | N | 4.3 ± 1.6 | 143 ± 53 | 8 | >1000 ± ND | >33649 ± ND | 7 | >1000 ± ND | >33649 ± ND | 4 | | >235 | >235 |
| T-mc0101 | N | 50.61 ± 14 | 1536.2 ± 370 | 2 | ND ± ND | ND ± ND | 0 | >1000 ± ND | >31260 ± ND | 2 | | ND | >19 |
| T-vc0101 | C | 0.64 ± 0.28 | 23.4 ± 10.7 | 17 | 0.60 ± 0.20 | 21.9 ± 7.2 | 7 | 0.73 ± 0.27 | 25.7 ± 9.9 | 14 | | 0.94 | 1.1 |
| T-vc8261 | C | 0.43 ± 0.1 | 15 ± 3.4 | 8 | 0.5 ± 0.2 | 17.1 ± 7.0 | 6 | 0.5 ± 0.2 | 18.2 ± 6.8 | 8 | | 1.1 | 1.2 |
| T-vc8254 | C | 0.44 ± ND | 16.6 ± ND | 1 | ND ± ND | ND ± ND | 0 | 0.58 ± ND | 21.7 ± ND | 1 | | ND | 1.31 |
| T-vc6780 | C | 0.73 ± ND | 25.8 ± ND | 1 | ND ± ND | ND ± ND | 0 | 0.56 ± ND | 19.8 ± ND | 1 | | ND | 0.77 |
| T-vc0131 | C | 0.61 ± ND | 20.2 ± ND | 1 | ND ± ND | ND ± ND | 0 | 0.59 ± ND | 19.8 ± ND | 1 | | ND | 0.98 | continued

FIG. 14 continued

| | | | | | | | | | | | | |
|---|---|---|---|---|---|---|---|---|---|---|---|---|
| T-vcMMAE | C | 0.54 ± 0.1 | 21.0 ± 3.2 | 2 | 0.8 ± ND | 32.2 ± ND | 1 | 0.9 ± ND | 36.8 ± ND | 1 | 1.5 | 1.8 |
| T(LCQ05+K222R)-AcLysvc0101 | C | 0.63 ± 0.23 | 46.9 ± 17.0 | 8 | 0.58 ± 0.25 | 43.4 ± 18.9 | 7 | 0.60 ± 0.24 | 45.2 ± 18.2 | 8 | 0.93 | 0.96 |
| T(N297Q+K222R)-AcLysvc0101 | C | 0.57 ± 0.09 | 21.5 ± 3.6 | 4 | 0.49 ± 0.01 | 18.5 ± 0.5 | 2 | 0.46 ± 0.06 | 17.2 ± 2.4 | 5 | 0.86 | 0.80 |
| T(N297A+K222R+LCQ05)-AcLysvc0101 | C | 0.62 ± 0.10 | 23.2 ± 3.7 | 2 | 0.57 ± ND | 21.4 ± ND | 1 | 0.57 ± 0.07 | 21.4 ± 2.7 | 2 | 0.92 | 0.92 |
| T(N297Q)-AcLysvc0101 | C | 0.56 ± 0.12 | 20.3 ± 4.3 | 5 | 0.58 ± 0.15 | 21.3 ± 5.5 | 5 | 0.64 ± 0.09 | 23.4 ± 3.6 | 5 | 1.0 | 1.20 |
| T(K290C+K334C)-vc0101 | C | 0.62 ± 0.21 | 22.7 ± 7.3 | 3 | 0.51 ± 0.17 | 18.8 ± 5.9 | 2 | 0.47 ± 0.08 | 17.3 ± 2.9 | 3 | 0.82 | 0.76 |
| T(K334C+K392C)-vc0101 | C | 0.71 ± 0.11 | 25.8 ± 4 | 3 | 0.63 ± ND | 22.9 ± ND | 1 | 0.59 ± 0.21 | 21.4 ± 7.5 | 3 | 0.89 | 0.83 |
| T(kK183C+K392C)-vc0101 | C | 0.66 ± 0.04 | 22.7 ± 1.4 | 3 | 0.54 ± ND | 18.8 ± ND | 1 | 0.49 ± 0.05 | 17.0 ± 1.8 | 4 | 0.83 | 0.75 |
| T(kK183C+K290C)-vc0101 | C | 0.72 ± 0.17 | 26.6 ± 5.6 | 2 | 0.63 ± ND | 23.7 ± ND | 1 | 0.71 ± 0.23 | 26.2 ± 8 | 2 | 0.88 | 0.99 |
| T(kK183C+K334C)-vc0101 | C | 1.59 ± ND | 62.4 ± ND | 1 | ND ± ND | ND ± ND | 0 | 1.4 ± ND | 56 ± ND | 1 | ND | 0.90 |
| T(K290C+K392C)-vc0101 | C | 0.65 ± 0.01 | 23.4 ± 0.2 | 2 | 0.67 ± ND | 24.5 ± ND | 1 | 0.65 ± 0.1 | 23.7 ± 3.6 | 2 | 1.0 | 1.0 |
| T(K290C)-vc0101 | C | 0.59 ± ND | 43.0 ± ND | 1 | ND ± ND | ND ± ND | 0 | 0.42 ± ND | 30.4 ± ND | 1 | ND | 0.71 |
| T(K334C)-vc0101 | C | 0.56 ± 0.02 | 40.5 ± 1.7 | 2 | ND ± ND | ND ± ND | ND | 0.51 ± 0.17 | 37.2 ± 12.3 | 2 | ND | 0.92 |
| T(K392C)-vc0101 | C | 0.55 ± 0.01 | 41.3 ± 0.2 | 2 | ND ± ND | ND ± ND | ND | 0.45 ± 0.17 | 33.6 ± 12.7 | 2 | ND | 0.81 |
| T(kK183C)-vc0101 | C | 0.62 ± ND | 45.1 ± ND | 1 | ND ± ND | ND ± ND | 0 | 0.6 ± ND | 46.6 ± ND | 1 | ND | 1.03 |
| DM1 | -- | 15.1 ± 8.5 | -- | 13 | 38.4 ± 17.53 | -- | 8 | 33.4 ± 8.9 | -- | 11 | 2.5 | 2.2 |
| 0101 | -- | 0.36 ± 0.09 | -- | 7 | 0.50 ± 0.11 | -- | 4 | 0.49 ± 0.12 | -- | 7 | 1.4 | 1.4 | continued

FIG. 14 continued

| | | | | | | | | | | | | |
|---|---|---|---|---|---|---|---|---|---|---|---|---|
| 8254 | -- | 0.59 ± 0.12 | -- | 4 | 1.1 ± 0.3 | -- | 3 | 1.0 ± 0.3 | -- | 4 | 1.9 | 1.7 |
| 6121 | -- | 0.15 ± 0.03 | -- | 2 | 0.32 ± ND | -- | 1 | 0.41 ± 0.11 | -- | 2 | 2.1 | 2.7 |
| Vinblastine | -- | 3.6 ± 0.1 | -- | 2 | 5.3 ± ND | -- | 1 | 5.7 ± 1.1 | -- | 2 | 1.5 | 1.6 |
| Paclitaxel | -- | 8.2 ± 4.0 | -- | 2 | 12.8 ± 9.0 | -- | 2 | 11.7 ± 6.5 | -- | 2 | 1.6 | 1.4 |
| Docetaxel | -- | 2.9 ± 1.4 | -- | 2 | 2.8 ± ND | -- | 1 | 4.1 ± 1.2 | -- | 2 | 0.95 | 1.4 |
| 5-fluorouracil | -- | 1611 ± 203 | -- | 2 | 3129 ± ND | -- | 1 | 3135 ± 1014 | -- | 2 | 1.9 | 1.9 |
| Gemcitabine | -- | 7.3 ± 2.2 | -- | 2 | 8.3 ± ND | -- | 1 | 8.4 ± 1.1 | -- | 2 | 1.1 | 1.1 |
| Doxorubicin | -- | 38.2 ± 13.5 | -- | 5 | 60.0 ± 18.5 | -- | 5 | 38.5 ± 7.5 | -- | 5 | 1.6 | 1.0 |
| Oxaliplatin | -- | 623 ± 471 | -- | 2 | 681 ± ND | -- | 1 | 1511 ± 1462 | -- | 2 | 1.1 | 2.4 |
| Camptothecin | -- | 20.6 ± 2.3 | -- | 2 | 11.0 ± ND | -- | 1 | 9.8 ± 3.3 | -- | 2 | 0.53 | 0.48 |

T-DM1

T-mc8261

T(N297Q+K222R)-AcLysvc0101

T(LCQ05+K222R)- AcLysvc0101

FIG. 19A

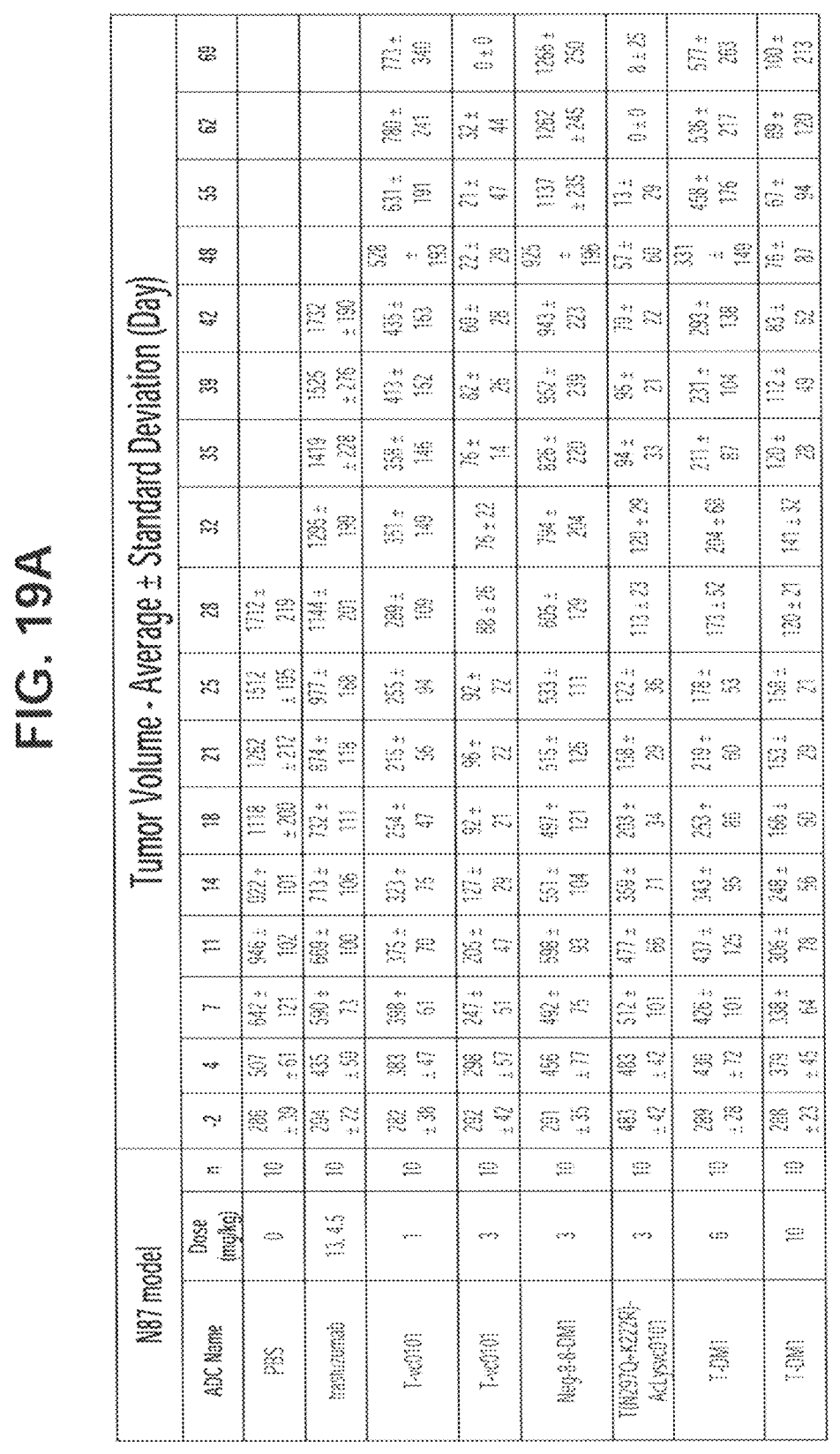

| N87 model | | | Tumor Volume - Average ± Standard Deviation (Day) | | | | | | | | | | | | | | | | |
|---|---|---|---|---|---|---|---|---|---|---|---|---|---|---|---|---|---|---|---|
| ADC Name | Dose (mg/kg) | n | -2 | 4 | 7 | 11 | 14 | 18 | 21 | 25 | 28 | 32 | 35 | 39 | 42 | 48 | 55 | 62 | 69 |
| PBS | 0 | 10 | 286 ± 39 | 507 ± 61 | 642 ± 121 | 946 ± 102 | 922 ± 101 | 1118 ± 200 | 1262 ± 212 | 1512 ± 195 | 1712 ± 219 | | | | | | | | |
| trastuzumab | 13.4.5 | 10 | 294 ± 22 | 435 ± 59 | 590 ± 73 | 669 ± 100 | 713 ± 106 | 732 ± 111 | 874 ± 118 | 977 ± 168 | 1144 ± 201 | 1295 ± 190 | 1419 ± 228 | 1525 ± 276 | 1732 ± 190 | | | | |
| T-vc0101 | 1 | 10 | 282 ± 38 | 383 ± 47 | 398 ± 61 | 375 ± 70 | 323 ± 76 | 254 ± 47 | 215 ± 56 | 255 ± 94 | 289 ± 109 | 351 ± 149 | 358 ± 146 | 413 ± 152 | 435 ± 163 | 528 ± 193 | 631 ± 191 | 780 ± 241 | 773 ± 340 |
| T-vc0101 | 3 | 10 | 292 ± 42 | 298 ± 57 | 247 ± 51 | 205 ± 47 | 127 ± 29 | 92 ± 21 | 96 ± 22 | 92 ± 22 | 88 ± 26 | 76 ± 22 | 76 ± 14 | 82 ± 26 | 60 ± 28 | 22 ± 29 | 21 ± 47 | 32 ± 44 | 0 ± 0 |
| Neg-8.8-DM1 | 3 | 10 | 291 ± 35 | 456 ± 77 | 492 ± 75 | 598 ± 93 | 551 ± 104 | 497 ± 121 | 515 ± 126 | 533 ± 111 | 605 ± 129 | 794 ± 204 | 826 ± 220 | 952 ± 239 | 943 ± 223 | 925 ± 196 | 1137 ± 235 | 1262 ± 245 | 1266 ± 250 |
| T(N297Q+K222R)-AcLysvc0101 | 3 | 10 | 483 ± 42 | 483 ± 42 | 512 ± 101 | 477 ± 66 | 359 ± 71 | 203 ± 34 | 158 ± 29 | 122 ± 36 | 113 ± 23 | 120 ± 29 | 94 ± 33 | 95 ± 21 | 79 ± 22 | 57 ± 60 | 13 ± 29 | 0 ± 0 | 8 ± 25 |
| T-DM1 | 6 | 10 | 289 ± 28 | 436 ± 72 | 426 ± 101 | 437 ± 125 | 343 ± 95 | 253 ± 86 | 219 ± 60 | 178 ± 53 | 173 ± 52 | 204 ± 68 | 211 ± 87 | 231 ± 104 | 293 ± 138 | 331 ± 149 | 458 ± 176 | 536 ± 217 | 577 ± 263 |
| T-DM1 | 10 | 10 | 288 ± 23 | 379 ± 45 | 338 ± 64 | 306 ± 78 | 248 ± 56 | 166 ± 60 | 153 ± 29 | 158 ± 21 | 120 ± 21 | 141 ± 32 | 120 ± 28 | 112 ± 49 | 83 ± 52 | 76 ± 87 | 67 ± 94 | 89 ± 120 | 100 ± 213 |

FIG. 19B

| N87-TM model: Study #1 | | | Tumor Volume - Average ± Standard Deviation (Day) | | | | | | | | | | | | | | | | | |
|---|---|---|---|---|---|---|---|---|---|---|---|---|---|---|---|---|---|---|---|---|
| ADC Name | Dose (mg/kg) | n | -1 | 3 | 7 | 10 | 14 | 17 | 21 | 24 | 28 | 31 | 35 | 38 | 43 | 49 | 56 | 65 | 72 | 78 |
| PBS | 0 | 10 | 256 ± 28 | 369 ± 49 | 503 ± 77 | 574 ± 70 | 610 ± 104 | 641 ± 110 | 1046 ± 119 | 1238 ± 101 | 1593 ± 208 | 1715 ± 259 | 1881 ± 284 | | | | | | | |
| trastuzumab | 13. 4.5 | 10 | 251 ± 20 | 278 ± 57 | 341 ± 92 | 411 ± 97 | 468 ± 112 | 640 ± 225 | 845 ± 201 | 997 ± 283 | 1150 ± 334 | 1404 ± 313 | 1589 ± 322 | | | | | | | |
| T-vc0101 | 1 | 10 | 255 ± 34 | 230 ± 47 | 333 ± 54 | 299 ± 58 | 297 ± 43 | 371 ± 90 | 493 ± 125 | 576 ± 93 | 692 ± 119 | 835 ± 179 | 1034 ± 214 | 1121 ± 190 | 1399 ± 278 | | | | | |
| T-vc0101 | 3 | 10 | 253 ± 21 | 240 ± 44 | 227 ± 53 | 152 ± 48 | 118 ± 38 | 104 ± 49 | 145 ± 41 | 125 ± 35 | 97 ± 35 | 103 ± 35 | 121 ± 48 | 84 ± 54 | 93 ± 58 | 123 ± 86 | 108 ± 154 | 81 ± 130 | | |
| Neg-8-8-DM1 | 3 | 10 | 252 ± 50 | 319 ± 62 | 341 ± 68 | 371 ± 85 | 406 ± 56 | 536 ± 89 | 628 ± 113 | 694 ± 164 | 822 ± 185 | 1055 ± 258 | 1125 ± 271 | 1168 ± 269 | 1455 ± 327 | | | | | |
| T(N297Q+K222R)-AcLysvc0101 | 3 | 10 | 254 ± 34 | 273 ± 38 | 268 ± 30 | 214 ± 33 | 176 ± 38 | 164 ± 33 | 194 ± 33 | 155 ± 26 | 154 ± 25 | 143 ± 33 | 134 ± 30 | 109 ± 41 | 106 ± 32 | 127 ± 39 | 114 ± 64 | 58 ± 44 | 147 ± 78 | 99 ± 69 |
| T-DM1 | 6 | 10 | 253 ± 33 | 294 ± 50 | 368 ± 69 | 435 ± 133 | 465 ± 116 | 570 ± 150 | 638 ± 149 | 783 ± 201 | 902 ± 326 | 1137 ± 312 | 1278 ± 291 | 1401 ± 327 | 1505 ± 336 | | | | | |
| T-DM1 | 10 | 15 | 243 ± 32 | 287 ± 41 | 343 ± 39 | 326 ± 65 | 315 ± 64 | 417 ± 92 | 530 ± 143 | 577 ± 135 | 706 ± 156 | 859 ± 187 | 978 ± 303 | 957 ± 251 | 1157 ± 341 | 1571 ± 339 | | | | |
| T-DM1, T(N297Q+K222R)-AcLysvc0101 | 10, 3 | 8 | 233 ± 32 | 302 ± 38 | 339 ± 27 | 312 ± 55 | 316 ± 66 | 422 ± 68 | 559 ± 163 | 593 ± 119 | 699 ± 155 | 855 ± 166 | 1079 ± 236 | 992 ± 202 | 966 ± 177 | 820 ± 129 | 590 ± 138 | 388 ± 82 | 510 ± 88 | 452 ± 160 |

FIG. 19C

| N87-TM model: Study #2 | | | Tumor Volume - Average ± Standard Deviation (Day) | | | | | | | | | | | | | | | | | | | |
|---|---|---|---|---|---|---|---|---|---|---|---|---|---|---|---|---|---|---|---|---|---|---|
| ADC Name | Dose (mg/kg) | n | -1 | 4 | 7 | 11 | 14 | 18 | 21 | 25 | 28 | 32 | 35 | 42 | 49 | 56 | 63 | 71 | 77 | 85 | 91 | 99 |
| PBS | 0 | 10 | 249 ± 24 | 353 ± 42 | 394 ± 62 | 522 ± 89 | 645 ± 112 | 811 ± 111 | 919 ± 113 | 1102 ± 180 | 1280 ± 187 | 1490 ± 240 | 1569 ± 248 | 1874 ± 292 | 2110 ± 196 | 2329 ± 314 | | | | | | |
| T(K290C+K334C)-vc0101 | 1 | 9 | 251 ± 36 | 301 ± 44 | 257 ± 56 | 240 ± 45 | 264 ± 31 | 249 ± 49 | 234 ± 50 | 268 ± 80 | 285 ± 111 | 322 ± 114 | 345 ± 132 | 528 ± 204 | 689 ± 281 | 892 ± 359 | 1340 ± 472 | 1437 ± 350 | 1696 ± 320 | 2337 ± 236 | | |
| T(K334C+K392C)-vc0101 | 1 | 9 | 248 ± 42 | 253 ± 32 | 252 ± 56 | 271 ± 41 | 300 ± 56 | 341 ± 97 | 304 ± 79 | 395 ± 123 | 464 ± 206 | 484 ± 197 | 519 ± 213 | 747 ± 280 | 1028 ± 337 | 1307 ± 384 | 1544 ± 349 | 1828 ± 326 | 2046 ± 288 | 2461 ± 439 | | |
| T(K290C+K334C)-vc0101 | 3 | 9 | 246 ± 33 | 246 ± 36 | 188 ± 24 | 141 ± 37 | 163 ± 42 | 170 ± 66 | 136 ± 17 | 148 ± 35 | 96 ± 17 | 123 ± 45 | 111 ± 24 | 98 ± 30 | 60 ± 21 | 76 ± 30 | 55 ± 18 | 102 ± 23 | 86 ± 32 | 84 ± 30 | 75 ± 24 | 92 ± 29 |
| T(K334C+K392C)-vc0101 | 3 | 9 | 250 ± 30 | 265 ± 55 | 210 ± 45 | 175 ± 30 | 171 ± 38 | 211 ± 42 | 180 ± 24 | 209 ± 59 | 137 ± 18 | 130 ± 27 | 83 ± 16 | 132 ± 25 | 96 ± 21 | 94 ± 30 | 67 ± 21 | 99 ± 11 | 91 ± 20 | 86 ± 16 | 84 ± 26 | 91 ± 24 |
| T(K392C)-vc0101 | 3 | 9 | 249 ± 40 | 233 ± 46 | 195 ± 27 | 172 ± 20 | 155 ± 21 | 166 ± 34 | 125 ± 37 | 143 ± 23 | 122 ± 32 | 133 ± 36 | 101 ± 48 | 151 ± 84 | 125 ± 93 | 95 ± 27 | 142 ± 163 | 272 ± 254 | 269 ± 333 | 441 ± 568 | 506 ± 693 | 438 ± 599 |
| T(K290C)-vc0101 | 3 | 9 | 248 ± 25 | 259 ± 32 | 216 ± 28 | 198 ± 41 | 172 ± 42 | 174 ± 39 | 127 ± 24 | 154 ± 29 | 147 ± 35 | 129 ± 43 | 127 ± 51 | 177 ± 101 | 204 ± 175 | 272 ± 258 | 342 ± 350 | 514 ± 498 | 557 ± 568 | 928 ± 903 | 403 ± 479 | 590 ± 633 |
| T(K334C)-vc0101 | 3 | 9 | 247 ± 19 | 238 ± 32 | 224 ± 59 | 173 ± 34 | 174 ± 17 | 177 ± 21 | 120 ± 20 | 161 ± 35 | 135 ± 22 | 123 ± 23 | 112 ± 33 | 135 ± 34 | 104 ± 44 | 122 ± 59 | 136 ± 120 | 202 ± 251 | 203 ± 273 | 274 ± 522 | 327 ± 703 | 105 ± 17 | continued

FIG. 19C continued

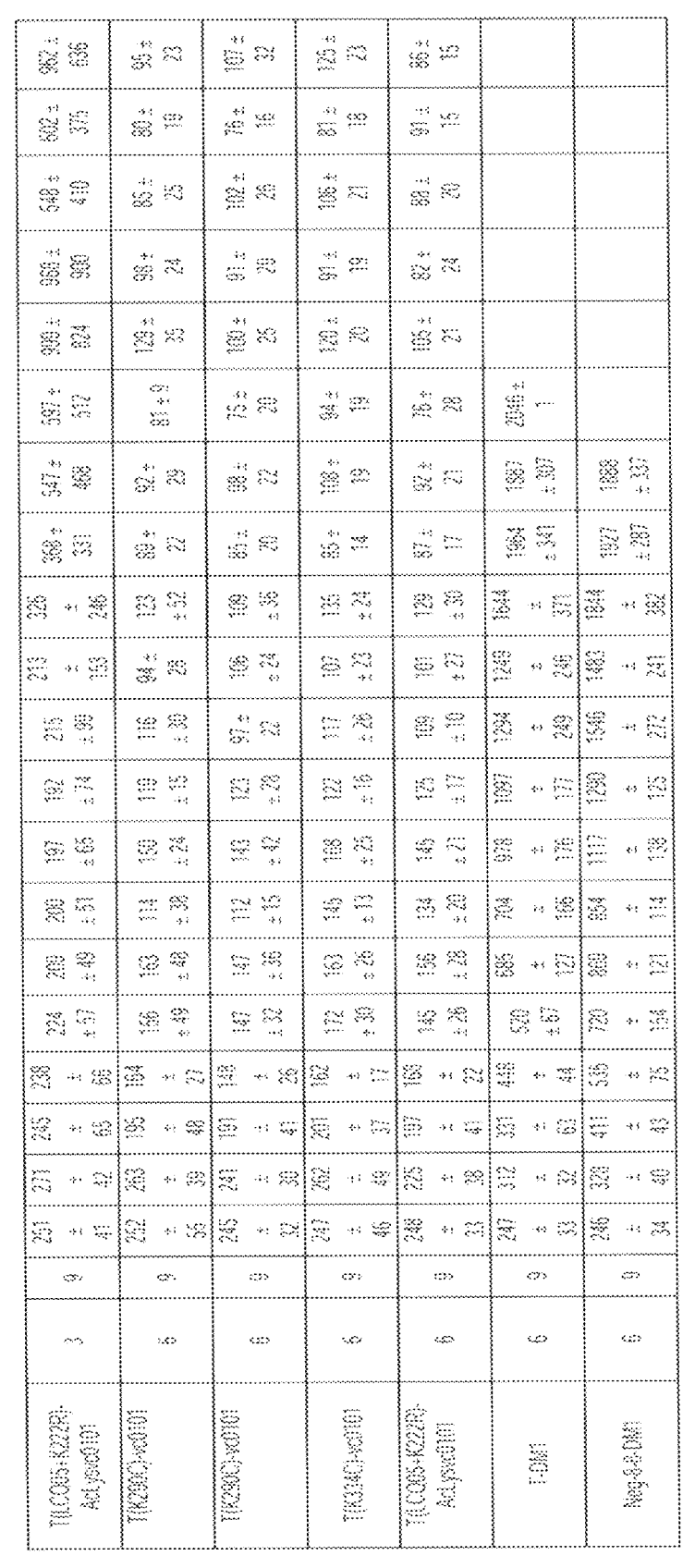

| | | | | | | | | | | | | | | | | | | | | | | | |
|---|---|---|---|---|---|---|---|---|---|---|---|---|---|---|---|---|---|---|---|---|---|---|---|
| T(LCQ05+K222R)-AcLysvc0101 | 3 | 9 | 251 ± 41 | 271 ± 42 | 245 ± 65 | 238 ± 66 | 224 ± 57 | 209 ± 49 | 200 ± 51 | 197 ± 65 | 192 ± 74 | 215 ± 98 | 213 ± 153 | 326 ± 246 | 368 ± 331 | 547 ± 468 | 597 ± 512 | 909 ± 824 | 968 ± 900 | 548 ± 410 | 602 ± 375 | 962 ± 636 |
| T(K290C)-vc0101 | 6 | 9 | 252 ± 56 | 263 ± 39 | 195 ± 48 | 164 ± 27 | 156 ± 49 | 163 ± 48 | 114 ± 38 | 150 ± 24 | 119 ± 15 | 116 ± 30 | 94 ± 28 | 123 ± 52 | 89 ± 22 | 92 ± 29 | 81 ± 9 | 129 ± 35 | 98 ± 24 | 85 ± 25 | 80 ± 19 | 95 ± 23 |
| T(K290C)-vc0101 | 6 | 9 | 245 ± 32 | 241 ± 30 | 191 ± 41 | 148 ± 26 | 147 ± 32 | 147 ± 36 | 112 ± 15 | 143 ± 42 | 123 ± 28 | 97 ± 22 | 106 ± 24 | 109 ± 36 | 85 ± 20 | 98 ± 22 | 75 ± 20 | 100 ± 25 | 91 ± 20 | 102 ± 26 | 76 ± 16 | 107 ± 32 |
| T(K334C)-vc0101 | 6 | 9 | 247 ± 46 | 262 ± 49 | 201 ± 37 | 162 ± 17 | 172 ± 30 | 163 ± 26 | 145 ± 13 | 188 ± 25 | 122 ± 16 | 117 ± 26 | 107 ± 23 | 135 ± 24 | 85 ± 14 | 108 ± 19 | 94 ± 19 | 120 ± 20 | 91 ± 19 | 106 ± 21 | 81 ± 18 | 125 ± 23 |
| T(LCQ05+K222R)-AcLysvc0101 | 6 | 9 | 248 ± 33 | 225 ± 38 | 197 ± 41 | 169 ± 22 | 145 ± 26 | 156 ± 28 | 134 ± 20 | 145 ± 21 | 125 ± 17 | 109 ± 10 | 101 ± 27 | 129 ± 30 | 87 ± 17 | 92 ± 21 | 76 ± 28 | 105 ± 21 | 82 ± 24 | 88 ± 20 | 91 ± 15 | 86 ± 15 |
| T-DM1 | 6 | 9 | 247 ± 33 | 312 ± 32 | 331 ± 63 | 448 ± 44 | 520 ± 67 | 685 ± 127 | 704 ± 166 | 978 ± 176 | 1097 ± 177 | 1294 ± 249 | 1249 ± 246 | 1644 ± 371 | 1964 ± 341 | 1887 ± 307 | 2046 ± 1 | | | | | |
| Neg-8-8-DM1 | 6 | 9 | 246 ± 34 | 328 ± 40 | 411 ± 43 | 535 ± 75 | 720 ± 154 | 869 ± 121 | 854 ± 114 | 1117 ± 138 | 1290 ± 125 | 1546 ± 272 | 1483 ± 241 | 1844 ± 382 | 1927 ± 287 | 1888 ± 337 | | | | | | |

Dose Schedule q4d (days 1,5,9,13)

Dose Schedule q4d (days 1,5,9,13)

SITE SPECIFIC HER2 ANTIBODY DRUG CONJUGATES

RELATED APPLICATIONS

This application claims the benefit of U.S. Provisional Application No. 62/260,854, filed Nov. 30, 2015, U.S. Provisional Application No. 62/289,744, filed Feb. 1, 2016, U.S. Provisional Application No. 62/289,727, filed Feb. 1, 2016, and U.S. Provisional Application No. 62/409,105, filed Oct. 17, 2016, which are hereby incorporated by referenced in their entireties.

SEQUENCE LISTING

This application is being filed electronically via EFS-Web and includes an electronically submitted sequence listing in .txt format. The .txt file contains a sequence listing entitled "PC72091A_SequenceListing_Substitute.txt" created on Nov. 4, 2019, and having a size of 171 KB. The sequence listing contained in this .txt file is part of the specification and is incorporated herein by reference in its entirety.

FIELD OF THE INVENTION

The present invention relates to site specific HER2 antibody drug conjugates. The present invention further relates to the methods of using such antibody drug conjugates for the treatment of cancer.

BACKGROUND OF THE INVENTION

Members of the ErbB family of transmembrane receptor tyrosine kinases are important mediators of cell growth, cell differentiation, cell migration, and apoptosis. The receptor family includes four distinct members, including epidermal growth factor receptor (EGFR or ErbB1), HER2 (ErbB2 or p185), HER3 (ErbB3) and HER4 (ErbB4 or tyro2).

HER2 was originally identified as the product of the transforming gene from neuroblastomas of chemically treated rats. HER2 overexpression has been validated as tumorigenic both in vitro (Di Fiore et al., 1987, Science 237(4811):178-82; Hudziak et al., 1987, PNAS 84(20):7159-63; Chazin et al., 1992, Oncogene 7(9):1859-66) and in animal models (Guy et al., 1992, PNAS 89(22):10578-82). Amplification of the gene encoding HER2 with consequent overexpression of the receptor occurs in breast and ovarian cancers and correlates with a poor prognosis (Slamon et al., 1987, Science 235(4785):177-82; Slamon et al., 1989, Science 244:707-12; Anbazhagan et al., 1991, Annals Oncology 2(1):47-53; Andrulis et al., 1998, J Clinical Oncology 16(4):1340-9). Overexpression of HER2 (frequently but not necessarily due to gene amplification) has also been observed in other tumor types including gastric, endometrial, non-small cell lung cancer, colon, pancreatic, bladder, kidney, prostate and cervical (Scholl et al., 2001, Annals Oncology 12 (Suppl. 1):581-7; Menard et al., 2001, Ann Oncol 12(Suppl 1):515-9; Martin et al., 2014, Future Oncology 10:1469-86).

Herceptin® (trastuzumab) is a humanized monoclonal antibody that binds to the extracellular domain of HER2 (Carter et al. 1992, PNAS 89:4285-9 and U.S. Pat. No. 5,821,337). Herceptin® received marketing approval from the Food and Drug Administration on Sep. 25, 1998 for the treatment of patients with metastatic breast cancer whose tumors overexpress the HER2 protein. Although Herceptin® is a breakthrough in treating patients with HER2-overexpressing breast cancers that have received extensive prior anti-cancer therapy, segments of patients in this population fail to respond, respond only poorly or become resistant to Herceptin® treatment.

Kadcyla® (trastuzumab-DM1 or T-DM1) is an antibody drug conjugate consisting of trastuzumab conjugated to the maytansinoid agent DM1 via the stable thioether linker MCC (4-[N-maleimidomethyl] cyclohexane-1-carboxylate) (Lewis et al., 2008, Cancer Res. 68:9280-90; Krop et al., 2010, J Clin Oncol. 28:2698-2704; U.S. Pat. No. 8,337,856). Kadcyla® received marketing approval from the Food and Drug Administration on Feb. 22, 2013 for the treatment of HER2 positive metastatic breast cancer in patients who had been previously treated with Herceptin® and a taxane drug and became Herceptin® refractory. Like seen with Herceptin®, there are segments of the patients in the HER2-overexpressing breast cancer population that do not experience successful long term therapy with Kadcyla®.

Therefore, there is a significant clinical need for developing further HER2-directed cancer therapies for those patients with HER2-overexpressing tumors or other diseases associated with HER2 overexpression that do not respond, respond poorly or become resistant to Herceptin® and/or Kadcyla® treatment.

SUMMARY OF THE INVENTION

The present invention provides site specific HER2 antibody drug conjugates (ADCs) and their use in treatment of HER2-expressing cancers. ADCs enable targeted delivery of therapeutics to cancer cells and offer potential for more selective therapy while reducing known off-target toxicities.

A site specific HER2 ADC of the invention is generally of the formula: Ab-(L-D), wherein Ab is an antibody, or antigen-binding fragment thereof, that binds to HER2; and L-D is a linker-drug moiety, wherein L is a linker, and D is a drug.

The antibody (Ab) of the ADCs of the invention can be any HER2-binding antibody. In some aspects of the invention, the Ab binds to the same epitope on HER2 as trastuzumab)(Herceptin®. In other aspects of the invention, the Ab has the same heavy chain and light chain CDRs as trastuzumab. In specific aspects of the invention, the Ab has the same heavy chain variable region ($V_H$) and the same light chain variable region ($V_L$) as trastuzumab.

The HER2 ADCs of the present invention are conjugated to the drug in a site specific manner. To accommodate this type of conjugation, the antibody must be derivatized to provide for either a reactive cysteine residue engineered at one or more specific sites or an acyl donor glutamine residue (either engineered at one or more specific sites or in an attached peptide tag). Such modifications should be at sites that do not disrupt the antigen binding capability of the antibody. In preferred embodiments, the one or more modifications are made in the constant region of the heavy and/or light chains of the antibody.

In some embodiments of the present invention, the site specific HER2 ADCs can use antibodies comprising heavy chain variable region CDRs and light chain variable region CDRs of trastuzumab ($V_H$ CDRs of SEQ ID NOs:2-4 and $V_L$ CDRs of SEQ ID NOs:8-10) and any combination of heavy and light chain constant regions disclosed in Table 1 with the proviso that when the heavy chain constant region is SEQ ID NO:5 then the light chain constant region is not SEQ ID NO:11. In such embodiments, the heavy chain constant region can be selected from any of SEQ ID NOs:17, 5, 13, 21, 23, 25, 27, 29, 31, 33, 35, 37 or 39 while the light chain constant region can be selected from any of SEQ ID NOs:41, 11 or 43 providing that the combination is not SEQ ID NO:5 and SEQ ID NO:11.

In a specific embodiment, the antibody used to make the site specific HER2 ADC comprises a $V_H$ domain with CDRs of SEQ ID NOs:2-4 and a $V_L$ domain with CDRs of SEQ ID NOs:8-10 attached to a heavy chain constant region of SEQ ID NO:17 and a light chain constant region of SEQ ID NO:41. In another specific embodiment, the antibody used to make the site specific HER2 ADC comprises a $V_H$ domain with CDRs of SEQ ID NOs:2-4 and a $V_L$ domain with CDRs of SEQ ID NOs:8-10 attached to a heavy chain constant region of SEQ ID NO:13 and a light chain constant region of SEQ ID NO:43.

In other embodiments, the ADCs of the invention can use antibodies comprising of any combination of heavy and light chains disclosed in Table 1 with the proviso that if the heavy chain is SEQ ID NO:6 then the light chain is not SEQ ID NO:12. In such embodiments, the heavy chain can be selected from any of SEQ ID NOs:18, 6, 14, 22, 24, 26, 28, 30, 32, 34, 36, 38 or 40 while the light chain can be selected from any of SEQ ID NOs: 42, 12 or 44 providing that the combination is not SEQ ID NO:6 and SEQ ID NO:12.

In a specific embodiment, the ADCs of the invention can use an antibody comprising a heavy chain of SEQ ID NO:18 and a light chain of SEQ ID NO:42. In another specific embodiment, the ADCs of the invention can use an antibody comprising a heavy chain of SEQ ID NO:14 and a light chain of SEQ ID NO:44.

Any of the site specific HER2 ADCs disclosed herein can be prepared with a drug (D) that is a therapeutic agent useful for treating cancer. In a specific embodiment, the therapeutic agent is an anti-mitotic agent. In another specific embodiment, the anti-mitotic agent drug component in the ADCs of the invention is an auristatin (e.g., 0101, 8261, 6121, 8254, 6780 and 0131). In a more specific embodiment, the auristatin drug component in the ADCs of the invention is 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (also known as 0101). Preferably, the drug component of the ADCs of the invention is membrane permeable.

Any of the site specific HER2 ADCs disclosed herein can be prepared with a linker (L) that is cleavable or non-cleavable. Preferably, the linker is cleavable. Cleavable linkers include, but are not limited to, vc, AcLysvc and m(H20)c-vc. More preferably, the linker is vc or AcLysvc.

In a particular aspect of the invention, site specific HER2 ADC of the formula Ab-(L-D) comprises (a) an antibody, Ab, comprising a heavy chain of SEQ ID NO:18 and a light chain of SEQ ID NO:42; and (b) a linker-drug moiety, L-D, wherein L is a linker, and D is a drug, wherein the linker is vc and wherein the drug is 0101.

In another particular aspect of the invention, site specific HER2 ADC of the formula Ab-(L-D) comprises (a) an antibody, Ab, comprising a heavy chain of SEQ ID NO:14 and a light chain of SEQ ID NO:44; and (b) a linker-drug moiety, L-D, wherein L is a linker, and D is a drug, wherein the linker is AcLysvc and wherein the drug is 0101.

Another aspect of the invention includes methods of making, methods of preparing, methods of synthesis, methods of conjugation and methods of purification of the antibody drug conjugates disclosed herein and the intermediates for the preparation, synthesis and conjugation of the antibody drug conjugates disclosed herein.

Further provided are pharmaceutical compositions comprising a site specific HER2 ADC disclosed herein and a pharmaceutically acceptable carrier.

Nucleic acids encoding the antibody portion of the site specific HER2 ADCs are contemplated by the invention. Additional vectors and host cells comprising the nucleic acids are also contemplate by the invention.

The present invention also provides method of use of the site specific HER2 ADCs in the treatment of HER2-expressing cancers. HER2-expressing cancer to be treated with the site specific HER2 ADCs of the invention can express HER2 at a high, moderate or low level. In some embodiments, the cancer to be treated is resistant to, refractory to and/or relapsed from treatment with trastuzumab and/or trastuzumab emtansine (T-DM1) either of which alone or in combination with a taxane. Cancers to be treated include, but are not limited to, breast cancer, ovarian cancer, lung cancer, gastric cancer, esophageal cancer, colorectal cancer, urothelial cancer, pancreatic cancer, salivary gland cancer and brain cancer or metastases of the aforementioned cancers. In a more specific embodiment, the breast cancer is estrogen receptor and progesterone receptor negative breast cancer or triple negative breast cancer (TNBC). In another embodiment, the lung cancer is non-small cell lung cancer (NSCLC).

These and other aspects of the invention will be appreciated by a review of the application as a whole.

BRIEF DESCRIPTION OF THE DRAWINGS

FIG. 5 depicts in vitro cytotoxicity data ($IC_{50}$) reported in nM payload concentration for a number of trastuzumab derived ADCs on a number of cell lines with different levels of HER2 expression.

FIG. 6 depicts in vitro cytotoxicity data ($IC_{50}$) reported in ng/ml antibody concentration for a number of trastuzumab derived ADCs on a number of cell lines with different levels of HER2 expression.

FIG. 14 depicts in vitro cytotoxicity data ($IC_{50}$) reported in nM payload concentration and ng/ml antibody concentration for a number of trastuzumab derived ADCs and free payloads on cells made resistant to T-DM1 in vitro (N87-TM1 and N87-TM2) or parental cells sensitive to T-DM1 (N87cells). N87 gastric cancer cells express high levels of HER2.

FIGS. 19A-19C depict sensitivity to trastuzumab and various trastuzumab derived ADCs of tumors generated in vivo from implantation of (A) T-DM1 sensitive N87 parental cells; (B) T-DM1 resistant N87-TM1 cells; (C) T-DM1 resistant N87-TM2 cells.

DETAILED DESCRIPTION OF THE INVENTION

Figure 1A:
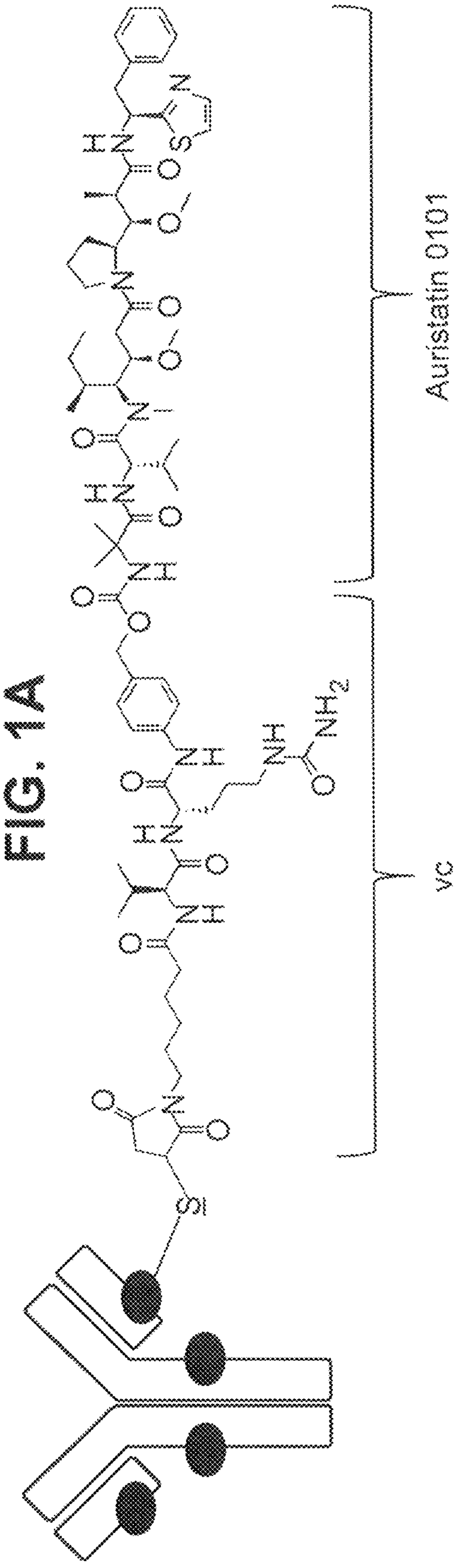
FIGS. 1A-1B depict (A) T(kK183C+K290C)-vc0101 ADC and (B) T(LCQ05+K222R)-AcLysvc0101 ADC. Each black circle represents a linker/payload that is conjugated to the monoclonal antibody. The structure of one such linker/payload is shown for each ADC. The underlined entity is supplied by the amino acid residue on the antibody through which conjugation occurs.

The present invention provides site specific HER2 antibody drug conjugates (ADCs), processes for preparing the conjugates using HER2 antibodies, linkers, and drug payloads and nucleic acids encoding the antibodies used in making the ADCs. The ADCs of the invention are useful for the preparation and manufacture of compositions, such as medicaments, that can be used in the treatment of HER2-expressing cancers.

ADCs consist of an antibody component conjugated to a drug payload through the use of a linker. Conventional conjugation strategies for ADCs rely on randomly conjugating the drug payload to the antibody through lysines or cysteines that are endogenously on the antibody heavy and/or light chain. Accordingly, such ADCs are a heterogeneous mixture of species showing different drug:antibody ratios (DAR). In contrast, the ADCs disclosed herein are site specific ADCs that conjugate the drug payload to the antibody at particular engineered residues on the antibody heavy and/or light chain. As such, the site specific ADCs are a homogeneous population of ADCs comprised of a species with a defined drug:antibody ratio (DAR). Thus, the site specific ADCs demonstrate uniform stoichiometry resulting in improved pharmacokinetics, biodistribution and safety profile of the conjugate. ADCs of the invention include antibodies of the invention conjugated to one or more linker/payload moieties.

The present invention provides antibody drug conjugates of the formula Ab-(L-D), wherein (a) Ab is an antibody, or antigen-binding fragment thereof, that binds to HER2, and (b) L-D is a linker-drug moiety, wherein L is a linker, and D is a drug.

Also encompassed by the present invention are antibody drug conjugates of the formula Ab-$(L\text{-}D)_p$, wherein (a) Ab is an antibody, or antigen-binding fragment thereof, that binds to HER2, (b) L-D is a linker-drug moiety, wherein L is a linker, and D is a drug and (c) p is the number of linker/drug moieties are attached to the antibody. For site specific ADCs, p is a whole number due to the homogeneous nature of the ADC. In some embodiments, p is 4. In other embodiments, p is 3. In other embodiments, p is 2. In other embodiments, p is 1. In other embodiments, p is greater than 4.

As used herein, the term "HER2" refers to a transmembrane tyrosine kinase receptor that belongs to the EGFR family. HER2 is also known as ErbB2, p185 and CD340. This family of receptors includes four members (EGFR/HER1, HER2, HER3 and HER4) that function by stimulating growth factor signaling pathways such as the PI3K-AKT-mTOR pathway. Amplification and/or overexpression of HER2 is associated with multiple human malignancies. The wild type human HER2 protein is described, for example, in Semba et al., 1985, PNAS 82:6497-6501 and Yamamoto et al., 1986, Nature 319:230-4 and Genbank Accession Number X03363.

As used herein, the term "Antibody (Ab)" refers to an immunoglobulin molecule capable of recognizing and binding to a specific target or antigen, such as a polypeptide, through at least one antigen recognition site located in the variable region of the immunoglobulin molecule. The term can encompass any type of antibody, including but not limited to monoclonal antibodies, antigen-binding fragments of intact antibodies that retain the ability to specifically bind to a given antigen (i.e., Fab, Fab', $F(ab')_2$, Fd, Fv, Fc, etc.) and mutants thereof.

Native or naturally occurring antibodies, and native immunoglobulins, are typically heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. The term "variable" refers to the fact that certain portions of the variable domains differ extensively in sequence among antibodies.

The antibody used in the present invention specifically binds to HER2. In a specific embodiment, the HER2 antibody binds to the same epitope on HER2 as trastuzumab) (Herceptin®. In a more specific embodiment, the HER2 antibody has the same variable region CDRs as trastuzumab) (Herceptin®. In yet a more specific embodiment, the HER2 antibody has the same variable regions (i.e., $V_H$ and $V_L$) as trastuzumab)(Herceptin®.

As used herein, the term "Linker (L)" describes the direct or indirect linkage of the antibody to the drug payload. Attachment of a linker to an antibody can be accomplished in a variety of ways, such as through surface lysines, reductive-coupling to oxidized carbohydrates, cysteine residues liberated by reducing interchain disulfide linkages, reactive cysteine residues engineered at specific sites, and acyl donor glutamine-containing tag or an endogenous glutamine made reactive by polypeptide engineering in the presence of transglutaminase and an amine. The present invention uses site specific methods to link the antibody to the drug payload. In one embodiment, conjugation occurs through cysteine residues that have been engineered into the antibody constant region. In another embodiment, conjugation occurs through acyl donor glutamine residues that have either been a) added to the antibody constant region via a peptide tag, b) engineered into the antibody constant region or c) made accessible/reactive by engineering surrounding residues. Linkers can be cleavable (i.e., susceptible to cleavage under intracellular conditions) or non-cleavable. In some embodiments, the linker is a cleavable linker.

As used herein, the term "Drug (D)" refers to any therapeutic agent useful in treating cancer. The drug has biological or detectable activity, for example, cytotoxic agents, chemotherapeutic agents, cytostatic agents, and immunomodulatory agents. In preferred embodiments, therapeutic agents have a cytotoxic effect on tumors including the depletion, elimination and/or the killing of tumor cells. The terms drug, payload, and drug payload are used interchangeably. In a specific embodiment, the drug is an anti-mitotic agent. In a more specific embodiment, the drug is an auristatin. In a yet more specific embodiment, the drug is 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (also known as 0101). In some embodiments, the drug is preferably membrane permeable.

As used herein, the term "L-D" refers to a linker-drug moiety resulting from a drug (D) linked to a linker (L).

Additional scientific and technical terms used in connection with the present invention, unless indicated otherwise herein, shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art.

I. HER2 Antibodies

For preparation of site specific HER2 ADCs of the invention, the antibody can be any antibody that specifically binds to the extracellular domain of HER2. In one embodiment, the antibody used to make the ADC binds to the same epitope of HER2 as trastuzumab and/or competes with trastuzumab for HER2 binding. In another embodiment, the antibody used to make the ADC has the same heavy chain variable region CDRs and light chain variable region CDRs as trastuzumab. In yet another embodiment, the antibody used to make the ADC has the same heavy chain variable region and light chain variable region as trastuzumab.

The term "compete", as used herein with regard to an antibody, means that a first antibody, or an antigen-binding fragment thereof, binds to an epitope in a manner sufficiently similar to the binding of a second antibody, or an antigen-binding fragment thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Trastuzumab (trade name Herceptin®) is a humanized monoclonal antibody that binds to the extracellular domain of HER2. The amino acid sequences of its variable domains are disclosed in U.S. Pat. No. 5,821,337 ($V_H$ is SEQ ID NO:42 and $V_L$ is SEQ ID NO:41 of U.S. Pat. No. 5,821,337) as well as in Table 1 infra (SEQ ID NOs:1 and 7, respectively). The amino acid sequences of the heavy chain variable region CDRs are SEQ ID NOs:2-4 while the amino acid sequences of the light chain CDRs are SEQ ID NOs: 6-10 (Table 1 infra). The amino acid sequences of the complete heavy and light chains are SEQ ID NOs:6 and 12, respectively (Table 1 infra).

T-DM1 (trade name Kadcyla®) is an antibody drug conjugate consisting of trastuzumab conjugated to the maytansinoid agent DM1 via the stable thioether linker MCC (4-[N-maleimidomethyl] cyclohexane-1-carboxylate) (U.S. Pat. No. 8,337,856). The antibody component of this ADC is identical to trastuzumab. Payload conjugation to trastuzumab is accomplished using conventional conjugation (rather than site specific) techniques such that the ADC is a heterogeneous population of species with different amounts of DM1 conjugated to each one. The DM1 payload inhibits cell proliferation by inhibiting the formation of microtubules during mitosis through inhibition of tubulin polymerization (Remillard et al., 1975, Science 189:1002-5). Kadcyla® is approved for the treatment of HER2 positive metastatic breast cancer in patients who had been previously treated with Herceptin® and a taxane drug and became Herceptin® refractory. T-DM1 used in the experiments described in the Examples Section was made internally using publically available information.

The ADCs of the present invention are conjugated to the payload in a site specific manner. To accommodate this type of conjugation, the antibody must be derivatized to provide for either a reactive cysteine residue engineered at one or more specific sites, an acyl donor glutamine-containing tag or an endogenous glutamine made reactive by polypeptide engineering in the presence of transglutaminase and an amine. Amino acid modifications can be made by any method known in the art and many such methods are well known and routine for the skilled artisan. For example, but not by way of limitation, amino acid substitutions, deletions and insertions may be accomplished using any well-known PCR-based technique. Amino acid substitutions may be made by site-directed mutagenesis (see, for example, Zoller and Smith, 1982, Nucl. Acids Res. 10:6487-6500; and Kunkel, 1985, PNAS 82:488).

In applications where retention of antigen binding is required, such modifications should be at sites that do not disrupt the antigen binding capability of the antibody. In preferred embodiments, the one or more modifications are made in the constant region of the heavy and/or light chains.

As used herein, the term "constant region" of an antibody refers to the constant region of the antibody light chain or the constant region of the antibody heavy chain, either alone or in combination. The constant regions of the antibodies used to make the ADCs of the invention may be derived from constant regions of any one of IgA, IgD, IgE, IgG, IgM, or any isotypes thereof as well as subclasses and mutated versions thereof.

The constant domains are not involved directly in binding an antibody to an antigen, but exhibit various effector functions, such as Fc receptor (FcR) binding, participation of the antibody in antibody-dependent cellular toxicity (ADCC), opsonization, initiation of complement dependent cytotoxicity, and mast cell degranulation. As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU Index of Kabat (Kabat et al., Sequences of Proteins of Immunological Interest, 5th Ed. Public Health Service, National Institutes of Health, Bethesda, Md., 1991). The Fc region of an immunoglobulin generally has two constant regions, CH2 and CH3.

There are two different light chains constant regions for use in antibodies, CLK and CLΔ. CLκ has known polymorphic loci CLκ-V/$A^{45}$ and CLκ-L/$V^{83}$ (using the Kabat numbering system as set forth in Kabat et al. (1991, NIH Publication 91-3242, National Technical Information Service, Springfield, Va.), so all Kappa and Lambda positions are numbered according to the Kabat system.) thus allowing for polymorphisms Km(1): CLκ-$V^{48}$/$L^{83}$; Km(1,2): CLκ-$A^{45}$/$L^{83}$; and Km(3): CLκ-$A^{48}$/$V^{83}$. Polypeptides, antibodies and ADCs of the invention can have antibody components with any of these light chain constant regions.

For clarity, unless otherwise specified, amino acid residues in the human IgG heavy constant domain of an antibody are numbered according the EU index of Edelman et al., 1969, Proc. Natl. Acad. Sci. USA 63(1):78-85 as described in Kabat et al., 1991, referred to herein as the "EU index of Kabat". Typically, the Fc domain comprises from about amino acid residue 236 to about 447 of the human IgG1 constant domain. Correspondence between C numberings can be found, e.g., at IGMT database. Amino acid residues of the light chain constant domain are numbered according to Kabat et al., 1991. Numbering of antibody constant domain amino acid residues is also shown in International Patent Publication No. WO 2013/093809. The only exception to the use of EU index of Kabat in IgG heavy constant domain is residue A114 described in the examples. A114 refers to Kabat numbering, and the corresponding EU index number is 118. This is because the initial publication of site specific conjugating at this site used Kabat numbering and referred this site as A114C, and has since been widely used in the art as the "114" site. See Junutula et al., Nature Biotechnology 26, 925-932 (2008). To be consistent with the common usage of this site in the art, "A114," "A114C," "C114" or "114C" are used in the examples.

Nucleic acids encoding the heavy and light chains of the antibodies used to make the ADCs of the invention can be cloned into a vector for expression or propagation. The sequence encoding the antibody of interest may be maintained in vector in a host cell and the host cell can then be expanded and frozen for future use.

As used herein, the term "vector" refers to a construct which is capable of delivering, and preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, the term "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a nucleic acids or vectors of this invention.

Table 1 provides the amino acid (protein) sequences and associated nucleic acid (DNA) sequences of humanized HER2 antibodies used in constructing the site specific ADCs of the invention. The CDRs shown are defined by Kabat numbering scheme.

The antibody heavy chains and light chains shown in Table 1 have the trastuzumab heavy chain variable region ($V_H$) and light chain variable region ($V_L$). The heavy chain constant region and light chain constant region are derivatized from trastuzumab and contain on or more modification to allow for site specific conjugation when making the ADCs of the invention.

Modifications to the amino acid sequences in the antibody constant region to allow for site specific conjugation are underlined and bolded. The nomenclature for the antibodies derivatized from trastuzumab is T (for trastuzumab) and then in parenthesis the position of the amino acid of modification flanked by the single letter amino acid code for the wild type residue and the single letter amino acid code for the residue that is now in that position in the derivatized antibody. Two exceptions to this nomenclature are "kK183C" which denotes that position 183 on the light (kappa) chain has been modified from a lysine to a cysteine and "LCQ05" which denotes an eight amino acid glutamine-containing tag that has been attached to the C terminus of the light chain constant region.

One of the modifications shown in Table 1 is not used for conjugation. The residue at position 222 on the heavy chain (using the EU Index of Kabat numbering scheme) can be altered to result in a more homogenous antibody and payload conjugate, better intermolecular crosslinking between the antibody and the payload and/or significant decrease in interchain crosslinking.

TABLE 1

Sequences of humanized HER2 antibodies

| SEQ ID NO. | Description | Sequence |
|---|---|---|
| 1 | Trastuzumab VH protein | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSS |
| 2 | VH CDR1 protein | DTYIH |

TABLE 1-continued

Sequences of humanized HER2 antibodies

| SEQ ID NO. | Description | Sequence |
|---|---|---|
| 3 | VH CDR2 protein | RIYPTNGYTRYADSVKG |
| 4 | VH CDR3 protein | WGGDGFYAMDY |
| 5 | Trastuzumab heavy chain constant region protein | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQ GNVFSCSVMHEALHNHYTQKSLSLSPG |
| 6 | Trastuzumab heavy chain protein | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVL DSDGSFFLYSKLTVDKSRWQQGNVFSCSVMHEALHNHYTQKSLSLSPG |
| 7 | Trastuzumab VL protein | DIQMTQSPSSLSASVGDRVTITCRASQDVNTAVAWYQQKPGKAPKWYSA SFLYSGVPSRFSGSRSGTDFTLTISSLQPEDFATYYCQQHYTTPPTFGQGT KVEIK |
| 8 | VL CDR1 protein | RASQDVNTAVA |
| 9 | VL CRD2 protein | SASFLYS |
| 10 | VL CDR3 protein | QQHYTTPPT |
| 11 | Trastuzumab light chain constant region protein | RTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKS FNRGEC |
| 12 | Trastuzumab light chain protein | DIQMTQSPSSLSASVGDRVTITCRASQDVNTAVAWYQQKPGKAPKWYSA SFLYSGVPSRFSGSRSGTDFTLTISSLQPEDFATYYCQQHYTTPPTFGQGT KVEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSS PVTKSFNRGEC |
| 13 | T(K222R) heavy chain constant region protein | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEPK SCDRTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQ GNVFSCSVMHEALHNHYTQKSLSLSPGK |
| 14 | T(K222R) heavy chain protein | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDRTHTCPPCPAPELLGGPSVFLFPPKP KDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVL DSDGSFFLYSKLTVDKSRWQQGNVFSCSVMHEALHNHYTQKSLSLSPGK |
| 15 | T(K246C) heavy chain constant region protein | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEPK SCDKTHTCPPCPAPELLGGPSVFLFPPCPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQ GNVFSCSVMHEALHNHYTQKSLSLSPG |

TABLE 1-continued

Sequences of humanized HER2 antibodies

| SEQ ID NO. | Description | Sequence |
|---|---|---|
| 16 | T(K246C) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPCP<br>KDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPG |
| 17 | T(K290C) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTCPREEQYNSTYRVVSVLTVLHQDWLNGKE<br>YKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPG |
| 18 | T(K290C) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTCPREEQYN<br>STYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPG |
| 19 | T(N297A) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTKPREEQYASTYRVVSVLTVLHQDWLNGKE<br>YKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPGK |
| 20 | T(N297A) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYA<br>STYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPGK |
| 21 | T(N297Q) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTKPREEQYQSTYRVVSVLTVLHQDWLNGKE<br>YKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPGK |
| 22 | T(N297Q) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYQ<br>STYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPGK |
| 23 | T(K334C) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKE<br>YKCKVSNKALPAPIECTISKAKGQPREPQVYTLPPSREEMTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPG |

TABLE 1-continued

Sequences of humanized HER2 antibodies

| SEQ ID NO. | Description | Sequence |
| --- | --- | --- |
| 24 | T(K334C) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYN<br>STYRVVSVLTVLHQDWLNGKEYKCKVSNKALPAPIECTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPG |
| 25 | T(K392C) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKE<br>YKCKVSNKALPAPIEKTISKAKGQPREPQVYTLPPSREEMTKNQVSLTCLV<br>KGFYPSDIAVEWESNGQPENNYCTTPPVLDSDGSFFLYSKLTVDKSRWQQ<br>GNVFSCSVMHEALHNHYTQKSLSLSPG |
| 26 | T(K392C) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQV<br>YTLPPSREEMTKNQVSLTCLVKGFYPSDIAVEWESNGQPENNYCTTPPVL<br>DSDGSFFLYSKLTVDKSRWQQGNVFSCSVMHEALHNHYTQKSLSLSPG |
| 27 | T(L443C) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKE<br>YKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQ<br>GNVFSCSVMHEALHNHYTQKSLSCSPG |
| 28 | T(L443C) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSCSPG |
| 29 | T(K290C + K334C) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTCPREEQYNSTYRVVSVLTVLHQDWLNGKE<br>YKCKVSNKALPAPIECTISKAKGQPREPQVYTLPPSREEMTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPG |
| 30 | T(K290C + K334C) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTCPREEQYN<br>STYRVVSVLTVLHQDWLNGKEYKCKVSNKALPAPIECTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPG |
| 31 | T(K290C + K392C) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTCPREEQYNSTYRVVSVLTVLHQDWLNGKE<br>YKCKVSNKALPAPIEKTISKAKGQPREPQVYTLPPSREEMTKNQVSLTCLV<br>KGFYPSDIAVEWESNGQPENNYCTTPPVLDSDGSFFLYSKLTVDKSRWQQ<br>GNVFSCSVMHEALHNHYTQKSLSLSPG |

TABLE 1-continued

Sequences of humanized HER2 antibodies

| SEQ ID NO. | Description | Sequence |
| --- | --- | --- |
| 32 | T(K290C + K392C) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTCPREEQYN<br>STYRVVSVLTVLHQDWLNGKEYKCKVSNKALPAPIEKTISKAKGQPREPQV<br>YTLPPSREEMTKNQVSLTCLVKGFYPSDIAVEWESNGQPENNYCTTPPVL<br>DSDGSFFLYSKLTVDKSRWQQGNVFSCSVMHEALHNHYTQKSLSLSPG |
| 33 | T(N297A + K222R) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDRTHTCPPCPAPELLGGPSVFLFPPKPKDTLMISRTPEVTCVVVDVSHE<br>DPEVKFNWYVDGVEVHNAKTKPREEQYASTYRVVSVLTVLHQDWLNGKE<br>YKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPGK |
| 34 | T(N297A + K222R) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDRTHTCPPCPAPELLGGPSVFLFPPKP<br>KDTLMISRTPEVTCVVVDVSHEDPEVKFNWYVDGVEVHNAKTKPREEQYA<br>STYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPGK |
| 35 | T(N297Q + K222R) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDRTHTCPPCPAPELLGGPSVFLFPPKPKDTLMISRTPEVTCVVVDVSHE<br>DPEVKFNWYVDGVEVHNAKTKPREEQYQSTYRVVSVLTVLHQDWLNGKE<br>YKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPGK |
| 36 | T(N297Q + K222R) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDRTHTCPPCPAPELLGGPSVFLFPPKP<br>KDTLMISRTPEVTCVVVDVSHEDPEVKFNWYVDGVEVHNAKTKPREEQYQ<br>STYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPGK |
| 37 | T(K334C + K392C) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKE<br>YKCKVSNKALPAPIECTISKAKGQPREPQVYTLPPSREEMTKNQVSLTCLV<br>KGFYPSDIAVEWESNGQPENNYCTTPPVLDSDGSFFLYSKLTVDKSRWQQ<br>GNVFSCSVMHEALHNHYTQKSLSLSPG |
| 38 | T(K334C + K392C) heavy chain protein | EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYN<br>STYRVVSVLTVLHQDWLNGKEYKCKVSNKALPAPIECTISKAKGQPREPQV<br>YTLPPSREEMTKNQVSLTCLVKGFYPSDIAVEWESNGQPENNYCTTPPVL<br>DSDGSFFLYSKLTVDKSRWQQGNVFSCSVMHEALHNHYTQKSLSLSPG |
| 39 | T(K392C + L443C) heavy chain constant region protein | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKE<br>YKCKVSNKALPAPIEKTISKAKGQPREPQVYTLPPSREEMTKNQVSLTCLV<br>KGFYPSDIAVEWESNGQPENNYCTTPPVLDSDGSFFLYSKLTVDKSRWQQ<br>GNVFSCSVMHEALHNHYTQKSLSCSPG |

TABLE 1-continued

Sequences of humanized HER2 antibodies

| SEQ ID NO. | Description | Sequence |
|---|---|---|
| 40 | T(K392C + L443C) heavy chain protein | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQV YTLPPSREEMTKNQVSLTCLVKGFYPSDIAVEWESNGQPENNYCTTPPVL DSDGSFFLYSKLTVDKSRWQQGNVFSCSVMHEALHNHYTQKSLSCSPG |
| 41 | T(kK183C) light chain constant region protein | RTVAAPSVFIFPPSDEQLKSGTASVVCLLNNFYPREAKVQWKVDNALQSG NSQESVTEQDSKDSTYSLSSTLTLSCADYEKHKVYACEVTHQGLSSPVTK SFNRGEC |
| 42 | T(kK183C) light chain protein | DIQMTQSPSSLSASVGDRVTITCRASQDVNTAVAWYQQKPGKAPKWYSA SFLYSGVPSRFSGSRSGTDFTLTISSLQPEDFATYYCQQHYTTPPTFGQGTK VEIKRTVAAPSVFIFPPSDEQLKSGTASVVCLLNNFYPREAKVQWKVDNAL QSGNSQESVTEQDSKDSTYSLSSTLTLSCADYEKHKVYACEVTHQGLSSP VTKSFNRGEC |
| 43 | T(LCQ05) light chain constant region protein | RTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKS FNRGECGGLLQGPP |
| 44 | T(LCQ05) light chain | DIQMTQSPSSLSASVGDRVTITCRASQDVNTAVAWYQQKPGKAPKWYSA SFLYSGVPSRFSGSRSGTDFTLTISSLQPEDFATYYCQQHYTTPPTFGQGT LQSGNSQESVTEQDSKDSTYSLSSTLTLSKADYEKHKVYACEVTHQGLSS PVTKSFNRGECGGLLQGPP |
| 45 | Trastuzumab VH DNA | GAGGTGCAGCTGGTGGAATCCGGCGGAGGCCTGGTCCAGCCTGGCGG ATCTCTGCGGCTGTCTTGCGCCGCCTCCGGCTTCAACATCAAGGACAC CTACATCCACTGGGTCCGACAGGCACCTGGCAAGGGACTGGAATGGGT GGCCCGGATCTACCCCACCAACGGCTACACCAGATACGCCGACTCCGT GAAGGGCCGGTTCACCATCTCCGCCGACACCTCCAAGAACACCGCCTA CCTGCAGATGAACTCCCTGCGGGCCGAGGACACCGCCGTGTACTACTG CTCCAGATGGGGAGGCGACGGCTTCTACGCCATGGACTACTGGGGCC AGGGCACCCTGGTCACCGTGTCTAGC |
| 46 | Trastuzumab heavy chain DNA | GAGGTGCAGCTGGTGGAATCCGGCGGAGGCCTGGTCCAGCCTGGCGG ATCTCTGCGGCTGTCTTGCGCCGCCTCCGGCTTCAACATCAAGGACAC CTACATCCACTGGGTCCGACAGGCACCTGGCAAGGGACTGGAATGGGT GGCCCGGATCTACCCCACCAACGGCTACACCAGATACGCCGACTCCGT GAAGGGCCGGTTCACCATCTCCGCCGACACCTCCAAGAACACCGCCTA CCTGCAGATGAACTCCCTGCGGGCCGAGGACACCGCCGTGTACTACTG CTCCAGATGGGGAGGCGACGGCTTCTACGCCATGGACTACTGGGGCC AGGGCACCCTGGTCACCGTGTCTAGCGCGTCGACCAAGGGCCCATCG GTCTTCCCCCTGGCACCCTCCTCCAAGAGCACCTCTGGGGGCACAGCG GCCCTGGGCTGCCTGGTCAAGGACTACTTCCCCGAACCGGTGACGGT GTCGTGGAACTCAGGCGCCCTGACCAGCGGCGTGCACACCTTCCCGG CTGTCCTACAGTCCTCAGGACTCTACTCCCTCAGCAGCGTGGTGACCG TGCCCTCCAGCAGCTTGGGCACCCAGACCTACATCTGCAACGTGAATC ACAAGCCCAGCAACACCAAGGTGGACAAGAAAGTTGAGCCCAAATCTT GTGACAAAACTCACACATGCCCACCGTGCCCAGCACCTGAACTCCTGG GGGGACCGTCAGTCTTCCTCTTCCCCCCAAAACCCAAGGACACCCTCA TGATCTCCCGGACCCCTGAGGTCACATGCGTGGTGGTGGACGTGAGC CACGAAGACCCTGAGGTCAAGTTCAACTGGTACGTGGACGGCGTGGAG GTGCATAATGCCAAGACAAAGCCGCGGGAGGAGCAGTACAACAGCAC GTACCGTGTGGTCAGCGTCCTCACCGTCCTGCACCAGGACTGGCTGAA TGGCAAGGAGTACAAGTGCAAGGTCTCCAACAAAGCCCTCCCAGCCCC CATCGAGAAAACCATCTCCAAAGCCAAAGGGCAGCCCCGAGAACCACA GGTGTACACCCTGCCCCCATCCCGGGAGGAGATGACCAAGAACCAGG TCAGCCTGACCTGCCTGGTCAAAGGCTTCTATCCCAGCGACATCGCCG TGGAGTGGGAGAGCAATGGGCAGCCGGAGAACAACTACAAGACCACG CCTCCCGTGCTGGACTCCGACGGCTCCTTCTTCCTCTATAGCAAGCTCA CCGTGGACAAGAGCAGGTGGCAGCAGGGGAACGTCTTCTCATGCTCC GTGATGCATGAGGCTCTGCACAACCACTACACGCAGAAGAGCCTCTCC CTGTCCCCGGGT |
| 47 | Trastuzumab VL DNA | GACATCCAGATGACCCAGTCCCCCTCCAGCCTGTCCGCCTCTGTGGGC GACAGAGTGACCATCACCTGTCGGGCCTCCCAGGACGTGAACACCGC CGTGGCCTGGTATCAGCAGAAGCCCGGCAAGGCCCCCAAGCTGCTGA TCTACTCCGCCTCCTTCCTGTACTCCGGCGTGCCCTCCCGGTTCTCCG |

TABLE 1-continued

Sequences of humanized HER2 antibodies

| SEQ ID NO. | Description | Sequence |
|---|---|---|
| | | GCTCCAGATCTGGCACCGACTTTACCCTGACCATCTCCAGCCTGCAGC CCGAGGACTTCGCCACCTACTACTGCCAGCAGCACTACACCACCCCCC CCACCTTTGGCCAGGGCACCAAGGTGGAAATCAAG |
| 48 | Trastuzumab light chain DNA | GACATCCAGATGACCCAGTCCCCCTCCAGCCTGTCCGCCTCTGTGGGC GACAGAGTGACCATCACCTGTCGGGCCTCCCAGGACGTGAACACCGC CGTGGCCTGGTATCAGCAGAAGCCCGGCAAGGCCCCCAAGCTGCTGA TCTACTCCGCCTCCTTCCTGTACTCCGGCGTGCCCTCCCGGTTCTCCG GCTCCAGATCTGGCACCGACTTTACCCTGACCATCTCCAGCCTGCAGC CCGAGGACTTCGCCACCTACTACTGCCAGCAGCACTACACCACCCCCC CCACCTTTGGCCAGGGCACCAAGGTGGAAATCAAGCGGACCGTGGCC GCTCCCTCCGTGTTCATCTTCCCACCCTCCGACGAGCAGCTGAAGTCC GGCACCGCCTCCGTCGTGTGCCTGCTGAACAACTTCTACCCCCGCGAG GCCAAGGTGCAGTGGAAGGTGGACAACGCCCTGCAGTCCGGCAACTC CCAGGAATCCGTCACCGAGCAGGACTCCAAGGACAGCACCTACTCCCT GTCCTCCACCCTGACCCTGTCCAAGGCCGACTACGAGAAGCACAAGGT GTACGCCTGCGAAGTGACCCACCAGGGCCTGTCCAGCCCCGTGACCA AGTCCTTCAACCGGGGCGAGTGC |
| 49 | T(K222R) heavy chain constant region DNA | GCCTCCACCAAGGGCCCATCGGTCTTCCCCCTGGCACCCTCCTCCAAG AGCACCTCTGGGGGCACAGCGGCCCTGGGCTGCCTGGTCAAGGACTA CTTCCCCGAACCGGTGACGGTGTCGTGGAACTCAGGCGCCCTGACCA GCGGCGTGCACACCTTCCCGGCTGTCCTACAGTCCTCAGGACTCTACT CCCTCAGCAGCGTAGTGACCGTGCCCTCCAGCAGCTTGGGCACCCAG ACCTACATCTGCAACGTGAATCACAAGCCCAGCAACACCAAGGTGGAC AAGAAAGTTGAGCCCAAATCTTGTGACCGTACTCACACATGCCCACCGT GCCCAGCACCTGAACTCCTGGGGGGACCGTCAGTCTTCCTCTTCCCCC CAAAACCCAAGGACACCCTCATGATCTCCCGGACCCCTGAGGTCACAT GCGTGGTGGTGGACGTGAGCCACGAAGACCCTGAGGTCAAGTTCAACT GGTACGTGGACGGCGTGGAGGTGCATAATGCCAAGACAAAGCCGCGG GAGGAGCAGTACAACAGCACGTACCGTGTGGTCAGCGTCCTCACCGTC CTGCACCAGGACTGGCTGAATGGCAAGGAGTACAAGTGCAAGGTCTCC AACAAAGCCCTCCCAGCCCCCATCGAGAAAACCATCTCCAAAGCCAAA GGGCAGCCCCGAGAACCACAGGTGTACACCCTGCCCCCATCCCGGGA GGAGATGACCAAGAACCAGGTCAGCCTGACCTGCCTGGTCAAAGGCTT CTATCCCAGCGACATCGCCGTGGAGTGGGAGAGCAATGGGCAGCCGG AGAACAACTACAAGACCACGCCTCCCGTGCTGGACTCCGACGGCTCCT TCTTCCTCTATAGCAAGCTCACCGTGGACAAGAGCAGGTGGCAGCAGG GGAACGTCTTCTCATGCTCCGTGATGCATGAGGCTCTGCACAACCACTA CACGCAGAAGAGCCTCTCCCTGTCTCCGGGAAAA |
| 50 | T(K222R) heavy chain DNA | GAGGTGCAGCTGGTGGAGTCCGGCGGCGGCCTGGTTCAGCCCGGCG GATCACTGAGGCTCTCCTGTGCCGCCAGCGGCTTCAACATCAAGGACA CATACATCCACTGGGTTCGCCAGGCTCCTGGCAAGGGACTGGAGTGG GTCGCTAGGATCTACCCCACCAATGGGTACACCAGGTACGCCGACTCC GTGAAGGGGCGGTTCACAATCTCAGCCGATACTAGCAAAAATACAGCC TACTTGCAGATGAACTCCCTGAGAGCAGAGGATACCGCCGTGTACTATT GCTCTCGCTGGGGCGGCGACGGCTTCTACGCTATGGATTATTGGGGCC AGGGAACCTTGGTCACCGTCTCCTCAGCCTCCACCAAGGGCCCATCGG TCTTCCCCCTGGCACCCTCCTCCAAGAGCACCTCTGGGGGCACAGCGG CCCTGGGCTGCCTGGTCAAGGACTACTTCCCCGAACCGGTGACGGTGT CGTGGAACTCAGGCGCCCTGACCAGCGGCGTGCACACCTTCCCGGCT GTCCTACAGTCCTCAGGACTCTACTCCCTCAGCAGCGTAGTGACCGTG CCCTCCAGCAGCTTGGGCACCCAGACCTACATCTGCAACGTGAATCAC AAGCCCAGCAACACCAAGGTGGACAAGAAAGTTGAGCCCAAATCTTGT GACCGTACTCACACATGCCCACCGTGCCCAGCACCTGAACTCCTGGGG GGACCGTCAGTCTTCCTCTTCCCCCCAAAACCCAAGGACACCCTCATG ATCTCCCGGACCCCTGAGGTCACATGCGTGGTGGTGGACGTGAGCCA CGAAGACCCTGAGGTCAAGTTCAACTGGTACGTGGACGGCGTGGAGGT GCATAATGCCAAGACAAAGCCGCGGGAGGAGCAGTACAACAGCACGTA CCGTGTGGTCAGCGTCCTCACCGTCCTGCACCAGGACTGGCTGAATGG CAAGGAGTACAAGTGCAAGGTCTCCAACAAAGCCCTCCCAGCCCCCAT CGAGAAAACCATCTCCAAAGCCAAAGGGCAGCCCCGAGAACCACAGGT GTACACCCTGCCCCCATCCCGGGAGGAGATGACCAAGAACCAGGTCA GCCTGACCTGCCTGGTCAAAGGCTTCTATCCCAGCGACATCGCCGTGG AGTGGGAGAGCAATGGGCAGCCGGAGAACAACTACAAGACCACGCCT CCCGTGCTGGACTCCGACGGCTCCTTCTTCCTCTATAGCAAGCTCACC GTGGACAAGAGCAGGTGGCAGCAGGGGAACGTCTTCTCATGCTCCGT GATGCATGAGGCTCTGCACAACCACTACACGCAGAAGAGCCTCTCCCT GTCTCCGGGAAAA |
| 51 | T(K246C) heavy chain constant region | GCGTCGACCAAGGGCCCATCGGTCTTCCCCCTGGCACCCTCCTCCAAG AGCACCTCTGGGGGCACAGCGGCCCTGGGCTGCCTGGTCAAGGACTA CTTCCCCGAACCGGTGACGGTGTCGTGGAACTCAGGCGCCCTGACCA |

TABLE 1-continued

Sequences of humanized HER2 antibodies

| SEQ ID NO. | Description | Sequence |
|---|---|---|
| | DNA | GCGGCGTGCACACCTTCCCGGCTGTCCTACAGTCCTCAGGACTCTACT<br>CCCTCAGCAGCGTGGTGACCGTGCCCTCCAGCAGCTTGGGCACCCAG<br>ACCTACATCTGCAACGTGAATCACAAGCCCAGCAACACCAAGGTGGAC<br>AAGAAAGTTGAGCCCAAATCTTGTGACAAAACTCACACATGCCCACCGT<br>GCCCAGCACCTGAACTCCTGGGGGGACCGTCAGTCTTCCTCTTCCCCC<br>CATGCCCCAAGGACACCCTCATGATCTCCCGGACCCCTGAGGTCACAT<br>GCGTGGTGGTGGACGTGAGCCACGAAGACCCTGAGGTCAAGTTCAACT<br>GGTACGTGGACGGCGTGGAGGTGCATAATGCCAAGACAAAGCCGCGG<br>GAGGAGCAGTACAACAGCACGTACCGTGTGGTCAGCGTCCTCACCGTC<br>CTGCACCAGGACTGGCTGAATGGCAAGGAGTACAAGTGCAAGGTCTCC<br>AACAAAGCCCTCCCAGCCCCCATCGAGAAAACCATCTCCAAAGCCAAA<br>GGGCAGCCCCGAGAACCACAGGTGTACACCCTGCCCCCATCCCGGGA<br>GGAGATGACCAAGAACCAGGTCAGCCTGACCTGCCTGGTCAAAGGCTT<br>CTATCCCAGCGACATCGCCGTGGAGTGGGAGAGCAATGGGCAGCCGG<br>AGAACAACTACAAGACCACGCCTCCCGTGCTGGACTCCGACGGCTCCT<br>TCTTCCTCTATAGCAAGCTCACCGTGGACAAGAGCAGGTGGCAGCAGG<br>GGAACGTCTTCTCATGCTCCGTGATGCATGAGGCTCTGCACAACCACTA<br>CACGCAGAAGAGCCTCTCCCTGTCCCCGGGT |
| 52 | T(K246C)<br>heavy chain<br>DNA | GAGGTGCAGCTGGTGGAATCCGGCGGAGGCCTGGTCCAGCCTGGCGG<br>ATCTCTGCGGCTGTCTTGCGCCGCCTCCGGCTTCAACATCAAGGACAC<br>CTACATCCACTGGGTCCGACAGGCACCTGGCAAGGGACTGGAATGGGT<br>GGCCCGGATCTACCCCACCAACGGCTACACCAGATACGCCGACTCCGT<br>GAAGGGCCGGTTCACCATCTCCGCCGACACCTCCAAGAACACCGCCTA<br>CCTGCAGATGAACTCCCTGCGGGCCGAGGACACCGCCGTGTACTACTG<br>CTCCAGATGGGGAGGCGACGGCTTCTACGCCATGGACTACTGGGGCC<br>AGGGCACCCTGGTCACCGTGTCTAGCGCGTCGACCAAGGGCCCATCG<br>GTCTTCCCCCTGGCACCCTCCTCCAAGAGCACCTCTGGGGGCACAGCG<br>GCCCTGGGCTGCCTGGTCAAGGACTACTTCCCCGAACCGGTGACGGT<br>GTCGTGGAACTCAGGCGCCCTGACCAGCGGCGTGCACACCTTCCCGG<br>CTGTCCTACAGTCCTCAGGACTCTACTCCCTCAGCAGCGTGGTGACCG<br>TGCCCTCCAGCAGCTTGGGCACCCAGACCTACATCTGCAACGTGAATC<br>ACAAGCCCAGCAACACCAAGGTGGACAAGAAAGTTGAGCCCAAATCTT<br>GTGACAAAACTCACACATGCCCACCGTGCCCAGCACCTGAACTCCTGG<br>GGGGACCGTCAGTCTTCCTCTTCCCCCCATGCCCCAAGGACACCCTCA<br>TGATCTCCCGGACCCCTGAGGTCACATGCGTGGTGGTGGACGTGAGC<br>CACGAAGACCCTGAGGTCAAGTTCAACTGGTACGTGGACGGCGTGGAG<br>GTGCATAATGCCAAGACAAAGCCGCGGGAGGAGCAGTACAACAGCAC<br>GTACCGTGTGGTCAGCGTCCTCACCGTCCTGCACCAGGACTGGCTGAA<br>TGGCAAGGAGTACAAGTGCAAGGTCTCCAACAAAGCCCTCCCAGCCCC<br>CATCGAGAAAACCATCTCCAAAGCCAAAGGGCAGCCCCGAGAACCACA<br>GGTGTACACCCTGCCCCCATCCCGGGAGGAGATGACCAAGAACCAGG<br>TCAGCCTGACCTGCCTGGTCAAAGGCTTCTATCCCAGCGACATCGCCG<br>TGGAGTGGGAGAGCAATGGGCAGCCGGAGAACAACTACAAGACCACG<br>CCTCCCGTGCTGGACTCCGACGGCTCCTTCTTCCTCTATAGCAAGCTCA<br>CCGTGGACAAGAGCAGGTGGCAGCAGGGGAACGTCTTCTCATGCTCC<br>GTGATGCATGAGGCTCTGCACAACCACTACACGCAGAAGAGCCTCTCC<br>CTGTCCCCGGGT |
| 53 | T(K290C)<br>heavy chain<br>constant region<br>DNA | GCGTCGACCAAGGGCCCATCGGTCTTCCCCCTGGCACCCTCCTCCAAG<br>AGCACCTCTGGGGGCACAGCGGCCCTGGGCTGCCTGGTCAAGGACTA<br>CTTCCCCGAACCGGTGACGGTGTCGTGGAACTCAGGCGCCCTGACCA<br>GCGGCGTGCACACCTTCCCGGCTGTCCTACAGTCCTCAGGACTCTACT<br>CCCTCAGCAGCGTGGTGACCGTGCCCTCCAGCAGCTTGGGCACCCAG<br>ACCTACATCTGCAACGTGAATCACAAGCCCAGCAACACCAAGGTGGAC<br>AAGAAAGTTGAGCCCAAATCTTGTGACAAAACTCACACATGCCCACCGT<br>GCCCAGCACCTGAACTCCTGGGGGGACCGTCAGTCTTCCTCTTCCCCC<br>CAAAACCCAAGGACACCCTCATGATCTCCCGGACCCCTGAGGTCACAT<br>GCGTGGTGGTGGACGTGAGCCACGAAGACCCTGAGGTCAAGTTCAACT<br>GGTACGTGGACGGCGTGGAGGTGCATAATGCCAAGACATGCCCGCGG<br>GAGGAGCAGTACAACAGCACGTACCGTGTGGTCAGCGTCCTCACCGTC<br>CTGCACCAGGACTGGCTGAATGGCAAGGAGTACAAGTGCAAGGTCTCC<br>AACAAAGCCCTCCCAGCCCCCATCGAGAAAACCATCTCCAAAGCCAAA<br>GGGCAGCCCCGAGAACCACAGGTGTACACCCTGCCCCCATCCCGGGA<br>GGAGATGACCAAGAACCAGGTCAGCCTGACCTGCCTGGTCAAAGGCTT<br>CTATCCCAGCGACATCGCCGTGGAGTGGGAGAGCAATGGGCAGCCGG<br>AGAACAACTACAAGACCACGCCTCCCGTGCTGGACTCCGACGGCTCCT<br>TCTTCCTCTATAGCAAGCTCACCGTGGACAAGAGCAGGTGGCAGCAGG<br>GGAACGTCTTCTCATGCTCCGTGATGCATGAGGCTCTGCACAACCACTA<br>CACGCAGAAGAGCCTCTCCCTGTCCCCGGGT |
| 54 | T(K290C)<br>heavy chain<br>DNA | GAGGTGCAGCTGGTGGAATCCGGCGGAGGCCTGGTCCAGCCTGGCGG<br>ATCTCTGCGGCTGTCTTGCGCCGCCTCCGGCTTCAACATCAAGGACAC<br>CTACATCCACTGGGTCCGACAGGCACCTGGCAAGGGACTGGAATGGGT |

TABLE 1-continued

Sequences of humanized HER2 antibodies

| SEQ ID NO. | Description | Sequence |
|---|---|---|
| | | GGCCCGGATCTACCCCACCAACGGCTACACCAGATACGCCGACTCCGT<br>GAAGGGCCGGTTCACCATCTCCGCCGACACCTCCAAGAACACCGCCTA<br>CCTGCAGATGAACTCCCTGCGGGCCGAGGACACCGCCGTGTACTACTG<br>CTCCAGATGGGGAGGCGACGGCTTCTACGCCATGGACTACTGGGGCC<br>AGGGCACCCTGGTCACCGTGTCTAGCGCGTCGACCAAGGGCCCATCG<br>GTCTTCCCCCTGGCACCCTCCTCCAAGAGCACCTCTGGGGGCACAGCG<br>GCCCTGGGCTGCCTGGTCAAGGACTACTTCCCCGAACCGGTGACGGT<br>GTCGTGGAACTCAGGCGCCCTGACCAGCGGCGTGCACACCTTCCCGG<br>CTGTCCTACAGTCCTCAGGACTCTACTCCCTCAGCAGCGTGGTGACCG<br>TGCCCTCCAGCAGCTTGGGCACCCAGACCTACATCTGCAACGTGAATC<br>ACAAGCCCAGCAACACCAAGGTGGACAAGAAAGTTGAGCCCAAATCTT<br>GTGACAAAACTCACACATGCCCACCGTGCCCAGCACCTGAACTCCTGG<br>GGGGACCGTCAGTCTTCCTCTTCCCCCCAAAACCCAAGGACACCCTCA<br>TGATCTCCCGGACCCCTGAGGTCACATGCGTGGTGGTGGACGTGAGC<br>CACGAAGACCCTGAGGTCAAGTTCAACTGGTACGTGGACGGCGTGGAG<br>GTGCATAATGCCAAGACATGCCCGCGGGAGGAGCAGTACAACAGCAC<br>GTACCGTGTGGTCAGCGTCCTCACCGTCCTGCACCAGGACTGGCTGAA<br>TGGCAAGGAGTACAAGTGCAAGGTCTCCAACAAAGCCCTCCCAGCCCC<br>CATCGAGAAAACCATCTCCAAAGCCAAAGGGCAGCCCCGAGAACCACA<br>GGTGTACACCCTGCCCCCATCCCGGGAGGAGATGACCAAGAACCAGG<br>TCAGCCTGACCTGCCTGGTCAAAGGCTTCTATCCCAGCGACATCGCCG<br>TGGAGTGGGAGAGCAATGGGCAGCCGGAGAACAACTACAAGACCACG<br>CCTCCCGTGCTGGACTCCGACGGCTCCTTCTTCCTCTATAGCAAGCTCA<br>CCGTGGACAAGAGCAGGTGGCAGCAGGGGAACGTCTTCTCATGCTCC<br>GTGATGCATGAGGCTCTGCACAACCACTACACGCAGAAGAGCCTCTCC<br>CTGTCCCCGGGT |
| 55 | T(N297A) heavy chain constant region DNA | GCCTCCACCAAGGGCCCATCGGTCTTCCCCCTGGCACCCTCCTCCAAG<br>AGCACCTCTGGGGGCACAGCGGCCCTGGGCTGCCTGGTCAAGGACTA<br>CTTCCCCGAACCGGTGACGGTGTCGTGGAACTCAGGCGCCCTGACCA<br>GCGGCGTGCACACCTTCCCGGCTGTCCTACAGTCCTCAGGACTCTACT<br>CCCTCAGCAGCGTAGTGACCGTGCCCTCCAGCAGCTTGGGCACCCAG<br>ACCTACATCTGCAACGTGAATCACAAGCCCAGCAACACCAAGGTGGAC<br>AAGAAAGTTGAGCCCAAATCTTGTGACAAAACTCACACATGCCCACCGT<br>GCCCAGCACCTGAACTCCTGGGGGGACCGTCAGTCTTCCTCTTCCCCC<br>CAAAACCCAAGGACACCCTCATGATCTCCCGGACCCCTGAGGTCACAT<br>GCGTGGTGGTGGACGTGAGCCACGAAGACCCTGAGGTCAAGTTCAACT<br>GGTACGTGGACGGCGTGGAGGTGCATAATGCCAAGACAAAGCCGCGG<br>GAGGAGCAGTACGCCAGCACGTACCGTGTGGTCAGCGTCCTCACCGT<br>CCTGCACCAGGACTGGCTGAATGGCAAGGAGTACAAGTGCAAGGTCTC<br>CAACAAAGCCCTCCCAGCCCCCATCGAGAAAACCATCTCCAAAGCCAA<br>AGGGCAGCCCCGAGAACCACAGGTGTACACCCTGCCCCCATCCCGGG<br>AGGAGATGACCAAGAACCAGGTCAGCCTGACCTGCCTGGTCAAAGGCT<br>TCTATCCCAGCGACATCGCCGTGGAGTGGGAGAGCAATGGGCAGCCG<br>GAGAACAACTACAAGACCACGCCTCCCGTGCTGGACTCCGACGGCTCC<br>TTCTTCCTCTATAGCAAGCTCACCGTGGACAAGAGCAGGTGGCAGCAG<br>GGGAACGTCTTCTCATGCTCCGTGATGCATGAGGCTCTGCACAACCAC<br>TACACGCAGAAGAGCCTCTCCCTGTCTCCGGGAAAA |
| 56 | T(N297A) heavy chain DNA | GAGGTGCAGCTGGTGGAGTCCGGCGGCGGCCTGGTTCAGCCCGGCG<br>GATCACTGAGGCTCTCCTGTGCCGCCAGCGGCTTCAACATCAAGGACA<br>CATACATCCACTGGGTTCGCCAGGCTCCTGGCAAGGGACTGGAGTGG<br>GTCGCTAGGATCTACCCCACCAATGGGTACACCAGGTACGCCGACTCC<br>GTGAAGGGGCGGTTCACAATCTCAGCCGATACTAGCAAAAATACAGCC<br>TACTTGCAGATGAACTCCCTGAGAGCAGAGGATACCGCCGTGTACTATT<br>GCTCTCGCTGGGGCGGCGACGGCTTCTACGCTATGGATTATTGGGGCC<br>AGGGAACCTTGGTCACCGTCTCCTCAGCCTCCACCAAGGGCCCATCGG<br>TCTTCCCCCTGGCACCCTCCTCCAAGAGCACCTCTGGGGGCACAGCGG<br>CCCTGGGCTGCCTGGTCAAGGACTACTTCCCCGAACCGGTGACGGTGT<br>CGTGGAACTCAGGCGCCCTGACCAGCGGCGTGCACACCTTCCCGGCT<br>GTCCTACAGTCCTCAGGACTCTACTCCCTCAGCAGCGTAGTGACCGTG<br>CCCTCCAGCAGCTTGGGCACCCAGACCTACATCTGCAACGTGAATCAC<br>AAGCCCAGCAACACCAAGGTGGACAAGAAAGTTGAGCCCAAATCTTGT<br>GACAAAACTCACACATGCCCACCGTGCCCAGCACCTGAACTCCTGGGG<br>GGACCGTCAGTCTTCCTCTTCCCCCCAAAACCCAAGGACACCCTCATG<br>ATCTCCCGGACCCCTGAGGTCACATGCGTGGTGGTGGACGTGAGCCA<br>CGAAGACCCTGAGGTCAAGTTCAACTGGTACGTGGACGGCGTGGAGGT<br>GCATAATGCCAAGACAAAGCCGCGGGAGGAGCAGTACGCCAGCACGT<br>ACCGTGTGGTCAGCGTCCTCACCGTCCTGCACCAGGACTGGCTGAATG<br>GCAAGGAGTACAAGTGCAAGGTCTCCAACAAAGCCCTCCCAGCCCCCA<br>TCGAGAAAACCATCTCCAAAGCCAAAGGGCAGCCCCGAGAACCACAGG<br>TGTACACCCTGCCCCCATCCCGGGAGGAGATGACCAAGAACCAGGTCA<br>GCCTGACCTGCCTGGTCAAAGGCTTCTATCCCAGCGACATCGCCGTGG<br>AGTGGGAGAGCAATGGGCAGCCGGAGAACAACTACAAGACCACGCCT |

TABLE 1-continued

Sequences of humanized HER2 antibodies

| SEQ ID NO. | Description | Sequence |
| --- | --- | --- |
| | | CCCGTGCTGGACTCCGACGGCTCCTTCTTCCTCTATAGCAAGCTCACC GTGGACAAGAGCAGGTGGCAGCAGGGGAACGTCTTCTCATGCTCCGT GATGCATGAGGCTCTGCACAACCACTACACGCAGAAGAGCCTCTCCCT GTCTCCGGGAAAA |
| 57 | T(N297Q) heavy chain constant region DNA | GCCTCCACCAAGGGCCCATCGGTCTTCCCCCTGGCACCCTCCTCCAAG AGCACCTCTGGGGGCACAGCGGCCCTGGGCTGCCTGGTCAAGGACTA CTTCCCCGAACCGGTGACGGTGTCGTGGAACTCAGGCGCCCTGACCA GCGGCGTGCACACCTTCCCGGCTGTCCTACAGTCCTCAGGACTCTACT CCCTCAGCAGCGTAGTGACCGTGCCCTCCAGCAGCTTGGGCACCCAG ACCTACATCTGCAACGTGAATCACAAGCCCAGCAACACCAAGGTGGAC AAGAAAGTTGAGCCCAAATCTTGTGACAAAACTCACACATGCCCACCGT GCCCAGCACCTGAACTCCTGGGGGGACCGTCAGTCTTCCTCTTCCCCC CAAAACCCAAGGACACCCTCATGATCTCCCGGACCCCTGAGGTCACAT GCGTGGTGGTGGACGTGAGCCACGAAGACCCTGAGGTCAAGTTCAACT GGTACGTGGACGGCGTGGAGGTGCATAATGCCAAGACAAAGCCGCGG GAGGAGCAGTACCAAAGCACGTACCGTGTGGTCAGCGTCCTCACCGTC CTGCACCAGGACTGGCTGAATGGCAAGGAGTACAAGTGCAAGGTCTCC AACAAAGCCCTCCCAGCCCCCATCGAGAAAACCATCTCCAAAGCCAAA GGGCAGCCCCGAGAACCACAGGTGTACACCCTGCCCCCATCCCGGGA GGAGATGACCAAGAACCAGGTCAGCCTGACCTGCCTGGTCAAAGGCTT CTATCCCAGCGACATCGCCGTGGAGTGGGAGAGCAATGGGCAGCCGG AGAACAACTACAAGACCACGCCTCCCGTGCTGGACTCCGACGGCTCCT TCTTCCTCTATAGCAAGCTCACCGTGGACAAGAGCAGGTGGCAGCAGG GGAACGTCTTCTCATGCTCCGTGATGCATGAGGCTCTGCACAACCACTA CACGCAGAAGAGCCTCTCCCTGTCTCCGGGAAAAGCCGCCAGCGGCTT CAACATCAAGGACACATACATCCACTGGGTTCGCCAGGCTCCTGGCAA GGG |
| 58 | T(N297Q) heavy chain DNA | GAGGTGCAGCTGGTGGAGTCCGGCGGCGGCCTGGTTCAGCCCGGCG GATCACTGAGGCTCTCCTGTGCCGCCAGCGGCTTCAACATCAAGGACA CATACATCCACTGGGTTCGCCAGGCTCCTGGCAAGGGACTGGAGTGG GTCGCTAGGATCTACCCCACCAATGGGTACACCAGGTACGCCGACTCC GTGAAGGGGCGGTTCACAATCTCAGCCGATACTAGCAAAAATACAGCC TACTTGCAGATGAACTCCCTGAGAGCAGAGGATACCGCCGTGTACTATT GCTCTCGCTGGGGCGGCGACGGCTTCTACGCTATGGATTATTGGGGCC AGGGAACCTTGGTCACCGTCTCCTCAGCCTCCACCAAGGGCCCATCGG TCTTCCCCCTGGCACCCTCCTCCAAGAGCACCTCTGGGGGCACAGCGG CCCTGGGCTGCCTGGTCAAGGACTACTTCCCCGAACCGGTGACGGTGT CGTGGAACTCAGGCGCCCTGACCAGCGGCGTGCACACCTTCCCGGCT GTCCTACAGTCCTCAGGACTCTACTCCCTCAGCAGCGTAGTGACCGTG CCCTCCAGCAGCTTGGGCACCCAGACCTACATCTGCAACGTGAATCAC AAGCCCAGCAACACCAAGGTGGACAAGAAAGTTGAGCCCAAATCTTGT GACAAAACTCACACATGCCCACCGTGCCCAGCACCTGAACTCCTGGGG GGACCGTCAGTCTTCCTCTTCCCCCCAAAACCCAAGGACACCCTCATG ATCTCCCGGACCCCTGAGGTCACATGCGTGGTGGTGGACGTGAGCCA CGAAGACCCTGAGGTCAAGTTCAACTGGTACGTGGACGGCGTGGAGGT GCATAATGCCAAGACAAAGCCGCGGGAGGAGCAGTACCAAAGCACGTA CCGTGTGGTCAGCGTCCTCACCGTCCTGCACCAGGACTGGCTGAATGG CAAGGAGTACAAGTGCAAGGTCTCCAACAAAGCCCTCCCAGCCCCCAT CGAGAAAACCATCTCCAAAGCCAAAGGGCAGCCCCGAGAACCACAGGT GTACACCCTGCCCCCATCCCGGGAGGAGATGACCAAGAACCAGGTCA GCCTGACCTGCCTGGTCAAAGGCTTCTATCCCAGCGACATCGCCGTGG AGTGGGAGAGCAATGGGCAGCCGGAGAACAACTACAAGACCACGCCT CCCGTGCTGGACTCCGACGGCTCCTTCTTCCTCTATAGCAAGCTCACC GTGGACAAGAGCAGGTGGCAGCAGGGGAACGTCTTCTCATGCTCCGT GATGCATGAGGCTCTGCACAACCACTACACGCAGAAGAGCCTCTCCCT GTCTCCGGGAAAAGCCGCCAGCGGCTTCAACATCAAGGACACATACAT CCACTGGGTTCGCCAGGCTCCTGGCAAGGG |
| 59 | T(K334C) heavy chain constant region DNA | GCGTCGACCAAGGGCCCATCGGTCTTCCCCCTGGCACCCTCCTCCAAG AGCACCTCTGGGGGCACAGCGGCCCTGGGCTGCCTGGTCAAGGACTA CTTCCCCGAACCGGTGACGGTGTCGTGGAACTCAGGCGCCCTGACCA GCGGCGTGCACACCTTCCCGGCTGTCCTACAGTCCTCAGGACTCTACT CCCTCAGCAGCGTGGTGACCGTGCCCTCCAGCAGCTTGGGCACCCAG ACCTACATCTGCAACGTGAATCACAAGCCCAGCAACACCAAGGTGGAC AAGAAAGTTGAGCCCAAATCTTGTGACAAAACTCACACATGCCCACCGT GCCCAGCACCTGAACTCCTGGGGGGACCGTCAGTCTTCCTCTTCCCCC CAAAACCCAAGGACACCCTCATGATCTCCCGGACCCCTGAGGTCACAT GCGTGGTGGTGGACGTGAGCCACGAAGACCCTGAGGTCAAGTTCAACT GGTACGTGGACGGCGTGGAGGTGCATAATGCCAAGACAAAGCCGCGG GAGGAGCAGTACAACAGCACGTACCGTGTGGTCAGCGTCCTCACCGTC CTGCACCAGGACTGGCTGAATGGCAAGGAGTACAAGTGCAAGGTCTCC AACAAAGCCCTCCCAGCCCCCATCGAGTGCACCATCTCCAAAGCCAAA |

TABLE 1-continued

| SEQ ID NO. | Description | Sequence |
| --- | --- | --- |
| | | Sequences of humanized HER2 antibodies |
| | | GGGCAGCCCCGAGAACCACAGGTGTACACCCTGCCCCCATCCCGGGA GGAGATGACCAAGAACCAGGTCAGCCTGACCTGCCTGGTCAAAGGCTT CTATCCCAGCGACATCGCCGTGGAGTGGGAGAGCAATGGGCAGCCGG AGAACAACTACAAGACCACGCCTCCCGTGCTGGACTCCGACGGCTCCT TCTTCCTCTATAGCAAGCTCACCGTGGACAAGAGCAGGTGGCAGCAGG GGAACGTCTTCTCATGCTCCGTGATGCATGAGGCTCTGCACAACCACTA CACGCAGAAGAGCCTCTCCCTGTCCCCGGGT |
| 60 | T(K334C) heavy chain DNA | GAGGTGCAGCTGGTGGAATCCGGCGGAGGCCTGGTCCAGCCTGGCGG ATCTCTGCGGCTGTCTTGCGCCGCCTCCGGCTTCAACATCAAGGACAC CTACATCCACTGGGTCCGACAGGCACCTGGCAAGGGACTGGAATGGGT GGCCCGGATCTACCCCACCAACGGCTACACCAGATACGCCGACTCCGT GAAGGGCCGGTTCACCATCTCCGCCGACACCTCCAAGAACACCGCCTA CCTGCAGATGAACTCCCTGCGGGCCGAGGACACCGCCGTGTACTACTG CTCCAGATGGGGAGGCGACGGCTTCTACGCCATGGACTACTGGGGCC AGGGCACCCTGGTCACCGTGTCTAGCGCGTCGACCAAGGGCCCATCG GTCTTCCCCCTGGCACCCTCCTCCAAGAGCACCTCTGGGGGCACAGCG GCCCTGGGCTGCCTGGTCAAGGACTACTTCCCCGAACCGGTGACGGT GTCGTGGAACTCAGGCGCCCTGACCAGCGGCGTGCACACCTTCCCGG CTGTCCTACAGTCCTCAGGACTCTACTCCCTCAGCAGCGTGGTGACCG TGCCCTCCAGCAGCTTGGGCACCCAGACCTACATCTGCAACGTGAATC ACAAGCCCAGCAACACCAAGGTGGACAAGAAAGTTGAGCCCAAATCTT GTGACAAAACTCACACATGCCCACCGTGCCCAGCACCTGAACTCCTGG GGGGACCGTCAGTCTTCCTCTTCCCCCCAAAACCCAAGGACACCCTCA TGATCTCCCGGACCCCTGAGGTCACATGCGTGGTGGTGGACGTGAGC CACGAAGACCCTGAGGTCAAGTTCAACTGGTACGTGGACGGCGTGGAG GTGCATAATGCCAAGACAAAGCCGCGGGAGGAGCAGTACAACAGCAC GTACCGTGTGGTCAGCGTCCTCACCGTCCTGCACCAGGACTGGCTGAA TGGCAAGGAGTACAAGTGCAAGGTCTCCAACAAAGCCCTCCCAGCCCC CATCGAGTGCACCATCTCCAAAGCCAAAGGGCAGCCCCGAGAACCACA GGTGTACACCCTGCCCCCATCCCGGGAGGAGATGACCAAGAACCAGG TCAGCCTGACCTGCCTGGTCAAAGGCTTCTATCCCAGCGACATCGCCG TGGAGTGGGAGAGCAATGGGCAGCCGGAGAACAACTACAAGACCACG CCTCCCGTGCTGGACTCCGACGGCTCCTTCTTCCTCTATAGCAAGCTCA CCGTGGACAAGAGCAGGTGGCAGCAGGGGAACGTCTTCTCATGCTCC GTGATGCATGAGGCTCTGCACAACCACTACACGCAGAAGAGCCTCTCC CTGTCCCCGGGT |
| 61 | T(K392C) heavy chain constant region DNA | GCGTCGACCAAGGGCCCATCGGTCTTCCCCCTGGCACCCTCCTCCAAG AGCACCTCTGGGGGCACAGCGGCCCTGGGCTGCCTGGTCAAGGACTA CTTCCCCGAACCGGTGACGGTGTCGTGGAACTCAGGCGCCCTGACCA GCGGCGTGCACACCTTCCCGGCTGTCCTACAGTCCTCAGGACTCTACT CCCTCAGCAGCGTGGTGACCGTGCCCTCCAGCAGCTTGGGCACCCAG ACCTACATCTGCAACGTGAATCACAAGCCCAGCAACACCAAGGTGGAC AAGAAAGTTGAGCCCAAATCTTGTGACAAAACTCACACATGCCCACCGT GCCCAGCACCTGAACTCCTGGGGGGACCGTCAGTCTTCCTCTTCCCCC CAAAACCCAAGGACACCCTCATGATCTCCCGGACCCCTGAGGTCACAT GCGTGGTGGTGGACGTGAGCCACGAAGACCCTGAGGTCAAGTTCAACT GGTACGTGGACGGCGTGGAGGTGCATAATGCCAAGACAAAGCCGCGG GAGGAGCAGTACAACAGCACGTACCGTGTGGTCAGCGTCCTCACCGTC CTGCACCAGGACTGGCTGAATGGCAAGGAGTACAAGTGCAAGGTCTCC AACAAAGCCCTCCCAGCCCCCATCGAGAAAACCATCTCCAAAGCCAAA GGGCAGCCCCGAGAACCACAGGTGTACACCCTGCCCCCATCCCGGGA GGAGATGACCAAGAACCAGGTCAGCCTGACCTGCCTGGTCAAAGGCTT CTATCCCAGCGACATCGCCGTGGAGTGGGAGAGCAATGGGCAGCCGG AGAACAACTACTGCACCACGCCTCCCGTGCTGGACTCCGACGGCTCCT TCTTCCTCTATAGCAAGCTCACCGTGGACAAGAGCAGGTGGCAGCAGG GGAACGTCTTCTCATGCTCCGTGATGCATGAGGCTCTGCACAACCACTA CACGCAGAAGAGCCTCTCCCTGTCCCCGGGT |
| 62 | T(K392C) heavy chain DNA | GAGGTGCAGCTGGTGGAATCCGGCGGAGGCCTGGTCCAGCCTGGCGG ATCTCTGCGGCTGTCTTGCGCCGCCTCCGGCTTCAACATCAAGGACAC CTACATCCACTGGGTCCGACAGGCACCTGGCAAGGGACTGGAATGGGT GGCCCGGATCTACCCCACCAACGGCTACACCAGATACGCCGACTCCGT GAAGGGCCGGTTCACCATCTCCGCCGACACCTCCAAGAACACCGCCTA CCTGCAGATGAACTCCCTGCGGGCCGAGGACACCGCCGTGTACTACTG CTCCAGATGGGGAGGCGACGGCTTCTACGCCATGGACTACTGGGGCC AGGGCACCTTGGTCACCGTGTCTAGCGCGTCGACCAAGGGCCCATCG GTCTTCCCCCTGGCACCCTCCTCCAAGAGCACCTCTGGGGGCACAGCG GCCCTGGGCTGCCTGGTCAAGGACTACTTCCCCGAACCGGTGACGGT GTCGTGGAACTCAGGCGCCCTGACCAGCGGCGTGCACACCTTCCCGG CTGTCCTACAGTCCTCAGGACTCTACTCCCTCAGCAGCGTGGTGACCG TGCCCTCCAGCAGCTTGGGCACCCAGACCTACATCTGCAACGTGAATC ACAAGCCCAGCAACACCAAGGTGGACAAGAAAGTTGAGCCCAAATCTT |

TABLE 1-continued

| Sequences of humanized HER2 antibodies | | |
|---|---|---|
| SEQ ID NO. | Description | Sequence |
| | | GTGACAAAACTCACACATGCCCACCGTGCCCAGCACCTGAACTCCTGG<br>GGGGACCGTCAGTCTTCCTCTTCCCCCCAAAACCCAAGGACACCCTCA<br>TGATCTCCCGGACCCCTGAGGTCACATGCGTGGTGGTGGACGTGAGC<br>CACGAAGACCCTGAGGTCAAGTTCAACTGGTACGTGGACGGCGTGGAG<br>GTGCATAATGCCAAGACAAAGCCGCGGGAGGAGCAGTACAACAGCAC<br>GTACCGTGTGGTCAGCGTCCTCACCGTCCTGCACCAGGACTGGCTGAA<br>TGGCAAGGAGTACAAGTGCAAGGTCTCCAACAAAGCCCTCCCAGCCCC<br>CATCGAGAAAACCATCTCCAAAGCCAAAGGGCAGCCCCGAGAACCACA<br>GGTGTACACCCTGCCCCCATCCCGGGAGGAGATGACCAAGAACCAGG<br>TCAGCCTGACCTGCCTGGTCAAAGGCTTCTATCCCAGCGACATCGCCG<br>TGGAGTGGGAGAGCAATGGGCAGCCGGAGAACAACTACTGCACCACG<br>CCTCCCGTGCTGGACTCCGACGGCTCCTTCTTCCTCTATAGCAAGCTCA<br>CCGTGGACAAGAGCAGGTGGCAGCAGGGGAACGTCTTCTCATGCTCC<br>GTGATGCATGAGGCTCTGCACAACCACTACACGCAGAAGAGCCTCTCC<br>CTGTCCCCGGGT |
| 63 | T(L443C)<br>heavy chain<br>constant region<br>DNA | GCGTCGACCAAGGGCCCATCGGTCTTCCCCCTGGCACCCTCCTCCAAG<br>AGCACCTCTGGGGGCACAGCGGCCCTGGGCTGCCTGGTCAAGGACTA<br>CTTCCCCGAACCGGTGACGGTGTCGTGGAACTCAGGCGCCCTGACCA<br>GCGGCGTGCACACCTTCCCGGCTGTCCTACAGTCCTCAGGACTCTACT<br>CCCTCAGCAGCGTGGTGACCGTGCCCTCCAGCAGCTTGGGCACCCAG<br>ACCTACATCTGCAACGTGAATCACAAGCCCAGCAACACCAAGGTGGAC<br>AAGAAAGTTGAGCCCAAATCTTGTGACAAAACTCACACATGCCCACCGT<br>GCCCAGCACCTGAACTCCTGGGGGGACCGTCAGTCTTCCTCTTCCCCC<br>CAAAACCCAAGGACACCCTCATGATCTCCCGGACCCCTGAGGTCACAT<br>GCGTGGTGGTGGACGTGAGCCACGAAGACCCTGAGGTCAAGTTCAACT<br>GGTACGTGGACGGCGTGGAGGTGCATAATGCCAAGACAAAGCCGCGG<br>GAGGAGCAGTACAACAGCACGTACCGTGTGGTCAGCGTCCTCACCGTC<br>CTGCACCAGGACTGGCTGAATGGCAAGGAGTACAAGTGCAAGGTCTCC<br>AACAAAGCCCTCCCAGCCCCCATCGAGAAAACCATCTCCAAAGCCAAA<br>GGGCAGCCCCGAGAACCACAGGTGTACACCCTGCCCCCATCCCGGGA<br>GGAGATGACCAAGAACCAGGTCAGCCTGACCTGCCTGGTCAAAGGCTT<br>CTATCCCAGCGACATCGCCGTGGAGTGGGAGAGCAATGGGCAGCCGG<br>AGAACAACTACAAGACCACGCCTCCCGTGCTGGACTCCGACGGCTCCT<br>TCTTCCTCTATAGCAAGCTCACCGTGGACAAGAGCAGGTGGCAGCAGG<br>GGAACGTCTTCTCATGCTCCGTGATGCATGAGGCTCTGCACAACCACTA<br>CACGCAGAAGAGCCTCTCCTGCTCCCCGGGT |
| 64 | T(L443C)<br>heavy chain<br>DNA | GAGGTGCAGCTGGTGGAATCCGGCGGAGGCCTGGTCCAGCCTGGCGG<br>ATCTCTGCGGCTGTCTTGCGCCGCCTCCGGCTTCAACATCAAGGACAC<br>CTACATCCACTGGGTCCGACAGGCACCTGGCAAGGGACTGGAATGGGT<br>GGCCCGGATCTACCCCACCAACGGCTACACCAGATACGCCGACTCCGT<br>GAAGGGCCGGTTCACCATCTCCGCCGACACCTCCAAGAACACCGCCTA<br>CCTGCAGATGAACTCCCTGCGGGCCGAGGACACCGCCGTGTACTACTG<br>CTCCAGATGGGGAGGCGACGGCTTCTACGCCATGGACTACTGGGGCC<br>AGGGCACCCTGGTCACCGTGTCTAGCGCGTCGACCAAGGGCCCATCG<br>GTCTTCCCCCTGGCACCCTCCTCCAAGAGCACCTCTGGGGGCACAGCG<br>GCCCTGGGCTGCCTGGTCAAGGACTACTTCCCCGAACCGGTGACGGT<br>GTCGTGGAACTCAGGCGCCCTGACCAGCGGCGTGCACACCTTCCCGG<br>CTGTCCTACAGTCCTCAGGACTCTACTCCCTCAGCAGCGTGGTGACCG<br>TGCCCTCCAGCAGCTTGGGCACCCAGACCTACATCTGCAACGTGAATC<br>ACAAGCCCAGCAACACCAAGGTGGACAAGAAAGTTGAGCCCAAATCTT<br>GTGACAAAACTCACACATGCCCACCGTGCCCAGCACCTGAACTCCTGG<br>GGGGACCGTCAGTCTTCCTCTTCCCCCCAAAACCCAAGGACACCCTCA<br>TGATCTCCCGGACCCCTGAGGTCACATGCGTGGTGGTGGACGTGAGC<br>CACGAAGACCCTGAGGTCAAGTTCAACTGGTACGTGGACGGCGTGGAG<br>GTGCATAATGCCAAGACAAAGCCGCGGGAGGAGCAGTACAACAGCAC<br>GTACCGTGTGGTCAGCGTCCTCACCGTCCTGCACCAGGACTGGCTGAA<br>TGGCAAGGAGTACAAGTGCAAGGTCTCCAACAAAGCCCTCCCAGCCCC<br>CATCGAGAAAACCATCTCCAAAGCCAAAGGGCAGCCCCGAGAACCACA<br>GGTGTACACCCTGCCCCCATCCCGGGAGGAGATGACCAAGAACCAGG<br>TCAGCCTGACCTGCCTGGTCAAAGGCTTCTATCCCAGCGACATCGCCG<br>TGGAGTGGGAGAGCAATGGGCAGCCGGAGAACAACTACAAGACCACG<br>CCTCCCGTGCTGGACTCCGACGGCTCCTTCTTCCTCTATAGCAAGCTCA<br>CCGTGGACAAGAGCAGGTGGCAGCAGGGGAACGTCTTCTCATGCTCC<br>GTGATGCATGAGGCTCTGCACAACCACTACACGCAGAAGAGCCTCTCC<br>TGCTCCCCGGGT |
| 65 | T(K290C + K334C)<br>heavy chain<br>constant region<br>DNA | GCGTCGACCAAGGGCCCATCGGTCTTCCCCCTGGCACCCTCCTCCAAG<br>AGCACCTCTGGGGGCACAGCGGCCCTGGGCTGCCTGGTCAAGGACTA<br>CTTCCCCGAACCGGTGACGGTGTCGTGGAACTCAGGCGCCCTGACCA<br>GCGGCGTGCACACCTTCCCGGCTGTCCTACAGTCCTCAGGACTCTACT<br>CCCTCAGCAGCGTGGTGACCGTGCCCTCCAGCAGCTTGGGCACCCAG<br>ACCTACATCTGCAACGTGAATCACAAGCCCAGCAACACCAAGGTGGAC |

TABLE 1-continued

Sequences of humanized HER2 antibodies

| SEQ ID NO. | Description | Sequence |
|---|---|---|
| | | AAGAAAGTTGAGCCCAAATCTTGTGACAAAACTCACACATGCCCACCGT<br>GCCCAGCACCTGAACTCCTGGGGGGACCGTCAGTCTTCCTCTTCCCCC<br>CAAAACCCAAGGACACCCTCATGATCTCCCGGACCCCTGAGGTCACAT<br>GCGTGGTGGTGGACGTGAGCCACGAAGACCCTGAGGTCAAGTTCAACT<br>GGTACGTGGACGGCGTGGAGGTGCATAATGCCAAGACATGCCCGCGG<br>GAGGAGCAGTACAACAGCACGTACCGTGTGGTCAGCGTCCTCACCGTC<br>CTGCACCAGGACTGGCTGAATGGCAAGGAGTACAAGTGCAAGGTCTCC<br>AACAAAGCCCTCCCAGCCCCCATCGAGTGCACCATCTCCAAAGCCAAA<br>GGGCAGCCCCGAGAACCACAGGTGTACACCCTGCCCCCATCCCGGGA<br>GGAGATGACCAAGAACCAGGTCAGCCTGACCTGCCTGGTCAAAGGCTT<br>CTATCCCAGCGACATCGCCGTGGAGTGGGAGAGCAATGGGCAGCCGG<br>AGAACAACTACAAGACCACGCCTCCCGTGCTGGACTCCGACGGCTCCT<br>TCTTCCTCTATAGCAAGCTCACCGTGGACAAGAGCAGGTGGCAGCAGG<br>GGAACGTCTTCTCATGCTCCGTGATGCATGAGGCTCTGCACAACCACTA<br>CACGCAGAAGAGCCTCTCCCTGTCCCCGGGT |
| 66 | T(K290C + K334C) heavy chain DNA | GAGGTGCAGCTGGTGGAATCCGGCGGAGGCCTGGTCCAGCCTGGCGG<br>ATCTCTGCGGCTGTCTTGCGCCGCCTCCGGCTTCAACATCAAGGACAC<br>CTACATCCACTGGGTCCGACAGGCACCTGGCAAGGGACTGGAATGGGT<br>GGCCCGGATCTACCCCACCAACGGCTACACCAGATACGCCGACTCCGT<br>GAAGGGCCGGTTCACCATCTCCGCCGACACCTCCAAGAACACCGCCTA<br>CCTGCAGATGAACTCCCTGCGGGCCGAGGACACCGCCGTGTACTACTG<br>CTCCAGATGGGGAGGCGACGGCTTCTACGCCATGGACTACTGGGGCC<br>AGGGCACCCTGGTCACCGTGTCTAGCGCGTCGACCAAGGGCCCATCG<br>GTCTTCCCCCTGGCACCCTCCTCCAAGAGCACCTCTGGGGGCACAGCG<br>GCCCTGGGCTGCCTGGTCAAGGACTACTTCCCCGAACCGGTGACGGT<br>GTCGTGGAACTCAGGCGCCCTGACCAGCGGCGTGCACACCTTCCCGG<br>CTGTCCTACAGTCCTCAGGACTCTACTCCCTCAGCAGCGTGGTGACCG<br>TGCCCTCCAGCAGCTTGGGCACCCAGACCTACATCTGCAACGTGAATC<br>ACAAGCCCAGCAACACCAAGGTGGACAAGAAAGTTGAGCCCAAATCTT<br>GTGACAAAACTCACACATGCCCACCGTGCCCAGCACCTGAACTCCTGG<br>GGGGACCGTCAGTCTTCCTCTTCCCCCCAAAACCCAAGGACACCCTCA<br>TGATCTCCCGGACCCCTGAGGTCACATGCGTGGTGGTGGACGTGAGC<br>CACGAAGACCCTGAGGTCAAGTTCAACTGGTACGTGGACGGCGTGGAG<br>GTGCATAATGCCAAGACATGCCCGCGGGAGGAGCAGTACAACAGCAC<br>GTACCGTGTGGTCAGCGTCCTCACCGTCCTGCACCAGGACTGGCTGAA<br>TGGCAAGGAGTACAAGTGCAAGGTCTCCAACAAAGCCCTCCCAGCCCC<br>CATCGAGTGCACCATCTCCAAAGCCAAAGGGCAGCCCCGAGAACCACA<br>GGTGTACACCCTGCCCCCATCCCGGGAGGAGATGACCAAGAACCAGG<br>TCAGCCTGACCTGCCTGGTCAAAGGCTTCTATCCCAGCGACATCGCCG<br>TGGAGTGGGAGAGCAATGGGCAGCCGGAGAACAACTACAAGACCACG<br>CCTCCCGTGCTGGACTCCGACGGCTCCTTCTTCCTCTATAGCAAGCTCA<br>CCGTGGACAAGAGCAGGTGGCAGCAGGGGAACGTCTTCTCATGCTCC<br>GTGATGCATGAGGCTCTGCACAACCACTACACGCAGAAGAGCCTCTCC<br>CTGTCCCCGGGT |
| 67 | T(K290C + K392C) heavy chain constant region DNA | GCGTCGACCAAGGGCCCATCGGTCTTCCCCCTGGCACCCTCCTCCAAG<br>AGCACCTCTGGGGGCACAGCGGCCCTGGGCTGCCTGGTCAAGGACTA<br>CTTCCCCGAACCGGTGACGGTGTCGTGGAACTCAGGCGCCCTGACCA<br>GCGGCGTGCACACCTTCCCGGCTGTCCTACAGTCCTCAGGACTCTACT<br>CCCTCAGCAGCGTGGTGACCGTGCCCTCCAGCAGCTTGGGCACCCAG<br>ACCTACATCTGCAACGTGAATCACAAGCCCAGCAACACCAAGGTGGAC<br>AAGAAAGTTGAGCCCAAATCTTGTGACAAAACTCACACATGCCCACCGT<br>GCCCAGCACCTGAACTCCTGGGGGGACCGTCAGTCTTCCTCTTCCCCC<br>CAAAACCCAAGGACACCCTCATGATCTCCCGGACCCCTGAGGTCACAT<br>GCGTGGTGGTGGACGTGAGCCACGAAGACCCTGAGGTCAAGTTCAACT<br>GGTACGTGGACGGCGTGGAGGTGCATAATGCCAAGACATGCCCGCGG<br>GAGGAGCAGTACAACAGCACGTACCGTGTGGTCAGCGTCCTCACCGTC<br>CTGCACCAGGACTGGCTGAATGGCAAGGAGTACAAGTGCAAGGTCTCC<br>AACAAAGCCCTCCCAGCCCCCATCGAGAAAACCATCTCCAAAGCCAAA<br>GGGCAGCCCCGAGAACCACAGGTGTACACCCTGCCCCCATCCCGGGA<br>GGAGATGACCAAGAACCAGGTCAGCCTGACCTGCCTGGTCAAAGGCTT<br>CTATCCCAGCGACATCGCCGTGGAGTGGGAGAGCAATGGGCAGCCGG<br>AGAACAACTACTGCACCACGCCTCCCGTGCTGGACTCCGACGGCTCCT<br>TCTTCCTCTATAGCAAGCTCACCGTGGACAAGAGCAGGTGGCAGCAGG<br>GGAACGTCTTCTCATGCTCCGTGATGCATGAGGCTCTGCACAACCACTA<br>CACGCAGAAGAGCCTCTCCCTGTCCCCGGGT |
| 68 | T(K290C + K392C) heavy chain DNA | GAGGTGCAGCTGGTGGAATCCGGCGGAGGCCTGGTCCAGCCTGGCGG<br>ATCTCTGCGGCTGTCTTGCGCCGCCTCCGGCTTCAACATCAAGGACAC<br>CTACATCCACTGGGTCCGACAGGCACCTGGCAAGGGACTGGAATGGGT<br>GGCCCGGATCTACCCCACCAACGGCTACACCAGATACGCCGACTCCGT<br>GAAGGGCCGGTTCACCATCTCCGCCGACACCTCCAAGAACACCGCCTA<br>CCTGCAGATGAACTCCCTGCGGGCCGAGGACACCGCCGTGTACTACTG |

TABLE 1-continued

| Sequences of humanized HER2 antibodies | | |
|---|---|---|
| SEQ ID NO. | Description | Sequence |
| | | CTCCAGATGGGGAGGCGACGGCTTCTACGCCATGGACTACTGGGGCC AGGGCACCCTGGTCACCGTGTCTAGCGCGTCGACCAAGGGCCCATCG GTCTTCCCCCTGGCACCCTCCTCCAAGAGCACCTCTGGGGGCACAGCG GCCCTGGGCTGCCTGGTCAAGGACTACTTCCCCGAACCGGTGACGGT GTCGTGGAACTCAGGCGCCCTGACCAGCGGCGTGCACACCTTCCCGG CTGTCCTACAGTCCTCAGGACTCTACTCCCTCAGCAGCGTGGTGACCG TGCCCTCCAGCAGCTTGGGCACCCAGACCTACATCTGCAACGTGAATC ACAAGCCCAGCAACACCAAGGTGGACAAGAAAGTTGAGCCCAAATCTT GTGACAAAACTCACACATGCCCACCGTGCCCAGCACCTGAACTCCTGG GGGGACCGTCAGTCTTCCTCTTCCCCCCAAAACCCAAGGACACCCTCA TGATCTCCCGGACCCCTGAGGTCACATGCGTGGTGGTGGACGTGAGC CACGAAGACCCTGAGGTCAAGTTCAACTGGTACGTGGACGGCGTGGAG GTGCATAATGCCAAGACATGCCCGCGGGAGGAGCAGTACAACAGCAC GTACCGTGTGGTCAGCGTCCTCACCGTCCTGCACCAGGACTGGCTGAA TGGCAAGGAGTACAAGTGCAAGGTCTCCAACAAAGCCCTCCCAGCCCC CATCGAGAAAACCATCTCCAAAGCCAAAGGGCAGCCCCGAGAACCACA GGTGTACACCCTGCCCCCATCCCGGGAGGAGATGACCAAGAACCAGG TCAGCCTGACCTGCCTGGTCAAAGGCTTCTATCCCAGCGACATCGCCG TGGAGTGGGAGAGCAATGGGCAGCCGGAGAACAACTACTGCACCACG CCTCCCGTGCTGGACTCCGACGGCTCCTTCTTCCTCTATAGCAAGCTCA CCGTGGACAAGAGCAGGTGGCAGCAGGGGAACGTCTTCTCATGCTCC GTGATGCATGAGGCTCTGCACAACCACTACACGCAGAAGAGCCTCTCC CTGTCCCCGGGT |
| 69 | T(N297A + K222R) heavy chain constant region DNA | GCCTCCACCAAGGGCCCATCGGTCTTCCCCCTGGCACCCTCCTCCAAG AGCACCTCTGGGGGCACAGCGGCCCTGGGCTGCCTGGTCAAGGACTA CTTCCCCGAACCGGTGACGGTGTCGTGGAACTCAGGCGCCCTGACCA GCGGCGTGCACACCTTCCCGGCTGTCCTACAGTCCTCAGGACTCTACT CCCTCAGCAGCGTAGTGACCGTGCCCTCCAGCAGCTTGGGCACCCAG ACCTACATCTGCAACGTGAATCACAAGCCCAGCAACACCAAGGTGGAC AAGAAAGTTGAGCCCAAATCTTGTGACCGTACTCACACATGCCCACCGT GCCCAGCACCTGAACTCCTGGGGGGACCGTCAGTCTTCCTCTTCCCCC CAAAACCCAAGGACACCCTCATGATCTCCCGGACCCCTGAGGTCACAT GCGTGGTGGTGGACGTGAGCCACGAAGACCCTGAGGTCAAGTTCAACT GGTACGTGGACGGCGTGGAGGTGCATAATGCCAAGACAAAGCCGCGG GAGGAGCAGTACGCCAGCACGTACCGTGTGGTCAGCGTCCTCACCGT CCTGCACCAGGACTGGCTGAATGGCAAGGAGTACAAGTGCAAGGTCTC CAACAAAGCCCTCCCAGCCCCCATCGAGAAAACCATCTCCAAAGCCAA AGGGCAGCCCCGAGAACCACAGGTGTACACCCTGCCCCCATCCCGGG AGGAGATGACCAAGAACCAGGTCAGCCTGACCTGCCTGGTCAAAGGCT TCTATCCCAGCGACATCGCCGTGGAGTGGGAGAGCAATGGGCAGCCG GAGAACAACTACAAGACCACGCCTCCCGTGCTGGACTCCGACGGCTCC TTCTTCCTCTATAGCAAGCTCACCGTGGACAAGAGCAGGTGGCAGCAG GGGAACGTCTTCTCATGCTCCGTGATGCATGAGGCTCTGCACAACCAC TACACGCAGAAGAGCCTCTCCCTGTCTCCGGGAAAA |
| 70 | T(N297A + K222R) heavy chain DNA | GAGGTGCAGCTGGTGGAGTCCGGCGGCGGCCTGGTTCAGCCCGGCG GATCACTGAGGCTCTCCTGTGCCGCCAGCGGCTTCAACATCAAGGACA CATACATCCACTGGGTTCGCCAGGCTCCTGGCAAGGGACTGGAGTGG GTCGCTAGGATCTACCCCACCAATGGGTACACCAGGTACGCCGACTCC GTGAAGGGGCGGTTCACAATCTCAGCCGATACTAGCAAAAATACAGCC TACTTGCAGATGAACTCCCTGAGAGCAGAGGATACCGCCGTGTACTATT GCTCTCGCTGGGGCGGCGACGGCTTCTACGCTATGGATTATTGGGGCC AGGGAACCTTGGTCACCGTCTCCTCAGCCTCCACCAAGGGCCCATCGG TCTTCCCCCTGGCACCCTCCTCCAAGAGCACCTCTGGGGGCACAGCGG CCCTGGGCTGCCTGGTCAAGGACTACTTCCCCGAACCGGTGACGGTGT CGTGGAACTCAGGCGCCCTGACCAGCGGCGTGCACACCTTCCCGGCT GTCCTACAGTCCTCAGGACTCTACTCCCTCAGCAGCGTAGTGACCGTG CCCTCCAGCAGCTTGGGCACCCAGACCTACATCTGCAACGTGAATCAC AAGCCCAGCAACACCAAGGTGGACAAGAAAGTTGAGCCCAAATCTTGT GACCGTACTCACACATGCCCACCGTGCCCAGCACCTGAACTCCTGGGG GGACCGTCAGTCTTCCTCTTCCCCCCAAAACCCAAGGACACCCTCATG ATCTCCCGGACCCCTGAGGTCACATGCGTGGTGGTGGACGTGAGCCA CGAAGACCCTGAGGTCAAGTTCAACTGGTACGTGGACGGCGTGGAGGT GCATAATGCCAAGACAAAGCCGCGGGAGGAGCAGTACGCCAGCACGT ACCGTGTGGTCAGCGTCCTCACCGTCCTGCACCAGGACTGGCTGAATG GCAAGGAGTACAAGTGCAAGGTCTCCAACAAAGCCCTCCCAGCCCCCA TCGAGAAAACCATCTCCAAAGCCAAAGGGCAGCCCCGAGAACCACAGG TGTACACCCTGCCCCCATCCCGGGAGGAGATGACCAAGAACCAGGTCA GCCTGACCTGCCTGGTCAAAGGCTTCTATCCCAGCGACATCGCCGTGG |

TABLE 1-continued

Sequences of humanized HER2 antibodies

| SEQ ID NO. | Description | Sequence |
|---|---|---|
| | | AGTGGGAGAGCAATGGGCAGCCGGAGAACAACTACAAGACCACGCCT CCCGTGCTGGACTCCGACGGCTCCTTCTTCCTCTATAGCAAGCTCACC GTGGACAAGAGCAGGTGGCAGCAGGGGAACGTCTTCTCATGCTCCGT GATGCATGAGGCTCTGCACAACCACTACACGCAGAAGAGCCTCTCCCT GTCTCCGGGAAAA |
| 71 | T(N297Q + K222R) heavy chain constant region DNA | GCCTCCACCAAGGGCCCATCGGTCTTCCCCCTGGCACCCTCCTCCAAG AGCACCTCTGGGGGCACAGCGGCCCTGGGCTGCCTGGTCAAGGACTA CTTCCCCGAACCGGTGACGGTGTCGTGGAACTCAGGCGCCCTGACCA GCGGCGTGCACACCTTCCCGGCTGTCCTACAGTCCTCAGGACTCTACT CCCTCAGCAGCGTAGTGACCGTGCCCTCCAGCAGCTTGGGCACCCAG ACCTACATCTGCAACGTGAATCACAAGCCCAGCAACACCAAGGTGGAC AAGAAAGTTGAGCCCAAATCTTGTGACCGTACTCACACATGCCCACCGT GCCCAGCACCTGAACTCCTGGGGGGACCGTCAGTCTTCCTCTTCCCCC CAAAACCCAAGGACACCCTCATGATCTCCCGGACCCCTGAGGTCACAT GCGTGGTGGTGGACGTGAGCCACGAAGACCCTGAGGTCAAGTTCAACT GGTACGTGGACGGCGTGGAGGTGCATAATGCCAAGACAAAGCCGCGG GAGGAGCAGTACCAAAGCACGTACCGTGTGGTCAGCGTCCTCACCGTC CTGCACCAGGACTGGCTGAATGGCAAGGAGTACAAGTGCAAGGTCTCC AACAAAGCCCTCCCAGCCCCCATCGAGAAAACCATCTCCAAAGCCAAA GGGCAGCCCCGAGAACCACAGGTGTACACCCTGCCCCCATCCCGGGA GGAGATGACCAAGAACCAGGTCAGCCTGACCTGCCTGGTCAAAGGCTT CTATCCCAGCGACATCGCCGTGGAGTGGGAGAGCAATGGGCAGCCGG AGAACAACTACAAGACCACGCCTCCCGTGCTGGACTCCGACGGCTCCT TCTTCCTCTATAGCAAGCTCACCGTGGACAAGAGCAGGTGGCAGCAGG GGAACGTCTTCTCATGCTCCGTGATGCATGAGGCTCTGCACAACCACTA CACGCAGAAGAGCCTCTCCCTGTCTCCGGGAAAAGCCGCCAGCGGCTT CAACATCAAGGACACATACATCCACTGGGTTCGCCAGGCTCCTGGCAA GGG |
| 72 | T(N297Q + K222R) heavy chain DNA | GAGGTGCAGCTGGTGGAGTCCGGCGGCGGCCTGGTTCAGCCCGGCG GATCACTGAGGCTCTCCTGTGCCGCCAGCGGCTTCAACATCAAGGACA CATACATCCACTGGGTTCGCCAGGCTCCTGGCAAGGGACTGGAGTGG GTCGCTAGGATCTACCCCACCAATGGGTACACCAGGTACGCCGACTCC GTGAAGGGGCGGTTCACAATCTCAGCCGATACTAGCAAAAATACAGCC TACTTGCAGATGAACTCCCTGAGAGCAGAGGATACCGCCGTGTACTATT GCTCTCGCTGGGGCGGCGACGGCTTCTACGCTATGGATTATTGGGGCC AGGGAACCTTGGTCACCGTCTCCTCAGCCTCCACCAAGGGCCCATCGG TCTTCCCCCTGGCACCCTCCTCCAAGAGCACCTCTGGGGGCACAGCGG CCCTGGGCTGCCTGGTCAAGGACTACTTCCCCGAACCGGTGACGGTGT CGTGGAACTCAGGCGCCCTGACCAGCGGCGTGCACACCTTCCCGGCT GTCCTACAGTCCTCAGGACTCTACTCCCTCAGCAGCGTAGTGACCGTG CCCTCCAGCAGCTTGGGCACCCAGACCTACATCTGCAACGTGAATCAC AAGCCCAGCAACACCAAGGTGGACAAGAAAGTTGAGCCCAAATCTTGT GACCGTACTCACACATGCCCACCGTGCCCAGCACCTGAACTCCTGGGG GGACCGTCAGTCTTCCTCTTCCCCCCAAAACCCAAGGACACCCTCATG ATCTCCCGGACCCCTGAGGTCACATGCGTGGTGGTGGACGTGAGCCA CGAAGACCCTGAGGTCAAGTTCAACTGGTACGTGGACGGCGTGGAGGT GCATAATGCCAAGACAAAGCCGCGGGAGGAGCAGTACCAAAGCACGTA CCGTGTGGTCAGCGTCCTCACCGTCCTGCACCAGGACTGGCTGAATGG CAAGGAGTACAAGTGCAAGGTCTCCAACAAAGCCCTCCCAGCCCCCAT CGAGAAAACCATCTCCAAAGCCAAAGGGCAGCCCCGAGAACCACAGGT GTACACCCTGCCCCCATCCCGGGAGGAGATGACCAAGAACCAGGTCA GCCTGACCTGCCTGGTCAAAGGCTTCTATCCCAGCGACATCGCCGTGG AGTGGGAGAGCAATGGGCAGCCGGAGAACAACTACAAGACCACGCCT CCCGTGCTGGACTCCGACGGCTCCTTCTTCCTCTATAGCAAGCTCACC GTGGACAAGAGCAGGTGGCAGCAGGGGAACGTCTTCTCATGCTCCGT GATGCATGAGGCTCTGCACAACCACTACACGCAGAAGAGCCTCTCCCT GTCTCCGGGAAAAGCCGCCAGCGGCTTCAACATCAAGGACACATACAT CCACTGGGTTCGCCAGGCTCCTGGCAAGGG |
| 73 | T(K334C + K39C2) heavy chain constant region DNA | GCGTCGACCAAGGGCCCATCGGTCTTCCCCCTGGCACCCTCCTCCAAG AGCACCTCTGGGGGCACAGCGGCCCTGGGCTGCCTGGTCAAGGACTA CTTCCCCGAACCGGTGACGGTGTCGTGGAACTCAGGCGCCCTGACCA GCGGCGTGCACACCTTCCCGGCTGTCCTACAGTCCTCAGGACTCTACT CCCTCAGCAGCGTGGTGACCGTGCCCTCCAGCAGCTTGGGCACCCAG ACCTACATCTGCAACGTGAATCACAAGCCCAGCAACACCAAGGTGGAC AAGAAAGTTGAGCCCAAATCTTGTGACAAAACTCACACATGCCCACCGT GCCCAGCACCTGAACTCCTGGGGGGACCGTCAGTCTTCCTCTTCCCCC CAAAACCCAAGGACACCCTCATGATCTCCCGGACCCCTGAGGTCACAT GCGTGGTGGTGGACGTGAGCCACGAAGACCCTGAGGTCAAGTTCAACT GGTACGTGGACGGCGTGGAGGTGCATAATGCCAAGACAAAGCCGCGG GAGGAGCAGTACAACAGCACGTACCGTGTGGTCAGCGTCCTCACCGTC CTGCACCAGGACTGGCTGAATGGCAAGGAGTACAAGTGCAAGGTCTCC |

TABLE 1-continued

| Sequences of humanized HER2 antibodies | | |
|---|---|---|
| SEQ ID NO. | Description | Sequence |
| | | AACAAAGCCCTCCCAGCCCCCATCGAGTGCACCATCTCCAAAGCCAAA GGGCAGCCCCGAGAACCACAGGTGTACACCCTGCCCCCATCCCGGGA GGAGATGACCAAGAACCAGGTCAGCCTGACCTGCCTGGTCAAAGGCTT CTATCCCAGCGACATCGCCGTGGAGTGGGAGAGCAATGGGCAGCCGG AGAACAACTACTGCACCACGCCTCCCGTGCTGGACTCCGACGGCTCCT TCTTCCTCTATAGCAAGCTCACCGTGGACAAGAGCAGGTGGCAGCAGG GGAACGTCTTCTCATGCTCCGTGATGCATGAGGCTCTGCACAACCACTA CACGCAGAAGAGCCTCTCCCTGTCCCCGGGT |
| 74 | T(K334C + K392C) heavy chain DNA | GAGGTGCAGCTGGTGGAATCCGGCGGAGGCCTGGTCCAGCCTGGCGG ATCTCTGCGGCTGTCTTGCGCCGCCTCCGGCTTCAACATCAAGGACAC CTACATCCACTGGGTCCGACAGGCACCTGGCAAGGGACTGGAATGGGT GGCCCGGATCTACCCCACCAACGGCTACACCAGATACGCCGACTCCGT GAAGGGCCGGTTCACCATCTCCGCCGACACCTCCAAGAACACCGCCTA CCTGCAGATGAACTCCCTGCGGGCCGAGGACACCGCCGTGTACTACTG CTCCAGATGGGGAGGCGACGGCTTCTACGCCATGGACTACTGGGGCC AGGGCACCCTGGTCACCGTGTCTAGCGCGTCGACCAAGGGCCCATCG GTCTTCCCCCTGGCACCCTCCTCCAAGAGCACCTCTGGGGGCACAGCG GCCCTGGGCTGCCTGGTCAAGGACTACTTCCCCGAACCGGTGACGGT GTCGTGGAACTCAGGCGCCCTGACCAGCGGCGTGCACACCTTCCCGG CTGTCCTACAGTCCTCAGGACTCTACTCCCTCAGCAGCGTGGTGACCG TGCCCTCCAGCAGCTTGGGCACCCAGACCTACATCTGCAACGTGAATC ACAAGCCCAGCAACACCAAGGTGGACAAGAAAGTTGAGCCCAAATCTT GTGACAAAACTCACACATGCCCACCGTGCCCAGCACCTGAACTCCTGG GGGGACCGTCAGTCTTCCTCTTCCCCCCAAAACCCAAGGACACCCTCA TGATCTCCCGGACCCCTGAGGTCACATGCGTGGTGGTGGACGTGAGC CACGAAGACCCTGAGGTCAAGTTCAACTGGTACGTGGACGGCGTGGAG GTGCATAATGCCAAGACAAAGCCGCGGGAGGAGCAGTACAACAGCAC GTACCGTGTGGTCAGCGTCCTCACCGTCCTGCACCAGGACTGGCTGAA TGGCAAGGAGTACAAGTGCAAGGTCTCCAACAAAGCCCTCCCAGCCCC CATCGAGTGCACCATCTCCAAAGCCAAAGGGCAGCCCCGAGAACCACA GGTGTACACCCTGCCCCCATCCCGGGAGGAGATGACCAAGAACCAGG TCAGCCTGACCTGCCTGGTCAAAGGCTTCTATCCCAGCGACATCGCCG TGGAGTGGGAGAGCAATGGGCAGCCGGAGAACAACTACTGCACCACG CCTCCCGTGCTGGACTCCGACGGCTCCTTCTTCCTCTATAGCAAGCTCA CCGTGGACAAGAGCAGGTGGCAGCAGGGGAACGTCTTCTCATGCTCC GTGATGCATGAGGCTCTGCACAACCACTACACGCAGAAGAGCCTCTCC CTGTCCCCGGGT |
| 75 | T(K392C + L443C) heavy chain constant region DNA | GCGTCGACCAAGGGCCCATCGGTCTTCCCCCTGGCACCCTCCTCCAAG AGCACCTCTGGGGGCACAGCGGCCCTGGGCTGCCTGGTCAAGGACTA CTTCCCCGAACCGGTGACGGTGTCGTGGAACTCAGGCGCCCTGACCA GCGGCGTGCACACCTTCCCGGCTGTCCTACAGTCCTCAGGACTCTACT CCCTCAGCAGCGTGGTGACCGTGCCCTCCAGCAGCTTGGGCACCCAG ACCTACATCTGCAACGTGAATCACAAGCCCAGCAACACCAAGGTGGAC AAGAAAGTTGAGCCCAAATCTTGTGACAAAACTCACACATGCCCACCGT GCCCAGCACCTGAACTCCTGGGGGGACCGTCAGTCTTCCTCTTCCCCC CAAAACCCAAGGACACCCTCATGATCTCCCGGACCCCTGAGGTCACAT GCGTGGTGGTGGACGTGAGCCACGAAGACCCTGAGGTCAAGTTCAACT GGTACGTGGACGGCGTGGAGGTGCATAATGCCAAGACAAAGCCGCGG GAGGAGCAGTACAACAGCACGTACCGTGTGGTCAGCGTCCTCACCGTC CTGCACCAGGACTGGCTGAATGGCAAGGAGTACAAGTGCAAGGTCTCC AACAAAGCCCTCCCAGCCCCCATCGAGAAAACCATCTCCAAAGCCAAA GGGCAGCCCCGAGAACCACAGGTGTACACCCTGCCCCCATCCCGGGA GGAGATGACCAAGAACCAGGTCAGCCTGACCTGCCTGGTCAAAGGCTT CTATCCCAGCGACATCGCCGTGGAGTGGGAGAGCAATGGGCAGCCGG AGAACAACTACTGCACCACGCCTCCCGTGCTGGACTCCGACGGCTCCT TCTTCCTCTATAGCAAGCTCACCGTGGACAAGAGCAGGTGGCAGCAGG GGAACGTCTTCTCATGCTCCGTGATGCATGAGGCTCTGCACAACCACTA CACGCAGAAGAGCCTCTCCTGCTCCCCGGGT |
| 76 | T(K392C + L443C) heavy chain DNA | GAGGTGCAGCTGGTGGAATCCGGCGGAGGCCTGGTCCAGCCTGGCGG ATCTCTGCGGCTGTCTTGCGCCGCCTCCGGCTTCAACATCAAGGACAC CTACATCCACTGGGTCCGACAGGCACCTGGCAAGGGACTGGAATGGGT GGCCCGGATCTACCCCACCAACGGCTACACCAGATACGCCGACTCCGT GAAGGGCCGGTTCACCATCTCCGCCGACACCTCCAAGAACACCGCCTA CCTGCAGATGAACTCCCTGCGGGCCGAGGACACCGCCGTGTACTACTG CTCCAGATGGGGAGGCGACGGCTTCTACGCCATGGACTACTGGGGCC AGGGCACCCTGGTCACCGTGTCTAGCGCGTCGACCAAGGGCCCATCG GTCTTCCCCCTGGCACCCTCCTCCAAGAGCACCTCTGGGGGCACAGCG GCCCTGGGCTGCCTGGTCAAGGACTACTTCCCCGAACCGGTGACGGT GTCGTGGAACTCAGGCGCCCTGACCAGCGGCGTGCACACCTTCCCGG CTGTCCTACAGTCCTCAGGACTCTACTCCCTCAGCAGCGTGGTGACCG TGCCCTCCAGCAGCTTGGGCACCCAGACCTACATCTGCAACGTGAATC |

TABLE 1-continued

Sequences of humanized HER2 antibodies

| SEQ ID NO. | Description | Sequence |
| --- | --- | --- |
| | | ACAAGCCCAGCAACACCAAGGTGGACAAGAAAGTTGAGCCCAAATCTT GTGACAAAACTCACACATGCCCACCGTGCCCAGCACCTGAACTCCTGG GGGGACCGTCAGTCTTCCTCTTCCCCCCAAAACCCAAGGACACCCTCA TGATCTCCCGGACCCCTGAGGTCACATGCGTGGTGGTGGACGTGAGC CACGAAGACCCTGAGGTCAAGTTCAACTGGTACGTGGACGGCGTGGAG GTGCATAATGCCAAGACAAAGCCGCGGGAGGAGCAGTACAACAGCAC GTACCGTGTGGTCAGCGTCCTCACCGTCCTGCACCAGGACTGGCTGAA TGGCAAGGAGTACAAGTGCAAGGTCTCCAACAAAGCCCTCCCAGCCCC CATCGAGAAAACCATCTCCAAAGCCAAAGGGCAGCCCCGAGAACCACA GGTGTACACCCTGCCCCCATCCCGGGAGGAGATGACCAAGAACCAGG TCAGCCTGACCTGCCTGGTCAAAGGCTTCTATCCCAGCGACATCGCCG TGGAGTGGGAGAGCAATGGGCAGCCGGAGAACAACTACTGCACCACG CCTCCCGTGCTGGACTCCGACGGCTCCTTCTTCCTCTATAGCAAGCTCA CCGTGGACAAGAGCAGGTGGCAGCAGGGGAACGTCTTCTCATGCTCC GTGATGCATGAGGCTCTGCACAACCACTACACGCAGAAGAGCCTCTCC TGCTCCCCGGGT |
| 77 | T(kK183C) light chain constant region DNA | CGGACCGTGGCCGCTCCCTCCGTGTTCATCTTCCCACCCTCCGACGAG CAGCTGAAGTCCGGCACCGCCTCCGTCGTGTGCCTGCTGAACAACTTC TACCCCCGCGAGGCCAAGGTGCAGTGGAAGGTGGACAACGCCCTGCA GTCCGGCAACTCCCAGGAATCCGTCACCGAGCAGGACTCCAAGGACA GCACCTACTCCCTGTCCTCCACCCTGACCCTGTCCTGCGCCGACTACG AGAAGCACAAGGTGTACGCCTGCGAAGTGACCCACCAGGGCCTGTCCA GCCCCGTGACCAAGTCCTTCAACCGGGGCGAGTGC |
| 78 | T(kK183C) light chain DNA | GACATCCAGATGACCCAGTCCCCCTCCAGCCTGTCCGCCTCTGTGGGC GACAGAGTGACCATCACCTGTCGGGCCTCCCAGGACGTGAACACCGC CGTGGCCTGGTATCAGCAGAAGCCCGGCAAGGCCCCCAAGCTGCTGA TCTACTCCGCCTCCTTCCTGTACTCCGGCGTGCCCTCCCGGTTCTCCG GCTCCAGATCTGGCACCGACTTTACCCTGACCATCTCCAGCCTGCAGC CCGAGGACTTCGCCACCTACTACTGCCAGCAGCACTACACCACCCCCC CCACCTTTGGCCAGGGCACCAAGGTGGAAATCAAGCGGACCGTGGCC GCTCCCTCCGTGTTCATCTTCCCACCCTCCGACGAGCAGCTGAAGTCC GGCACCGCCTCCGTCGTGTGCCTGCTGAACAACTTCTACCCCCGCGAG GCCAAGGTGCAGTGGAAGGTGGACAACGCCCTGCAGTCCGGCAACTC CCAGGAATCCGTCACCGAGCAGGACTCCAAGGACAGCACCTACTCCCT GTCCTCCACCCTGACCCTGTCCTGCGCCGACTACGAGAAGCACAAGGT GTACGCCTGCGAAGTGACCCACCAGGGCCTGTCCAGCCCCGTGACCA AGTCCTTCAACCGGGGCGAGTGC |
| 79 | T(LCQ05) light chain constant region DNA | CGTACGGTGGCTGCACCATCTGTCTTCATCTTCCCGCCATCTGATGAGC AGTTGAAATCTGGAACTGCCTCTGTTGTGTGCCTGCTGAATAACTTCTAT CCCAGAGAGGCCAAAGTACAGTGGAAGGTGGATAACGCCCTCCAATCG GGTAACTCCCAGGAGAGTGTCACAGAGCAGGACAGCAAGGACAGCAC CTACAGCCTCAGCAGCACCCTGACGCTGAGCAAAGCAGACTACGAGAA ACACAAAGTCTACGCCTGCGAAGTCACCCATCAGGGCCTGAGCTCGCC CGTCACAAAGAGCTTCAACAGGGGAGAGTGT GGTGGCCTGCTTCAGGGCCCACCA |
| 80 | T(LCQ05) light chain DNA | GATATCCAGATGACACAGTCCCCCTCCAGCCTCTCCGCTAGTGTCGGA GATAGAGTGACAATTACATGTCGGGCAAGCCAGGACGTCAATACCGCC GTGGCCTGGTATCAGCAGAAGCCAGGAAAGGCCCCAAAACTCCTGATC TACTCCGCCTCCTTCCTGTACTCAGGGGTCCCTTCACGCTTCTCCGGTT CCCGGAGCGGCACCGACTTCACTCTGACTATCTCAAGCTTGCAGCCCG AGGACTTCGCCACATACTATTGCCAGCAGCACTATACCACCCCCCCTAC CTTCGGTCAGGGAACTAAGGTGGAAATTAAACGTACGGTGGCTGCACC ATCTGTCTTCATCTTCCCGCCATCTGATGAGCAGTTGAAATCTGGAACT GCCTCTGTTGTGTGCCTGCTGAATAACTTCTATCCCAGAGAGGCCAAAG TACAGTGGAAGGTGGATAACGCCCTCCAATCGGGTAACTCCCAGGAGA GTGTCACAGAGCAGGACAGCAAGGACAGCACCTACAGCCTCAGCAGCA CCCTGACGCTGAGCAAAGCAGACTACGAGAAACACAAAGTCTACGCCT GCGAAGTCACCCATCAGGGCCTGAGCTCGCCCGTCACAAAGAGCTTCA ACAGGGGAGAGTGTGGTGGCCTGCTTCAGGGCCCACCA |

In some embodiments, the ADCs of the invention can use antibodies comprising heavy chain variable region CDRs and light chain variable region CDRs of trastuzumab ($V_H$ CDRs of SEQ ID NOs:2-4 and $V_L$ CDRs of SEQ ID NOs:8-10) and any combination of heavy and light chain constant regions disclosed in Table 1 with the proviso that when the heavy chain constant region is SEQ ID NO:5 then the light chain constant region is not SEQ ID NO:11 (due to the fact that this combination recreates wild type trastuzumab and would thus not allow for site specific conjugation). In such embodiments, the heavy chain constant region can be selected from any of SEQ ID NOs:17, 5, 13, 21, 23, 25, 27, 29, 31, 33, 35, 37 or 39 while the light chain constant region can be selected from any of SEQ ID NOs:41, 11 or 43 providing that the combination is not SEQ ID NO:5 and SEQ ID NO:11 as discussed supra.

In more specific embodiments, the ADCs of the invention can use antibodies comprising heavy chain variable region CDRs and light chain variable region CDRs of trastuzumab ($V_H$ CDRs of SEQ ID NOs:2-4 and $V_L$ CDRs of SEQ ID NOs:8-10) and a heavy and light chain constant region combination selected from:

(a) a heavy chain constant region of SEQ ID NO:17 and a light chain constant region of SEQ ID NO:41;
(b) a heavy chain constant region of SEQ ID NO:5 and a light chain constant region of SEQ ID NO:41;
(c) a heavy chain constant region of SEQ ID NO:17 and a light chain constant region of SEQ ID NO:11;
(d) a heavy chain constant region of SEQ ID NO:21 and a light chain constant region of SEQ ID NO:11;
(e) a heavy chain constant region of SEQ ID NO:23 and a light chain constant region of SEQ ID NO:11;
(f) a heavy chain constant region of SEQ ID NO:25 and a light chain constant region of SEQ ID NO:11;
(g) a heavy chain constant region of SEQ ID NO:27 and a light chain constant region of SEQ ID NO:11;
(h) a heavy chain constant region of SEQ ID NO:23 and a light chain constant region of SEQ ID NO:41;
(i) a heavy chain constant region of SEQ ID NO:25 and a light chain constant region of SEQ ID NO:41;
(j) a heavy chain constant region of SEQ ID NO:27 and a light chain constant region of SEQ ID NO:41;
(k) a heavy chain constant region of SEQ ID NO:29 and a light chain constant region of SEQ ID NO:11;
(l) a heavy chain constant region of SEQ ID NO:31 and a light chain constant region of SEQ ID NO:11;
(m) a heavy chain constant region of SEQ ID NO:33 and a light chain constant region of SEQ ID NO:43;
(n) a heavy chain constant region of SEQ ID NO:35 and a light chain constant region of SEQ ID NO:11;
(o) a heavy chain constant region of SEQ ID NO:37 and a light chain constant region of SEQ ID NO:11;
(p) a heavy chain constant region of SEQ ID NO:39 and a light chain constant region of SEQ ID NO:11; or
(q) a heavy chain constant region of SEQ ID NO:13 and a light chain constant region of SEQ ID NO:43.

In yet a more specific embodiment, an ADC of the invention comprises an antibody with $V_H$ CDRs of SEQ ID NOs:2-4 and $V_L$ CDRs of SEQ ID NOs:8-10 and a heavy chain constant region of SEQ ID NO:17 and a light chain constant region of SEQ ID NO:41.

In another more specific embodiment, an ADC of the invention comprises an antibody with $V_H$ CDRs of SEQ ID NOs:2-4 and $V_L$ CDRs of SEQ ID NOs:8-10 and a heavy chain constant region of SEQ ID NO:13 and a light chain constant region of SEQ ID NO:43.

In other embodiments, the ADCs of the invention can use antibodies comprising any combination of heavy and light chains disclosed in Table 1 with the proviso that if the heavy chain is SEQ ID NO:6 then the light chain is not SEQ ID NO:12 (due to the fact that this combination recreates wild type trastuzumab and would thus not allow for site specific conjugation). In such embodiments, the heavy chain can be selected from any of SEQ ID NOs:18, 6, 14, 22, 24, 26, 28, 30, 32, 34, 36, 38 or 40 while the light chain can be selected from any of SEQ ID NOs: 42, 12 or 44 providing that the combination is not SEQ ID NO:6 and SEQ ID NO:12 as discussed supra.

In more specific embodiments, the ADCs of the invention can use antibodies comprising a heavy chain and light chain combination selected from:

(a) a heavy chain of SEQ ID NO:18 and a light chain of SEQ ID NO:42;
(b) a heavy chain of SEQ ID NO:6 and a light chain of SEQ ID NO:42;
(c) a heavy chain of SEQ ID NO:18 and a light chain of SEQ ID NO:12;
(d) a heavy chain of SEQ ID NO:22 and a light chain of SEQ ID NO:12;
(e) a heavy chain of SEQ ID NO:24 and a light chain of SEQ ID NO:12;
(f) a heavy chain of SEQ ID NO:26 and a light chain of SEQ ID NO:12;
(g) a heavy chain of SEQ ID NO:28 and a light chain of SEQ ID NO:12;
(h) a heavy chain of SEQ ID NO:24 and a light chain of SEQ ID NO:42;
(i) a heavy chain of SEQ ID NO:26 and a light chain of SEQ ID NO:42;
(j) a heavy chain of SEQ ID NO:28 and a light chain of SEQ ID NO:42;
(k) a heavy chain of SEQ ID NO:30 and a light chain of SEQ ID NO:12;
(l) a heavy chain of SEQ ID NO:32 and a light chain of SEQ ID NO:12;
(m) a heavy chain of SEQ ID NO:34 and a light chain of SEQ ID NO:44;
(n) a heavy chain of SEQ ID NO:36 and a light chain of SEQ ID NO:12;
(o) a heavy chain of SEQ ID NO:38 and a light chain of SEQ ID NO:12;
(p) a heavy chain of SEQ ID NO:40 and a light chain of SEQ ID NO:12; or
(q) a heavy chain of SEQ ID NO:14 and a light chain of SEQ ID NO:44.

In yet a more specific embodiment, an ADC of the invention comprises an antibody with a heavy chain of SEQ ID NO:18 and a light chain of SEQ ID NO:42. Plasmids containing nucleic acids encoding the heavy chain of SEQ ID NO:18 and the light chain of SEQ ID NO:42 have been deposited with the American Type Culture Collection (ATCC), 10801 University Blvd., Manassas, Va. 20110-2209 on Nov. 17, 2015 and given Accession Nos. PTA-122672 and PTA-122673, respectively. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

In another more specific embodiment, an ADC of the invention comprises an antibody with a heavy chain of SEQ ID NO:14 and a light chain of SEQ ID NO:44.

In some aspects of the invention, the ADC of the invention includes an antibody having a heavy chain and/or a light chain comprising an amino acid sequence that is at least 90%, 95%, 98%, or 99% identical to any of the heavy or light chains disclosed supra. Residues that have been altered can be in the variable region or in the constant region of the antibody. In some embodiments, there are no more than 1, 2, 3, 4 or 5 residues that have been altered as compared to any of the heavy or light chains disclosed supra. In other embodiments, there are no altered residues in any of the variable region CDRs.

The term "percent identical" (or "% identical") in the context of amino acid sequences means the number of residues in two sequences that are the same when aligned for maximum correspondence. There are a number of different algorithms known in the art which can be used to measure amino acid percent identity (i.e., the Basic Local Alignment Tool or BLAST®. Unless otherwise specified, default parameters for a particular program or algorithm are used.

For use in preparation of ADCs, HER2 antibodies described herein may be substantially pure, i.e., at least 50% pure (i.e., free from contaminants), more preferably, at least 90% pure, more preferably, at least 95% pure, yet more preferably, at least 98% pure, and most preferably, at least 99% pure.

II. Drugs

Drugs useful in preparation of the site specific HER2 ADCs of the invention include any therapeutic agent useful in the treatment of cancer including, but not limited to, cytotoxic agents, cytostatic agents, immunomodulating agents and chemotherapeutic agents. A cytotoxic effect refers to the depletion, elimination and/or the killing of a target cell (i.e., tumor cell). A cytotoxic agent refers to an agent that has a cytotoxic effect on a cell. A cytostatic effect refers to the inhibition of cell proliferation. A cytostatic agent refers to an agent that has a cytostatic effect on a cell, thereby inhibiting the growth and/or expansion of a specific subset of cells (i.e., tumor cells). An immunomodulating agent refers to an agent that stimulates the immune response through the production of cytokines and/or antibodies and/or modulating T cell function thereby inhibiting or reducing the growth of a subset of cells (i.e., tumor cells) either directly or indirectly by allowing another agent to be more efficacious. A chemotherapeutic agent refers to an agent that is a chemical compound useful in the treatment of cancer. A drug may also be a drug derivative, wherein a drug has been functionalized to enable conjugation with an antibody of the invention.

In some embodiments the drug is a membrane permeable drug. In such embodiments, the payload (i.e. drug) can elicit a bystander effect wherein cells surrounding the cell that initially internalized the ADC are killed by the payload. This occurs when the payload is released from the antibody (i.e., by cleaving of a cleavable linker) and crosses the cellular membrane and, upon diffusion, induces the killing of surrounding cells.

In accordance with the disclosed methods, the drugs are used to prepare antibody drug conjugates of the formula Ab-(L-D), wherein (a) Ab is an antibody that binds to HER2; and (b) L-D is a linker-drug moiety, wherein L is a linker, and D is a drug.

The drug-to-antibody ratio (DAR) or drug loading indicates the number of drug (D) molecules that are conjugated per antibody. The antibody drug conjugates of the present invention use site specific conjugation such that there is essentially a homogeneous population of ADCs having one DAR in a composition of ADCs. In some embodiments, the DAR is 1. In some embodiments, the DAR is 2. In other embodiments, the DAR is 3. In other embodiments, the DAR is 4. In other embodiments, the DAR is greater than 4.

Using conventional conjugation (rather than site specific conjugation) results in a heterogeneous population of different species of ADCs, each of which has a different individual DAR. Compositions of ADCs prepared in this way include a plurality of antibodies, each antibody conjugated to a particular number of drug molecules. As such, the compositions have an average DAR. T-DM1 (Kadcyla®) uses conventional conjugation on lysine residues and has an average DAR of around 4 with a broad distribution which includes ADCs loaded with 0, 1, 2, 3, 4, 5, 6, 7 or 8 drug molecules (Kim et al., 2014, Bioconj Chem 25(7):1223-32).

Compositions, batches, and/or formulations of a plurality of ADCs may be characterized by an average DAR. DAR and average DAR can be determined by various conventional means such as UV spectroscopy, mass spectroscopy, ELISA assay, radiometric methods, hydrophobic interaction chromatography (HIC), electrophoresis and HPLC.

In aspects of the invention, an HER2 ADC may have a DAR of 1, a DAR of 2, a DAR of 3, a DAR of 4, a DAR of 5, a DAR of 6, a DAR of 7, a DAR of 8, a DAR of 9, a DAR of 10, a DAR of 11, a DAR of 12 or a DAR greater than 12. In aspects of the invention, an HER2 ADC may have one drug molecule, or 2 drug molecules, or 3 drug molecules, or 4 drug molecules, or 5 drug molecules, or 6 drug molecules, or 7 drug molecules, or 8 drug molecules, or 9 drug molecules, or 10 drug molecules, or 11 drug molecules, or 12 drug molecules or greater than 12 molecules.

In aspects of the invention, an HER2 ADC may have average DAR in the range of about 2 to about 4, or an average DAR in the range of about 3 to about 5, or an average DAR in the range of about 4 to about 6, or an average DAR in the range of about 5 to about 7, or an average DAR in the range of about 6 to about 8, or an average DAR in the range of about 7 to about 9, or an average DAR in the range of about 8 to about 10, or an average DAR in the range of about 9 to about 11, or an average DAR in the range of about 10 to about 12, etc. In some aspects the compositions, batches and/or formulations of HER2 ADCs may have an average DAR of about 1, or an average DAR of about 2, an average DAR of about 3, or an average DAR of about 4, or an average DAR of about 5, or an average DAR of about 6, or an average DAR of about 7, or an average DAR of about 8, or an average DAR of about 9, or an average DAR of about 10, or an average DAR of about 11, or an average DAR of about 12 or an average DAR greater than 12. As used in the foregoing ranges of average DAR, the term "about" means+/−0.5%.

A composition, batch, and/or formulation of HER2 ADCs may be characterized by a preferred range of average DAR, e.g., an average DAR in the range of about 3 to about 5, an average DAR in the range of about 3 to about 4, or an average DAR in the range of about 4 to about 5. Further, a composition, batch, and/or formulation of HER2 ADCs may be characterized by a preferred range of average DAR, e.g., an average DAR in the range of 3 to 5, an average DAR in the range of 3 to 4, or an average DAR in the range of 4 to 5.

In some aspects of the invention, a composition, batch, and/or formulation of HER2 ADCs may be characterized by an average DAR of about 1.0, or an average DAR of 1.0, or an average DAR of 1.1, or an average DAR of 1.2, or an average DAR of 1.3, or an average DAR of 1.4, or an average DAR of 1.5, or an average DAR of 1.6, or an average DAR of 1.7, or an average DAR of 1.8, or an average DAR of 1.9. In another aspect, a composition, batch, and/or formulation of HER2 ADCs may be characterized by an average DAR of about 2.0, or an average DAR of 2.0, or an average DAR of 2.1, or an average DAR of 2.2, or an average DAR of 2.3, or an average DAR of 2.4, or an average DAR of 2.5, or an average DAR of 2.6, or an average DAR of 2.7, or an average DAR of 2.8, or an average DAR of 2.9. In another aspect, a composition, batch, and/or formulation of HER2 ADCs may be characterized by an average DAR of about 3.0, or an average DAR of 3.0, or an average DAR of 3.1, or an average DAR of 3.2, or an average DAR of 3.3, or an average DAR of 3.4, or an average DAR of 3.5, or an average DAR of 3.6, or an average DAR of 3.7, or an average DAR of 3.8, or an average DAR of 3.9. In another aspect, a composition, batch, and/or formulation of HER2 ADCs may be characterized by an average DAR of about 4.0, or an average DAR of 4.0, or an average DAR of 4.1, or an average DAR of 4.2, or an average DAR of 4.3, or an average DAR of 4.4, or an average DAR of 4.5, or an average DAR of 4.6, or an average DAR of 4.7, or an average DAR of 4.8, or an average DAR of 4.9, or an average DAR of 5.0.

In another aspect, a composition, batch, and/or formulation of HER2 ADCs may be characterized by an average DAR of 12 or less, an average DAR of 11 or less, an average DAR of 10 or less, an average DAR of 9 or less, an average DAR of 8 or less, an average DAR of 7 or less, an average DAR of 6 or less, an average DAR of 5 or less, an average DAR of 4 or less, an average DAR of 3 or less, an average DAR of 2 or less or an average DAR of 1 or less.

In other aspects, a composition, batch, and/or formulation of HER2 ADCs may be characterized by an average DAR of 11.5 or less, an average DAR of 10.5 or less, an average DAR of 9.5 or less, an average DAR of 8.5 or less, an average DAR of 7.5 or less, an average DAR of 6.5 or less, an average DAR of 5.5 or less, an average DAR of 4.5 or less, an average DAR of 3.5 or less, an average DAR of 2.5 or less, an average DAR of 1.5 or less.

In some aspects of the present invention, the methods for conventional conjugation via cysteine residues and purification conditions disclosed herein provide a composition, batch, and/or formulation of HER2 ADCs with an optimized average DAR in the range of about 3 to 5, preferably about 4.

In some aspects of the present invention, the methods for site-specific conjugation via engineered cysteine residues and purification conditions disclosed herein provide a composition, batch, and/or formulation of HER2 ADCs with an optimized average DAR in the range of about 3 to 5, preferably about 4.

In some aspects of the present invention, the methods for site-specific conjugation via transglutaminase-based conjugation and purification conditions disclosed herein provide a composition, batch, and/or formulation of HER2 ADCs with an optimized average DAR in the range of about 1 to 3, preferably about 2.

Also encompassed by the present invention are antibody drug conjugates of the formula Ab-(L-D)p, wherein (a) Ab is an antibody, or antigen-binding fragment thereof, that binds to HER2, (b) L-D is a linker-drug moiety, wherein L is a linker, and D is a drug and (c) p is the number of linker/drug moieties that are attached to the antibody. For site specific ADCs, p is a whole number due to the homogeneous nature of the ADC. In some embodiments, p is 4. In other embodiments, p is 3. In other embodiments, p is 2. In other embodiments, p is 1. In other embodiments, p is greater than 4.

In one embodiment, the drug component of the ADCs of the invention is an anti-mitotic drug. In a specific embodiment, the anti-mitotic drug is an auristatin (e.g., 0101, 8261, 6121, 8254, 6780 and 0131; see Table 2 infra). In a more specific embodiment, the auristatin drug is 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (also known as 0101).

Auristatins inhibit cell proliferation by inhibiting the formation of microtubules during mitosis through inhibition of tubulin polymerization. PCT International Publication No. WO 2013/072813, which is incorporated by reference in its entirety, discloses auristatins that are useful in the manufacture of the ADCs of the invention and provides methods of producing those auristatins.

TABLE 2

| Drugs | | |
|---|---|---|
| Name | Structure | IUPAC Name |
| 0101 | 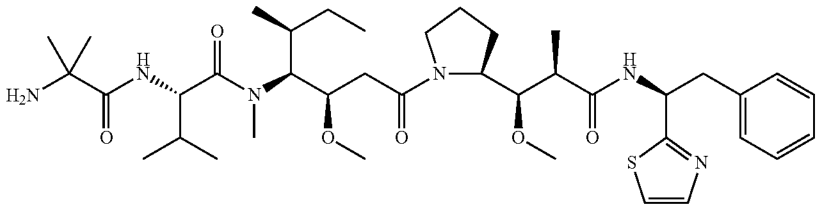 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C] | 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |

TABLE 2-continued

| Drugs | | |
|---|---|---|
| Name | Structure | IUPAC Name |
| 8261 | 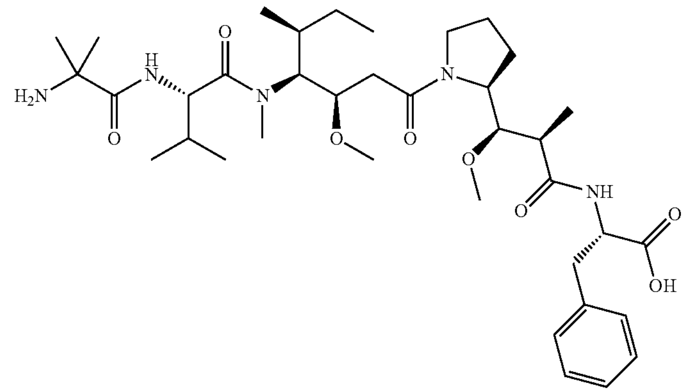 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)N)C(C)C] | 2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| 6121 | 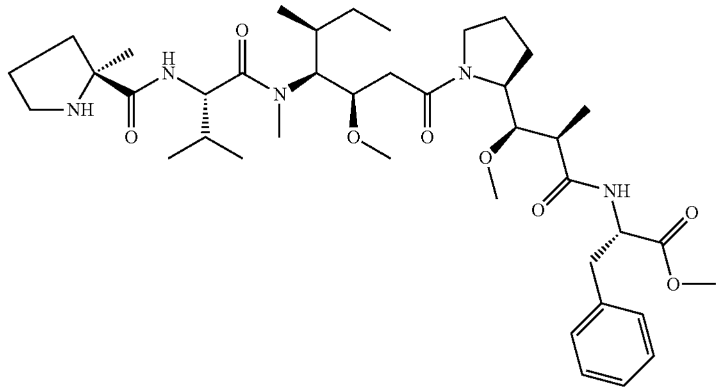 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1)C(C)C] | 2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide |
| 8254 | 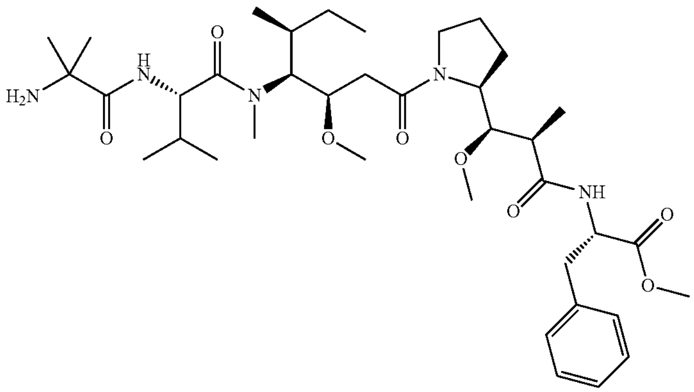 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)C(C)(C)N)C(C)C] | 2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide |
| 6780 | 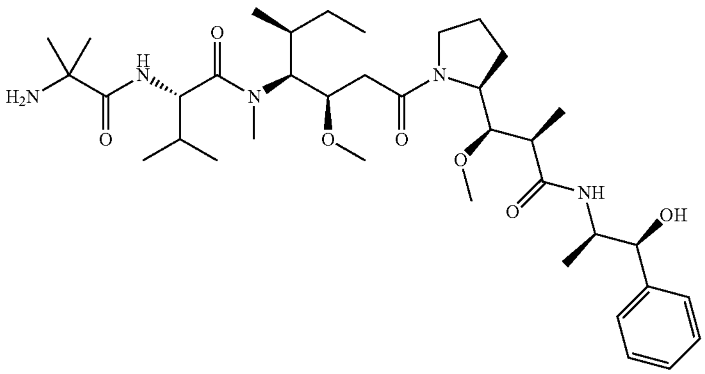 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)C(C)(C)N)C(C)C] | 2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |

TABLE 2-continued

Drugs

| Name | Structure | IUPAC Name |
|---|---|---|
| 0131 | 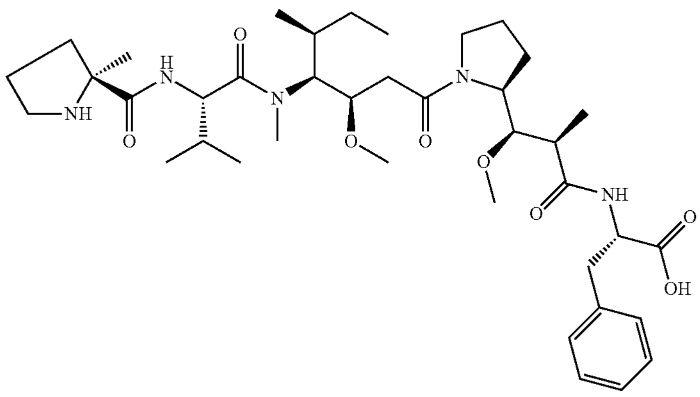 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C] | 2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |
| MMAD | 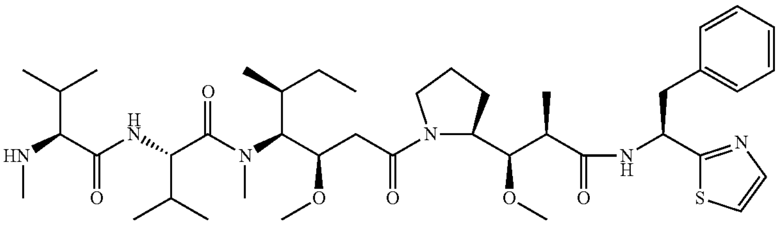 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@@H](NC)C(C)C)C(C)C] | N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide |
| MMAE | 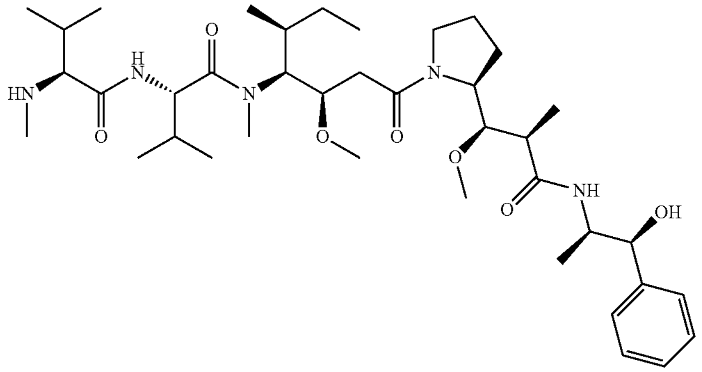 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C] | N-methyl-L-valyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide |
| MMAF | 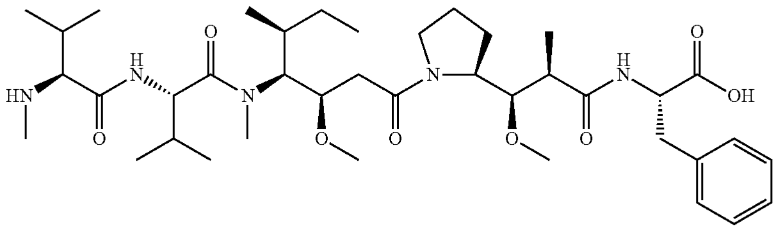 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C] | N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide |

In some aspects of the invention, the cytotoxic agent can be made using a liposome or biocompatible polymer. The HER2 antibodies as described herein can be conjugated to the biocompatible polymer to increase serum half-life and bioactivity, and/or to extend in vivo half-lives. Examples of biocompatible polymers include water-soluble polymers, such as polyethylene glycol (PEG) or derivatives thereof and zwitterion-containing biocompatible polymers (e.g., a phosphorylcholine containing polymer).

III. Linkers

Site specific HER2 ADCs of the invention are prepared using a linker to link or conjugate a drug to an HER2 antibody. A linker is a bifunctional compound which can be used to link a drug and an antibody to form an antibody drug conjugate (ADC). Such conjugates allow the selective delivery of drugs to tumor cells. Suitable linkers include, for example, cleavable and non-cleavable linkers. A cleavable linker is typically susceptible to cleavage under intracellular conditions. Major mechanisms by which a conjugated drug is cleaved from an antibody include hydrolysis in the acidic pH of the lysosomes (hydrazones, acetals, and cis-aconitate-like amides), peptide cleavage by lysosomal enzymes (the cathepsins and other lysosomal enzymes), and reduction of disulfides. As a result of these varying mechanisms for cleavage, mechanisms of linking the drug to the antibody also vary widely and any suitable linker can be used.

Suitable cleavable linkers include, but are not limited to, a peptide linker cleavable by an intracellular protease, such as lysosomal protease or an endosomal protease such as maleimidocaproyl-valine-citrulline-p-aminobenzyloxycarbonyl (vc), N~2~-acetyl-L-lysyl-L-valyl-L-citruline-p-aminobenzyloxycarbonyl-N,N'-dimethylaminoethyl-CO-(AcLysvc) and m(H20)c-vc (Table 3 infra). In specific embodiments, the linker is a cleavable linker such that the payload can induce a bystander effect once the linker is cleaved. The bystander effect is when a membrane permeable drug is released from the antibody (i.e., by cleaving of a cleavable linker) and crosses the cellular membrane and, upon diffusion, induces killing of cells surrounding the cell that initially internalized the ADC.

Suitable non-cleavable linkers include, but are not limited to, maleimidocaproyl (mc), maleimide-(polyethylene glycol)$_6$ (MalPeg6), Mal-PEG2C2, Mal-PEG3C2 and m(H20)c (Table 3 infra).

Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

In particular aspects of the invention, the linkers in the site specific HER2 ADCs of the invention are cleavable and may be vc or AcLysvc.

Many of the therapeutic agents (drugs) conjugated to antibodies have little, if any, solubility in water and that can limit drug loading on the conjugate due to aggregation of the conjugate. One approach to overcoming this is to add solublizing groups to the linker. Conjugates made with a linker consisting of PEG and a dipeptide can been used, including those having a PEG di-acid, thiol-acid, or maleimide-acid attached to the antibody, a dipeptide spacer, and an amide bond to the amine of an anthracycline or a duocarmycin analogue. Another example is a conjugate prepared with a PEG-containing linker disulfide bonded to a cytotoxic agent and amide bonded to an antibody. Approaches that incorporate PEG groups may be beneficial in overcoming aggregation and limits in drug loading.

TABLE 3

Linkers

| Name | Structure |
| --- | --- |
| vc | 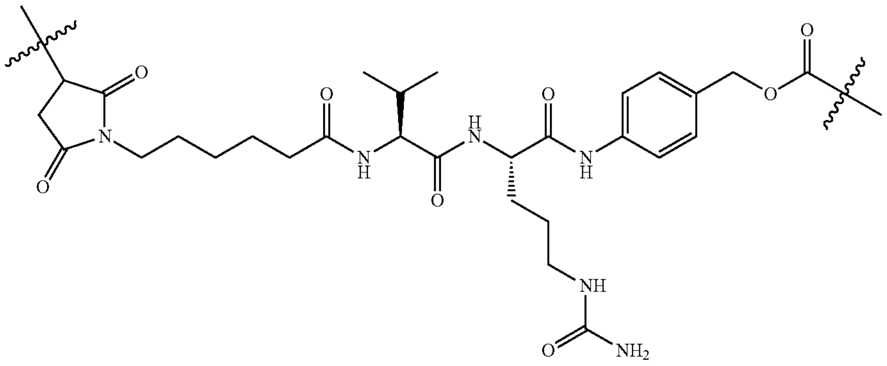 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1] |
| AcLysvc | 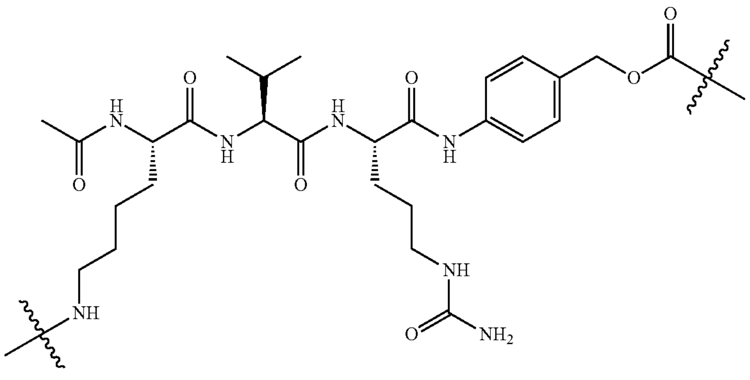 [SMILES: *NCCCC[C@H](NC(C)=O)C(=O)N[C@H](C(=O)N[C@@H](CCCNC(N)=O)C(=O)Nc1ccc(COC(*)=O)cc1)C(C)C] |
| mc | 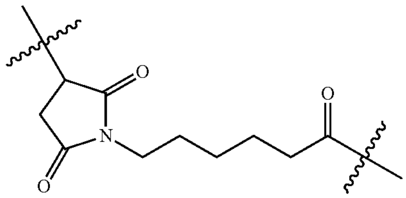 [SMILES: *C(=O)CCCCCN1C(=O)CC(*)C1=O] |

TABLE 3-continued

| Linkers | |
|---|---|
| Name | Structure |
| MalPeg6 | 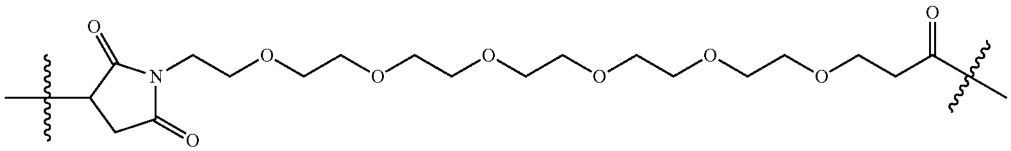 [SMILES: *C(=O)CCOCCOCCOCCOCCOCCOCCN1C(=O)CC(*)C1=O] |
| m(H2O)c | 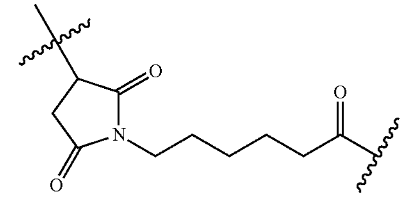 or 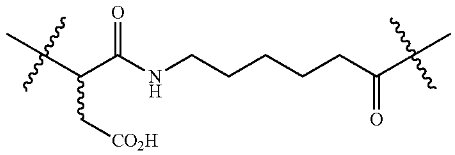 |
| m(H2O)c-vc | 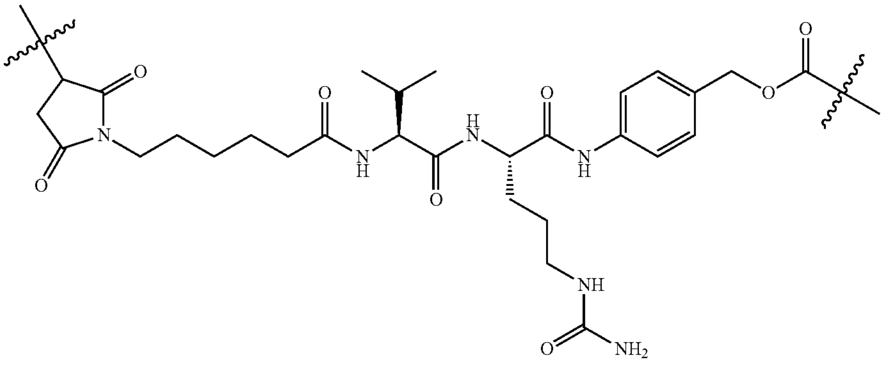 or 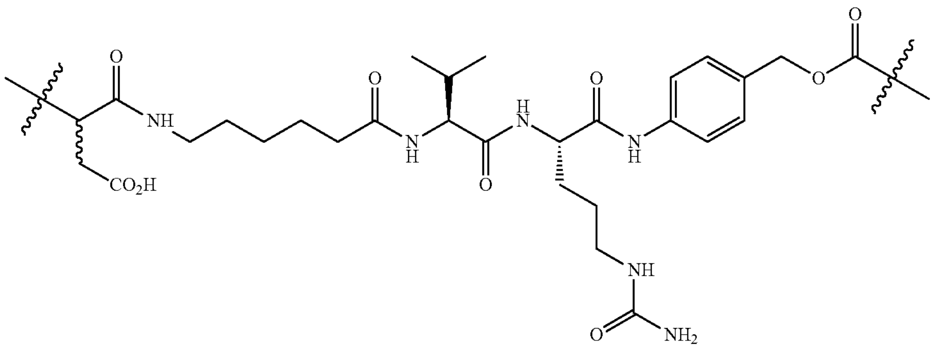 [SMILES: *C(=O)OCc1ccc(NC(=O)[C@H](CCCNC(N)=O)NC(=O)[C@@H](NC(=O)CCCCCNC(=O)C(*)CC(=O)O)C(C)C)cc1] |

Linkers are attached to the monoclonal antibody via the left side of the molecule and the drug via the right side of the molecule as depicted in Table 3.

IV. Methods of Preparing Site Specific HER2 ADCs

Also provided are methods for preparing antibody drug conjugates of the present invention. For example, a process for producing a site specific HER2 ADC as disclosed herein can include (a) linking the linker to the drug; (b) conjugating the linker-drug moiety to the antibody; and (c) purifying the antibody drug conjugate.

The HER2 ADCs of the present invention use site specific methods to conjugate the HER2 antibody to the drug payload.

In one embodiment, the site specific conjugation occurs through one or more cysteine residues that have been engineered into an antibody constant region. Methods of preparing HER2 antibodies for site specific conjugation through cysteine residues can be performed as described in PCT Publication No. WO2013/093809, which is incorporated by reference in its entirety. One or more of the following positions (using EU Index of Kabat numbering for the IgG1 constant region and Kabat numbering for the Kappa chain constant region) can be altered to be a cysteine and thus serve as a site for conjugation: a) on the heavy chain constant region, residues 114, 246, 249, 265, 267, 270, 276, 278, 283, 290, 292, 293, 294, 300, 302, 303, 314, 315, 318, 320, 327, 332, 333, 334, 336, 345, 347, 354, 355, 358, 360, 362, 370, 373, 375, 376, 378, 380, 382, 386, 388, 390, 392, 393, 401, 404, 411, 413, 414, 416, 418, 419, 421, 428, 431, 432, 437, 438, 439, 443, and 444 and/or b) on the Kappa chain constant region, residues 111, 149, 183, 188, 207, and 210.

In a specific embodiment, the one or more positions (using EU Index of Kabat numbering) that can be altered to be a cysteine a) on the heavy chain constant region are 290, 334, 392 and/or 443 and/or b) on the light chain constant region is 183 (Kabat numbering).

In a more specific embodiment, positions 290 on the heavy chain constant region and position 183 on the light chain constant region are altered to cysteine for conjugation.

In another embodiment, the site specific conjugation occurs through one or more acyl donor glutamine residues that have been engineered into the antibody constant region. Methods of preparing HER2 antibodies for site specific conjugation through glutamine residues can be performed as described in PCT Publication No. WO2012/059882, which is incorporated by reference in its entirety. Antibodies can be engineered to express the glutamine residue used for site specific conjugation in three different ways.

The short peptide tag containing the glutamine residue can be incorporated into a number of different positions of the light and/or heavy chain (i.e., at the N-terminus, at the C-terminus, internally). In a first embodiment, a short peptide tag containing the glutamine residue can be attached to the C-terminus of the heavy and/or light chain. One or more of the following glutamine containing tags can be attached to serve as the acyl donor for drug conjugation: GGLLQGPP (SEQ ID NO:81), GGLLQGG (SEQ ID NO:82), LLQGA (SEQ ID NO:83), GGLLQGA (SEQ ID NO:84), LLQG (SEQ ID NO: 85), LLQGPG (SEQ ID NO: 86), LLQGPA (SEQ ID NO: 87), LLQGP (SEQ ID NO: 88), LLQP (SEQ ID NO: 89), LLQPGK (SEQ ID NO: 90), LLQGAPGK (SEQ ID NO: 91), LLQGAPG (SEQ ID NO: 92), LLQGAP (SEQ ID NO: 93), $LLQX_1X_2X_3X_4X_5$, wherein $X_1$ is G or P, wherein $X_2$ is A, G, P, or absent, wherein $X_3$ is A, G, K, P, or absent, wherein $X_4$ is G, K or absent, and wherein $X_5$ is K or absent (SEQ ID NO: 94), or $LLQX_1X_2X_3X_4X_5$, wherein $X_1$ is any naturally occurring amino acid and wherein $X_2$, $X_3$, $X_4$, and $X_5$ are any naturally occurring amino acids or absent (SEQ ID NO: 95).

In a specific embodiment, GGLLQGPP (SEQ ID NO:81) is attached to the C-term inus of the light chain.

In a second embodiment, a residue on the heavy and/or light chain can be altered to a glutamine residue by site directed mutagenesis. In a specific embodiment, the residue at position 297 on the heavy chain (using EU Index of Kabat numbering) can be altered to be a glutamine (Q) and thus serve as a site for conjugation.

In a third embodiment, a residue on the heavy chain or light chain can be altered resulting in aglycosylation at that position such that one or more endogenous glutamine becomes accessible/reactive for conjugation. In a specific embodiment, the residue at position 297 on the heavy chain (using EU Index of Kabat numbering) is altered to an alanine (A). In such cases, the glutamine (Q) at position 295 on the heavy chain is then capable for use in conjugation.

Optimal reaction conditions for formation of a conjugate may be empirically determined by variation of reaction variables such as temperature, pH, linker-payload moiety input, and additive concentration. Conditions suitable for conjugation of other drugs may be determined by those skilled in the art without undue experimentation. Site specific conjugation through engineered cysteine residues is exemplified in Example 5A infra. Site specific conjugation through glutamine residues is exemplified in Example 5B infra.

To further increase the number of drug molecules per antibody drug conjugate, the drug may be conjugated to polyethylene glycol (PEG), including straight or branched polyethylene glycol polymers and monomers. A PEG monomer is of the formula: $-(CH_2CH_2O)-$. Drugs and/or peptide analogs may be bound to PEG directly or indirectly, i.e. through appropriate spacer groups such as sugars. A PEG-antibody drug composition may also include additional lipophilic and/or hydrophilic moieties to facilitate drug stability and delivery to a target site in vivo. Representative methods for preparing PEG-containing compositions may be found in, e.g., U.S. Pat. Nos. 6,461,603; 6,309,633; and 5,648,095.

Following conjugation, the conjugates may be separated and purified from unconjugated reactants and/or aggregated forms of the conjugates by conventional methods. This can include processes such as size exclusion chromatography (SEC), ultrafiltration/diafiltration, ion exchange chromatography (IEC), chromatofocusing (CF) HPLC, FPLC, or Sephacryl S-200 chromatography. The separation may also be accomplished by hydrophobic interaction chromatography (HIC). Suitable HIC media includes Phenyl Sepharose 6 Fast Flow chromatographic medium, Butyl Sepharose 4 Fast Flow chromatographic medium, Octyl Sepharose 4 Fast Flow chromatographic medium, Toyopearl Ether-650M chromatographic medium, Macro-Prep methyl HIC medium or Macro-Prep t-Butyl HIC medium.

Table 4 infra shows HER2 ADCs used to generate data in the Examples Section set forth herein. The site specific HER2 ADCs shown in Table 4 (in rows 1-17) are examples of site specific ADCs of the invention.

To make a site specific HER2 ADC of the invention any HER2 antibody disclosed in Section I supra can be conjugated using site specific techniques to any drug disclosed in Section II supra via any linker disclosed in Section III supra. In preferred embodiments, the linker is cleavable (e.g., vc or AcLysvc). In other preferred embodiments, the drug is an auristatin (e.g., 0101).

In a particular aspect of the invention, site specific HER2 ADC of the formula Ab-(L-D) comprises (a) an antibody, Ab, comprising a heavy chain of SEQ ID NO:18 and a light chain of SEQ ID NO:42; and (b) a linker-drug moiety, L-D, wherein L is a linker, and D is a drug, wherein the linker is vc and wherein the drug is 0101. A schematic of such an ADC is shown in FIG. 1A.

Figure 1B:
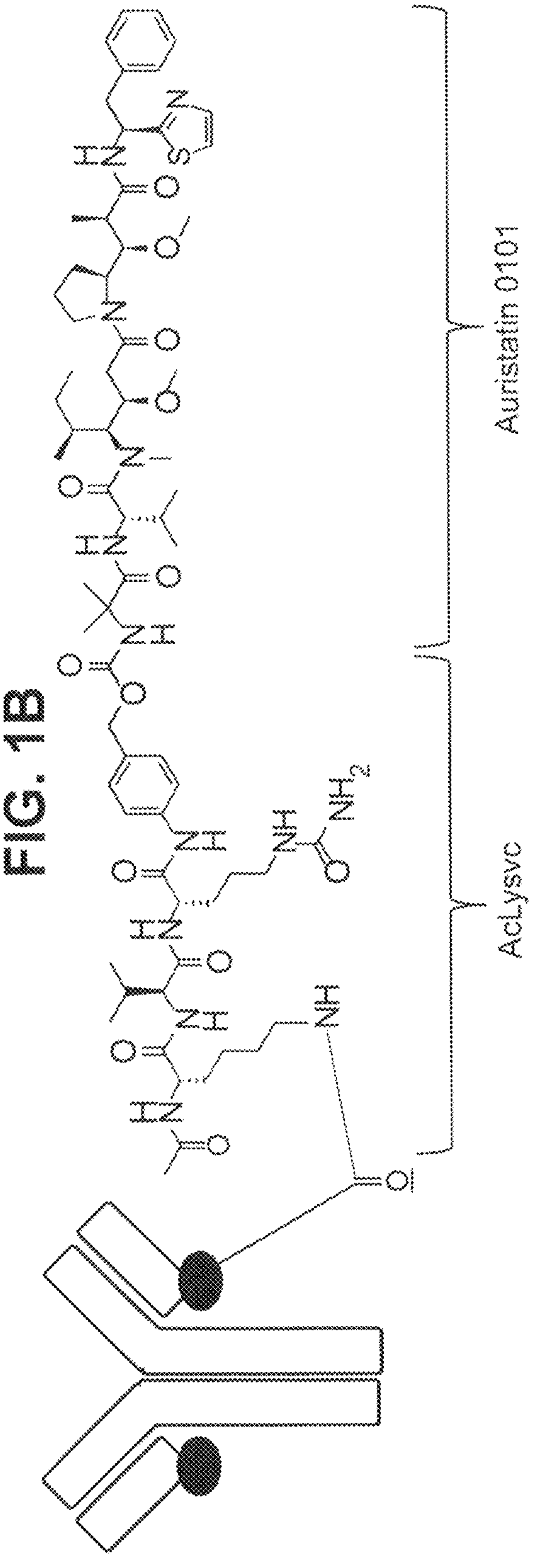
Figure 2A:
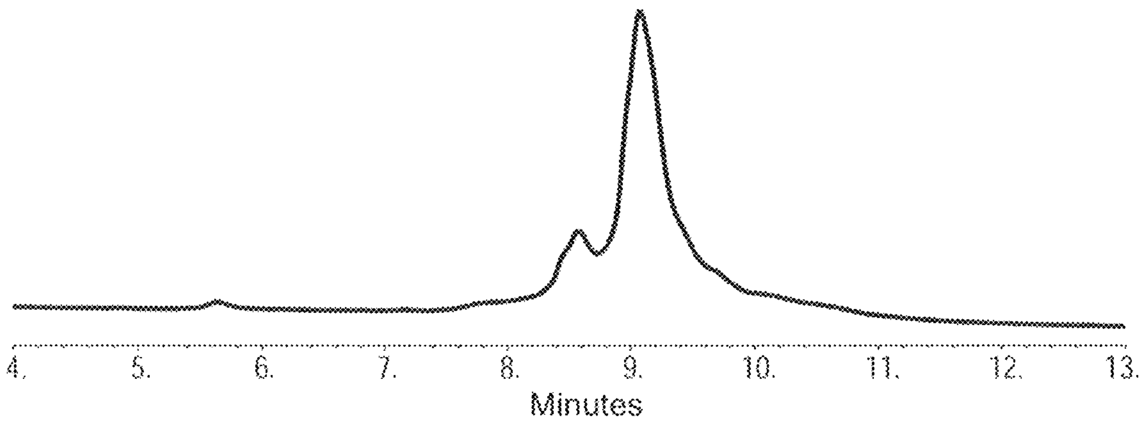
FIGS. 2A-2E depict spectra of selected ADCs from hydrophobic interaction chromatography (HIC) showing changes in retention times upon conjugation of trastuzumab derived antibodies to different linker payloads.
Figure 2B:
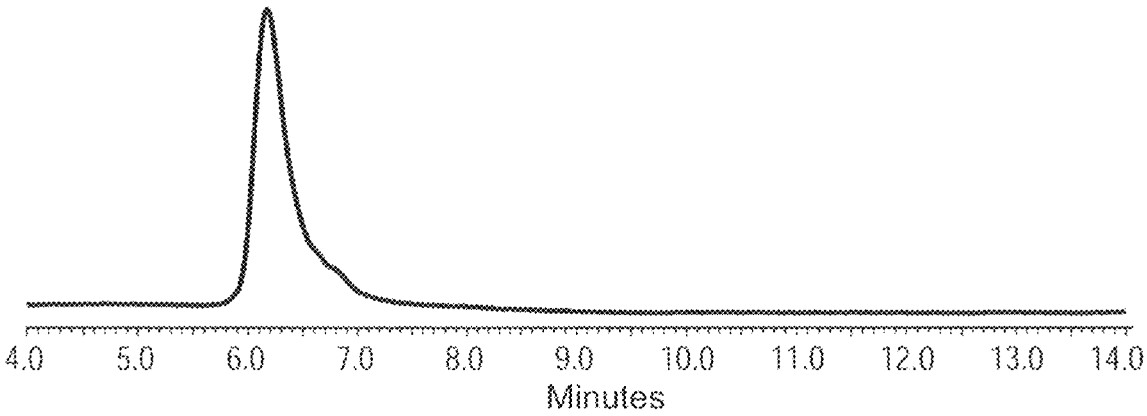
Figure 2C:
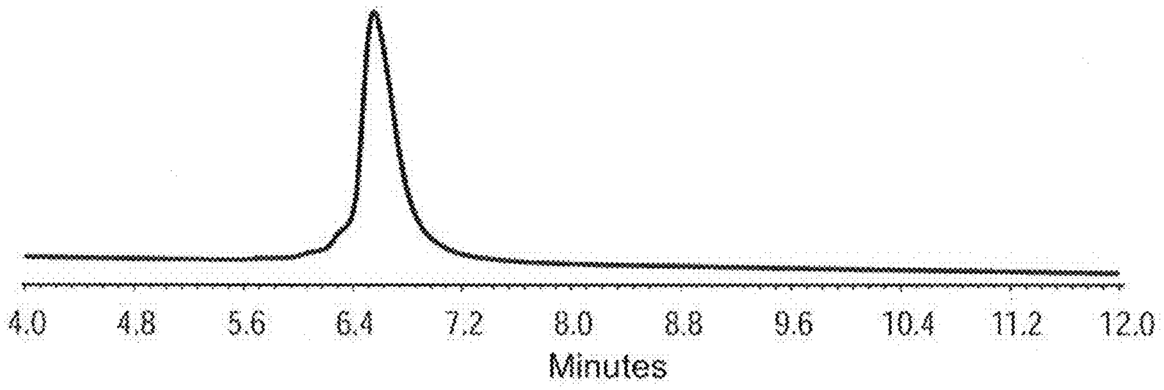
Figure 2D:
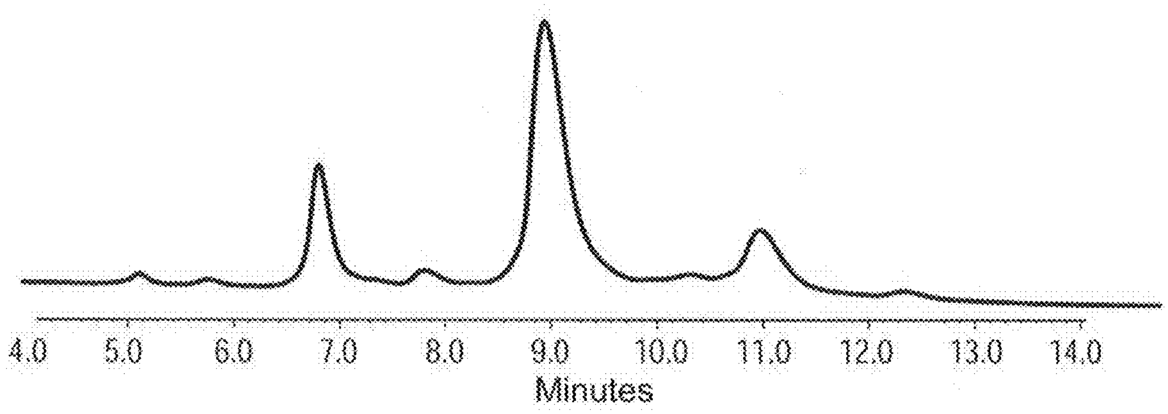
Figure 2E:
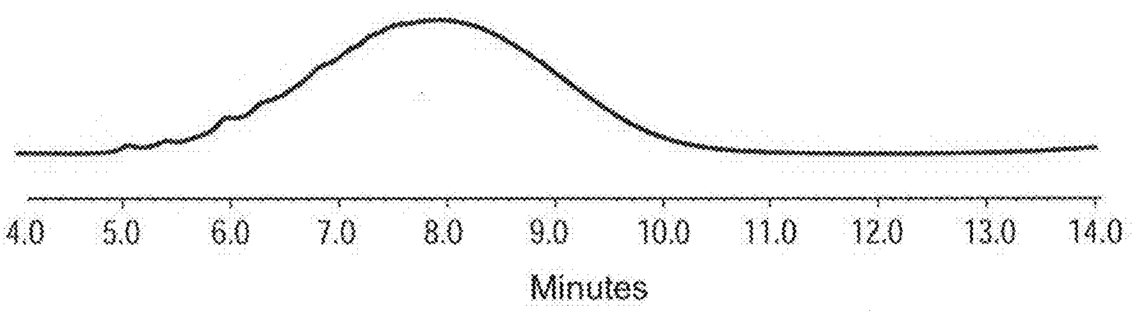

In another particular aspect of the invention, site specific HER2 ADC of the formula Ab-(L-D) comprises (a) an antibody, Ab, comprising a heavy chain of SEQ ID NO:14 and a light chain of SEQ ID NO:44; and (b) a linker-drug moiety, L-D, wherein L is a linker, and D is a drug, wherein the linker is AcLysvc and wherein the drug is 0101. A schematic of such an ADC is shown in FIG. 1B.

In another particular aspect of the invention, site specific HER2 ADC of the formula Ab-(L-D) comprises (a) an antibody, Ab, comprising a heavy chain of SEQ ID NO:24 and a light chain of SEQ ID NO:42; and (b) a linker-drug moiety, L-D, wherein L is a linker, and D is a drug, wherein the linker is vc and wherein the drug is 0101.

In another particular aspect of the invention, site specific HER2 ADC of the formula Ab-(L-D) comprises (a) an antibody, Ab, comprising a heavy chain of SEQ ID NO:26 and a light chain of SEQ ID NO:42; and (b) a linker-drug moiety, L-D, wherein L is a linker, and D is a drug, wherein the linker is vc and wherein the drug is 0101.

In another particular aspect of the invention, site specific HER2 ADC of the formula Ab-(L-D) comprises (a) an antibody, Ab, comprising a heavy chain of SEQ ID NO:28 and a light chain of SEQ ID NO:42; and (b) a linker-drug moiety, L-D, wherein L is a linker, and D is a drug, wherein the linker is vc and wherein the drug is 0101.

In another particular aspect of the invention, site specific HER2 ADC of the formula Ab-(L-D) comprises (a) an antibody, Ab, comprising a heavy chain of SEQ ID NO:30 and a light chain of SEQ ID NO:12; and (b) a linker-drug moiety, L-D, wherein L is a linker, and D is a drug, wherein the linker is vc and wherein the drug is 0101.

In another particular aspect of the invention, site specific HER2 ADC of the formula Ab-(L-D) comprises (a) an antibody, Ab, comprising a heavy chain of SEQ ID NO:32 and a light chain of SEQ ID NO:12; and (b) a linker-drug moiety, L-D, wherein L is a linker, and D is a drug, wherein the linker is vc and wherein the drug is 0101.

In another particular aspect of the invention, site specific HER2 ADC of the formula Ab-(L-D) comprises (a) an antibody, Ab, comprising a heavy chain of SEQ ID NO:34 and a light chain of SEQ ID NO:44; and (b) a linker-drug moiety, L-D, wherein L is a linker, and D is a drug, wherein the linker is AcLysvc and wherein the drug is 0101.

In another particular aspect of the invention, site specific HER2 ADC of the formula Ab-(L-D) comprises (a) an antibody, Ab, comprising a heavy chain of SEQ ID NO:36 and a light chain of SEQ ID NO:12; and (b) a linker-drug moiety, L-D, wherein L is a linker, and D is a drug, wherein the linker is AcLysvc and wherein the drug is 0101.

In another particular aspect of the invention, site specific HER2 ADC of the formula Ab-(L-D) comprises (a) an antibody, Ab, comprising a heavy chain of SEQ ID NO:38 and a light chain of SEQ ID NO:12; and (b) a linker-drug moiety, L-D, wherein L is a linker, and D is a drug, wherein the linker is vc and wherein the drug is 0101.

In another particular aspect of the invention, site specific HER2 ADC of the formula Ab-(L-D) comprises (a) an antibody, Ab, comprising a heavy chain of SEQ ID NO:40 and a light chain of SEQ ID NO:12; and (b) a linker-drug moiety, L-D, wherein L is a linker, and D is a drug, wherein the linker is vc and wherein the drug is 0101.

TABLE 4

HER2 ADCS

| ADC | Heavy Chain variable region | Heavy Chain constant region | Heavy Chain | Light Chain variable region | Light Chain constant region | Light Chain | Linker | Payload | Linker Type[1] |
|---|---|---|---|---|---|---|---|---|---|
| T(kK183C)-vc0101 | 1 | 5 | 6 | 7 | 41 | 42 | vc | 0101 | C |
| T(K290C)-vc0101 | 1 | 17 | 18 | 7 | 11 | 12 | vc | 0101 | C |
| T(N297Q)-AcLysvc0101 | 1 | 21 | 22 | 7 | 11 | 12 | AcLysvc | 0101 | C |
| T(K334C)-vc0101 | 1 | 23 | 24 | 7 | 11 | 12 | vc | 0101 | C |
| T(K392C)-vc0101 | 1 | 25 | 26 | 7 | 11 | 12 | vc | 0101 | C |
| T(L443C)-vc0101 | 1 | 27 | 28 | 7 | 11 | 12 | vc | 0101 | C |
| T(kK183C+K290C)-vc0101 | 1 | 17 | 18 | 7 | 41 | 42 | vc | 0101 | C |
| T(kK183C+K334C)-vc0101 | 1 | 23 | 24 | 7 | 41 | 42 | vc | 0101 | C |
| T(kK183C+K392C)-vc0101 | 1 | 25 | 26 | 7 | 41 | 42 | vc | 0101 | C |
| T(kK183C+L443C)-vc0101 | 1 | 27 | 28 | 7 | 41 | 42 | vc | 0101 | C |
| T(K290C+K334C)-vc0101 | 1 | 29 | 30 | 7 | 11 | 12 | vc | 0101 | C |
| T(K290C+K392C)-vc0101 | 1 | 31 | 32 | 7 | 11 | 12 | vc | 0101 | C |
| T(N297A+K222R+LCQ05)-AcLysvc0101 | 1 | 33 | 34 | 7 | 43 | 44 | AcLysvc | 0101 | C |
| T(N297Q+K222R)-AcLysvc0101 | 1 | 35 | 36 | 7 | 11 | 12 | AcLysvc | 0101 | C |
| T(K334C+K392C)-vc0101 | 1 | 37 | 38 | 7 | 11 | 12 | vc | 0101 | C |
| T(K392C+L443C)-vc0101 | 1 | 39 | 40 | 7 | 11 | 12 | vc | 0101 | C |
| T(LCQ05+K222R)-AcLysvc0101 | 1 | 13 | 14 | 7 | 43 | 44 | AcLysvc | 0101 | C |
| T-mc8261 | 1 | 5 | 6 | 7 | 11 | 12 | mc | 8261 | N |
| T-m(H20)c8261 | 1 | 5 | 6 | 7 | 11 | 12 | m(H20)c | 8261 | N |
| T-MalPeg8261 | 1 | 5 | 6 | 7 | 11 | 12 | MalPeg6 | 8261 | N |
| T-vc8261 | 1 | 5 | 6 | 7 | 11 | 12 | vc | 8261 | C |
| T-mc6121 | 1 | 5 | 6 | 7 | 11 | 12 | mc | 6121 | N |
| T-MalPeg6121 | 1 | 5 | 6 | 7 | 11 | 12 | MalPeg6 | 6121 | N |
| T-mc0101 | 1 | 5 | 6 | 7 | 11 | 12 | mc | 0101 | N |
| T-vc0101 | 1 | 5 | 6 | 7 | 11 | 12 | vc | 0101 | C |
| T-vc8254 | 1 | 5 | 6 | 7 | 11 | 12 | vc | 8254 | C |
| T-vc6780 | 1 | 5 | 6 | 7 | 11 | 12 | vc | 6780 | C |
| T-vc0131 | 1 | 5 | 6 | 7 | 11 | 12 | vc | 0131 | C |
| T-MalPegMMAD | 1 | 5 | 6 | 7 | 11 | 12 | MalPeg6 | MMAD | N |
| T-vcMMAE | 1 | 5 | 6 | 7 | 11 | 12 | vc | MMAE | C |
| T-DM1 | 1 | 5 | 6 | 7 | 11 | 12 | mcc | DM1 | N |

[1] C = cleavable; N = non-cleavable

V. Use of Site Specific HER2 Antibody Drug Conjugates

The antibody drug conjugates of the present invention are useful in therapeutic methods to treat HER2-expressing cancer. In some aspects of the invention, provided is a method of inhibiting tumor growth or progression in a subject who has a HER2-expressing tumor, including administering to the subject in need thereof an effective amount of a composition (i.e., a pharmaceutical composition) having one or more ADCs described herein. In other aspects of the invention, provided is a method of inhibiting metastasis of HER2-expressing cancer cells in a subject, including administering to the subject in need thereof an effective amount of a composition (i.e., a pharmaceutical composition) having one or more ADCs described herein. In other aspects of the invention, provided is a method of inducing regression of a HER2-expressing tumor in a subject, including administering to the subject in need thereof an effective amount of a composition (i.e., a pharmaceutical composition) having one or more ADCs described herein. In other aspects, the invention provides a pharmaceutical composition comprising one or more ADCs described herein for use in a method as described above. In other aspects, the invention provides the use of one or more ADCs as described herein or a pharmaceutical composition comprising the ADCs as described herein in the manufacture of a medicament for use in the methods described above.

Desired outcomes of the disclosed therapeutic methods are generally quantifiable measures as compared to a control or baseline measurement. As used herein, relative terms such as "improve," "increase," or "reduce" indicate values relative to a control, such as a measurement in the same individual prior to initiation of treatment described herein, or a measurement in a control individual (or multiple control individuals) in the absence of the treatment described herein. A representative control individual is an individual afflicted with the same form of cancer as the individual being treated, who is about the same age as the individual being treated (to ensure that the stages of the disorder in the treated individual and the control individual are comparable).

Changes or improvements in response to therapy are generally statistically significant. As used herein, the term "significance" or "significant" relates to a statistical analysis of the probability that there is a non-random association between two or more entities. To determine whether or not a relationship is "significant" or has "significance," statistical manipulations of the data can be "p-value." Those p-values that fall below a user-defined cut-off point are regarded as significant. A p-value less than or equal to 0.1, less than 0.05, less than 0.01, less than 0.005, or less than 0.001 may be regarded as significant.

V.A. Cancers

The ADCs of the present invention are useful in treating HER2-expressing cancers. In one embodiment, the HER2-expressing cancer is a solid tumor. In a more specific embodiment, HER2-expressing solid tumors include, but are not limited to, breast cancer (e.g., estrogen and progesterone receptor negative breast cancer, triple negative breast cancer), ovarian cancer, lung cancer (e.g., non-small cell lung cancer (including adenocarcinomas, squamous cell carcinomas and large cell carcinomas) and small cell lung cancer), gastric cancer, esophageal cancer, colorectal cancer, urothelial cancer (e.g., micropapillary urothelial cancer and typical urothelial cancer), pancreatic cancer, salivary gland cancer (e.g., mucoepidermoid carcinomas, adenoid cystic carcinomas and terminal duct adenocarcinoma) and brain cancer or metastases of the aforementioned cancers (i.e., lung metastasis from HER2+ breast cancer) (Martin et al., 2014, Future Oncol. 10(8):1469-86).

In an even more specific embodiment, HER2-expressing solid tumors include, but are not limited to, breast cancer, ovarian cancer, lung cancer and gastric cancer.

In another embodiment, the breast cancer is estrogen receptor and progesterone receptor negative. In a more specific embodiment, the breast cancer is triple negative breast cancer (TNBC).

In another embodiment, the lung cancer is non-small cell lung cancer (NSCLC).

In one aspect of the invention, ADCs disclosed herein can be used to treat HER2-expressing cancers that have not been previously treated with a therapeutic agent (i.e., as a first line treatment).

In another aspect of the invention, ADCs disclosed herein can be used to treat HER2-expressing cancers that are resistant to, refractory to and/or relapsed from treatment with another therapeutic agent (i.e., as a second line treatment). In one embodiment, the prior treatment was trastuzumab (trastuzumab or Herceptin®) either alone or in combination with an additional therapeutic agent (i.e., a taxane such as paclitaxel, docetaxel, cabazitaxel, etc.). In another embodiment, the prior treatment was trastuzumab emtansine (T-DM1 or Kadcyla®) either alone or in combination with an additional therapeutic agent (i.e., a taxane such as paclitaxel, docetaxel, cabazitaxel, etc.).

In another aspect of the invention, ADCs disclosed herein can be used to treat HER2-expressing cancers that are resistant to, refractory to and/or relapsed from treatment with more than one other therapeutic agent (i.e., as a third line treatment or a fourth line treatment, etc.).

ADCs of the present invention can be used to treat cancers that express high levels of HER2 (i.e., IHC 3+), moderate levels of HER2 (i.e., 2+ IHC or 2+/3+ IHC) or low levels of HER2 (i.e., IHC 1+, IHC 2+ or IHC 1+/2+) (see Section IVB for methods of HER2 detection). This is in contrast to trastuzumab and T-DM1 where they are not efficacious in low or moderate HER2-expressing cancers (Burris et al., 2011, J Clinical Oncology 29(4):398-405).

ADCs of the present invention can be used to treat cancers that are homogeneous in nature where the majority of tumor cells express a similar amount of HER2. Alternatively, the ADCs of the present invention can be used to treat cancers that are heterogeneous in nature where there are different tumor cell populations expressing different levels of HER2.

V.B. HER2 Detection Methods

Aspects regarding the best way to assess HER2 expression levels on a tumor have been discussed and clinical implications have been outlined (Sauter et al., 2009, J Clin Oncol. 27:1323-33; Wolff et al., 2007, J Clinical Oncology 25:118-45; Wolff et al., 2013, J Clinical Oncology 31:3997-4014). Currently, HER2 status can be assessed by immunohistochemistry (IHC), fluorescent in situ hybridization (FISH) and chromogenic in situ hybridization (CISH).

IHC identifies HER2 protein expression on the cell membrane. Results are usually expressed using a semiquantitative scoring system ranging from 0+ (no expression) to 3+(high expression). Tumors that show no (0+) or low levels (1+) of expression are considered HER2-negative; vice-versa tumors that show high levels (3+) of expression should be considered as HER2-positive. This method is economically advantageous and readily available, but suffers from low sensitivity and high interobserver variability (Gancberg et al., 2002, Breast Cancer Res Treat. 74:113-20).

There are four FDA-approved commercial kits available for HER2 detection using IHC: HercepTest™ (by Dako Denmark A/S); Pathway (by Ventana Medical Systems, Inc.); Insite HER2/NEU kit (by Biogenex Laboratories, Inc.) and Bond Oracle HER2 IHC System (by Leica Biosystems). These are highly standardized, semiquantitative assays which stratify HER2 expression levels into; 0 (<20,000 receptors per cell, no visible expression), 1+ (~100,000 receptors per cell, partial membrane staining, <10% of cells overexpressing HER-2), 2+ (~500,000 receptors per cell, light to moderate complete membrane staining, >10% of cells overexpressing HER-2), and 3+ (~2,000,000 receptors per cell, strong complete membrane staining, >10% of cells overexpressing HER-2). The presence of cytoplasmic expression is disregarded.

FISH detects HER2 gene amplification with a DNA probe and is more specific and sensitive than IHC (Owens et al., 2004, Clin Breast Cancer. 5:63-69; Press et al., 2005, Clin Cancer Res. 11:6598-6607; Vogel et al., 2002, J Clinical Oncology 20(3):719-726). FISH offers quantitative results on the number of HER2 gene copies per chromosome 17 centromeres. Results are reported as a ratio of the number of HER2 signals to chromosome 17 centromere signals. A ratio of less than 1.8 is considered within normal limits. A ratio of 1.8-2.0 is equivocal and requires further testing. A ratio of greater than 2.0 is consistent with amplification of HER2 gene sequences.

There are four FDA-approved commercial kits available for HER2 detection using FISH: HER2 FISH Pharm Dx™ kit (by Dako Denmark A/S); Pathvysion HER2 DNA Probe Kit (by Abbott Molecular Inc.); Inform HER2/NEU and Inform HER2 Dual ISH DNA Probe Cocktail (both by Ventana Medical Systems, Inc.).

Another method to assess HER2 gene amplification is CISH. CISH is very similar to FISH but utilizes conventional peroxidase or alkaline phosphatase reactions visualized under a standard bright-field microscope. There are two FDA-approved commercial kits available for HER2 detection using CISH: HER2 CISH PharmDx Kit (by Dako Denmark A/S) and Spot-Light HER2 CISH Kit (by Life Technologies, Inc.).

Both gene amplification detected by FISH or CISH and protein expression by IHC are commonly used as initial test to assess HER2 status. There is a good correlation between the two methods (Jacobs et al., 1999, J Clinical Oncology 17(7):1974-82). However in cases where the tumor is scored as equivocal (i.e., IHC 2+ or FISH/CISH ratio of 1.8-2.2 or average HER2 gene copy number of four to six signals per nucleus), a common approach is to test the tumor with an alternative method (Wolff et al., 2007, J Clinical Oncology 25:118-45).

Thus, HER2 expression is considered high in tumors with a 3+ level as determined by immunohistochemistry (IHC) and/or a fluorescence in situ hybridization (FISH) amplification ratio of ≥2.0. HER2 expression is considered moderate in tumors with a 2+ level as determined by immunohistochemistry (IHC) and/or a fluorescence in situ hybridization (FISH) amplification ratio of <2.0. HER2 expression is considered low in tumors with a 1+ level as determined by immunohistochemistry (IHC) and/or a fluorescence in situ hybridization (FISH) amplification ratio of <2.0.

In one embodiment, HER2 levels are determined by IHC. In a more specific embodiment, IHC is performed using a Dako Hercptest™ assay.

In another embodiment, HER2 levels are determined by FISH. In a more specific embodiment, FISH is performed using a Dako HER2 FISH Pharm Dx™ assay.

Representative tumor samples include any biological or clinical sample which contains tumor cells, for example, a tissue sample, a biopsy, a blood sample, a plasma sample, a saliva sample, a urine sample, etc.

VI. Formulations

The present invention provides pharmaceutical compositions including any of the site specific HER2 antibody drug conjugates disclosed herein and a pharmaceutically acceptable carrier. Further, the compositions can include more than one of the site specific HER2 ADCs disclosed herein.

The compositions used in the present invention can further include pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). "Pharmaceutically acceptable salt" as used herein refers to pharmaceutically acceptable organic or inorganic salts of a molecule or macromolecule. Pharmaceutically acceptable excipients are further described herein.

Various formulations of one or more site specific HER2 ADCs may be used for administration including, but not limited to formulations comprising one or more pharmaceutically acceptable excipients. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some aspects of the invention, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Therapeutic formulations of the site specific HER2 ADCs used in accordance with the present invention are prepared for storage by mixing an ADC having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may include buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the site specific HER2 ADCs can be prepared by methods known in the art, such as described in Eppstein, et al., 1985, PNAS 82:3688-92; Hwang, et al., 1908, PNAS 77:4030-4; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition including phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic site specific HER2 ADC compositions are generally placed into a container having a sterile access port, for example, an intravenous solution bag or vial having a stopper pierceable by a hypodermic injection needle.

Suitable surface-active agents include, in particular, non-ionic agents, such as polyoxyethylenesorbitans (e.g. TWEEN™ 20, 40, 60, 80 or 85) and other sorbitans (e.g. Span™ 20, 40, 60, 80 or 85). Compositions with a surface-active agent will conveniently include between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can include fat droplets between 0.1 and 1.0 μm, particularly 0.1 and 0.5 μm, and have a pH in the range of 5.5 to 8.0. The emulsion compositions can be those prepared by mixing a site specific HER2 ADC with INTRALIPID™ or the components thereof (soybean oil, egg phospholipids, glycerol and water).

The invention also provides kits for use in the instant methods. Kits of the invention include one or more containers including one or more site specific HER2 ADCs as described herein and instructions for use in accordance with any of the methods of the invention described herein. Generally, these instructions include a description of administration of the site specific HER2 ADC for the above described therapeutic treatments.

The instructions relating to the use of the site specific HER2 ADCs as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a site specific HER2 ADC. The container may further include a second pharmaceutically active agent.

Kits may optionally provide additional components such as buffers and interpretive information. Normally, the kit includes a container and a label or package insert(s) on or associated with the container.

VII. Dose and Administration

For in vivo applications, site specific HER2 ADCs are provided or administered in an effective dosage. The phrases "effective dosage" or "effective amount" as used herein refer to an amount of a drug, compound or pharmaceutical composition necessary to achieve any one or more beneficial or desired therapeutic results either directly or indirectly. For example, when administered to a cancer-bearing subject, an effective dosage includes an amount sufficient to elicit anti-cancer activity, including cancer cell cytolysis, inhibition of cancer cell proliferation, induction of cancer cell apoptosis, reduction of cancer cell antigens, delayed tumor growth, and/or inhibition of metastasis. Tumor shrinkage is well accepted as a clinical surrogate marker for efficacy. Another well accepted marker for efficacy is progression-free survival.

An effective dosage can be administered in one or more administrations. An effective dosage of a drug, compound, or pharmaceutical composition may or may not be achieved in conjunction with another drug, compound, or pharmaceutical composition. Thus, an effective dosage may be considered in the context of administering one or more therapeutic agents, and a single agent may be considered to be given in an effective amount if, in conjunction with one or more other agents, a desirable result may be or is achieved.

The site specific HER2 ADCs can be administered to an individual via any suitable route. It should be understood by persons skilled in the art that the examples described herein are not intended to be limiting but to be illustrative of the techniques available. Accordingly, in some aspects of the invention, the site specific HER2 ADC is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the site specific HER2 ADC can be aerosolized using a fluorocarbon formulation and a metered dose inhaler, or inhaled as a lyophilized and milled powder.

In some aspects of the invention, the site specific HER2 ADC is administered via site-specific or targeted local delivery techniques. Examples of site-specific or targeted local delivery techniques include various implantable depot sources of site specific HER2 ADC or local delivery catheters, such as infusion catheters, indwelling catheters, or needle catheters, synthetic grafts, adventitial wraps, shunts and stents or other implantable devices, site specific carriers, direct injection, or direct application. See, e.g. PCT International Publication No. WO 2000/53211 and U.S. Pat. No. 5,981,568.

For the purpose of the present invention, the appropriate dosage of the site specific HER2 ADCs will depend on the particular ADC (or compositions thereof) employed, the type and severity of symptoms to be treated, whether the agent is administered for therapeutic purposes, previous therapy, the patient's clinical history and response to the agent, the patient's clearance rate for the administered agent, and the discretion of the attending physician. The clinician may administer a site specific HER2 ADC until a dosage is reached that achieves the desired result and beyond. Dose and/or frequency can vary over course of treatment, but may stay constant as well. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration of symptoms, e.g., tumor growth inhibition or delay, etc. Alternatively, sustained continuous release formulations of site specific HER2 ADCs may be appropriate. Various formulations and devices for achieving sustained release are known in the art.

Generally, for administration of a site specific HER2 ADC, an initial candidate dosage can be about 2 mg/kg. For the purpose of the present invention, a typical daily dosage might range from about any of 3 μg/kg to 30 μg/kg to 300 μg/kg to 3 mg/kg, to 30 mg/kg, to 100 mg/kg or more. For example, dosage of about 1 mg/kg, about 2.5 mg/kg, about 5 mg/kg, about 10 mg/kg, and about 25 mg/kg may be used. For repeated administrations over several days or longer, depending on the disorder, the treatment is sustained until a desired suppression of symptoms occurs or until sufficient therapeutic levels are achieved, for example, to inhibit or delay tumor growth/progression or metastases of cancer cells. An exemplary dosing regimen includes administering an initial dose of about 2 mg/kg, followed by a weekly maintenance dose of about 1 mg/kg of the site specific HER2 ADC, or followed by a maintenance dose of about 1 mg/kg every other week. Other exemplary dosing regimens include administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some aspects of the invention, dosing from one to four times a week is contemplated. In other aspects, dosing once a month or once every other month or every three months is contemplated, as well as weekly, bi-weekly and every three weeks. The progress of this therapy may be easily monitored by conventional techniques and assays. The dosing regimen (including the particular site specific HER2 ADC used) can vary over time.

VIII. Combination Therapies

In some aspects of the invention, the methods described herein further include a step of treating a subject with an additional form of therapy. In some aspects, the additional form of therapy is an additional anti-cancer therapy including, but not limited to, chemotherapy, radiation, surgery, hormone therapy, and/or additional immunotherapy.

The disclosed site specific HER2 ADCs may be administered as an initial treatment, or for treatment of cancers that are unresponsive to conventional therapies. In addition, the site specific HER2 ADCs may be used in combination with other therapies (e.g., surgical excision, radiation, additional anti-cancer drugs etc.) to thereby elicit additive or potentiated therapeutic effects and/or reduce cytotoxicity of some anti-cancer agents. Site specific HER2 ADCs of the invention may be co-administered or co-formulated with additional agents, or formulated for consecutive administration with additional agents in any order.

Site specific HER2 ADCs of the invention may be used in combination with other therapeutic agents including, but not limited to, therapeutic antibodies, ADCs, immunomodulating agents, cytotoxic agents, and cytostatic agents. A cytotoxic effect refers to the depletion, elimination and/or the killing of a target cells (i.e., tumor cells). A cytotoxic agent refers to an agent that has a cytotoxic and/or cytostatic effect on a cell. A cytostatic effect refers to the inhibition of cell proliferation. A cytostatic agent refers to an agent that has a cytostatic effect on a cell, thereby inhibiting the growth and/or expansion of a specific subset of cells (i.e., tumor cells). An immunomodulating agent refers to an agent that stimulates the immune response though the production of cytokines and/or antibodies and/or modulating T cell function thereby inhibiting or reducing the growth of a subset of cells (i.e., tumor cells) either directly or indirectly by allowing another agent to be more efficacious.

For combination therapies, a site specific HER2 ADC and/or one or more additional therapeutic agents are administered within any time frame suitable for performance of the intended therapy. Thus, the single agents may be administered substantially simultaneously (i.e., as a single formulation or within minutes or hours) or consecutively in any order. For example, single agent treatments may be administered within about 1 year of each other, such as within about 10, 8, 6, 4, or 2 months, or within 4, 3, 2 or 1 week(s), or within about 5, 4, 3, 2 or 1 day(s).

The disclosed combination therapies may elicit a synergistic therapeutic effect, i.e., an effect greater than the sum of their individual effects or therapeutic outcomes. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1: Preparation of Trastuzumab Derived Antibodies for Site Specific Conjugation A. For Conjugation Via Cysteine Methods of preparing trastuzumab derivatives for site specific conjugation through cysteine residues were generally performed as described in PCT Publication WO2013/093809 (which is incorporated herein in its entirety). One or more residues on either the light chain (183 using the Kabat numbering scheme) or the heavy chain (290, 334, 392 and/or 443 using the EU index of Kabat numbering scheme) were altered to a cysteine (C) residue by site directed mutagenesis.

B. For Conjugation Via Transglutaminase

Methods of preparing trastuzumab derivatives for site specific conjugation through glutamine residues were generally performed as described in PCT Publication WO2012/059882 (which is incorporated herein in its entirety). Trastuzumab was engineered to express the glutamine residue used for conjugation in three different ways.

For the first method, an 8 amino acid residue tag (LCQ05) containing the glutamine residue was attached to the C-terminus of the light chain (i.e., SEQ ID NO:81).

For the second method, a residue on the heavy chain (position 297 using the EU index of Kabat numbering scheme) was altered from an asparagine (N) to a glutamine (Q) residue by site directed mutagenesis.

For the third method, a residue on the heavy chain (position 297 using the EU index of Kabat numbering system) was altered from an asparagine (N) to an alanine (A). This results in aglycosylation at position 297 and accessible/reactive endogenous glutamine at position 295.

Additionally, some of the trastuzumab derivatives have an alteration that is not used for conjugation. The residue at position 222 on the heavy chain (using the EU Index of Kabat numbering scheme) was altered from a lysine (K) to an arginine (R) residue. The K222R substitution was found to result in more homogenous antibody and payload conjugate, better intermolecular crosslinking between the antibody and the payload, and/or significant decrease in interchain crosslinking with the glutamine tag on the C terminus of the antibody light chain.

Example 2: Production of Stably Transfected Cells Expressing Trastuzumab Derived Antibodies A. Cysteine Mutants To determine that the single and double cysteine engineered trastuzumab derived antibody variants could be stably expressed in cells and large-scale produced, CHO cells were transfected with DNA encoding nine trastuzumab derived antibody variants (T(κK183C), T(K290C), T(K334C), T(K392C), T(κK183C+K290C), T(κK183C+K392C), T(K290C+K334C), T(K334C+K392C) and T(K290C+K392C)) and stable high production pools were isolated using standard procedures well-known in the art. To produce T(κK183C+K334C) for conjugation studies, HEK-293 cells (ATCC Accession # CRL-1573) were transiently co-transfected with heavy and light chain DNA encoding this double-cysteine engineered antibody variant using standard methods. A two-column process, i.e. Protein-A affinity capture followed by a TMAE column or a three-column process, i.e. Protein-A affinity capture followed by a TMAE column and then CHA-TI column, was used to isolate these trastuzumab variants from the concentrated CHO pool starting material. Using these purification process, all engineered cysteine trastuzumab derived antibody variant preparations contained >97% peak-of-interest (POI) as determined by analytical size-exclusion chromatography (Table 5). These results shown in Table 5 demonstrate that acceptable levels of high molecular weight (HMW) aggregated species were detected following elution from Protein A resin for all ten trastuzumab derived cysteine variants and that this undesirable HMW species could be removed using size exclusion chromatography. Additionally, the data demonstrated that the Protein A binding site in the human IgG1 constant region was not altered by the presence of the engineered cysteine residues.

TABLE 5

Production of Trastuzumab Derived Cysteine Antibody Variants

| Variant | Purification Process | ProA Eluate (% POI) | Yield (ProA) | Final (% POI) | Yield (Final) |
|---|---|---|---|---|---|
| T(κK183C) | 2 column | ND | ND | >99% | 768 mg/L |
| T(K290C) | 2 column | >99% | ND | >99% | 100 mg/L |
| T(K334C) | 2 column | >99% | ND | >99% | 100 mg/L |
| T(K392C | 2 column | >99% | ND | >99% | 110 mg/L |
| T(κK183C+K290C) | 3 column | 93% | 567 mg/L | >99% | 248 mg/L |

TABLE 5-continued

Production of Trastuzumab Derived Cysteine Antibody Variants

| Variant | Purification Process | ProA Eluate (% POI) | Yield (ProA) | Final (% POI) | Yield (Final) |
|---|---|---|---|---|---|
| T(K290C+K334C) | 3 column | 91.2% | 470 mg/L | >99% | 240 mg/L |
| T(K334C+K392C) | 3 column | 92.4% | 410 mg/L | >99% | 220 mg/L |
| T(κK183C+K334C) | 3 column | ND | ND | >99% | 64 mg/L |
| T(K290C+K392C) | 2 column | 93.1% | 700 mg/L | 97.9% | 420 mg/L |
| T(κK183C+K392C) | 2 column | 91.4 | ND | 97.8 | 600 mg/L |

ND = Not Determined

Example 3: Integrity of Trastuzumab Derived Antibodies

Molecular assessment of the engineered cysteine and transglutaminase variants was performed to evaluate key biophysical properties relative to the trastuzumab wild type antibody to ensure the variants would be amenable to a standard antibody manufacturing platform process.

A. Cysteine Mutants

To determine integrity of the purified engineered cysteine antibody variant preparations produced via stable CHO expression, the percent purity of peaks was calculated using non-reduced capillary gel electrophoresis (Caliper LabChip GXII: Perkin Elmer Waltham, Mass.). Results show that the engineered cysteine antibody variants T(κK183C+K290C) and T(K290C+K334C) contained low levels of both fragments and high molecular mass species (HMMS) similar to the trastuzumab wild type antibody. In contrast, T(K334C+K392C) contained high levels of fragmented antibody peaks relative to the other double engineered cysteine variants evaluated (Table 6). These results suggest that specific combinations of engineered cysteines can impact integrity of the antibody intended for site-specific conjugation.

TABLE 6

Percent Purity of Peaks Calculated from Non-Reduced Electropherogram

| Antibody | Main Peak (%) | Fragments (%) | HMMS (%) |
|---|---|---|---|
| trastuzumab WT | 95 | 5 | 0 |
| T(κK183C + K290C) | 95.78 | 4.18 | 0.04 |

TABLE 6-continued

Percent Purity of Peaks Calculated from Non-Reduced Electropherogram

| Antibody | Main Peak (%) | Fragments (%) | HMMS (%) |
|---|---|---|---|
| T(K290C + K334C) | 94.6 | 5.2 | 0.2 |
| T(K334C + K392C) | 80.7 | 19.3 | 0 |

Example 4: Generation of Payload Drug Compounds

The auristatin drug compounds 0101, 0131, 8261, 6121, 8254 and 6780 were made according to the methods described in PCT Publication WO2013/072813 (which is incorporated herein in its entirety). In published application, the auristatin compounds are indicated by the numbering system shown in Table 7.

TABLE 7

| Auristatin Drug Compound | Designation in WO2013/072813 |
|---|---|
| 0101 | #54 |
| 0131 | #118 |
| 8261 | #69 |
| 6121 | #117 |
| 8254 | #70 |
| 6780 | #112 |

According to PCT Publication WO2013/072813 drug compound 0101 was made according to the following procedure.

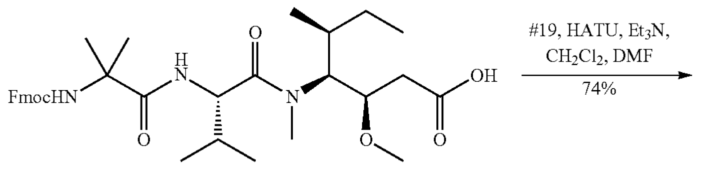

#32

-continued

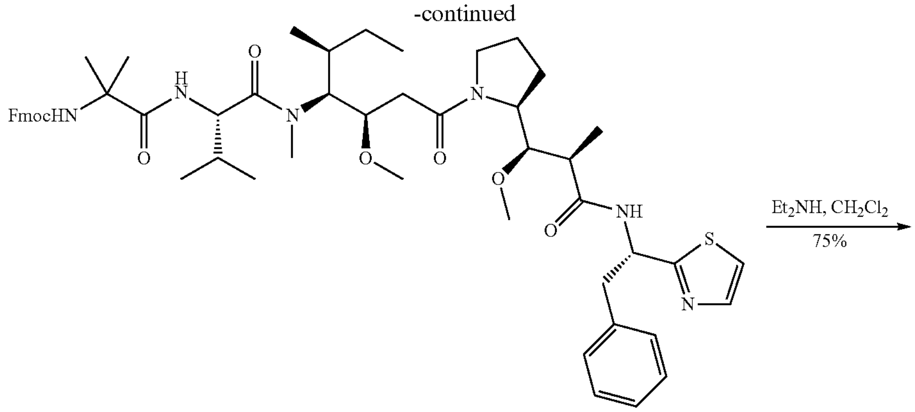

#53

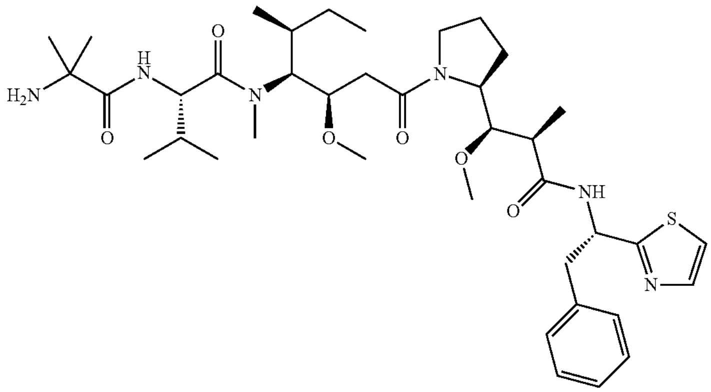

#54

Step 1. Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#53)

According to general procedure D, from #32 (2.05 g, 2.83 mmol, 1 eq.) in dichloromethane (20 mL, 0.1 M) and N,N-dimethylformamide (3 mL), the amine #19 (2.5 g, 3.4 mmol, 1.2 eq.), HATU (1.29 g, 3.38 mmol, 1.2 eq.) and triethylamine (1.57 mL, 11.3 mmol, 4 eq.) was synthesized the crude desired material, which was purified by silica gel chromatography (Gradient: 0% to 55% acetone in heptane), producing #53 (2.42 g, 74%) as a solid. LC-MS: m/z 965.7 [M+H$^+$], 987.6 [M+Na$^+$], retention time=1.04 minutes; HPLC (Protocol A): m/z 965.4 [M+H$^+$], retention time=11.344 minutes (purity>97%); $^1$H NMR (400 MHz, DMSO-d$_6$), presumed to be a mixture of rotamers, characteristic signals: δ 7.86-7.91 (m, 2H), [7.77 (d, J=3.3 Hz) and 7.79 (d, J=3.2 Hz), total 1H], 7.67-7.74 (m, 2H), [7.63 (d, J=3.2 Hz) and 7.65 (d, J=3.2 Hz), total 1H], 7.38-7.44 (m, 2H), 7.30-7.36 (m, 2H), 7.11-7.30 (m, 5H), [5.39 (ddd, J=11.4, 8.4, 4.1 Hz) and 5.52 (ddd, J=11.7, 8.8, 4.2 Hz), total 1H], [4.49 (dd, J=8.6, 7.6 Hz) and 4.59 (dd, J=8.6, 6.8 Hz), total 1H], 3.13, 3.17, 3.18 and 3.24 (4 s, total 6H), 2.90 and 3.00 (2 br s, total 3H), 1.31 and 1.36 (2 br s, total 6H), [1.05 (d, J=6.7 Hz) and 1.09 (d, J=6.7 Hz), total 3H].

Step 2. Synthesis of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54 or 0101)

According to general procedure A, from #53 (701 mg, 0.726 mmol) in dichloromethane (10 mL, 0.07 M) was synthesized the crude desired material, which was purified by silica gel chromatography (Gradient: 0% to 10% methanol in dichloromethane). The residue was diluted with diethyl ether and heptane and was concentrated in vacuo to afford #54 (or 0101) (406 mg, 75%) as a white solid. LC-MS: m/z 743.6 [M+H$^+$], retention time=0.70 minutes; HPLC (Protocol A): m/z 743.4 [M+H$^+$], retention time=6.903 minutes, (purity>97%); $^1$H NMR (400 MHz, DMSO-d$_6$), presumed to be a mixture of rotamers, characteristic signals: δ [8.64 (br d, J=8.5 Hz) and 8.86 (br d, J=8.7 Hz), total 1H], [8.04 (br d, J=9.3 Hz) and 8.08 (br d, J=9.3 Hz), total 1H], [7.77 (d, J=3.3 Hz) and 7.80 (d, J=3.2 Hz), total 1H], [7.63 (d, J=3.3 Hz) and 7.66 (d, J=3.2 Hz), total 1H], 7.13-7.31 (m, 5H), [5.39 (ddd, J=11, 8.5, 4 Hz) and 5.53 (ddd, J=12, 9, 4 Hz), total 1H], [4.49 (dd, J=9, 8 Hz) and 4.60 (dd, J=9, 7 Hz), total 1H], 3.16, 3.20, 3.21 and 3.25 (4 s, total 6H), 2.93 and 3.02 (2 br s, total 3H), 1.21 (s, 3H), 1.13 and 1.13 (2 s, total 3H), [1.05 (d, J=6.7 Hz) and 1.10 (d, J=6.7 Hz), total 3H], 0.73-0.80 (m, 3H).

Drug compounds MMAD, MMAE and MMAF were made in-house according to methods disclosed in PCT Publication WO 2013/072813.

Drug compound DM1 was made in-house from purchased maytansinol via procedures outlined in U.S. Pat. No. 5,208,020.

Example 5: Bioconjugation of Trastuzumab-Derived Antibodies

The trastuzumab-derived antibodies of the present invention were conjugated to payload via linkers to generate ADCs. The conjugation method used was either site specific (i.e., via particular cysteine residues or particular glutamine residues) or conventional conjugation.

A. Cysteine Site Specific

The ADCs of Table 8 were conjugated via cysteine site specific methods described below.

TABLE 8

| | |
|---|---|
| T(kK183C)-vc0101 | T(kK183C + K334C)-vc0101 |
| T(K290C)-vc0101 | T(kK183C + K392C)-vc0101 |
| T(K334C)-vc0101 | T(K290C + K334C)-vc0101 |
| T(K392C)-vc0101 | T(K290C + K392C)-vc0101 |
| T(kK183C + K290C)-vc0101 | T(K334C + K392C)-vc0101 |

A 500 mM tris(2-carboxyethyl)phosphine hydrochloride (TCEP) solution (50 to 100 molar equivalents) was added to the antibody (5 mg) such that the final antibody concentration was 5-15 mg/mL in PBS containing 20 mM EDTA. After allowing the reaction to stand at 37° C. for 2.5 hour, the antibody was buffer exchanged into PBS containing 5 mM EDTA using a gel filtration column (PD-10 desalting column, GE Healthcare). The resulting antibody (5-10 mg/mL) in PBS containing 5 mM EDTA was treated with a freshly prepared 50 mM solution of DHA in 1:1 PBS/EtOH (final DHA concentration=1 mM-4 mM) and allowed to stand at 4° C. overnight.

The antibody/DHA mixture was buffer exchanged into PBS containing 5 mM EDTA (pH of the equilibration buffer adjusted to ~7.0 using phosphoric acid) and concentrated using a 50 kD MW cutoff spin concentration device. The resulting antibody in PBS (antibody concentration ~5-10 mg/ml) containing 5 mM EDTA was treated with 5-7 molar equivalents of 10 mM maleimide payload in DMA. After standing for 1.5-2.5 hours, the material was buffer exchanged (PD-10). Purification by SEC was performed (as needed) to remove any aggregated material and remaining free payload.

B. Transglutaminase Site Specific

The ADCs of Table 9 were conjugated via transglutaminase site specific methods described below.

TABLE 9

| |
|---|
| T(N297Q)-AcLysvc0101 |
| T(LCQ05+K222R)-AcLysvc0101 |
| T(N297Q+K222R)-AcLysvc0101 |
| T(N297A+K222R-LCQ05)-AcLysvc0101 |

In the transamidation reaction, the glutamine on the antibody acted as an acyl donor, and the amine-containing compound acted as an acyl acceptor (amine donor). Purified HER2 antibody in the concentration of 33 µM was incubated with a 10-25 M excess acyl acceptor, ranging between 33-83.3 µM AcLysvc-0101, in the presence of 2% (w/v) *Streptoverticillium mobaraense* transglutaminase (ACTIVA™, Ajinomoto, Japan) in 150-mM sodium chloride and Tris HCl buffer at pH range 7.5-8, with 0.31 mM reduced glutathione unless noted. The reaction conditions were adjusted for individual acyl donors, with T(LCQ05+K222R) using 10M excess acyl acceptor at pH 8.0 without reduced glutathione, T(N297Q+K222R) and T(N297Q) using 20M excess acyl acceptor at pH 7.5 and T(N297A+K222R+LCQ05) using 25M excess acyl acceptor at pH 7.5. Following incubation at 37° C. for 16-20 hours, the antibody was purified on MabSelect SuReÔ resin or Butyl Sepharose High Performance (GE Healthcare, Piscataway, N.J.) using standard chromatography methods known to persons skilled in the art, such as commercial affinity chromatography and hydrophobic interaction chromatography from GE Healthcare.

C. Conventional Conjugation

The ADCs of Tables 10 and 11 were conjugated via conventional conjugation methods described below.

TABLE 10

| | |
|---|---|
| T-DM1 | T-mc0101 |
| T-mc8261 | T-vc0101 |
| T-MalPeg8261 | T-vc8261 |
| T-mc6121 | T-vc8254 |
| T-MalPeg6121 | T-vc6780 |
| T-MalPegMMAD | T-vc0131 |
| | T-vcMMAE |

TABLE 11

| |
|---|
| T-m(H20)c8261 |
| T-m(H20)cvc0101 |

The antibody was dialyzed into Dulbecco's Phosphate Buffered Saline (DPBS, Lonza). The dialyzed antibody was diluted to 15 mg/mL with PBS containing 5 mM 2, 2',2'',2'''-(ethane-1, 2-diyldinitrilo)tetraacetic acid (EDTA), pH 7. The resulting antibody was treated with 2-3 equivalents of tris(2-carboxyethyl)phosphine hydrochloride (TCEP, 5 mM in distilled water) and allowed to stand 37° C. for 1-2 hours. Upon cooling to room temperature, dimethylacetamide (DMA) was added to achieve 10% (v/v) total organic. The mixture was treated with 8-10 equivalents of the appropriate linker-payload as a 10 mM stock solution in DMA. The reaction was allowed to stand for 1-2 hours at room temperature and then buffer exchanged into DPBS (pH 7.4) using GE Healthcare Sephadex G-25 M buffer exchange columns per manufacturer's instructions.

Material that was to remain ring-closed (ADCs of Table 10) was purified by size exclusion chromatography (SEC) using GE AKTA Explorer system with GE Superdex200 column and PBS (pH 7.4) eluent. Final samples were concentrated to ~5 mg/mL protein, filter sterilized, and checked for loading using the mass spectroscopy conditions outlined below.

Material used for succinimide ring hydrolysis (ADCs of Table 11) were immediately buffer exchanged into a 50 mM borate buffer (pH 9.2) using an ultrafiltration device (50 kd MW cutoff). The resulting solution was heated to 45° C. for 48 h. The resulting solution was cooled, buffer-exchanged into PBS, and purified by SEC (as described below) in order to remove any aggregated material. Final samples were concentrated to ~5 mg/mL protein and filter sterilized and checked for loading using the mass spectroscopy conditions outlined below.

D. T-DM1 Conjugation

Trastuzumab-maytansinoid conjugate (T-DM1) is structurally similar to trastuzumab emtansine (Kadcyla®). T-DM1 is comprised of the trastuzumab antibody covalently bound to the DM1 maytansinoid through the bifunctional linker sulfosuccinim idyl 4-(N-maleimidomethyl) cyclohexane-1-carboxylate (sulfo-SMCC). Sulfo-SMCC is first conjugated to the free amines on the antibody for one hour at 25° C. in 50 mM potassium phosphate, 2 mM EDTA, pH 6.8, at a 10:1 reaction stoichiometry, and unbound linker is then desalted from the conjugated antibody. This antibody-MCC intermediate is then conjugated to the DM1 sulfide at the free maleimido end on the MCC linker antibody overnight at 25° C. in 50 mM potassium phosphate, 50 mM NaCl, 2 mM EDTA, pH 6.8, at a 10:1 reaction stoichiometry. Remaining unreacted maleimide is then capped with L-cysteine, and the ADC is fractionated through a Superdex200 column to remove non-monomeric species (Chari et al., 1992, Cancer Res 52:127-31).

Example 6: Purification of ADCs

The ADCs were generally purified and characterized using size-exclusion chromatography (SEC) as described below. The loading of the drug onto the intended site of conjugation was determined using a variety of methods including mass spectrometry (MS), reverse phase HPLC, and hydrophobic interaction chromatography (HIC), as more fully described below. The combination of these three analytical methods provides a variety of ways to verify and quantitate the loading of the payload onto the antibody thereby providing an accurate determination of the DAR for each conjugate.

A. Preparative SEC

ADCs were generally purified using SEC chromatography using a Waters Superdex200 10/300GL column on an Akta Explorer FPLC system in order to remove protein aggregate and to remove traces of payload-linker left in the reaction mixture. On occasion, ADCs were free of aggregate and small molecule prior to SEC purification and were therefore not subjected to preparative SEC. The eluent used was PBS at 1 mL/min flow. Under these conditions, aggregated material (eluting at about 10 minutes at room temperature) was easily separated from non-aggregated material (eluting at about 15 minutes at room temperature). Hydrophobic payload-linker combinations frequently resulted in a "right-shift" of the SEC peaks. Without wishing to be bound by any particular theory, this SEC peak shift may be due to hydrophobic interactions of the linker-payload with the stationary phase. In some cases, this right-shift allowed for conjugated protein to be partially resolved from non-conjugated protein.

B. Analytical SEC

Analytical SEC was carried out on an Agilent 1100 HPLC using PBS as eluent to assess the purity and monomeric status of the ADCs. The eluent was monitored at 220 and 280 nM. When the column was a TSKGel G3000SW column (7.8×300 mm, catalog number R874803P), the mobile phase used was PBS with a flow rate of 0.9 mL/min for 30 minutes When the column was a BiosepSEC3000 column (7.8×300 mm), the mobile phase used was PBS with a flow rate of 1.0 mL/min for 25 minutes.

Example 7: Characterization of ADCs

A. Mass Spectroscopy (MS)

Samples were prepped for LCMS analysis by combining approximately 20 μl of sample (approximately 1 mg/ml ADC in PBS) with 20 μl of 20 mM dithiothreitol (DTT). After allowing the mixture to stand at room temperature for 5 minutes, the samples were injected into an Agilent 110 HPLC system fitted with an Agilent Poroshell 300SB-C8 (2.1×75 mm) column. The system temperature was set to 60° C. A 5 minute gradient from 20% to 45% acetonitrile in water (with 0.1% formic acid modifier) was utilized. The eluent was monitored by UV (220 nM) and by a Waters Micromass ZQ mass spectrometer (ESI ionization; cone voltage: 20V; Source temp: 120° C.; Desolvation temp: 350° C.). The crude spectrum containing the multiple-charged species was deconvoluted using MaxEnt1 within MassLynx 4.1 software package according to the manufacturer's instructions.

B. MS Determination of Loading Per Antibody

The total loading of the payload to the antibody to make an ADC is referred to as the Drug Antibody Ratio or DAR. The DAR was calculated for each of the ADCs made (Table 12).

The spectra for the entire elution window (usually 5 minutes) were combined into a single summed spectrum (i.e., a mass spectrum that represents the MS of the entire sample). MS results for ADC samples were compared directly to the corresponding MS of the identical non-loaded control antibody. This allowed for the identification of loaded/nonloaded heavy chain (HC) peaks and loaded/non-loaded light chain (LC) peaks. The ratio of the various peaks can be used to establish loading based on the equation below (Equation 1). Calculations are based on the assumption that loaded and non-loaded chains ionize equally which has been determined to be a generally valid assumption.

The following calculation was performed in order to establish the DAR:

$$\text{Loading}=2*[LC1/(LC1+LC0)]+2*[HC1/(HC0+HC1+HC2)]+4*[HC2/(HC0+HC1+HC2)] \quad \text{Equation 1:}$$

Where the indicated variables are the relative abundance of: LC0=unloaded light chain, LC1=single loaded light chain, HC0=unloaded heavy chain, HC1=single loaded heavy chain, and HC2=double loaded heavy chain. One of ordinary skill in the art would appreciate that the invention encompasses expansion of this calculation to encompass higher loaded species such as LC2, LC3, HC3, HC4, HC5, and the like.

Equation 2, below, is used to estimate the amount of loading onto non-engineered cysteine residues. For engineered Fc mutants, loading onto the light chain (LC) was considered, by definition, to be nonspecific loading. Moreover, it was assumed that loading only the LC was the result of inadvertent reduction of the HC-LC disulfide bridge (i.e., the antibody was "over-reduced"). Given that a large excess of maleimide electrophile was used for the conjugation reactions (generally approximately 5 equivalents for single mutants and 10 equivalents for double mutants), it was assumed that any nonspecific loading onto the light chain was accompanied by a corresponding amount of non-specific loading onto the heavy chain (i.e., the other "half" of the broken HC-LC disulfide). With these assumptions in mind, the following equation (Equation 2) was used to estimate the amount of non-specific loading onto the protein:

$$\text{Nonspecific loading}=4*[LC1/(LC1+LC0)] \quad \text{Equation 2:}$$

Where the indicated variables are the relative abundance of: LC0=unloaded light chain, LC1=single loaded light chain.

TABLE 12

| Drug Antibody Ratio (DAR) of ADCs | |
|---|---|
| ADC | DAR |
| T(kK183C)-vc0101 | 2 |
| T(K290C)-vc0101 | 2 |
| T(K334C)-vc0101 | 2 |
| T(K392C)-vc0101 | 2 |
| T(kK183C+K290C)-vc0101 | 4 |
| T(kK183C+K334C)-vc0101 | 4 |
| T(kK183C+K392C)-vc0101 | 4 |
| T(K290C+K334C)-vc0101 | 4 |
| T(K290C+K392C)-vc0101 | 4 |
| T(K334C+K392C)-vc0101 | 4 |
| T(N297Q)-AcLysvc0101 | 4 |
| T(N297Q+K222R)-AcLysvc0101 | 4 |
| T(N297A+K222R+LCQ05)-AcLysvc0101 | 4 |
| T(LCQ05+K222R)-AcLysvc0101 | 2 |
| T-mc8261 | 4.2 |
| T-m(H20)c8261 | 3.6 |
| T-MalPeg8261 | 3.1 |
| T-vc8261 | 4.3 |
| T-mc6121 | 3.5 |
| T-MalPeg6121 | 3.6 |
| T-mc0101 | 4.8 |
| T-vc0101 | 4.2 |
| T-vc8254 | 4 |
| T-vc6780 | 4.2 |
| T-vc0131 | 4.5 |
| T-MalPegMMAD | 4.4 |
| T-vcMMAE | 3.8 |
| T-DM1 | 4.2 |

C. Proteolysis with FabRICATOR® to Establish the Site of Loading

For the cysteine mutant ADCs, any nonspecific loading of the electrophillic payload onto the antibody is presumed to occur at the “interchain” also referred to as the “internal” cysteine residues (i.e., those that are typically part of the HC-HC or HC-LC disulfide bridges). In order to distinguish loading of electrophile onto the engineered cysteines in the Fc domain versus loading onto the internal cysteine residues (otherwise typically forming the S—S bonds between HC-HC or HC-LC), the conjugates were treated with a protease known to cleave between the Fab domains and the Fc domain of the antibody. One such protease is the cysteine protease IdeS, marketed as “FabRICATOR®” by Genovis, and described in von Pawel-Rammingen et al., 2002, EMBO J. 21:1607.

Briefly, following the manufacturer’s suggested conditions, the ADC was treated with FabRICATOR® protease and the sample was incubated at 37° C. for 30 minutes. Samples were prepped for LCMS analysis by combining approximately 20 μl of sample (approximately 1 mg/mL in PBS) with 20 μl of 20 mM dithiothreitol (DTT) and allowing the mixture to stand at room temperature for 5 minutes. This treatment of human IgG1 resulted in three antibody fragments, all ranging from about 23 to 26 kD in size: the LC fragment comprising an internal cysteine which typically forms an LC-HC interchain disulfide bond; the N-terminal HC fragment comprising three internal cysteines (where one typically forms an LC-HC disulfide bond and the other two cysteines found in the hinge region of the antibody and which typically form HC-HC disulfide bonds between the two heavy chains of the antibody); and the C-terminal HC fragment which contains no reactive cysteines other than those introduced by mutation in the constructs disclosed herein. The samples were analyzed by MS as described above. Loading calculations were performed in the same manner as previously described (above) in order to quantitate the loading of the LC, the N-terminal HC, and the C-terminal HC. Loading on the C-terminal HC is considered “specific” loading while loading onto the LC and the N-terminal HC is considered “nonspecific” loading.

To cross-check the loading calculations, a subset of ADCs were also assessed for loading using alternative methods (reverse phase high performance liquid chromatography [rpHPLC]-based and hydrophobic interaction chromatography [HIC]-based methods) as more fully described in the sections below.

D. Reverse Phase HPLC Analysis

Samples were prepped for reverse-phase HPLC analysis by combining approximately 20 μl of sample (approximately 1 mg/mL in PBS) with 20 μl of 20 mM dithiothreitol (DTT). After allowing the mixture to stand at room temperature for 5 minutes, the samples were injected into an Agilent 1100 HPLC system fitted with an Agilent Poroshell 300SB-C8 (2.1×75 mm) column. The system temperature was set to 60° C. and the eluent was monitored by UV (220 nM and 280 nM). A 20-minute gradient from 20% to 45% acetonitrile in water (with 0.1% TFA modifier) was utilized: T=0 min: 25% acetonitrile; T=2 min: 25% acetonitrile; T=19 min: 45% acetonitrile; and T=20 min: 25% acetonitrile. Using these conditions, the HC and LC of the antibody were baseline separated. The results of this analysis indicate that the LC remains largely unmodified (except for T(kK183C) and T(LCQ05) containing antibodies) while the HC is modified (data not shown).

E. Hydrophobic Interaction Chromatography (HIC)

Compounds were prepared for HIC analysis by diluting samples to approximately 1 mg/ml with PBS. The samples were analyzed by auto-injection of 15 μl onto an Agilent 1200 HPLC with a TSK-GEL Butyl NPR column (4.6×3.5 mm, 2.5 μm pore size; Tosoh Biosciences part #14947). The system includes an auto-sampler with a thermostat, a column heater and a UV detector.

The gradient method was used as follows:

Mobile phase A: 1.5M ammonium sulfate, 50 mM potassium phosphate dibasic (pH7); Mobile phase B: 20% isopropyl alcohol, 50 mM potassium phosphate dibasic (pH 7); T=0 min. 100% A; T=12 min., 0% A.

Retention times are shown in Table 13. Selected spectra are shown in FIGS. 2A-2E. ADCs using site-specific conjugation (T(kK183C+K290C)-vc0101, T(K334C+K392C)-vc0101 and T(LCQ05+K222R)-AcLysvc0101) (FIGS. 1A-1C) showed primarily one peak while ADCs using conventional conjugation (T-vc0101 and T-DM1) (FIGS. 2D-2E) showed a mixture of differentially loaded conjugates.

TABLE 13

| ADC retention times by hydrophobic interaction chromatography (HIC) | | |
|---|---|---|
| ADC | RT (min) | RRT |
| T-vc0101 | 8.8 ± 0.1 | 1.68 |
| T(kK183C)-vc0101 | 7.2 ± 0.1 | 1.40 |
| T(K334C)-vc0101 | ND | |
| T(K392C)-vc0101 | 6.7 ± 0.1 | 1.29 |
| T(L443C)-vc0101 | 10.1 ± 0.1 | 1.98 |
| T(kK183C+K290C)-vc0101 | 9.0 ± 0.0 | 1.77 |
| T(kK183C+K334C)-vc0101 | ND | |
| T(kK183C+K392C)-vc0101 | 7.7 ± 0.1 | 1.54 |
| T(kK183C+L443C)-vc0101 | 10.6 | 2.04 |
| T(K290C+K334C)-vc0101 | 6.3 ± 0.0 | 1.21 |

TABLE 13-continued

ADC retention times by hydrophobic interaction chromatography (HIC)

| ADC | RT (min) | RRT |
|---|---|---|
| T(K290C+K392C)-vc0101 | 7.8 ± 0.0 | 1.54 |
| T(K334C+K392C)-vc0101 | 6.0 ± 0.3 | 1.18 |
| T(K392C+L443C)-vc0101 | 10.8 ± 0.0 | 2.08 |
| T(LCQ05+K222R)- AcLys-vc0101 | 6.5 | 1.27 |
| T(N297A+K222R+LCQ05)-AcLys-vc0101 | 6.3 ± 0.1 | 1.24 |

ND = not determined
RT = retention time (min) on HIC
RRT = mean relative retention time, calculated by RT of ADC divided by RT of benchmark unconjugated wild type trastuzumab having a typical retention time of 5.0-5.2 min

TABLE 14

Thermal Stability of Engineered Trastuzumab Derived Variants

| Antibody | Tm1 (° C.) | Tm2 (° C.) | Tm3 (° C.) |
|---|---|---|---|
| T(κK183C) | 72.17 ± 0.029 | 80.78 ± 0.37 | 82.81 ± 0.055 |
| T(L443C) | 72.02 ± 0.06 | 80.98 ± 1.10 | 82.96 ± 0.11 |
| T(LCQ05) | 72.22 ± 0.027 | 81.16 ± 0.19 | 82.88 ± 0.033 |
| T(κK183C+K290C) | 75.4 | 81.1 | 82.9 |
| T(κK183C+K392C) | 75 | 81 | 83 |
| T(κK183C+L443C) | 72.24 ± 0.05 | 80.89 ± 0.89 | 82.87 ± 0.16 |
| T(K290C+K334C) | 75.0 ± 0.14 | 83.0 ± 0.1 | 81.1 ± 0.4 |
| T(K334C+K392C) | 75.3 ± 0.25 | 82.7 ± 0.53 | 81.0 ± 2.9 |
| T(K290C+K392C) | 77 | 81 | 83 |
| T(K392C+L443C) | 73.95 ± 0.29 | 80.54 ± 0.70 | 82.81 ± 0.17 |

TABLE 15

Thermal Stability of Site-Specific Conjugates Conjugated to Auristatin 0101

| Site-Specific Conjugate | Tm1 (° C.) | Tm2 (° C.) | Tm3 (° C.) | $Tm1_{SSC}$ − $Tm1_{Ab}$ |
|---|---|---|---|---|
| T(κK183C)-vc0101 | 70.16 ± 0.03 | 80.45 ± 0.12 | 82.04 ± 0.03 | −2.01 |
| T(L443C)-vc0101 | 72.34 ± 0.10 | 80.20 ± 0.59 | 82.44 ± 0.10 | 0.32 |
| T(κK183C+L443C)-vc0101 | 70.11 ± 0.02 | 78.89 ± 0.59 | 81.38 ± 0.10 | −2.13 |
| T(K392C+L443C)-vc0101 | 69.60 ± 0.35 | 79.21 ± 0.43 | 82.10 ± 0.05 | −4.35 |

F. Thermostability

Differential Scanning calorimetry (DCS) was used to determine the thermal stability of the engineered cysteine and transglutaminase antibody variants, and corresponding Aur-06380101 site-specific conjugates. For this analysis, samples formulated in PBS-CMF pH 7.2 were dispensed into the sample tray of a MicroCal VP-Capillary DSC with Autosampler (GE Healthcare Bio-Sciences, Piscataway, N.J.), equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, Mass.) was used to fit the data to an MN2-State Model with an appropriate number of transitions.

All single and double cysteine engineered antibody variants as well as the engineered LCQ05 acyl donor glutamine-containing tag antibody exhibited excellent thermal stability as determined by the first melting transition (Tm1)>65° C. (Table 14).

Trastuzumab derived monoclonal antibodies conjugated to 0101 using site specific conjugation methods were also evaluated and shown to have exceptional thermal stability as well (Table 15). However, the Tm1 for T(K392C+L443C)-vc0101 ADC was most impacted by conjugation of the payload since it was −4.35° C. relative to the unconjugated antibody.

Taken together these results demonstrated that both the engineered cysteine and acyl donor glutamine-containing tag antibody variants were thermally stable and that site-specific conjugation of 0101 via a vc linker yielded conjugates with excellent thermal stability. Furthermore, the lower thermal stability observed for T(K392C+L443C)-vc0101 relative to the unconjugated antibody indicated that conjugation of 0101 via a vc linker to certain combinations of engineered cysteine residues can impact stability of the ADC.

Example 8: ADC Binding to HER2

A. Direct Binding

BT474 cells (HTB-20) were trypsinized, spun down and re-suspended in fresh media. The cells were then incubated with a serial of dilutions of either the ADCs or unconjugated trastuzumab with starting concentration of 1 μg/ml for one hour at 4° C. The cells were then washed twice with ice cold PBS and incubated with anti-human Alexafluor 488 secondary antibody (Cat # A-11013, Life technologies) for 30 min. The cells were then washed twice and then re-suspended in PBS. The mean fluorescence intensity was read using Accuri flow cytometer (BD Biosciences San Jose, Calif.).

TABLE 16

ADC binding to HER2

| ADC/Ab | $EC_{50}$ |
|---|---|
| trastuzumab | 0.37 |
| T(kK183C+K392C)-vc0101 | 0.56 |
| T(kK183C+K290C)-vc0101 | 0.47 |
| T(K290C+K392C)-vc0101 | 0.32 |
| T-DM1 (Kadcyla) | 0.40 |
| T(LCQ05+K222R)-AcLysvc0101 | 0.37 |
| T(N297Q+K222R)-AcLysvc0101 | 0.36 |

EC50 = the concentration of an antibody or ADC that gives half-maximal binding.

Figure 3A:
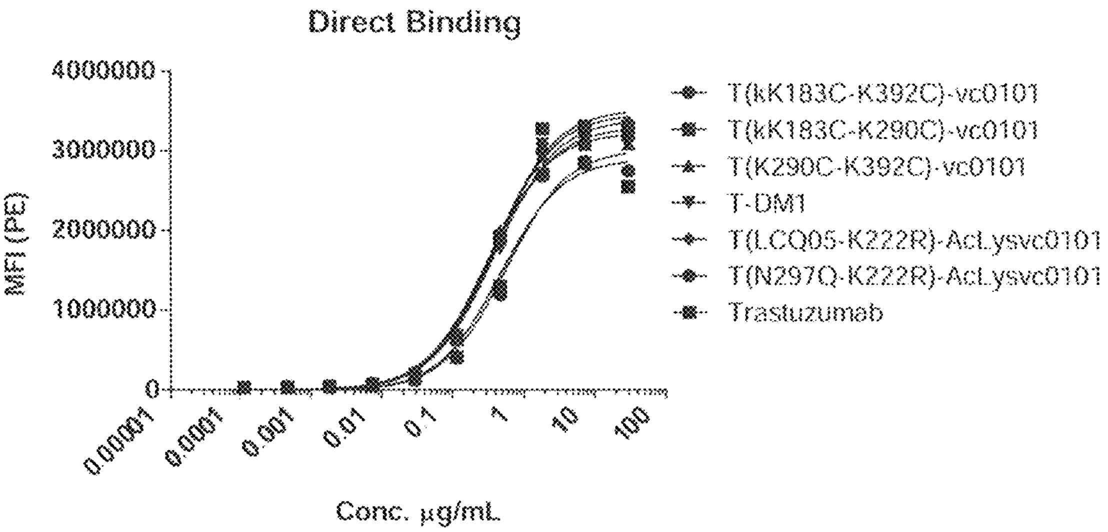
FIGS. 3A-3B depict graphs of ADCs binding to HER2. (A) direct binding to HER2 positive BT474 cells and (B) competitive binding with PE labelled trastuzumab to BT474 cells. These results indicate that the binding properties of antibody in these ADCs were unaltered by the conjugation process.

As shown in FIG. 3A and Table 16, ADCs T(LCQ05+K222R)-AcLysvc0101, T(N297Q+K222R)-AcLysvc0101, T(kK183C+K290C)-vc0101, T(kK183C+K392C)-vc0101, T(K290C+K392C)-vc0101 had similar binding affinities as T-DM1 and trastuzumab by direct binding. This indicates that the modifications to the antibody in the ADCs of the present invention and the addition of the linker-payload did not significantly affect binding.

B. Competitive Binding by FACS

BT474 cells were trypsinized, spun down and re-suspended in fresh media. The cells were then incubated for one hour at 4° C. with serial dilutions of either the ADCs or the unconjugated trastuzumab combined with 1 μg/mL of trastuzumab-PE (custom synthesized 1:1 PE labeled trastuzumab by eBiosciences (San Diego, Calif.)). The cells were then washed twice and then re-suspended in PBS. The mean fluorescence intensity was read using Accuri flow cytometer (BD Biosciences San Jose, Calif.).

Figure 3B:
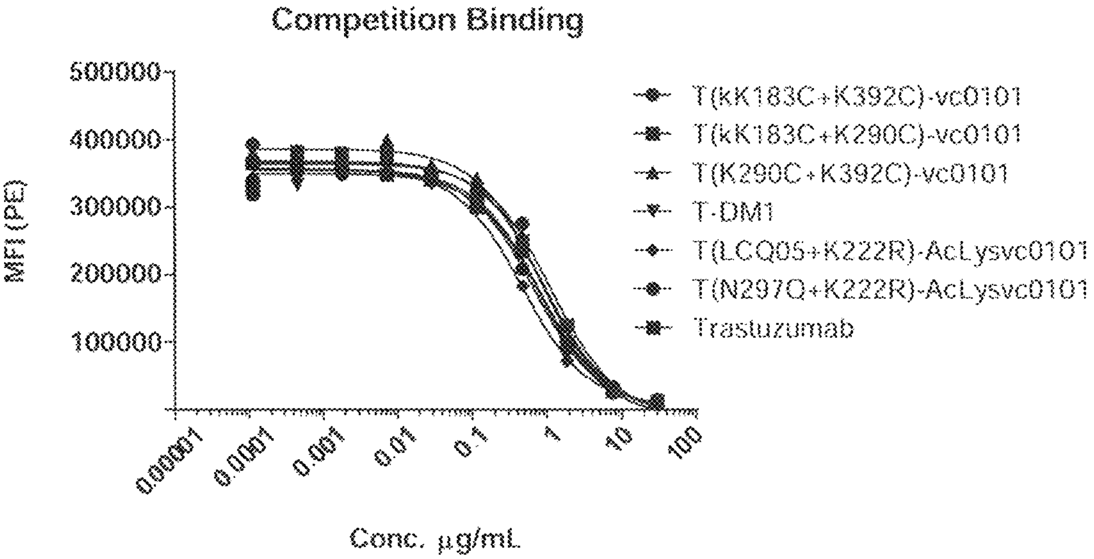

As shown in FIG. 3B, ADCs T(LCQ05+K222R)-AcLysvc0101, T(N297Q+K222R)-AcLysvc0101, T(kK183C+K290C)-vc0101, T(kK183C+K392C)-vc0101, T(K290C+K392C)-vc0101 had similar binding affinities as T-DM1 and trastuzumab by competition binding to PE labeled trastuzumab. This indicates that the modifications to the antibody in the ADCs of the present invention and the addition of the linker-payload did not significantly affect binding.

Example 9: ADC Binding to Human FcRn

It is believed in the art that FcRn interacts with IgG regardless of subtype in a pH dependent manner and protects the antibody from degradation by preventing it from entering the lysosomal compartment where it is degraded. Therefore, a consideration for selecting positions for introduction of reactive cysteines into the wild type IgG1-Fc region was to avoid altering the FcRn binding properties and half-life of the antibody comprising the engineered cysteine.

BIAcore® analysis was performed to determine the steady-state affinity (KD) for the trastuzumab derived monoclonal antibodies and their respective ADCs for binding to human FcRn. BIAcore® technology utilizes changes in the refractive index at the surface layer of a sensor upon binding of the trastuzumab derived monoclonal antibodies or their respective ADCs to human FcRn protein immobilized on the layer. Binding was detected by surface plasmon resonance (SPR) of laser light refracting from the surface. Human FcRn was specifically biotinylated through an engineered Avi-tag using the BirA reagent (Catalog #: BIRA500, Avidity, LLC, Aurora, Colo.) and immobilized onto a streptavidin (SA) sensor chip to enable uniform orientation of the FcRn protein on the sensor. Next, various concentrations of the trastuzumab derived monoclonal antibodies or their respective ADCs or in 20 mM MES (2-(N-morpholino)ethanesulfonic acid pH 6.0, with 150 mM NaCl, 3 mM EDTA (ethylenediaminetetraacetic acid), 0.5% Surfactant P20 (MES-EP) were injected over the chip surface. The surface was regenerated using HBS-EP+0.05% Surfactant P20 (GE Healthcare, Piscataway, N.J.), pH 7.4, between injection cycles. The steady-state binding affinities were determined for the trastuzumab derived monoclonal antibodies or their respective ADCs, and these were compared with the wild type trastuzumab antibody (comprising no cysteine mutations in the IgG1 Fc region, no TGase engineered tag or site-specific conjugation of a payload).

These data demonstrated that incorporation of engineered cysteine residues into the IgG-Fc region at the indicated positions of the invention did not alter affinity to FcRn (Table 17).

TABLE 17

Steady-State Affinities of Site-Specific Conjugates Binding Human FcRn

| | KD [nM] Experiment 1 | KD [nM] Experiment 2 | KD [nM] Experiment 3 |
|---|---|---|---|
| Trastuzumab WT | 1050.0 | 705.8 | 859.2 |
| T-DM1 | ND | 500.8 | ND |
| T(K290C+K334C) | 987.0 | ND | ND |
| T(K290C+K334C)-vc0101 | 1218.0 | ND | ND |
| T(K334C+K392C) | 834.1 | ND | ND |
| T(K334C+K392C)-vc0101 | 1404.0 | ND | ND |
| T(κK183C+K290C) | 1173.0 | ND | ND |
| T(κK183C+K290C)-vc0101 | 473.8 | ND | ND |
| T(κK183C+K392C) | 1009.0 | ND | ND |
| T(κK183C+K392C)-vc0101 | 672.5 | ND | ND |
| T(κK183C)-vc0101 | 961.5 | ND | ND |
| T(LCQ05) | 900.9 | ND | ND |
| T(LCQ05)-vc0101 | 1050.0 | ND | ND |
| T(K392C) | ND | 468.3 | ND |
| T(K392C)-vc0101 | ND | 518.8 | ND |
| T(N297Q)-vc0101 | ND | 647.9 | ND |
| T(κK183C+K334C)-vc0101 | ND | 416.5 | ND |
| T(κK183C+K443C) | ND | 542.8 | ND |
| T(κK183C+K443C)-vc0101 | ND | 287.5 | ND |
| T(K290C) | ND | ND | 650.3 |
| T(K290C)-vc0101 | ND | ND | 874.6 |
| T(K290C+K392C)-vc0101 | ND | ND | 554.7 |
| T(K334C) | ND | ND | 631.6 |
| T(K334C)-vc0101 | ND | ND | 791.2 |
| T(K392C+K443C) | ND | ND | 601.7 |
| T(K392C+K443C)-vc0101 | ND | ND | 197.9 |

ND = Not Determined

Example 10: ADC Binding to Fcγ Receptors

Binding of the ADCs using site-specific conjugation to human Fc-γ receptors was evaluated in order to understand if conjugation to a payload alters binding which can impact antibody related functionality properties such as antibody-dependent cell-mediated cytotoxicity (ADCC). FcγIIIa (CD16) is expressed on NK cells and macrophages, and co-engagement of this receptor with the target expressing cells via antibody binding induces ADCC. BIAcore® analysis was used to examine binding of the trastuzumab derived monoclonal antibodies and their respective ADCs to Fc-γ receptors IIa (CD32a), IIb (CD32b), IIIa (CD16) and FcγRI (CD64).

For this surface plasmon resonance (SPR) assay, recombinant human epidermal growth factor receptor 2 (Her2/neu) extra-cellular domain protein (Sino Biological Inc., Beijing, P.R. China) was immobilized on a CM5 chip (GE Healthcare, Piscataway, N.J.) and ~300-400 response units (RU) of either a trastuzumab derived monoclonal antibody or its respective ADC was captured. The T-DM1 was included in this evaluation as a positive control since it has been shown to retain binding properties post-conjugation to Fcγ receptors comparable to the unconjugated trastuzumab antibody. Next, various concentrations of the Fcγ receptors FcγIIa (CD32a), FcγIIb(CD32b), FcγIIIa (CD16a) and FcγRI (CD64) were injected over the surface and binding was determined.

FcγRs IIa, IIb and IIIa exhibited rapid on/off rates and therefore the sensorgrams were fit to steady state model to obtain Kd values. FcγRI exhibited slower on/off rates so data was fit to a kinetic model to obtain Kd values.

Conjugation of payload at the engineered cysteine positions 290 and 334 showed a moderate loss in FcγR affinity, specifically to CD16a, CD32a and CD64 compared to their unconjugated counterpart antibodies and T-DM1 (Table 18). However, simultaneous conjugation at sites 290, 334 and 392 resulted in a substantial loss of affinity to CD16a, CD32a and CD32b, but not CD64 as observed with the T(K290C+K334C)-vc0101 and T(K334C+K392C)-vc0101 (Table 18). Interestingly, T(κK183C+K290C)-vc0101 exhibited comparable binding to all FcγR evaluated in this study despite harboring drug payload on the K290C position (Table 18). As expected the transglutaminase mediated conjugated T(N297Q+K222R)-AcLysvc0101 did not bind to any of the Fcγ receptors evaluated since location of the acyl donor glutamine-containing tag removes N-linked glycosylation. Contrary, T(LCQ05+K222R)-AcLysvc0101 retained full binding to the Fcγ receptors as the glutamine-containing tag is engineered within the human Kappa light chain constant region.

Taken together, these results suggested that location of the conjugated payload can impact binding of the ADC to FcγR and may impact the antibody functionality of the conjugate.

TABLE 18

Binding Affinity of Site-Specific Conjugates for Fcγ Receptors binding to the CD16a, CD32a, CD32b and CD64

| | $K_D$ [M] | | | |
|---|---|---|---|---|
| | FcγRIIIa (CD16a) [μM] | FcγRIIa (CD32a) [μM] | FcγRIIb (CD32b) [μM] | FcγRI (CD64) [pM] |
| Trastuzumab WT mAb | 0.36 | 0.74 | 4.08 | 23 |
| T-DM1 ADC | 0.30 | 0.53 | 2.97 | 27 |
| T(K290C)-vc0101 | 1.20 | 1.70 | 3.74 | 185 |
| T(K334C)-vc0101 | 0.81 | 1.42 | 4.74 | ND |
| T(K290C+K334C)-vc0101 | 5.14 | 6.30 | 6.38 | 110 |
| T(K334C+K392C)-vc0101 | 2.38 | 4.18 | 11.30 | 43 |
| T(K392C)-vc0101 | 0.45 | 0.73 | 4.33 | ND |
| T(KK183C+K290C)-0101 | 0.47 | 0.70 | 3.63 | 37 |
| T(LCQ05+K222R)-AcLysvc0101 | 0.43 | 0.62 | 3.41 | 32 |
| T(N297Q-K222R)-AcLysvc0101 | NB | NB | NB | NB |

ND = Not Determined,
NB = No Binding

Example 11: ADCC Activities

In ADCC assays, Her2-expressing cell lines BT474 and SKBR3 were used as target cells while NK-92 cells (an interleukin-2 dependent natural killer cell line derived from peripheral blood mononuclear cells from a 50 year old Caucasian male by Conkwest) or human peripheral blood mononucleocytes (PBMC) isolated from the freshly drawn blood from a healthy donor (#179) were used as effector cells.

Target cells (BT474 or SKBR3) of $1\times10^4$ cells/100 μl/well were placed in 96-well plate and cultured overnight in RPMI1640 media at 37° C./5% $CO_2$. The next day, the media was removed and replaced with 60 μl assay buffer (RPMI1640 media containing 10 mM HEPES), 20 μl of 1 μg/ml antibody or ADC, followed by addition of 20 μl $1\times10^5$ (for SKBR3) or $5\times10^5$ (for BT474) PBMC suspension or $2.5\times10^5$ NK92 cells for both cell lines to each well to achieve effector to target ratio of 50:1 for BT474 or of 25:1 for SKBR3 for PBMC, 10:1 for NK92. All samples were run in triplicate.

Assay plates were incubated at 37° C./5% $CO_2$ for 6 hours and then equilibrated to room temperature. LDH release from cell lysis was measured using CytoTox-One™ reagent at an excitation wavelength of 560 nm and an emission wavelength of 590 nm. As a positive control, 8 μL of Triton was added to generate a maximum LDH release in control wells. The specific cytotoxicity shown in FIG. 4 was calculated using the following formula:

$$\%\ \text{Specific Cytotoxicity} = \frac{\text{Experimental} - \text{effector spontaneous} - \text{target spontaneous}}{\text{Target maximum} - \text{Target spontaneous}} \times 100$$

"Experimental" corresponds to the signal measured in one of the condition described above.

"Effector spontaneous" corresponds to the signal measured in the presence of PBMC alone.

"Target spontaneous" corresponds to the signal measured in the presence of target cells alone.

"Target Maximum" corresponds to the signal measured in the presence of detergent-lysed target cells alone.

Figure 4:
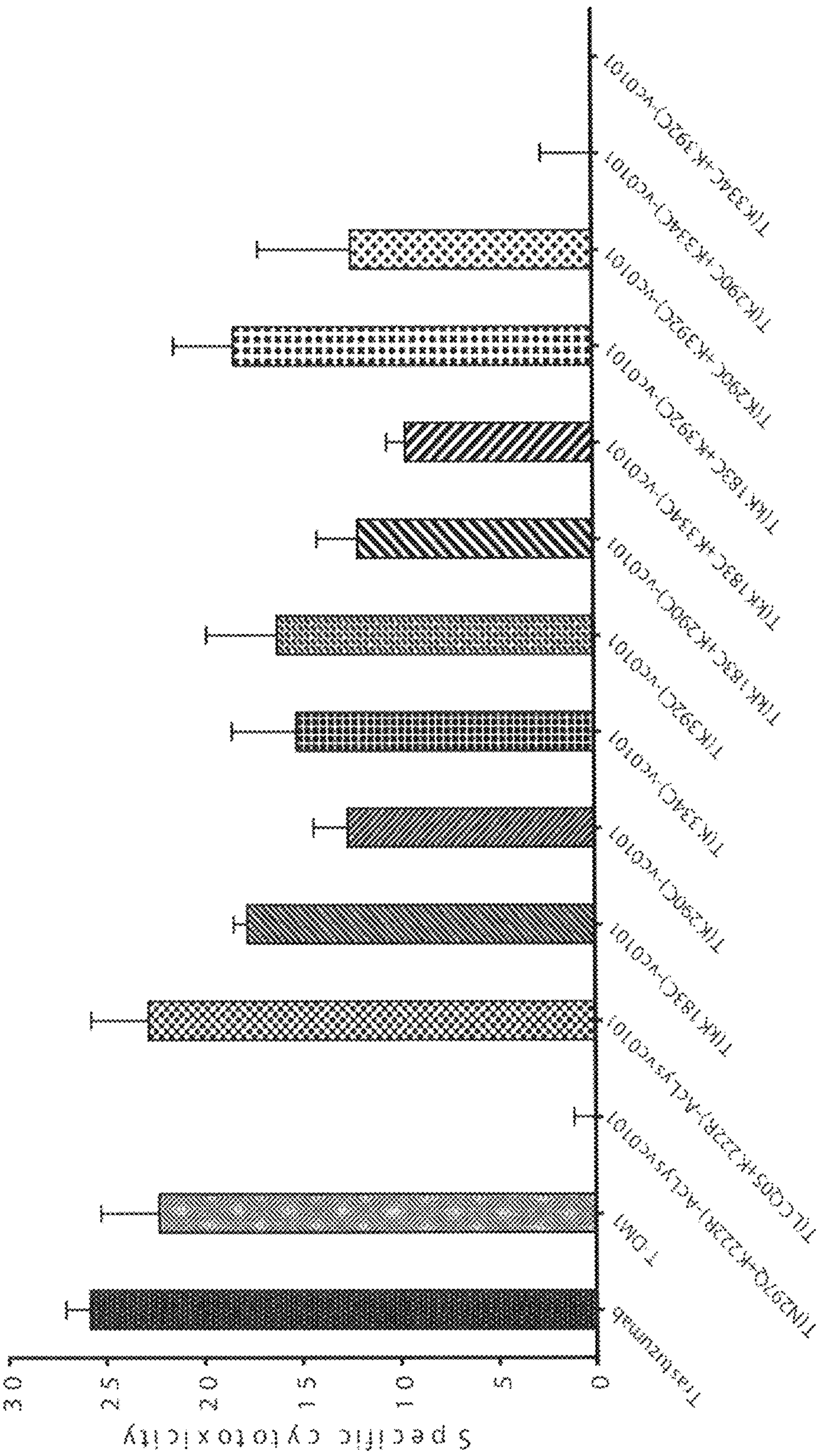
FIG. 4 depicts ADCC activities of trastuzumab derived ADCs.

FIG. 4 shows the ADCC activities tested for trastuzumab, T-DM1 and vc0101 ADC conjugates. The data conform the reported ADCC activities of Trastuzumab and T-DM1. Since the mutation of N297Q is at the glycosylation site, T(N297Q+K222R)-AcLysvc0101 was not expected to have ADCC activities which was also confirmed in the assays. For single mutant (K183C, K290C, K334C, K392C including LCQ05) ADCs, ADCC activities were maintained. Surprisingly, for double mutant (K183C+K290C, K183C+K392C, K183C+K334C K290C+K392C, K290C+K334C, K334C+K392C) ADCs, ADCC activities were maintained in all except two double mutant ADCs associated with K334C site (K290C+K334C and K334C+K392C).

Example 12: In Vitro Cytotoxicity Assays

Antibody-drug conjugates were prepared as indicated in Example 3. Cells were seeded in 96-well plates at low density, then treated the following day with ADCs and unconjugated payloads at 3-fold serial dilutions at 10 concentrations in duplicate. Cells were incubated for 4 days in a humidified 37° C./5% $CO_2$ incubator. The plates were harvested by incubating with CellTiter® 96 AQueous One MTS Solution (Promega, Madison, Wis.) for 1.5 hours and absorbance measured on a Victor plate reader (Perkin-Elmer, Waltham, Mass.) at wavelength 490 nm. $IC_{50}$ values were calculated using a four-parameter logistic model with XLfit (IDBS, Bridgewater, N.J.) and reported as nM payload concentration in FIG. 5 and ng/ml antibody concentration in FIG. 6. The $IC_{50}$ are shown +/−the standard deviation with the number of independent determinations in parenthesis.

The ADCs containing vc-0101 or AcLysv-0101 linker-payloads were highly potent against Her2-positive cell models and selective against Her2-negative cells, compared with the benchmark ADC, T-DM1 (Kadcyla).

ADCs synthesized with site-specific conjugation to trastuzumab showed high level potency and selectivity against Her2 cell models. Notably, several trastuzumab-vc0101 ADCs are more potent than T-DM1 in moderate or low Her2-expressing cell models. For example, the in vitro cytotoxicity $IC_{50}$ for T(kK183C+K290C)-vc0101 in MDA-MB-175-VII cells (with 1+ Her2 expression) is 351 ng/ml, compared with 3626 ng/ml for T-DM1 (~10-fold lower). For cells with 2++ level Her2 expression such as MDA-MB- 361-DYT2 and MDA-MB-453 cells, the $IC_{50}$ for T(kK183C+K290C)-vc0101 is 12-20 ng/ml, compared with 38-40 ng/ml for T-DM1.

Example 13: Xenograft Models

Trastuzumab derived ADCs of the invention tested in an N87 gastric cancer xenograft model, 37622 lung cancer xenograft model, and a number of breast cancer xenograft models (i.e., HCC 1954, JIMT-1, MDA-MB-361(DYT2) and 144580 (PDX) models). For each model described below the first dose was given on Day 1. The tumors were measured at least once a week and their volume was calculated with the formula: tumor volume ($mm^3$)=0.5×(tumor width$^2$)(tumor length). The mean tumor volumes (±S.E.M.) for each treatment group were calculated having a maximum of 8-10 animals and a minimum of 6-8 animals to be included.

A. N87 Gastric Xenografts

The effects of Trastuzumab derived ADCs were examined in immunodeficient mice on the in vivo growth of human tumor xenografts that were established from the N87 cell line (ATCC CRL-5822) which has high level HER2 expression. To generate xenografts, nude (Nu/Nu, Charles River Lab, Wilmington, Mass.) female mice were implanted subcutaneously with 7.5×10$^6$ N87 cells in 50% Matrigel (BD Biosciences). When the tumors reached a volume of 250 to 450 $mm^3$, the tumors were staged to ensure uniformity of the tumor mass among various treatment groups. The N87 gastric model was dosed 4 times intravenously 4 days apart (Q4dx4) with PBS vehicle, Trastuzumab ADCs (at 0.3, 1 and 3 mg/kg) or T-DM1 (1, 3 and 10 mg/kg) (FIG. 7).

The data demonstrates that Trastuzumab derived ADCs inhibited growth of N87 gastric xenografts in a dose-dependent manner (FIGS. 7A-7H).

Figure 7A:
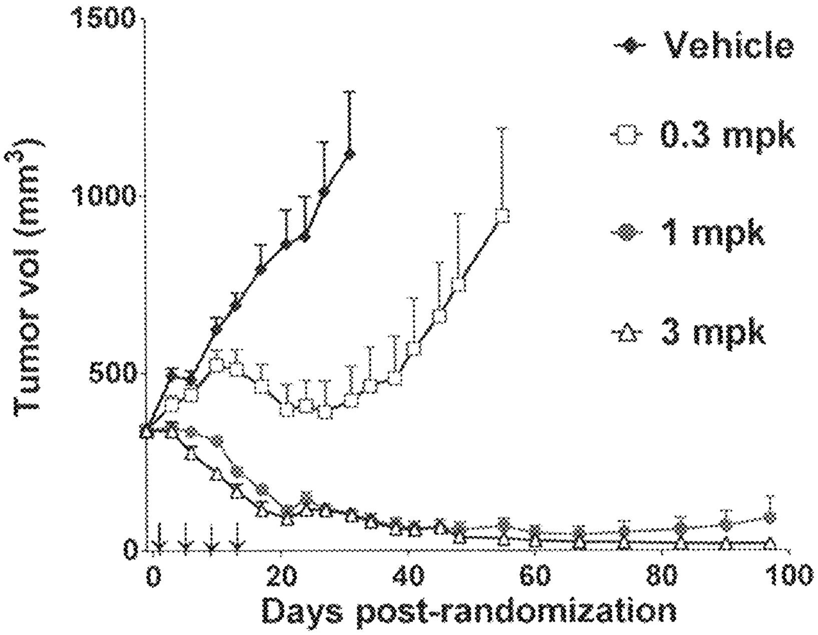
FIGS. 7A-7I depict anti-tumor activity of nine trastuzumab derived ADCs on N87 xenografts with tumor volume was plotted over time. (A) T(kK183C+K290C)-vc0101; (B) T(kK183C)-vc0101; (C) T(K290C)-vc0101; (D) T(LCQ05+K222R)-AcLysvc0101; (E) T(K290C+K334C)-vc0101; (F) T(K334C+K392C)-vc0101; (G) T(N297Q+K222R)-AcLysvc0101; (H) T-vc0101; (I) T-DM1. N87 gastric cancer cells express high levels of HER2.
Figure 7B:
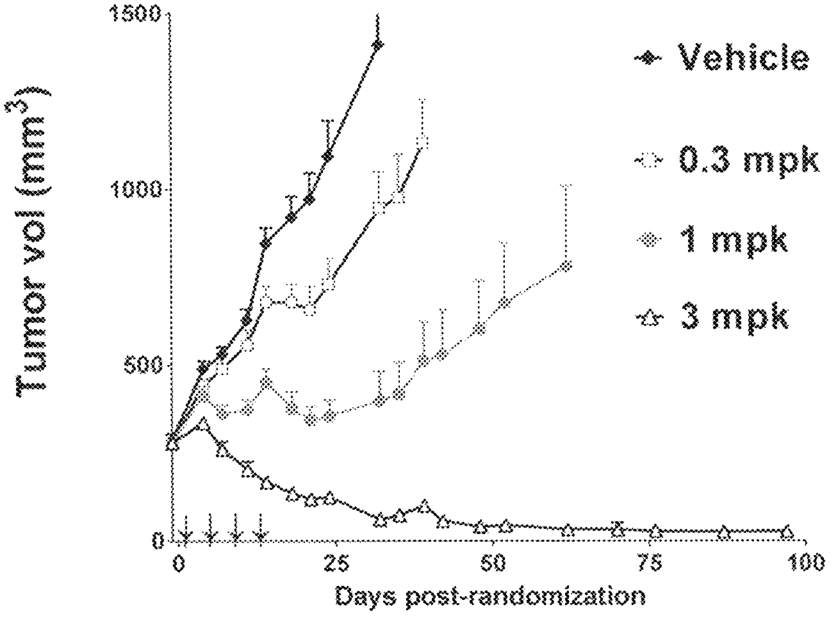
Figure 7C:
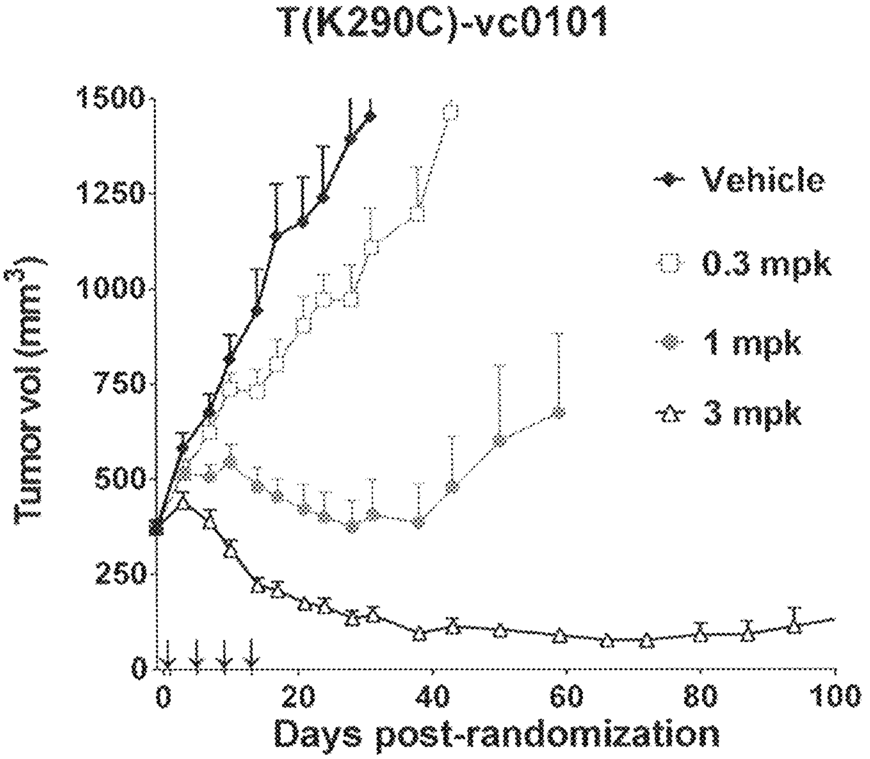
Figure 7D:
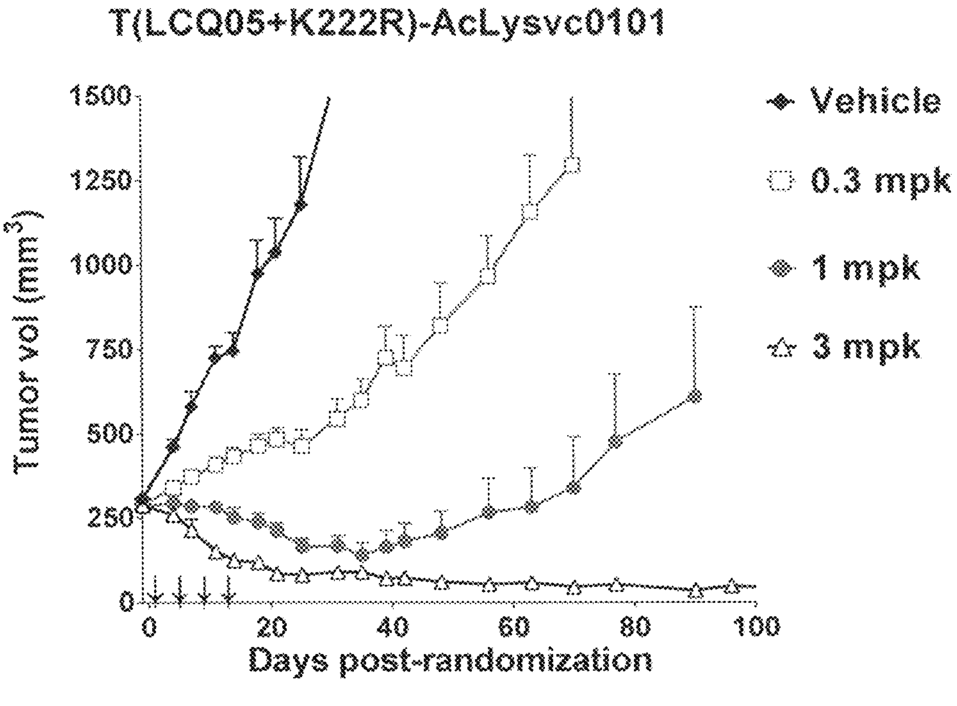
Figure 7E:
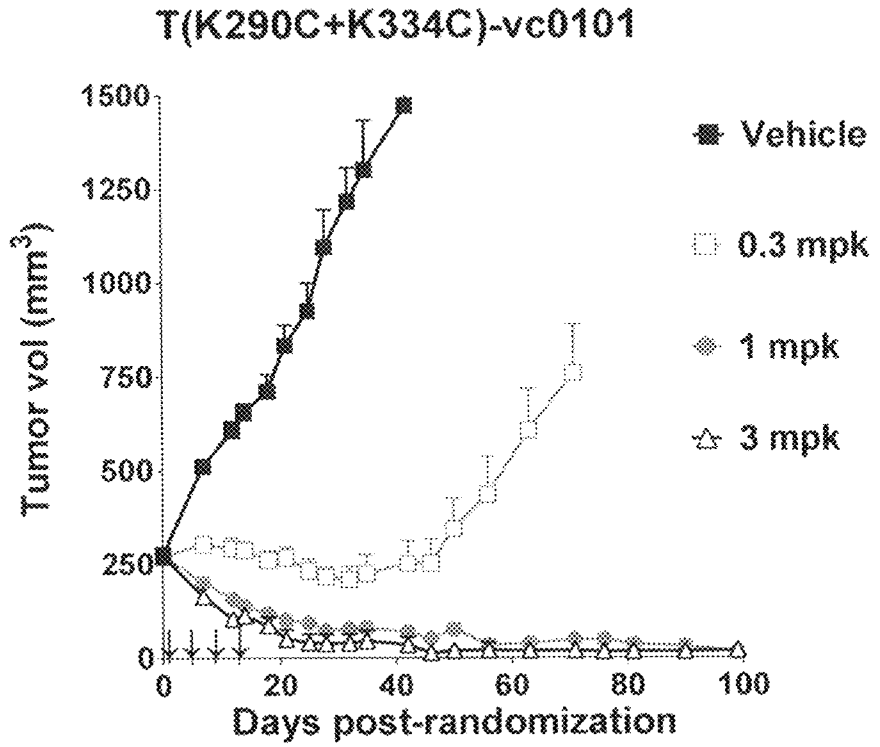
Figure 7F:
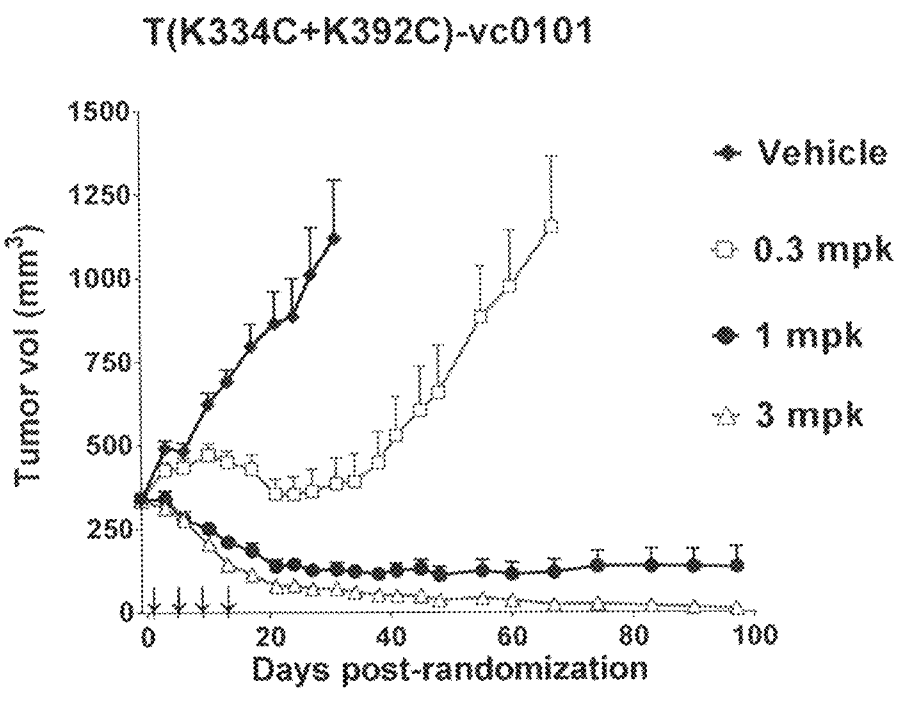
Figure 7G:
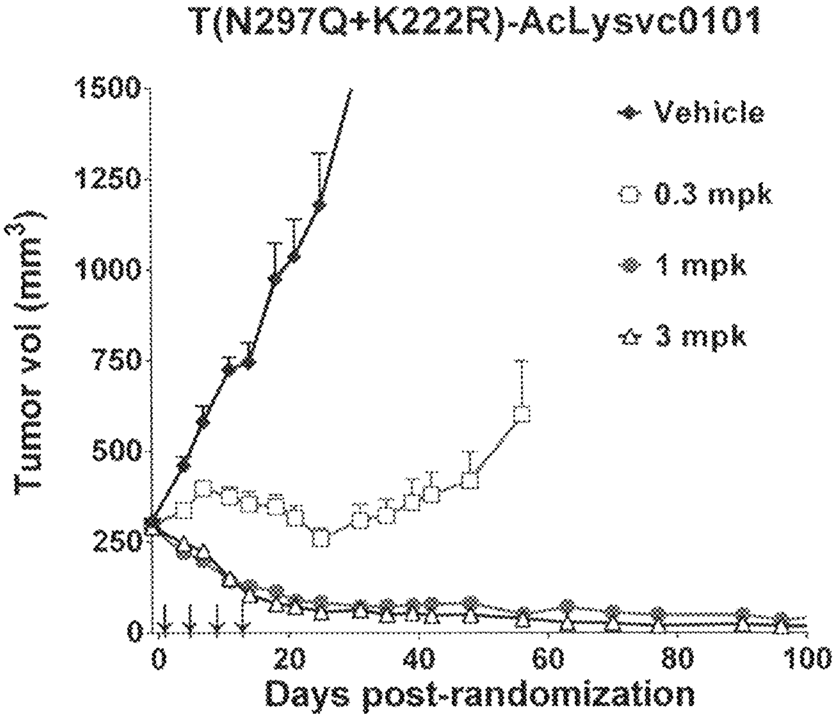
Figure 7H:
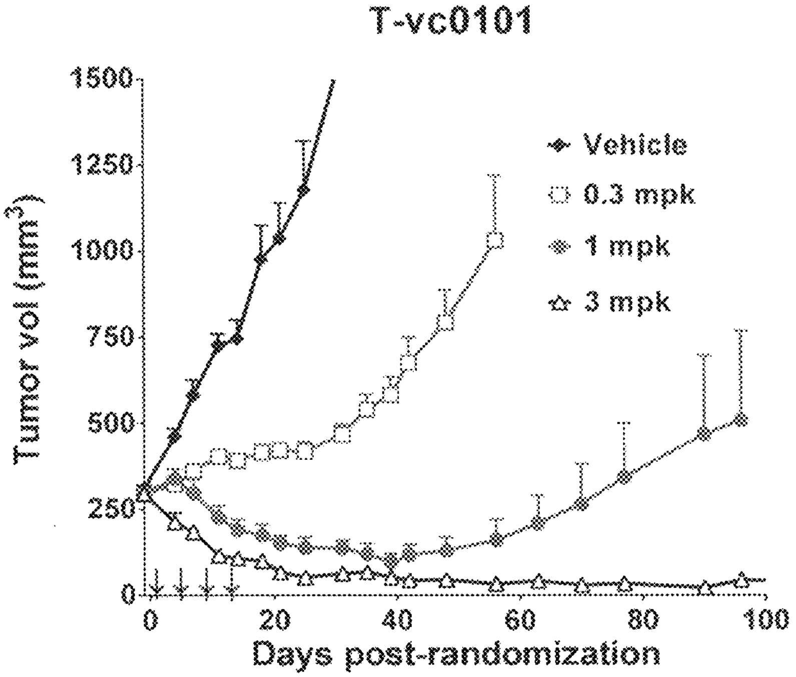
Figure 7I:
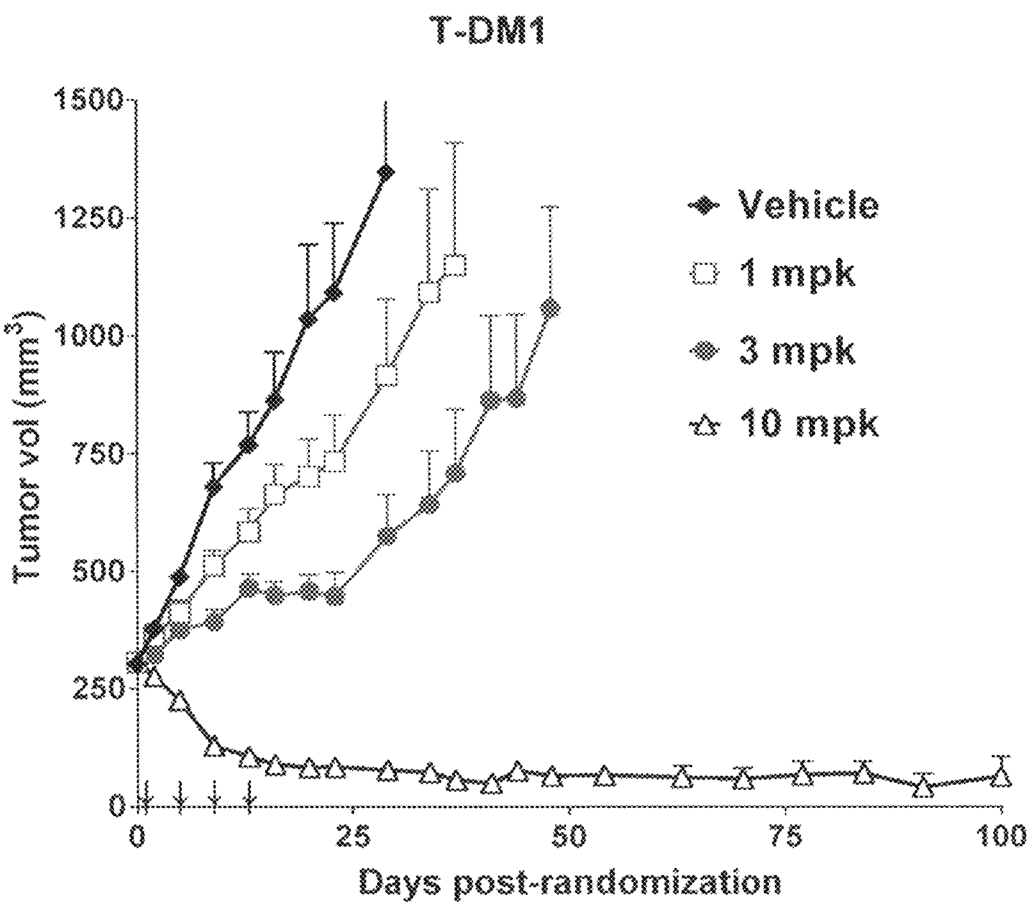

As illustrated in FIG. 7I, T-DM1 had delayed tumor growth at 1 and 3 mg/kg and had complete regression of tumors at 10 mg/kg. However, T(kK183C+K290C)-vc0101 provided complete regression at 1 and 3 mg/kg and partial regression at 0.3 mg/kg (FIG. 7A). The data shows that T(kK183C+K290C)-vc0101 is significantly more potent (~10 times) than T-DM1 in this model.

Similar in vivo efficacy from ADCs with DAR4 (FIGS. 6E, 6F and 6G) were obtained compared to 183+290 (FIG. 7A). In addition, single mutants were evaluated that are DAR2 ADCs (FIGS. 7B, 7C and 7D). In general, these ADCs are less efficacious compared to DAR4 ADCs but more efficacious than T-DM1. Among DAR2 ADCs, it appears LCQ05 is the most potent ADC based on the in vivo efficacy data.

B. HCC1954 Breast Xenografts

HCC1954 (ATCC # CRL-2338) is a high HER2 expression breast cancer cell line. To generate xenografts, SHO female mice (Charles River, Wilmington, Mass.) were implanted subcutaneously with 5×10$^6$ HCC1954 cells in 50% Matrigel (BD Biosciences). When the tumors reached a volume of 200 to 250 $mm^3$, the tumors were staged to ensure uniformity of the tumor mass among various treatment groups. The HCC1954 breast model was dosed intravenously Q4dx4 with PBS vehicle, Trastuzumab derived ADCs and negative control ADC (FIGS. 8A-8E).

Figure 8A:
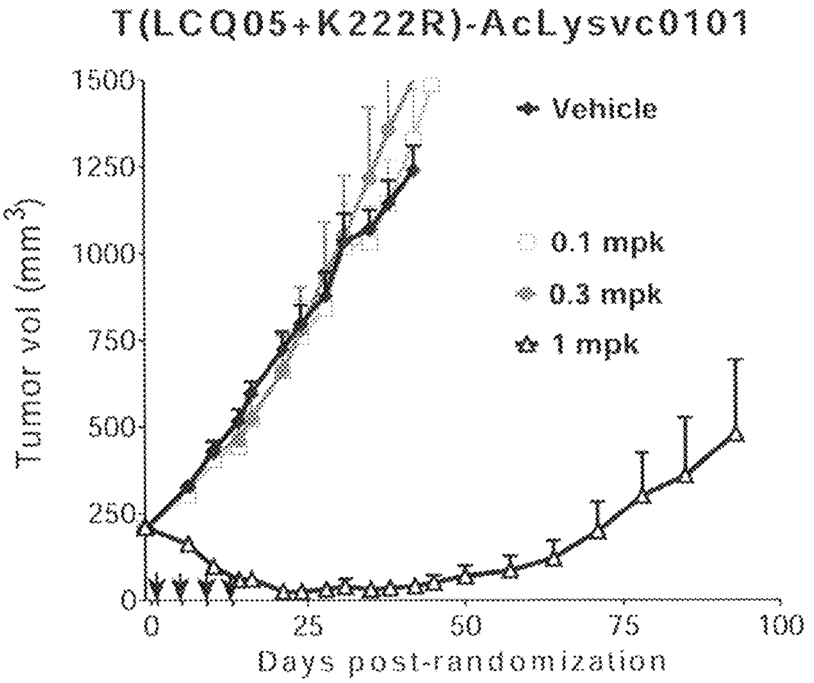
FIGS. 8A-8E depict anti-tumor activity of six trastuzumab derived ADCs on HCC1954 xenografts with tumor volume plotted over time. (A) T(LCQ05+K222R)-AcLysvc0101; (B) T(K290C+K334C)-vc0101; (C) T(K334C+K392C)-vc0101; (D) T(N297Q+K222R)-AcLysvc0101; (E) T-DM1. HCC1954 breast cancer cells express high levels of HER2.
Figure 8B:
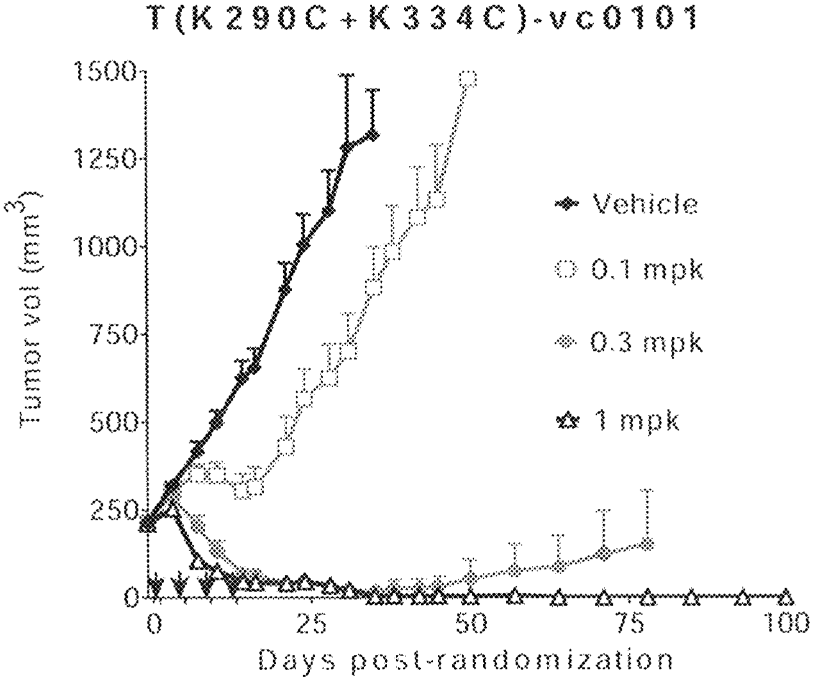
Figure 8C:
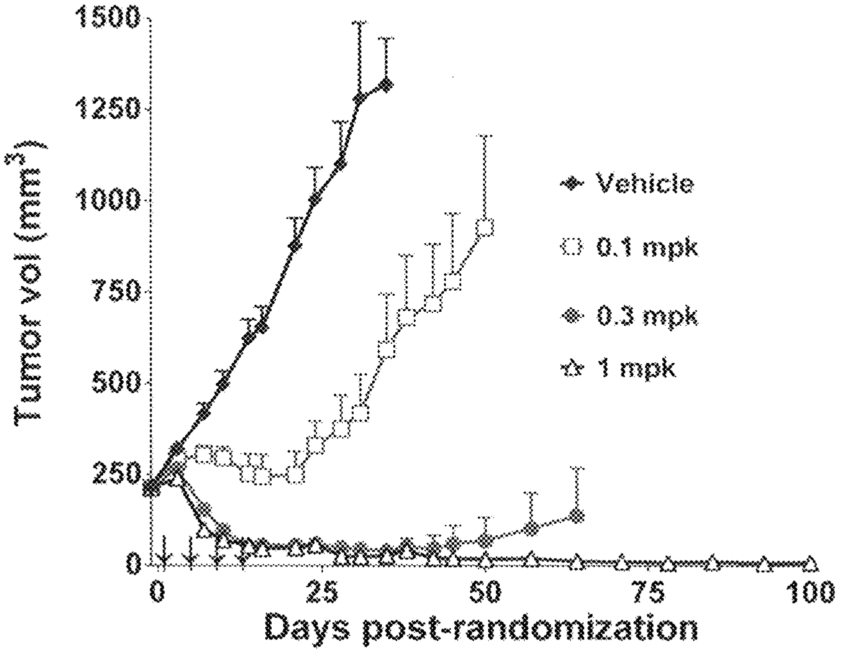
Figure 8D:
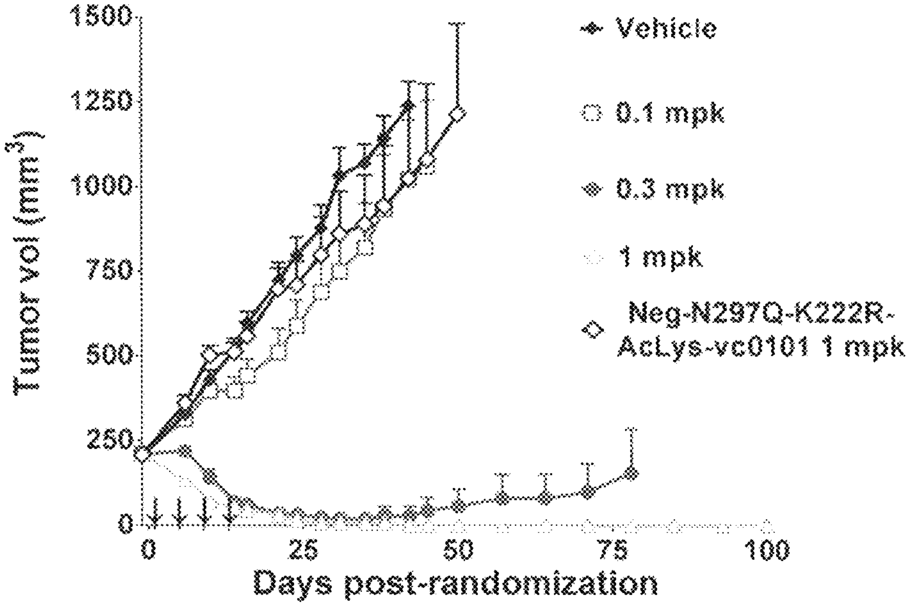
Figure 8E:
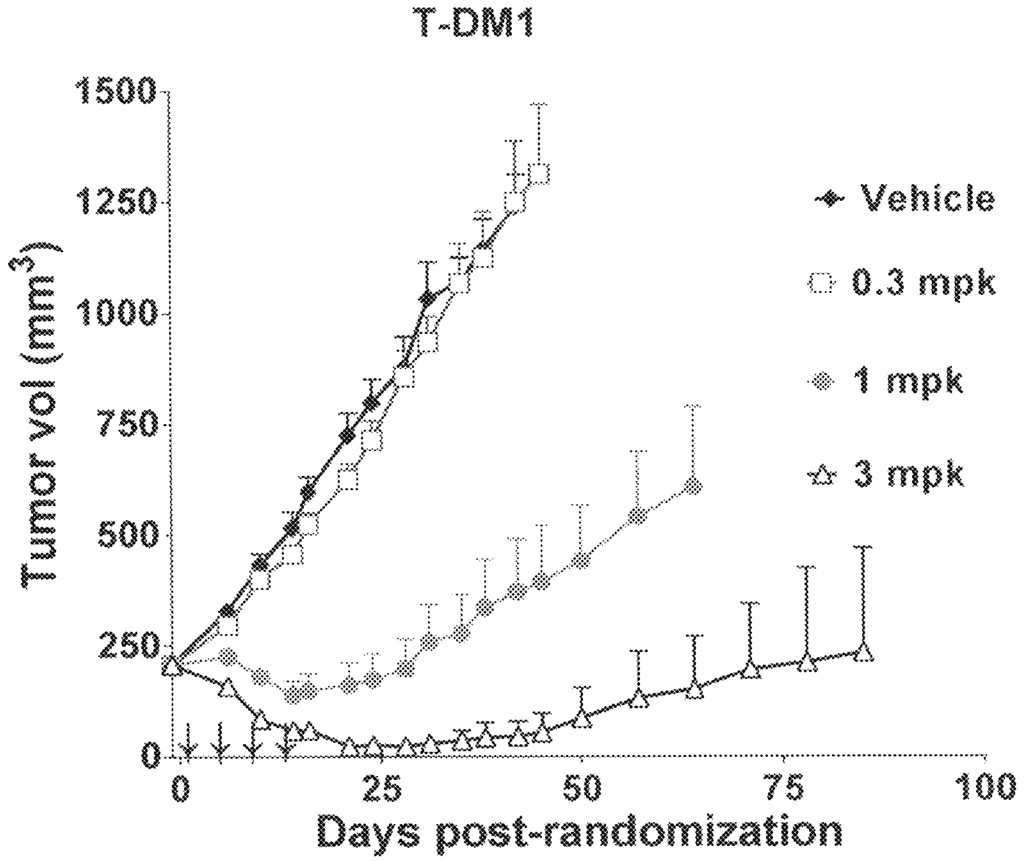

The data demonstrates that Trastuzumab ADCs inhibited growth of HCC1954 breast xenografts in a dose-dependent manner. Comparing the 1 mg/kg dose, vc0101 conjugates were more efficacious than T-DM1. Comparing the 0.3 mg/kg dose, DAR4 loaded ADCs (FIGS. 8B, 8C and 8D) are more efficacious than a DAR2 loaded ADC (FIG. 8A). Further, the negative control ADC at 1 mg/kg had very minimal impact on tumor growth compared to vehicle control (FIG. 8D). However, T(N297Q+K222R)-AcLysvc0101 completely regressed the tumors indicating the target specificity.

C. JIMT-1 Breast Xenografts

Figure 9A:
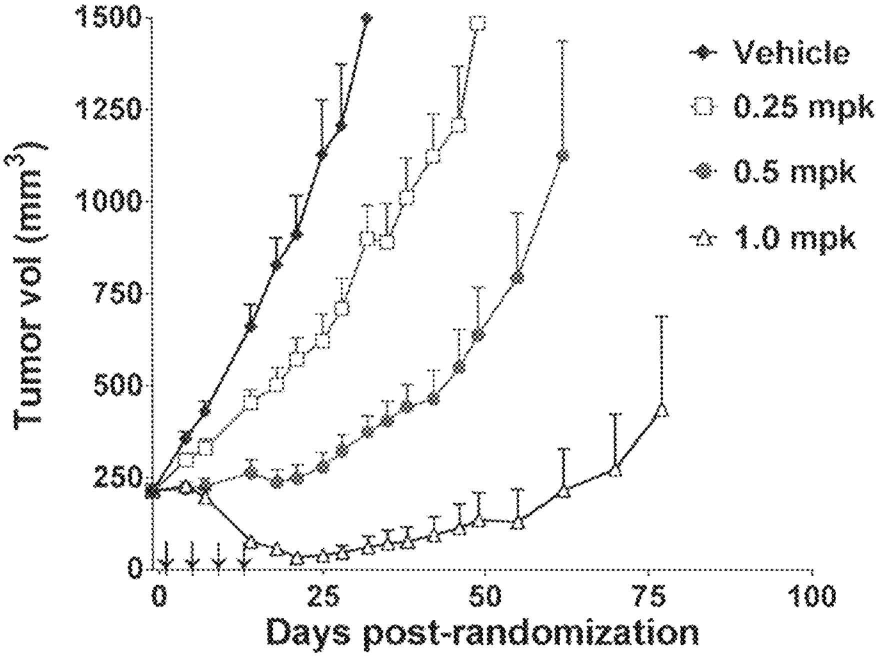
FIGS. 9A-9G depict anti-tumor activity of seven trastuzumab derived ADCs on JIMT-1 xenografts with tumor volume plotted over time. (A) T(kK183C+K290C)-vc0101; (B) T(LCQ05+K222R)-AcLysvc0101; (C) T(K290C+K334C)-vc0101; (D) T(K334C+K392C)-vc0101; (E) T(N297Q+K222R)-AcLysvc0101; (F) T-vc0101; (G) T-DM1. JIMT-1 breast cancer cells express moderate/low levels of HER2.
Figure 9B:
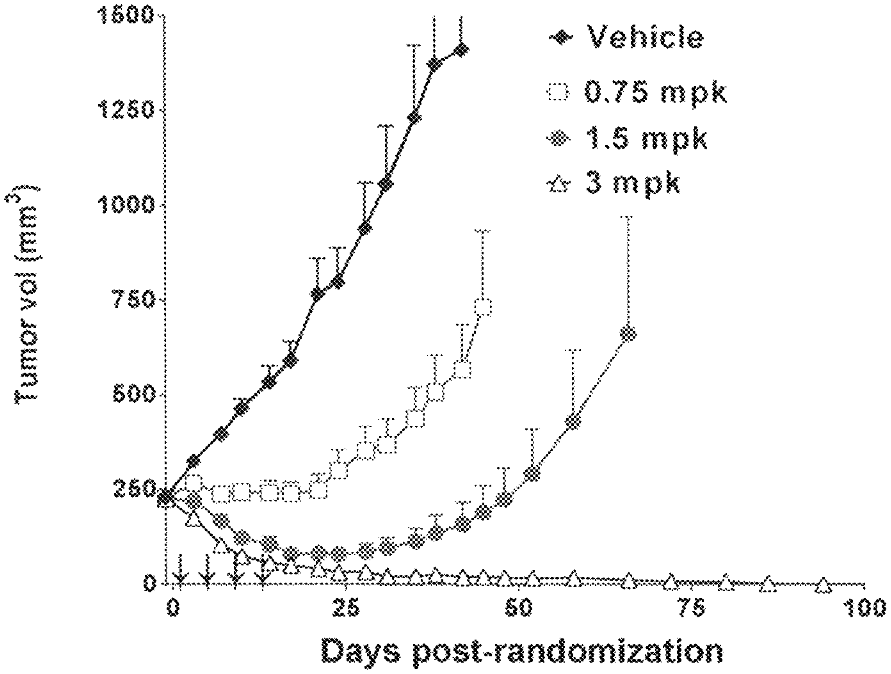
Figure 9C:
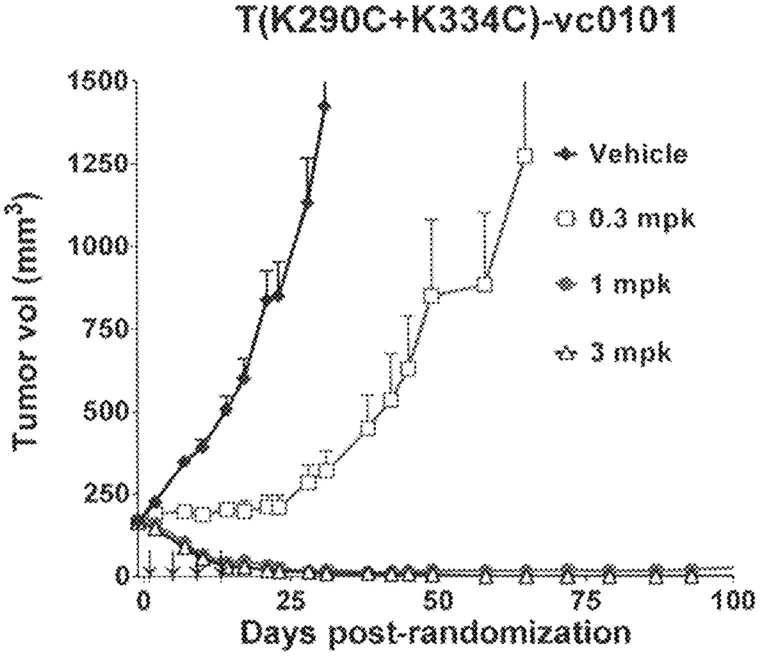
Figure 9D:
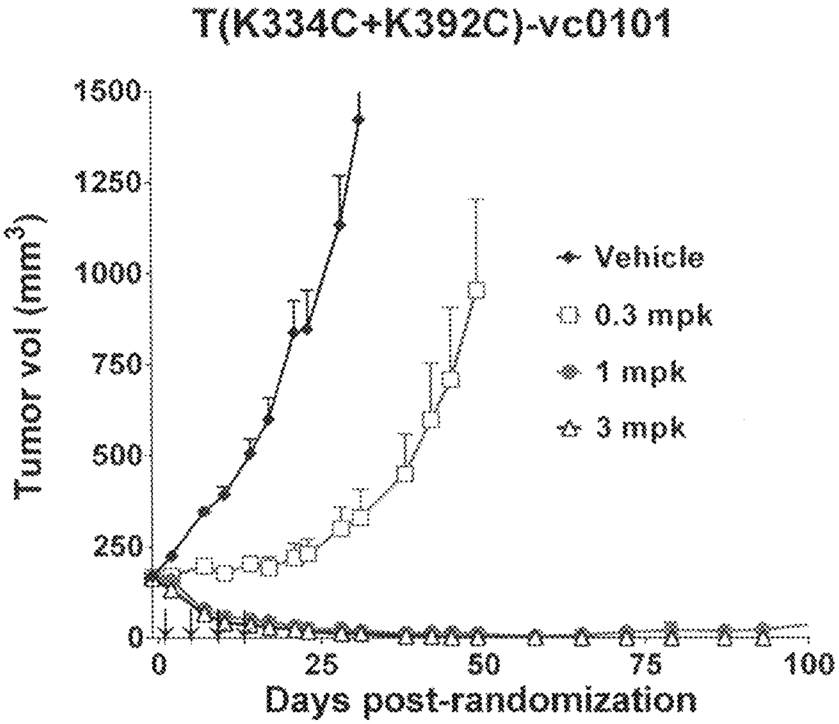
Figure 9E:
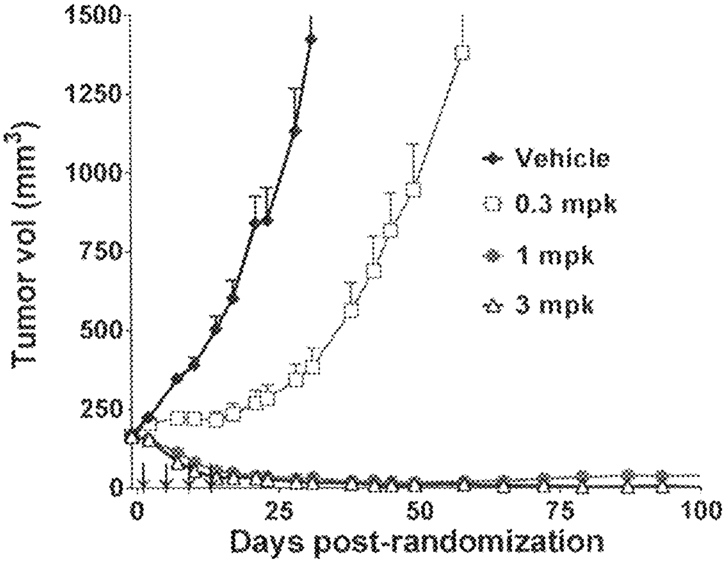
Figure 9F:
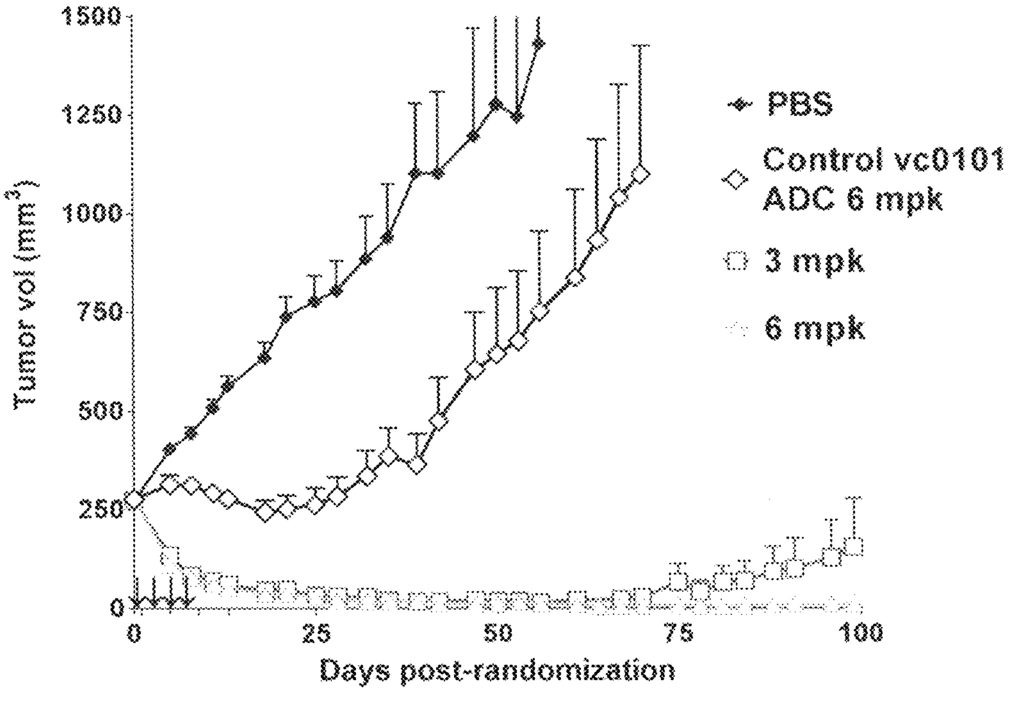
Figure 9G:
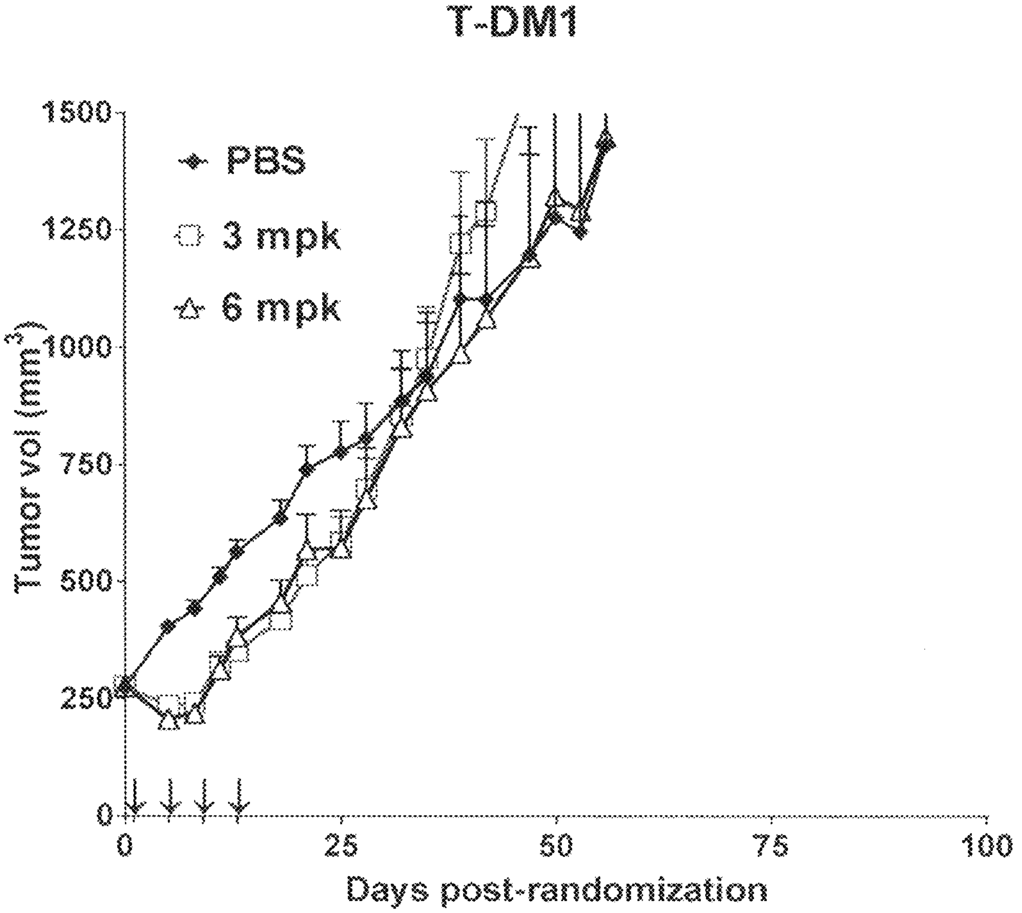
Figure 10A:
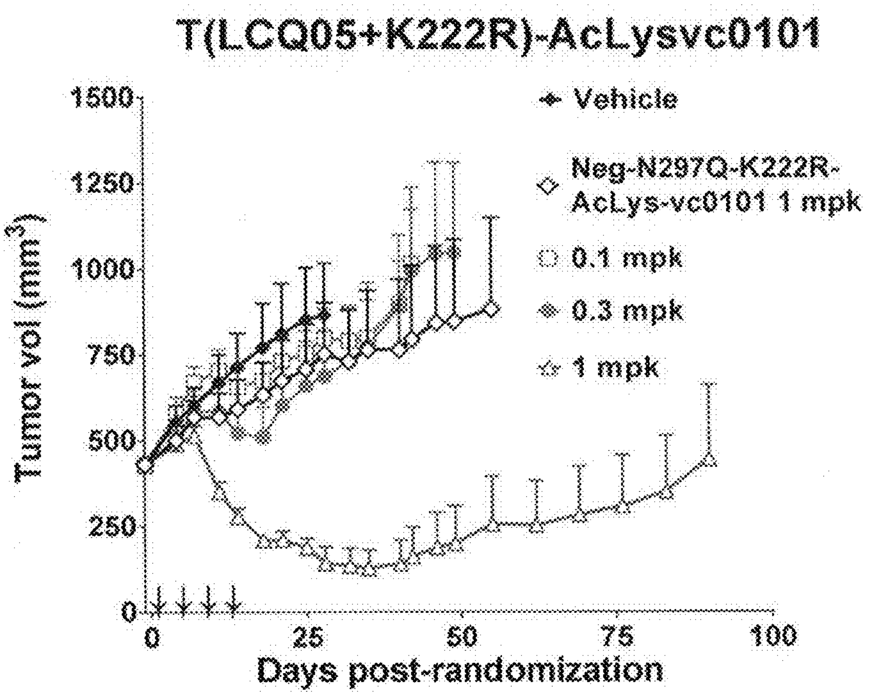
FIGS. 10A-10D depict anti-tumor activity of five trastuzumab derived ADCs on MDA-MB-361(DYT2) xenografts with tumor volume plotted over time. (A) T(LCQ05+K222R)-AcLysvc0101; (B) T(N297Q+K222R)-AcLysvc0101; (C) T-vc0101; (D) T-DM1. MDA-MB-361 (DYT2) breast cancer cells express moderate/low levels of HER2.
Figure 10B:
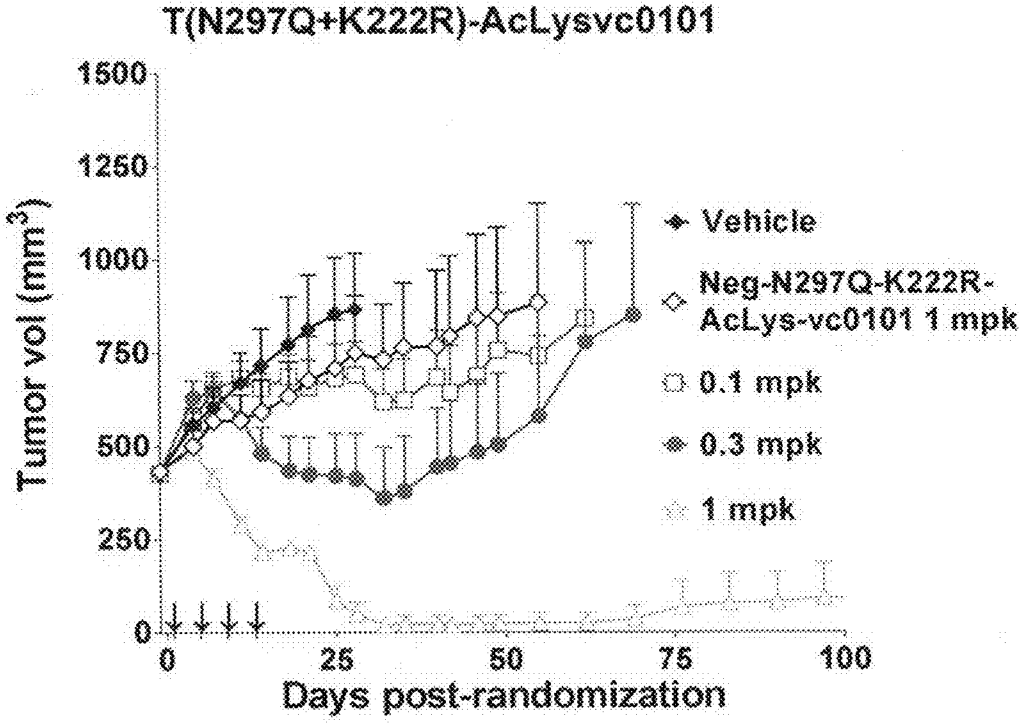
Figure 10C:
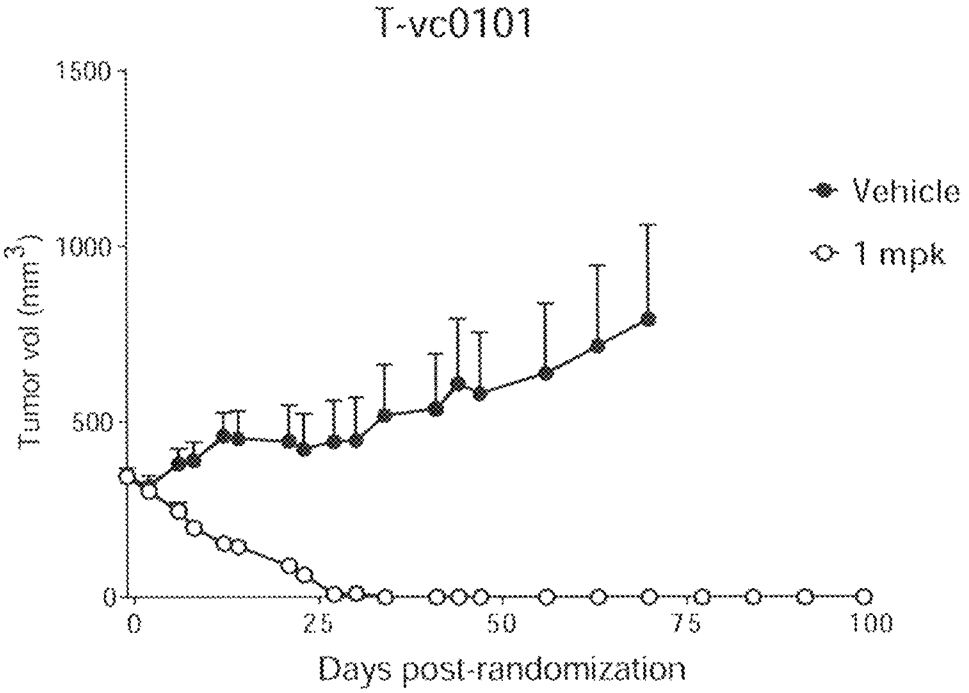
Figure 10D:
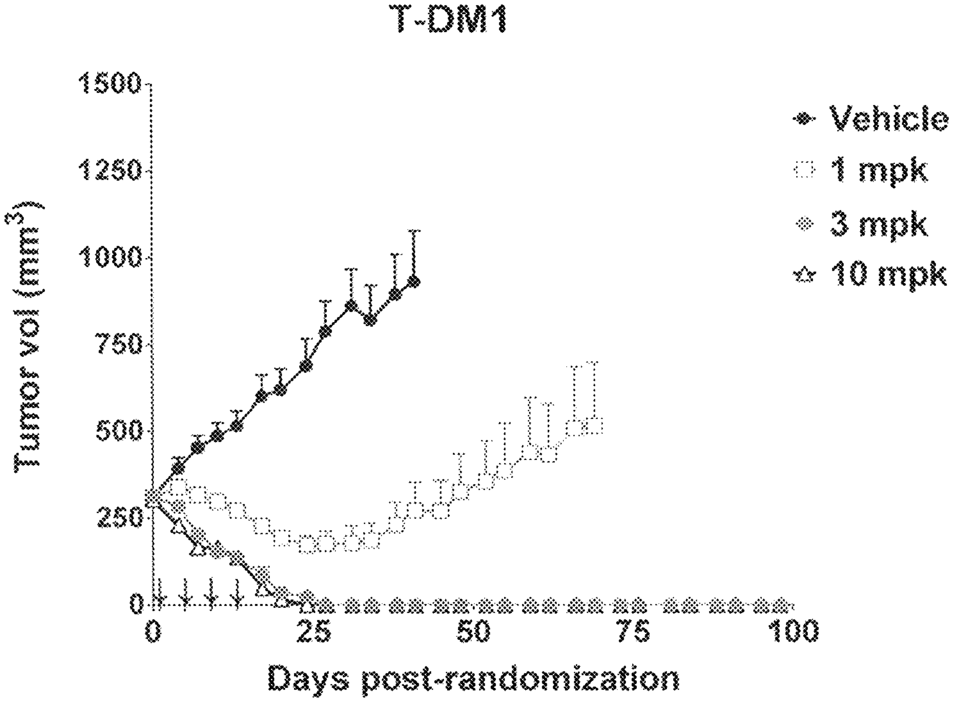
Figure 11A:
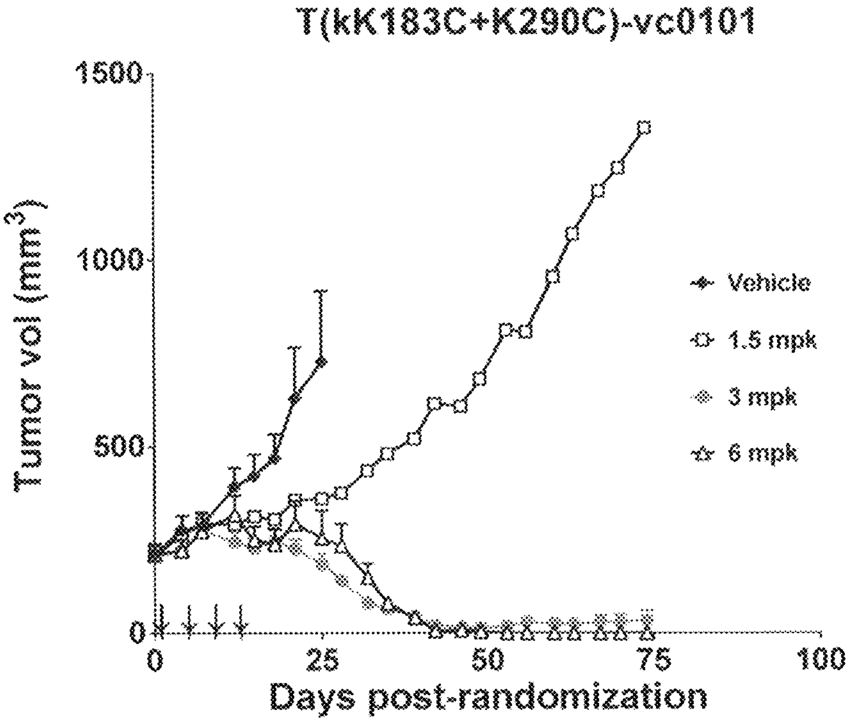
FIGS. 11A-11E depict anti-tumor activity of five trastuzumab derived ADCs on PDX-144580 patient derived xenografts with tumor volume plotted over time. (A) T(kK183C+K290C)-vc0101; (B) T(LCQ05+K222R)-AcLysvc0101; (C) T(N297Q+K222R)-AcLysvc0101; (D) T-vc0101; (E) T-DM1. PDX-144580 patient derived cells are a TNBC PDX model.
Figure 11B:
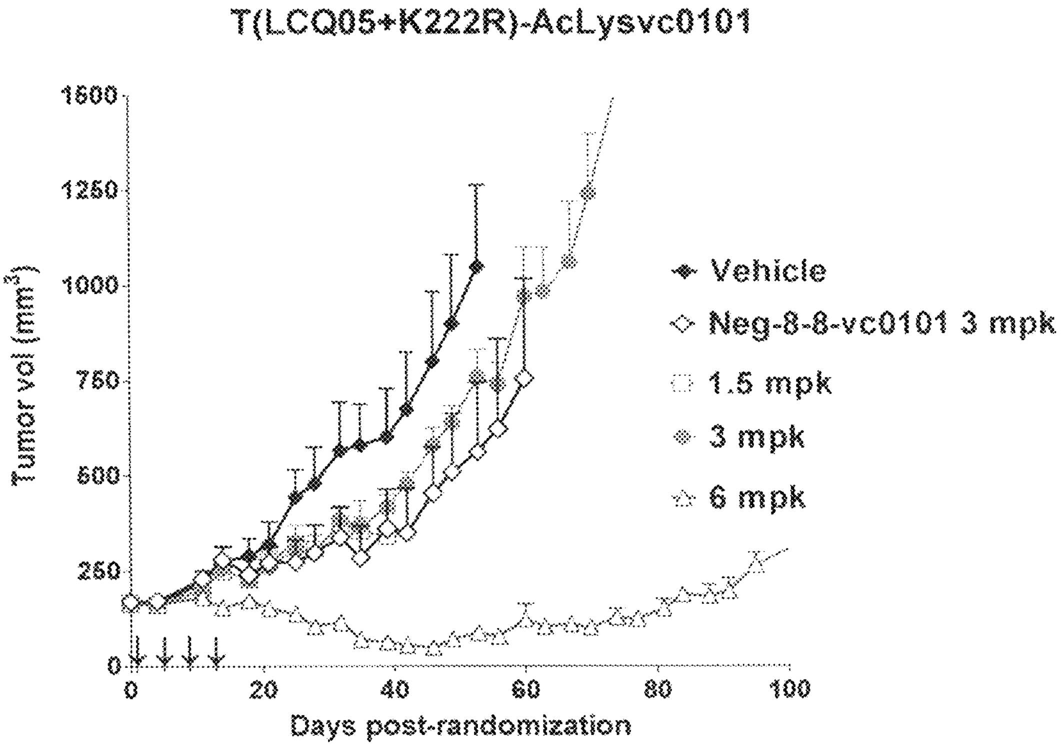
Figure 11C:
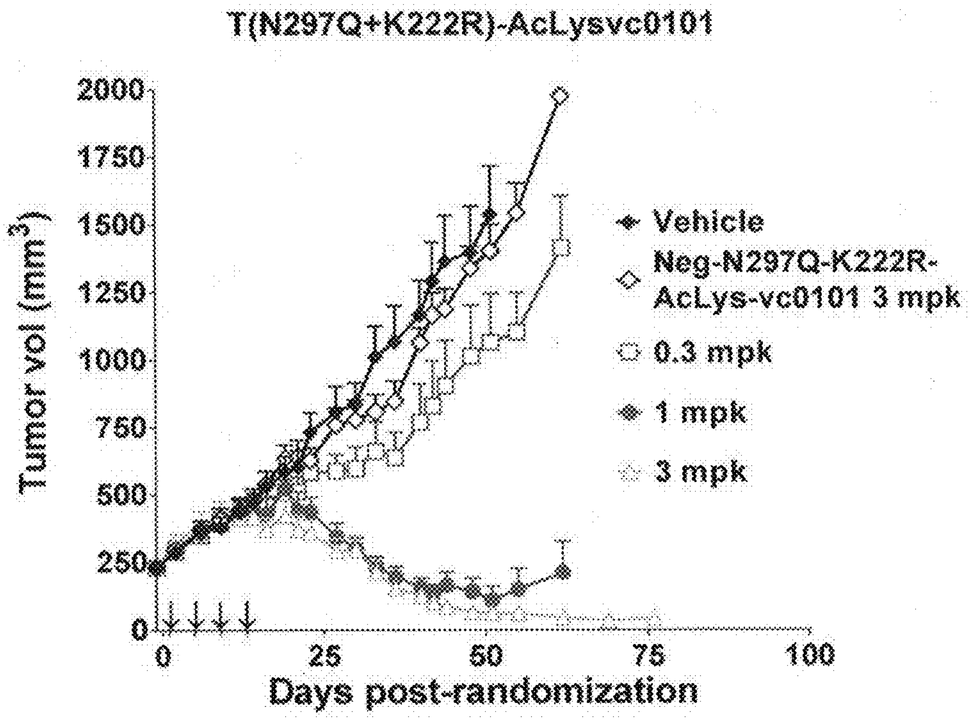
Figure 11D:
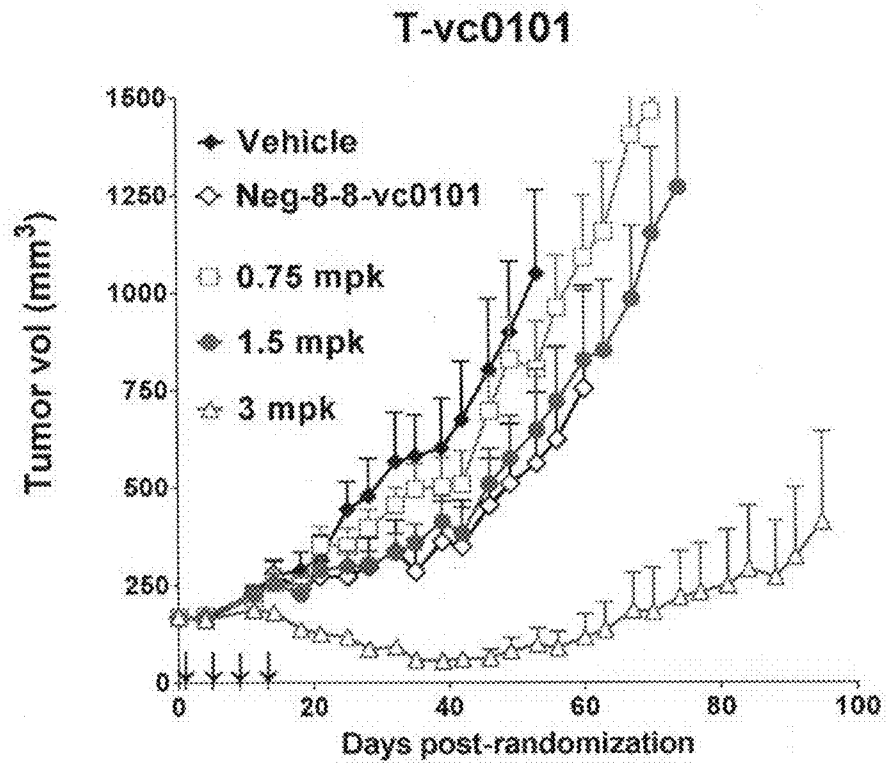
Figure 11E:
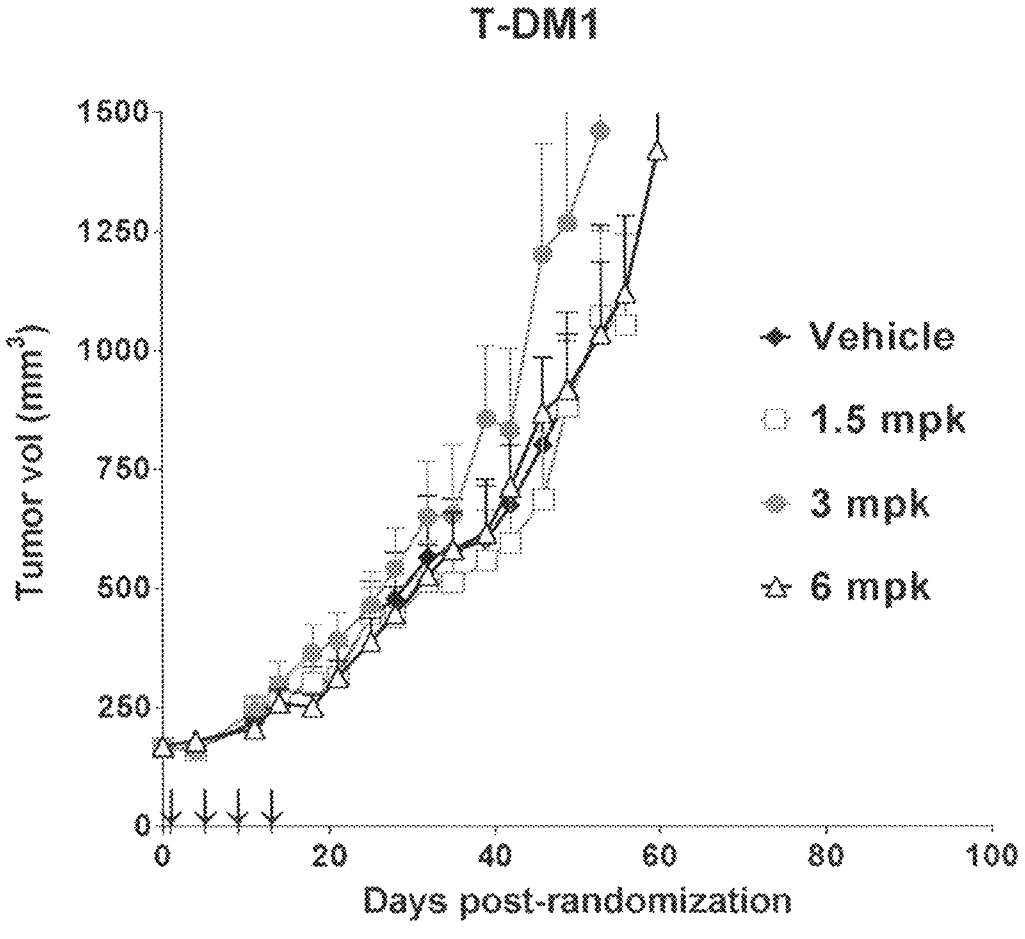

JIMT-1 is a breast cancer cell line expressing moderate/low Her2 and is inherently resistant to trastuzumab. To generate xenografts, nude (Nu/Nu) female mice were implanted subcutaneously with 5×10$^6$ JIMT-1 cells (DSMZ # ACC-589) in 50% Matrigel (BD Biosciences). When the tumors reached a volume of 200 to 250 $mm^3$, the tumors were staged to ensure uniformity of the tumor mass among various treatment groups. The JIMT-1 breast model was dosed intravenously Q4dx4 with PBS vehicle, T-DM1 (FIG. 9G), trastuzumab derived ADCs using site specific conjugation (FIGS. 9A-9E), trastuzumab derived ADC using conventional conjugation (FIG. 9F) and negative control huNeg-8.8 ADC.

The data demonstrates that all the tested vc0101 conjugates cause tumor reduction in a dose-dependent manner. These ADCs can cause tumor regression at 1 mg/kg. However, T-DM1 is inactive in this moderate/low Her2 expressing model even at 6 mg/kg.

D. MDA-MB-361(DYT2) Breast Xenografts

MDA-MB-361(DYT2) is a breast cancer cell line expressing moderate/low Her2. To generate xenografts, nude (Nu/Nu) female mice were irradiated at 100 cGy/min for 4 minutes and three days later implanted subcutaneously with 1.0×10$^7$ MDA-MB-361(DYT2) cells (ATCC # HTB-27) in 50% Matrigel (BD Biosciences). When the tumors reached a volume of 300 to 400 $mm^3$, the tumors were staged to ensure uniformity of the tumor mass among various treatment groups. The DYT2 breast model was dosed intravenously Q4dx4 with PBS vehicle, trastuzumab derived ADCs using site specific and conventional conjugation, T-DM1 and negative control ADC (FIGS. 10A-10D).

The data demonstrates that trastuzumab ADCs inhibited growth of DYT2 breast xenografts in a dose-dependent manner. Although DYT2 is moderate/low Her2 expression cell lines, it is more sensitive to micro-tubule inhibitors than other Her2 low/moderate expressing cell lines.

E. 144580 Patient-Derived Breast Cancer Xenografts

The effects of Trastuzumab derived ADCs were examined in immunodeficient mice on the in vivo growth of human tumor xenografts that were established from fragments of freshly resected 144580 breast tumors obtained in accordance with appropriate consent procedures. The tumor characterization of 144580 when fresh biopsy was taken was as a triple negative (ER−, PR−, and HER2−) breast cancer tumor. The 144580 breast patient-derived xenografts were subcutaneously passaged in vivo as fragments from animal to animal in nude (Nu/Nu) female mice. When the tumors reached a volume of 150 to 300 $mm^3$, they were staged to ensure uniformity of the tumor size among various treatment groups. The 144580 breast model was dosed intravenously four times every four days (Q4dx4) with PBS vehicle, trastuzumab ADCs using site specific conjugation, trastuzumab derived ADC using conventional conjugation and negative control ADC (FIGS. 11A-11E).

In this HER2− (by clinical definition) PDX model, T-DM1 was ineffective at all doses tested (1, 5, 3 and 6 mg/kg) (FIG. 10E). For DAR4 vc0101 ADCs (FIGS. 11A, 11C and 11D), 3 mg/kg is able to cause tumor regression (even at 1 mg/kg in FIG. 11C). The DAR2 vc0101 ADC (FIG. 11B) is less efficacious than DAR4 ADCs at 3 mg/kg. However, the DAR 2 vc0101 ADC is efficacious at 6 mg/kg unlike T-DM1.

F. 37622 Patient-Derived Non-Small Cell Lund Cancer Xenograft

Several ADCs were tested in patient-derived Non-Small Cell Lung Cancer xenograft model of 37622 obtained in accordance with appropriate consent procedures. The 37622 patient-derived xenografts were subcutaneously passaged in vivo as fragments from animal to animal in nude (Nu/Nu) female mice. When the tumors reached a volume of 150 to 300 $mm^3$, they were staged to ensure uniformity of the tumor size among various treatment groups. The 37622 PDX model was dosed intravenously four times every four days (Q4dx4) with PBS vehicle, trastuzumab derived ADCs using site specific conjugation, T-DM1 and negative control ADC (FIGS. 12A-12D).

Figure 12A:
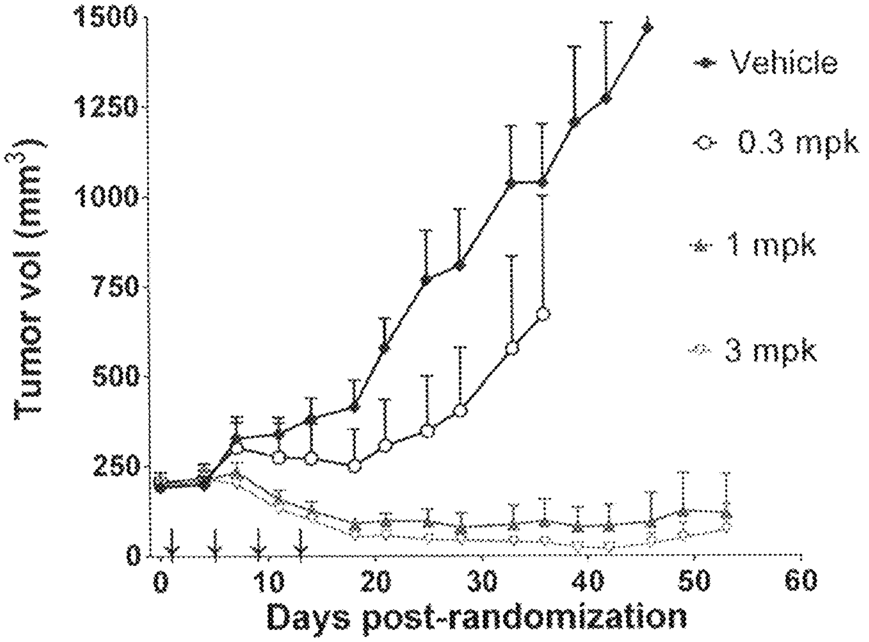
FIGS. 12A-12D depict anti-tumor activity of four trastuzumab derived ADCs on PDX-37622 patient derived xenografts with tumor volume plotted over time. (A) T(kK183C+K290C)-vc0101; (B) T(N297Q+K222R)-AcLysvc0101; (C) T(K297C+K334C)-vc0101; (D) T-DM1. PDX-37622 patient derived cells are a NSCLC PDX model expressing moderate levels of HER2.
Figure 12B:
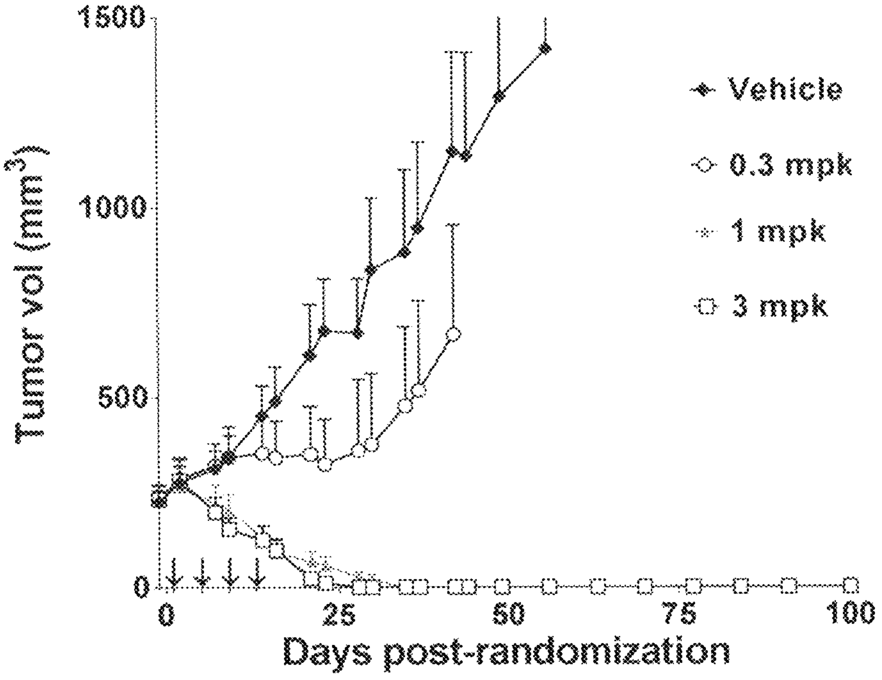
Figure 12C:
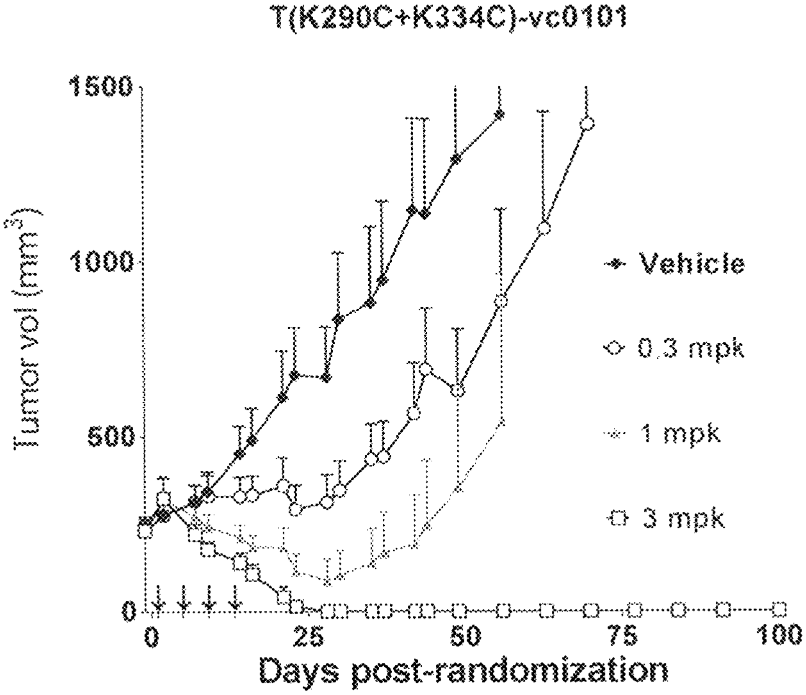
Figure 12D:
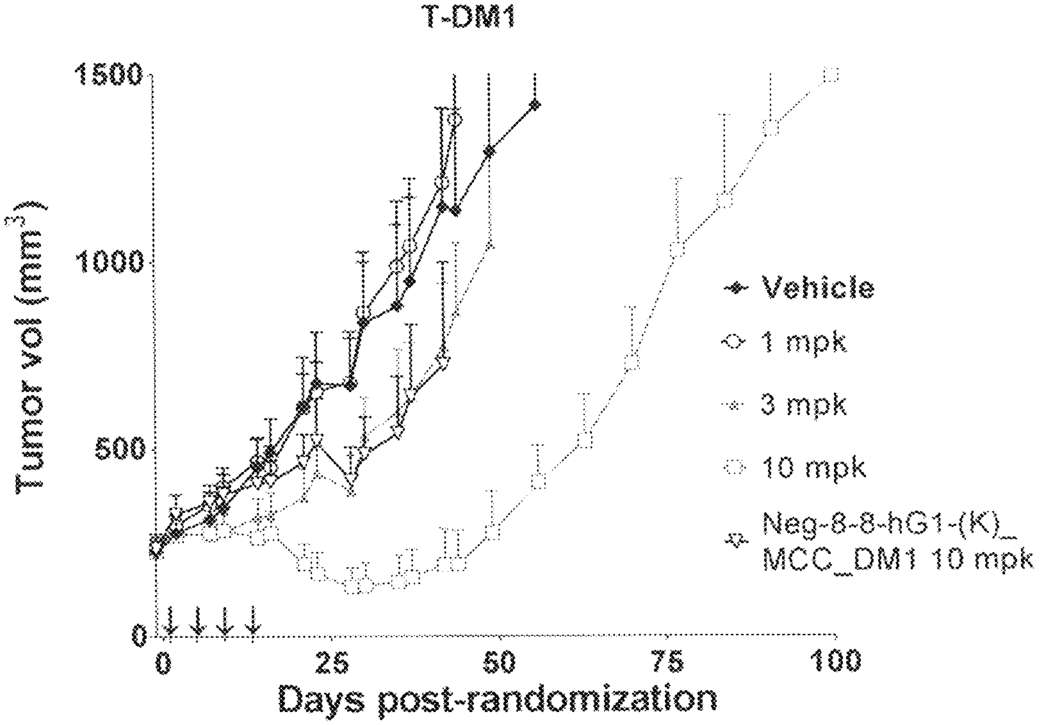

Expression of Her2 was profiled by modified Hercept test and was classified as 2+ with more heterogeneity than seen in cell lines. The ADCs conjugated with vc0101 as a linker-payload (FIGS. 12A-12C) were efficacious at 1 and 3 mg/kg causing tumor regression. However, T-DM1 only provided some therapeutic benefit at 10 mg/kg (FIG. 12D). It appears vc0101 ADCs are 10-times more potent than T-DM1 by comparing results at 10 mg/kg from T-DM1 to 1 mg/kg from vc0101 ADCs. It is possible that the bystander effect is important for efficacy for a heterogeneic tumor.

G. GA0044 Patient-Derived Gastric Cancer Xenograft

Figure 30:
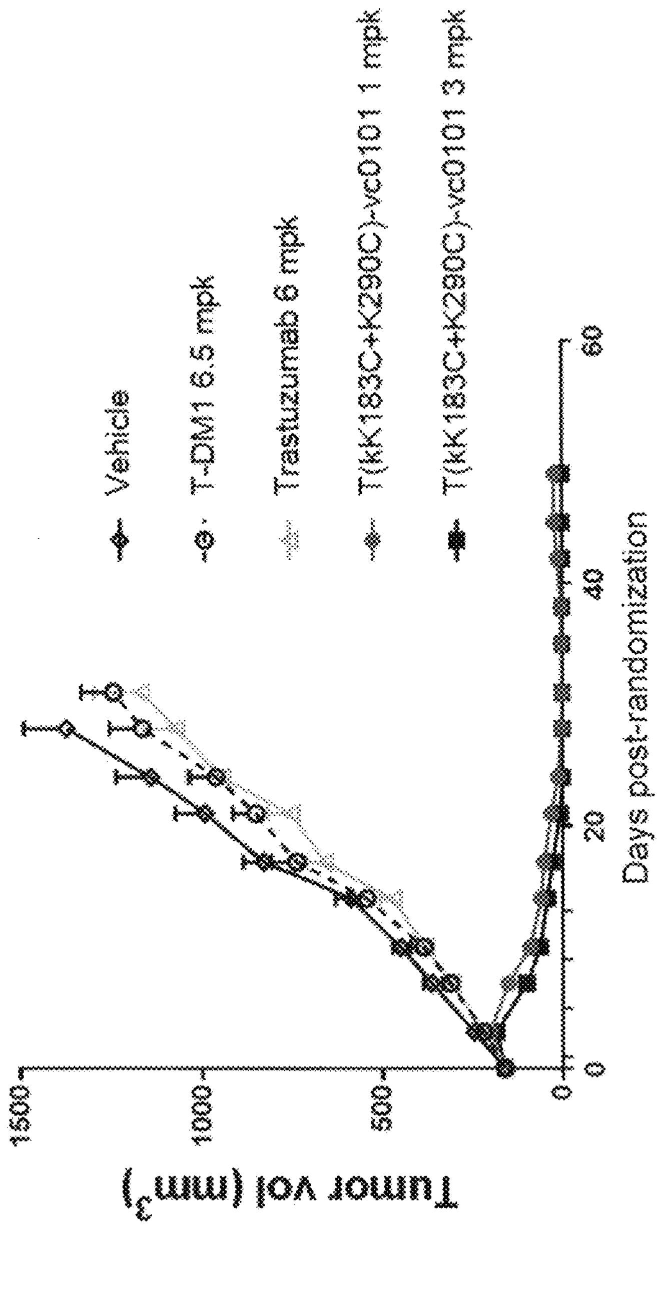
FIG. 30 depicts anti-tumor activity of trastuzumab and two trastuzumab derived ADCs on PDX-GA0044 patient derived xenografts with tumor volume plotted over time. Animals were treated with vehicle (hollow diamonds), trastuzumab (hollow triangles), T-DM1 (hollow circles), or T(kK183C+K290C)-vc0101 (solid circles and solid squares). PDX-GA0044 patient derived cells are a Gastric PDX model expressing moderate levels of HER2.

Trastuzumab and anti-HER2 ADCs were tested in a patient-derived Gastric xenograft model (GA0044) obtained in accordance with appropriate consent procedures. The GA0044 patient-derived xenografts were subcutaneously passaged in vivo as fragments from animal to animal in nude (Nu/Nu) female mice. When the tumors reached a volume of 150 to 300 $mm^3$, they were staged to ensure uniformity of the tumor size among various treatment groups. The GA0044 PDX model was dosed intravenously four times every four days (Q4dx4) with PBS vehicle, trastuzumab, T-DM1 or a trastuzumab derived ADC using site-specific conjugation to vc0101 (FIG. 30).

Expression of HER2 in GA0044 was profiled by modified Hercept test and was classified as 2+ with heterogeneous distribution. The ADC conjugated with vc0101 as the payload (namely, T(kK183C+K290C)-vc0101) was efficacious and resulted in complete tumor regressions at 1 and 3 mg/kg doses. Trastuzumab and T-DM1 showed no appreciable difference in tumor growth as compared to vehicle treated tumors. It is possible that the bystander effect is important for efficacy in this tumor with heterogenous target (i.e. HER2) expression.

H. Demonstration of Bystander Effect of T-Vc0101 ADC in N87 Gastric Xenograft

Figure 13A:
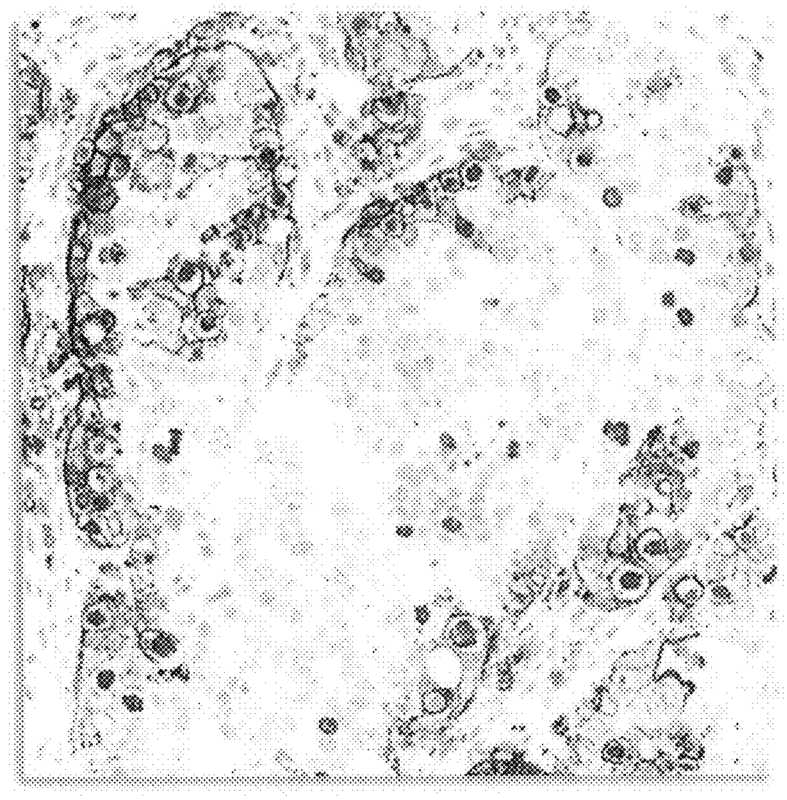
FIGS. 13A-13B depict immunohistocytochemistry of N87 tumor xenografts treated with either (A) T-DM1 or (B) T-vc0101 and stained for phosphohistone H3 and IgG antibody. Bystander activity is observed with T-vc0101.
Figure 13B:
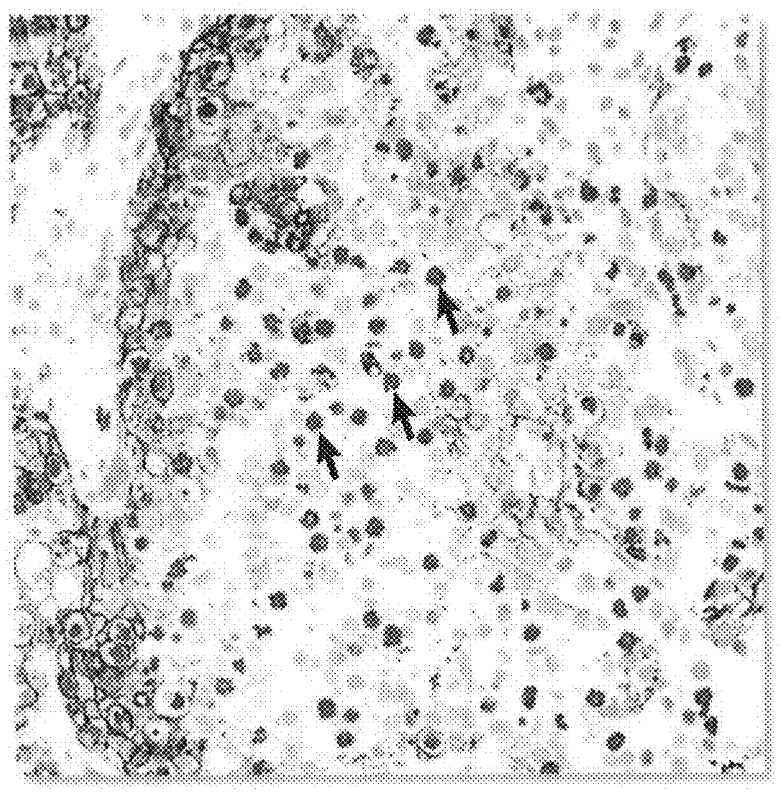

The released metabolite of the T-DM1 ADC has been shown to be the lysine-capped mcc-DM1 linker payload (i.e., Lys-mcc-DM1) which is a membrane impermeable compound (Kovtun et al., 2006, Cancer Res 66:3214-21; Xie et al., 2004, J Pharmacol Exp Ther 310:844). However, the released metabolite from the T-vc0101 ADC is auristatin 0101, a compound with more membrane permeability than Lys-mcc-DM1. The ability of a released ADC payload to kill neighboring cells is known as the bystander effect. Due to a release of a membrane permeable payload, T-vc0101 is able to elicit a strong bystander effect whereas T-DM1 is not. FIG. 13 shows immunohistocytochemistry from N87 cell line xenograft tumors which received a single dose of either T-DM1 at 6 mg/kg (FIG. 13A) or T-vc0101 at 3 mg/kg (FIG. 13B) and then harvested and processed in formalin fixation 96 hours later. Tumor sections were stained for human IgG to detect ADC bound to tumor cells and phospho-histone H3 (pHH3) to detect mitotic cells as a readout of the proposed mechanism of action for the payloads of both ADCs.

ADC is detected in the periphery of the tumors in both cases. In T-DM1 treated tumors (FIG. 13A), the majority of pHH3 positive tumor cells are located near the ADC. However, in T-vc0101 treated tumors (FIG. 13B), the majority of pHH3 positive tumor cells extend beyond the location of the ADC (black arrows highlight a few examples) and are in the tumor interior. These data suggest that an ADC with a cleavable linker and a membrane permeable payload can elicit a strong bystander effect in vivo.

Example 14: In Vitro T-DM1 Resistance Models

A. Generation of T-DM1 Resistant Cells In Vitro

Figure 15A:
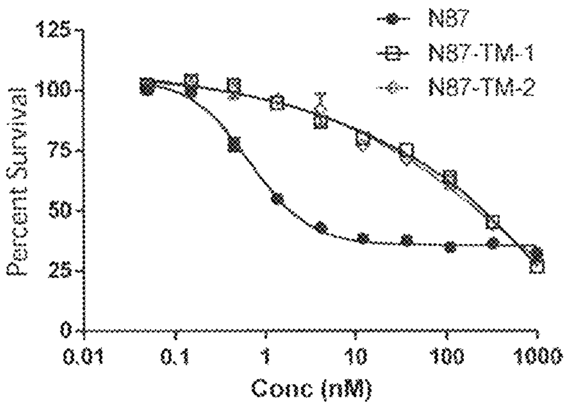
FIGS. 15A-15G depict anti-tumor activity of seven trastuzumab derived ADCs on T-DM1 sensitive (N87 cells) and resistant (N87-TM1 and N87-TM2) gastric cancer cells. (A) T-DM1; (B) T-mc8261; (C) T(297Q+K222R)-AcLysvc0101; (D) T(LCQ05+K222R)-AcLysvc0101; (E) T(K290C+K334C)-vc0101; (F) T(K334C+K392C)-vc0101; (G) T(kK183C+K290C)-vc0101.

N87 cells were passaged into two separate flasks and each flask was treated identically with respect to the resistance-generation protocol to enable biological duplicates. Cells were exposed to five cycles of T-DM1 conjugate at approximately $IC_{80}$ concentrations (10 nM payload concentration) for 3 days, followed by approximately 4 to 11 days recovery without treatment. After the five cycles at 10 nM of the T-DM1 conjugate, the cells were exposed to six additional cycles of 100 nM T-DM1 in a similar fashion. The procedure was intended to simulate the chronic, multi-cycle (on/off) dosing at maximally tolerated doses typically used for cytotoxic therapeutics in the clinic, followed by a recovery period. Parental cells derived from N87 are referred to as N87, and cells chronically exposed to T-DM1 are referred to as N87-TM. Moderate- to high-level drug resistance developed within 4 months for N87-TM cells. Drug selection pressure was removed after ~3-4 months of cycle treatments when the level of resistance no longer increased after continued drug exposure. Responses and phenotypes remained stable in the cultured cell lines for approximately 3-6 months thereafter. Thereafter, a reduction in the magnitude of the resistance phenotype as measured by cytotoxicity assays was occasionally observed, in which case early passage cryo-preserved T-DM1 resistant cells were thawed for additional studies. All reported characterizations were conducted after removal of T-DM1 selection pressure for at least 2-8 weeks to ensure stabilization of the cells. Data were collected from various thawed cryopreserved populations derived from a single selection, over approximately 1-2 years after model development to ensure consistency in the results. The gastric cancer cell line N87 was selected for resistance to trastuzumab-maytansinoid antibody-drug conjugate (T-DM1) by treatment cycles at doses that were approximately the $IC_{80}$ (~10 nM payload concentration) for the respective cell line. Parental N87 cells were inherently sensitive to the conjugate ($IC_{50}$=1.7 nM payload concentration; 62 ng/ml antibody concentration) (FIG. 14). Two populations of parental N87 cells were exposed to the treatment cycles and, after only approximately four months exposure cycling at 100 nM T-DM1, these two populations (henceforth named N87-TM-1 and N87-TM-2) became refractory to the ADC by 114- and 146-fold, respectively, compared with parental cells (FIG. 14 and FIG. 15A). Interestingly, minimal cross-resistance (~2.2-2.5×) to the corresponding unconjugated maytansinoid free drug, DM1, was observed (FIG. 14).

B. Cytotoxicity Studies

ADCs were prepared as indicated in Example 3. Unconjugated maytansine analog (DM1) and auristatin analogs were prepared by Pfizer Worldwide Medicinal Chemistry (Groton, Conn.). Other standard-of-care chemotherapeutics were purchased from Sigma (St. Louis, Mo.). Cells were seeded in 96-well plates at low density, then treated the following day with ADCs and unconjugated payloads at 3-fold serial dilutions at 10 concentrations in duplicate. Cells were incubated for 4 days in a humidified 37° C./5% $CO_2$ incubator. The plates were harvested by incubating with CellTiter® 96 AQueous One MTS Solution (Promega, Madison, Wis.) for 1.5 hours and absorbance measured on a Victor plate reader (Perkin-Elmer, Waltham, Mass.) at wavelength 490 nm. $IC_{50}$ values were calculated using a four-parameter logistic model with XLfit (IDBS, Bridgewater, N.J.).

Figure 15B:
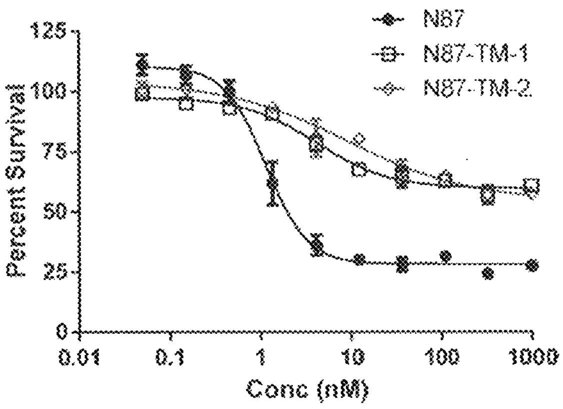

The cross-resistance profile to other trastuzumab derived ADCs was determined. Significant cross-resistance to many trastuzumab derived ADCs composed of non-cleavable linkers and delivering payloads with anti-tubulin mechanisms of action was observed (FIG. 14). For example, in N87-TM vs. N87-parental cells, >330- and >272-fold reduced potency was observed to T-mc8261 (FIG. 14 and FIG. 15B) and T-MalPeg8261 (FIG. 14), which represent an auristatin-based payload linked to trastuzumab via non-cleavable maleimidocaproyl or Mal-PEG linkers, respectively. Over 235-fold resistance was observed in N87-TM cells against T-mcMalPegMMAD, another trastuzumab ADC with a different non-cleavable linker delivering monomethyl dolastatin (MMAD) (FIG. 14).

Figure 15C:
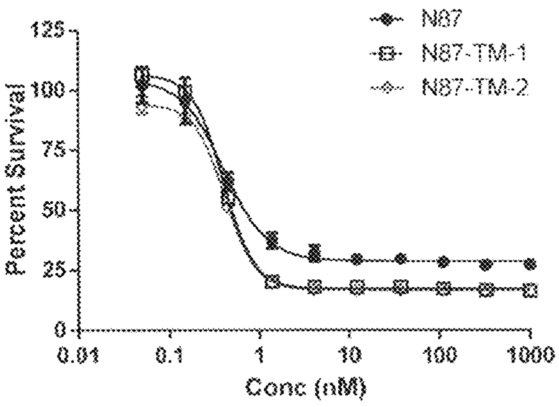
Figure 15D:
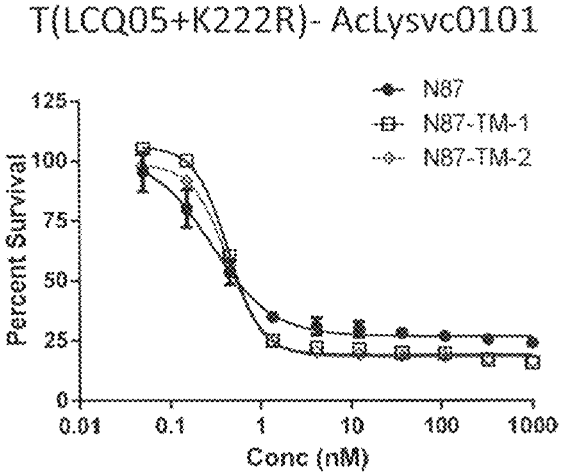
Figure 15E:
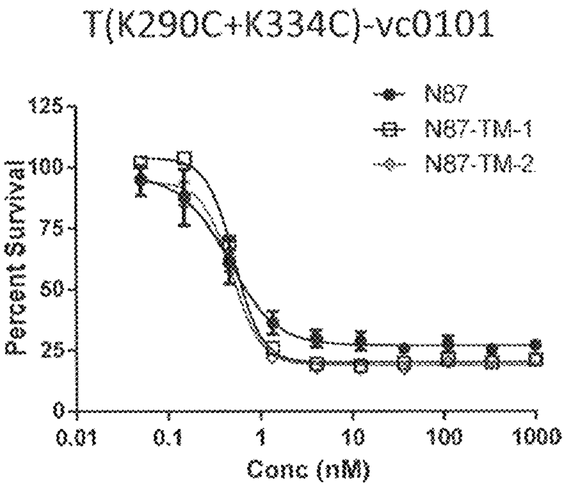
Figure 15F:
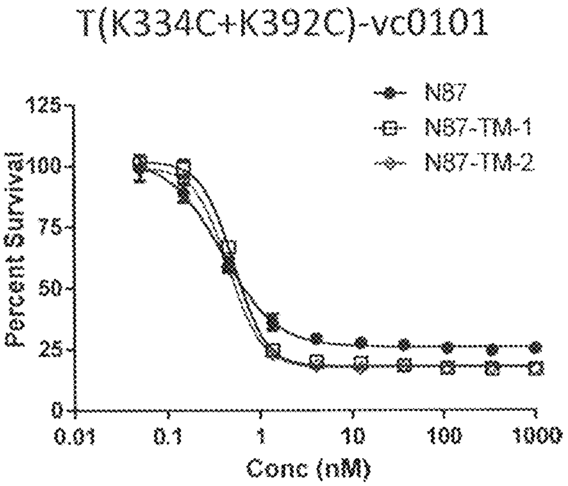
Figure 15G:
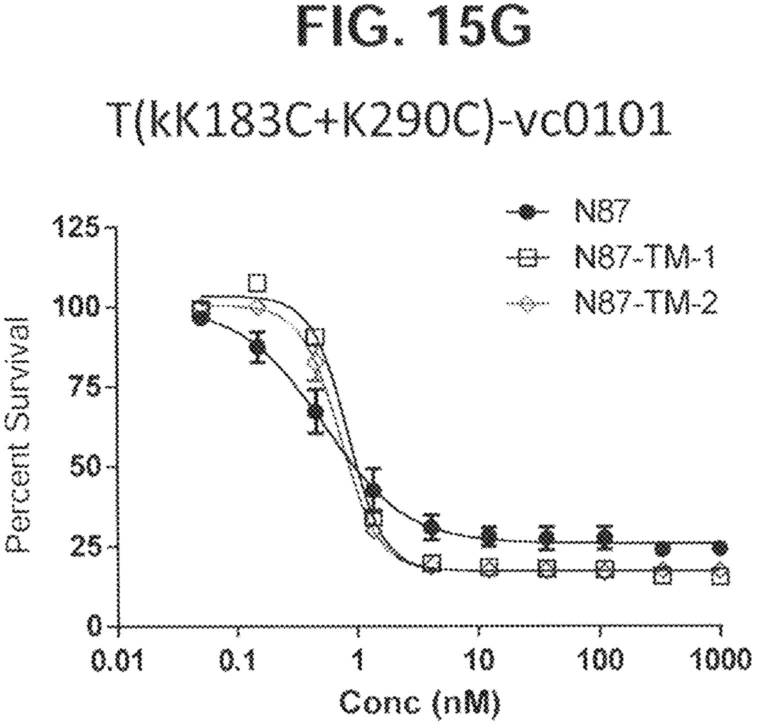

Remarkably, it was observed that the N87-TM cell line retained sensitivity to payloads when delivered via a cleavable linker, even though these drugs functionally inhibit similar targets (i.e., microtubule depolymerization). Examples of ADCs which overcome resistance include, but are not limited to, T(N297Q+K222R)-AcLysvc0101 (FIG. 14 and FIG. 15C), T(LCQ05+K222R)-AcLysvc0101 (FIG. 14 and FIG. 15D), T(K290C+K334C)-vc0101 (FIG. 10 and FIG. 11E), T(K334C+K392C)-vc0101 (FIG. 14 and FIG. 15F) and T(kK183C+K290C)-vc0101 (FIG. 14 and FIG. 15G). These represent trastuzumab-based ADCs delivering the auristatin analog 0101, but where the payloads are released intracellularly by proteolytic cleavage of the vc linker.

In order to determine whether these ADC-resistant cancer cells were broadly resistant to other therapies, the N87-TM cell models were treated with a panel of standard-of-care chemotherapeutics with various mechanisms of action. In general, small molecule inhibitors of microtubule and DNA function remained effective against the N87-TM resistant cell lines (FIG. 14). While these cells were made resistant against an ADC delivering an analog of the microtubule depolymerizing agent, maytansine, minimal or no cross-resistance was observed to several tubulin depolymerizing or polymerizing agents. Similarly, both cell lines retained sensitivity to agents which interfere with DNA function, including topoisomerase inhibitors, anti-metabolites, and alklyating/cross-linking agents. In general, the N87-TM cells were not refractory to a broad range of cytotoxics, ruling out generic growth or cell cycle defects which might mimic drug resistance.

Both N87-TM populations also retained sensitivity to the corresponding unconjugated drugs (i.e., DM1 and 0101; FIG. 14). Hence, N87-TM cells made refractory to a trastuzumab-maytansinoid conjugate displayed cross-resistance to other microtubule-based ADCs when delivered via non-cleavable linkers, but remained sensitive to unconjugated microtubule inhibitors and other chemotherapeutics.

Figure 16B:
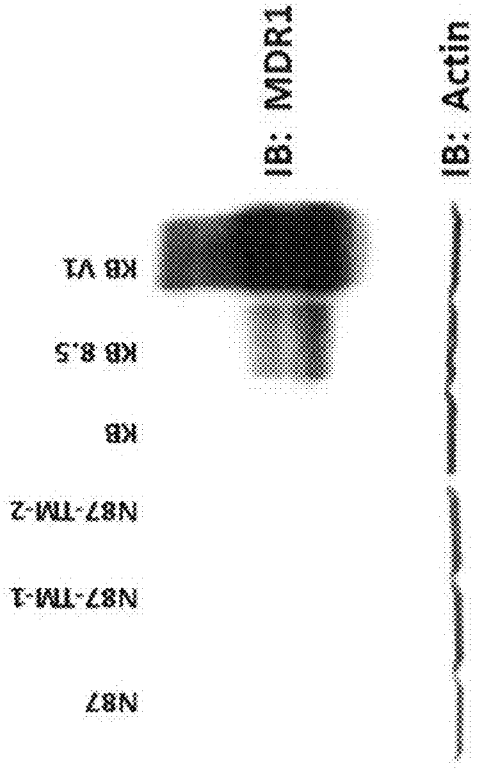
FIGS. 16A-16B depict western blots showing (A) MRP1 drug efflux pump and (B) MDR1 drug efflux pump protein expression on T-DM1 sensitive (N87 cells) and resistant (N87-TM1 and N87-TM2) gastric cancer cells.
Figure 16A:
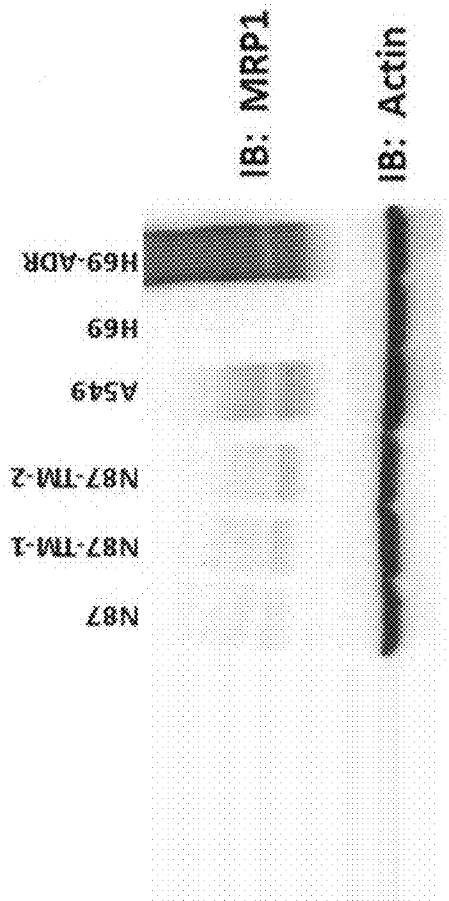

To determine the molecular mechanism of resistance to T-DM1 in the N87-TM cells protein expression levels of MDR1 and MRP1 drug efflux pumps were determined. This was because small molecule tubulin inhibitors are known substrates of the MDR1 and MRP1 drug efflux pumps (Thomas and Coley, 2003, Cancer Control 10(2):159-165). The protein expression levels of these two proteins from total cell lysates of the parental N87 and N87-TM resistant cells was determined (FIG. 16). Immunoblot analysis showed that the N87-TM resistant cells do not significantly overexpress the MRP1 (FIG. 16A) or MDR1 (FIG. 16B) proteins. Taken together, these data combined with the lack of cross-resistance to known substrates of drug efflux pumps (e.g. paclitaxel, doxorubicin) in the N87-TM cells suggests that drug efflux pump overexpression is not the molecular mechanism of T-DM1 resistance in N87-TM cells.

Figure 17A:
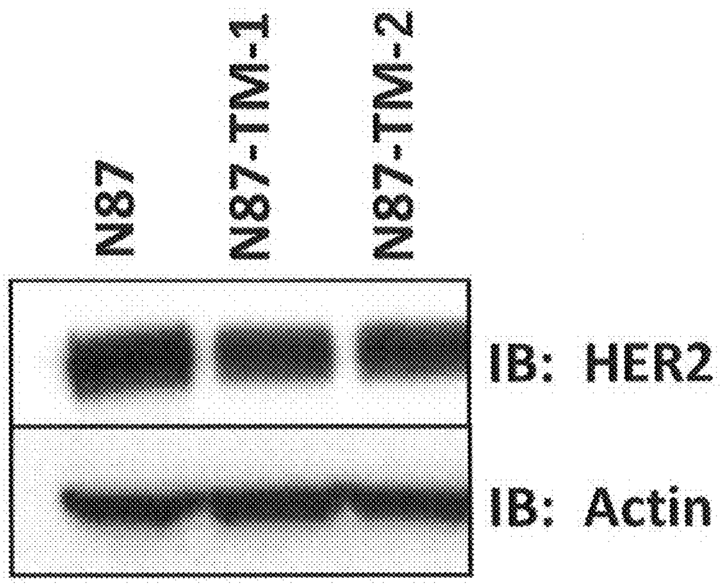
FIGS. 17A-17B depict HER2 expression and binding to trastuzumab of T-DM1 sensitive (N87 cells) and resistant (N87-TM1 and N87-TM2) gastric cancer cells. (A) a western blot showing HER2 protein expression and (B) trastuzumab binding to cell surface HER2.

Since the mechanism of action for ADCs requires binding to a specific antigen, antigen depletion or reduced antibody binding may account for T-DM1 resistance in N87-TM cells. To determine if the antigen for T-DM1 had been significantly depleted in N87-TM cells, HER2 protein expression levels from total cell lysates of the parental N87 and N87-TM resistant cells were compared (FIG. 17A). Immunoblot analysis showed that the N87-TM cells did not have a markedly reduced amount of HER2 protein expression compared with the parental N87 cells.

Figure 17B:
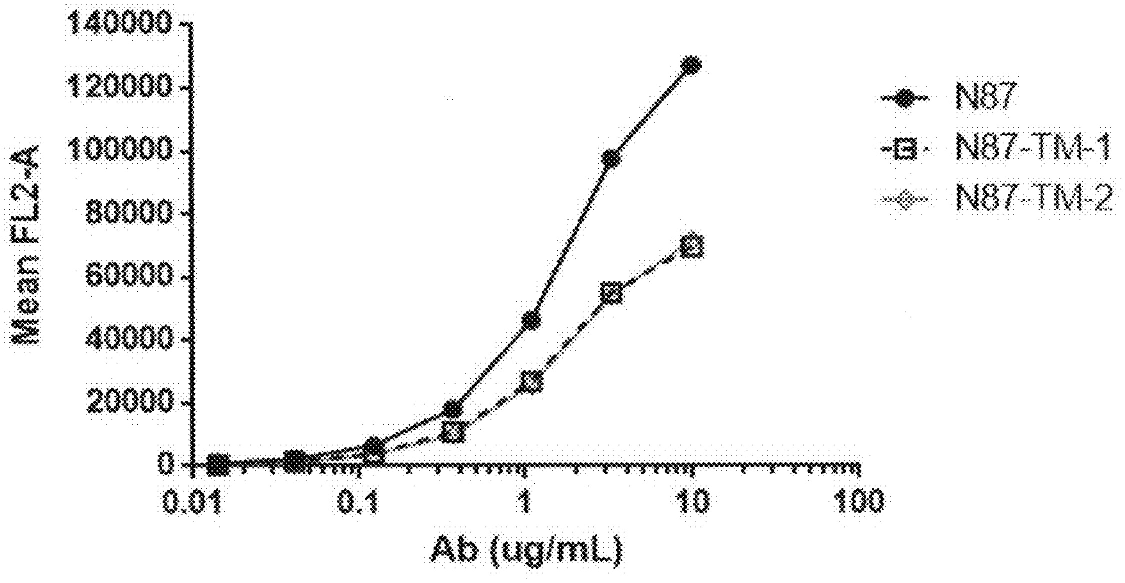

The amount of antibody binding to cell surface HER2 antigens of the N87-TM cells was determined. In a cell surface binding study using fluorescence activated cell sorting, the N87-TM cells did have ~50% decrease in trastuzumab binding to cell surface antigens (FIG. 17B). Since N87 cells are high expressers of HER2 protein among cancer cell lines (Fujimoto-Ouchi et al., 2007, Cancer Chemother Pharmacol 59(6):795-805), a ~50% reduction in HER2 antibody binding in these cells probably does not represent the driving mechanism of resistance to T-DM1 in N87-TM cells. Evidence supporting this interpretation is that the N87-TM resistant cells remain sensitive to other HER2 binding trastuzumab derived ADCs with different linkers and payloads (FIG. 14).

Figure 18A:
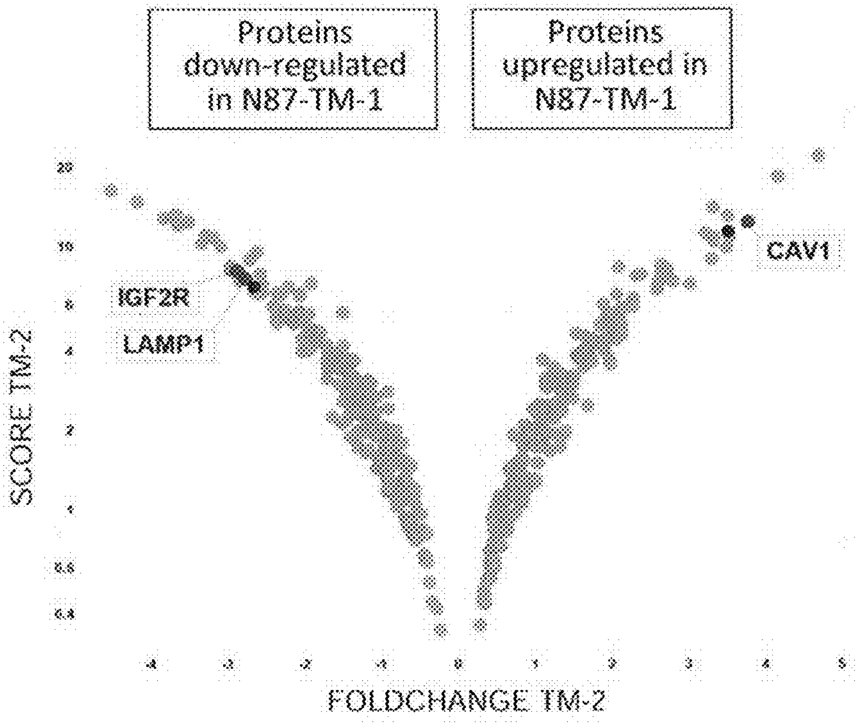
FIGS. 18A-18D depict characterization of protein expression levels in T-DM1 sensitive (N87 cells) and resistant (N87-TM1 and N87-TM2) gastric cancer cells. (A) protein expression level changes in 523 proteins; (B) western blots showing protein expression of IGF2R, LAMP1 and CTSB; (C) western blot showing protein expression of CAV1; (D) IHC of CAV1 protein expression in tumors generated in vivo from implantation of N87 cells (left panel) and N87-TM2 cells (right panel).
Figure 18B:
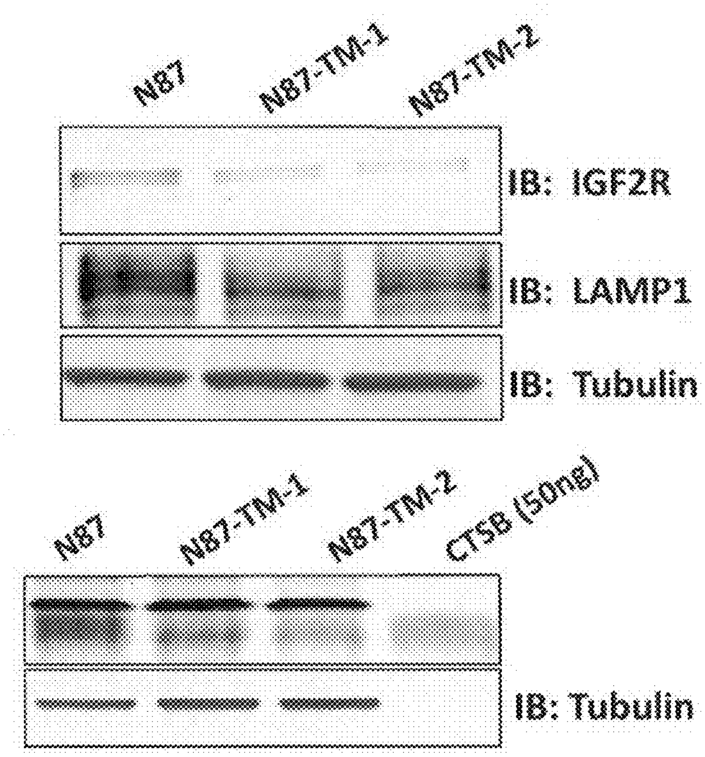
Figure 18C:
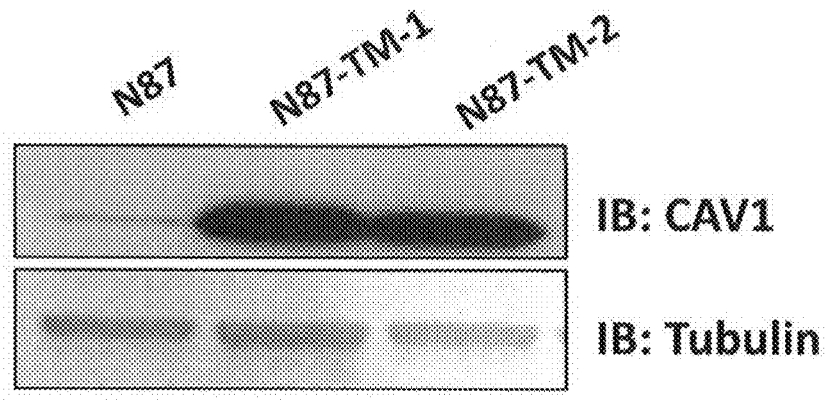
Figure 18D:
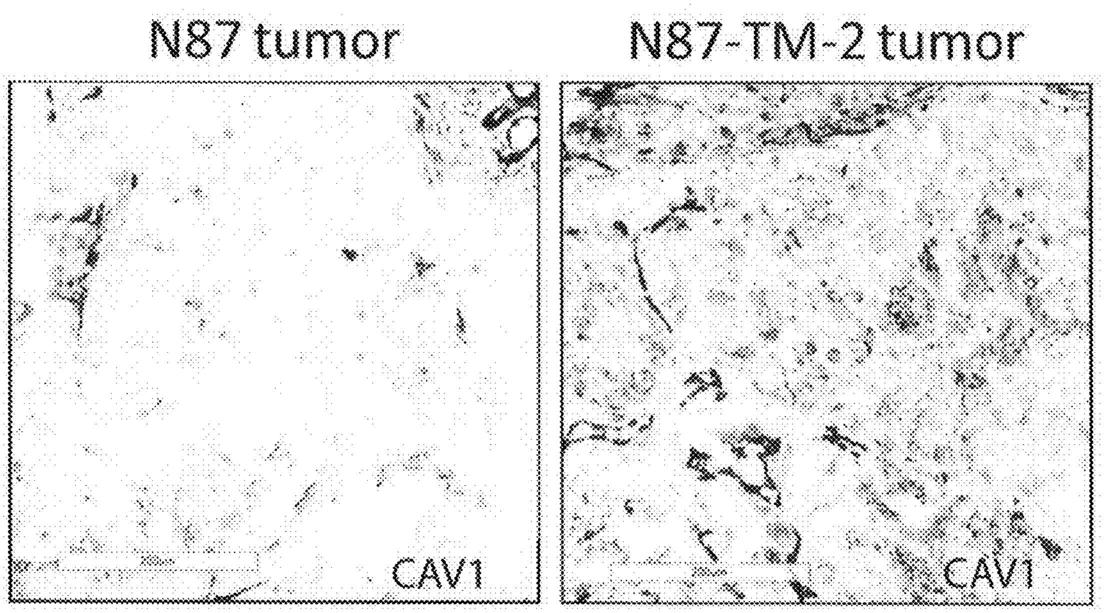

In order to determine potential mechanisms of T-DM1 resistance in an unbiased approach, the parental N87 and N87-TM resistant cell models were profiled via a proteomic approach in order to globally identify changes in membrane protein expression levels that may be responsible for T-DM1 resistance. Significant expression level changes in 523 proteins between both cell line models was observed (FIG. 18A). To validate a selection of these predicted protein changes, immunoblots on N87 and N87-TM whole cell lysates were performed for proteins predicted to be under-expressed (IGF2R, LAMP1, CTSB) (FIG. 18B) and over-expressed (CAV1) (FIG. 18C) in the N87-TM cells relative to the N87 cells. In vivo tumors were generated by subcutaneous implantation of the N87 and N87-TM-2 cells into NSG mice to assess if protein changes observed in vivo mimic those seen in vitro. N87-TM-2 tumors retained over-expression of the CAV1 protein compared with the N87 tumors (FIG. 18D). While CAV1 staining in the mouse stroma in both models is expected, epithelial CAV1 staining was only seen in the N87-TM-2 model.

C. In Vivo Efficacy Studies

In order to determine if the resistance observed in cell culture was recapitulated in vivo, parental N87 cells and N87-TM-2 cells were expanded and injected into the flanks of Female NOD scid gamma (NSG) immunodeficient mice (NOD.Cg-Prkdcscid Il2rgtm1WjI/SzJ) obtained from The Jackson Laboratory (Bar Harbor, Me.). Mice were injected subcutaneously in the right flank with suspensions of either N87 or N87-TM cells ($7.5\times10^6$ cells per injection, with 50%

Matrigel). Mice were randomized into study groups when tumors reached ~0.3 g (~250 $mm^3$). T-DM1 conjugate or vehicle, were administered intravenously in saline on day 0 and repeated for a total of four doses, four days apart (Q4Dx4). Tumors were measured weekly and mass calculated as volume=(width×width×length)/2. Time-to-event analysis (tumor doubling) was conducted and significance evaluated by Log-rank (Mantel-Cox) test. No weight loss was observed in mice in all treatment groups in these studies.

Figure 20A:
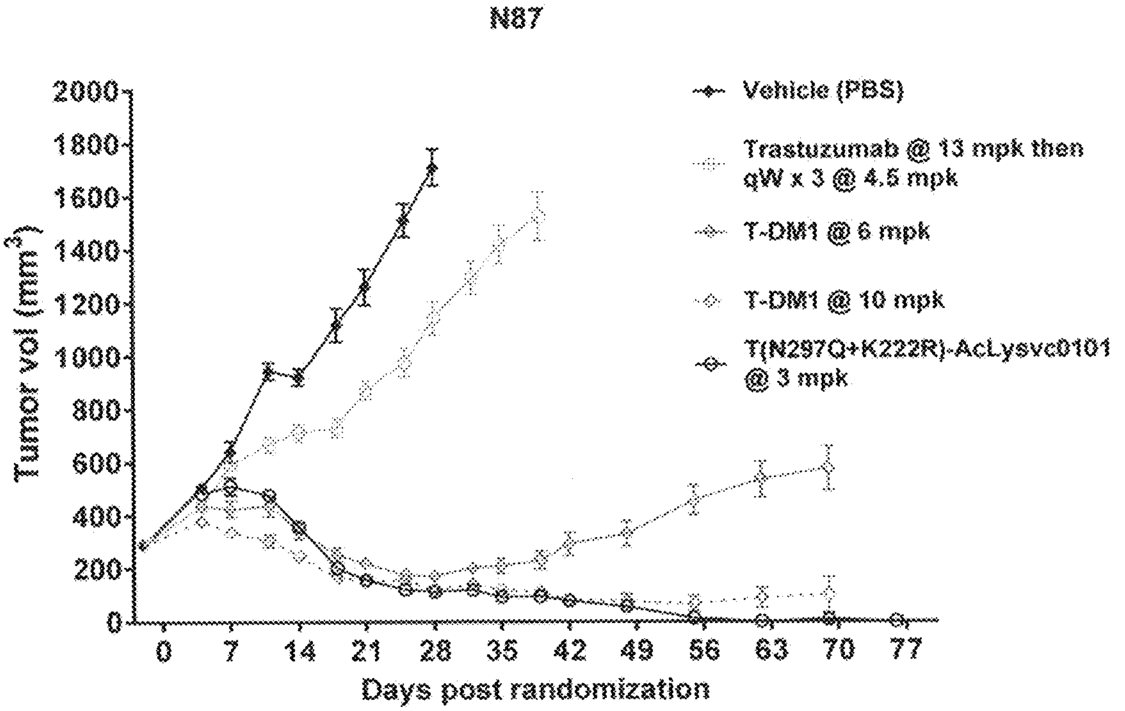
FIGS. 20A-20F depict sensitivity to trastuzumab and various trastuzumab derived ADCs of tumors generated in vivo from implantation of T-DM1 sensitive N87 parental cells and T-DM1 resistant N87-TM2 or N87-TM1 cells. (A) N87 tumor size was plotted over time in the presence of trastuzumab or two trastuzumab derived ADCs; (B) N87-TM2 tumor size was plotted over time in the presence of trastuzumab or two trastuzumab derived ADCs; (C) time for N87 cell tumor to double in size in the presence of in the presence of trastuzumab or two trastuzumab derived ADCs; (D) time for N87-TM2 cell tumor to double in size in the presence of trastuzumab or two trastuzumab derived ADCs; (E) N87-TM2 tumor size was plotted over time in the presence of seven different trastuzumab derived ADCs; (F) N87-TM1 tumor size was plotted over time with a trastuzumab derived ADC added at day 14.
Figure 20B:
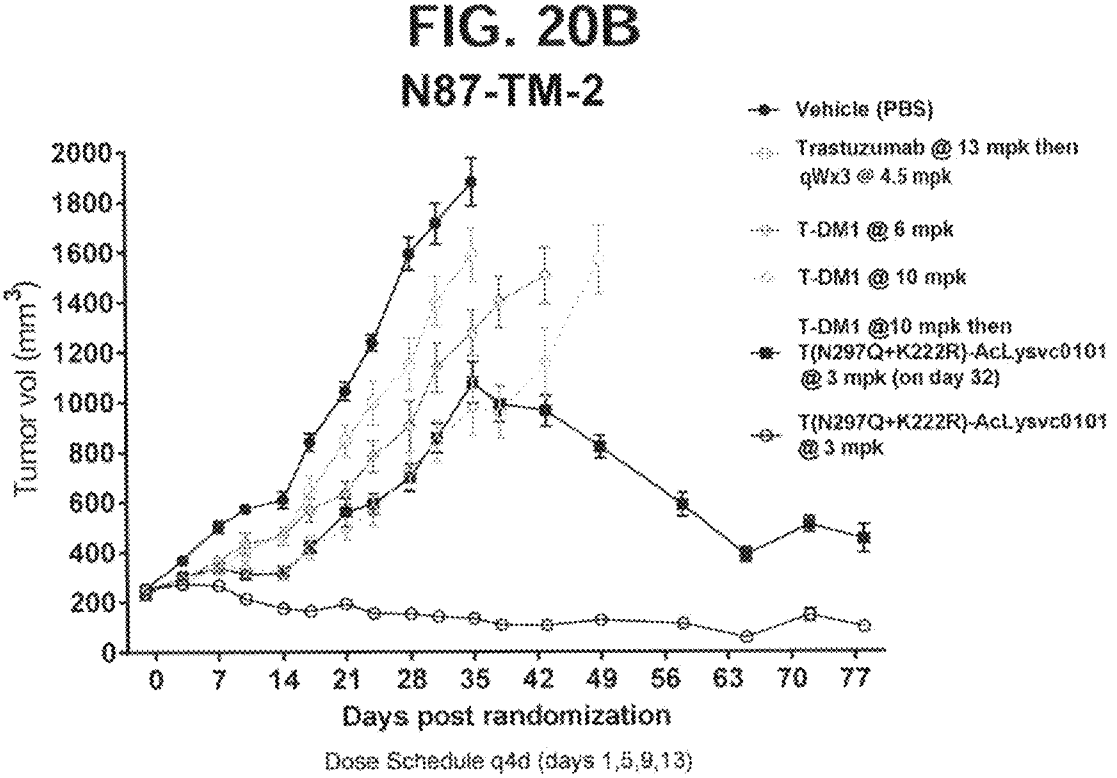
Figure 20C:
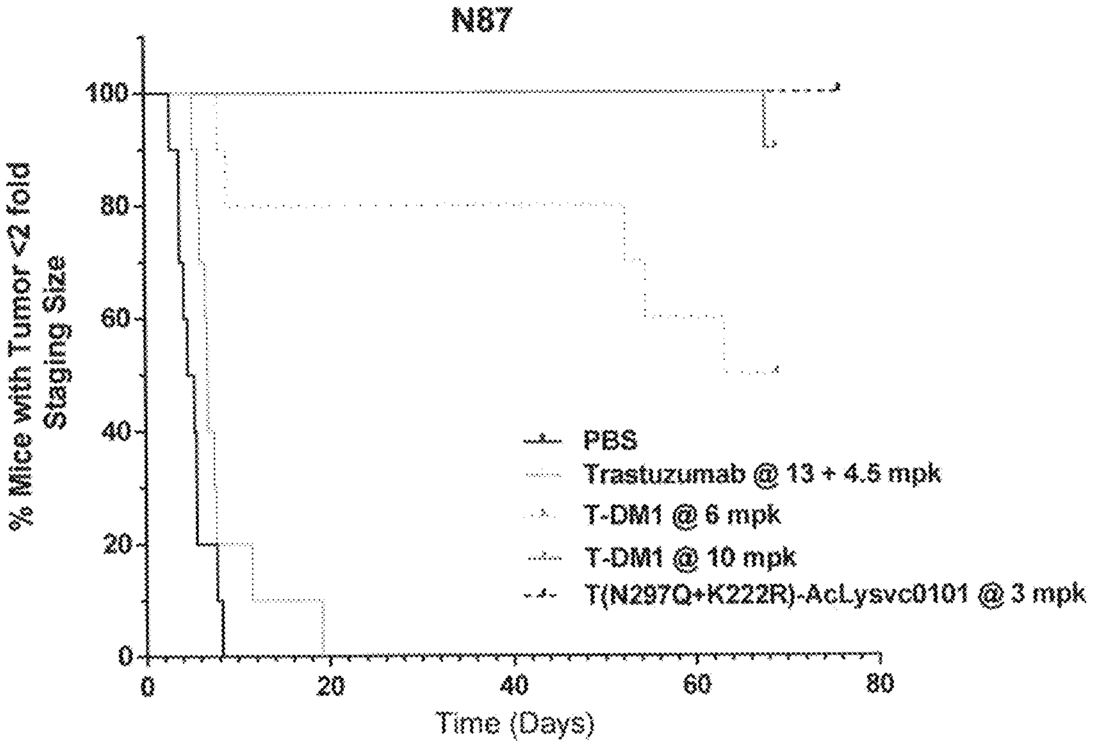
Figure 20D:
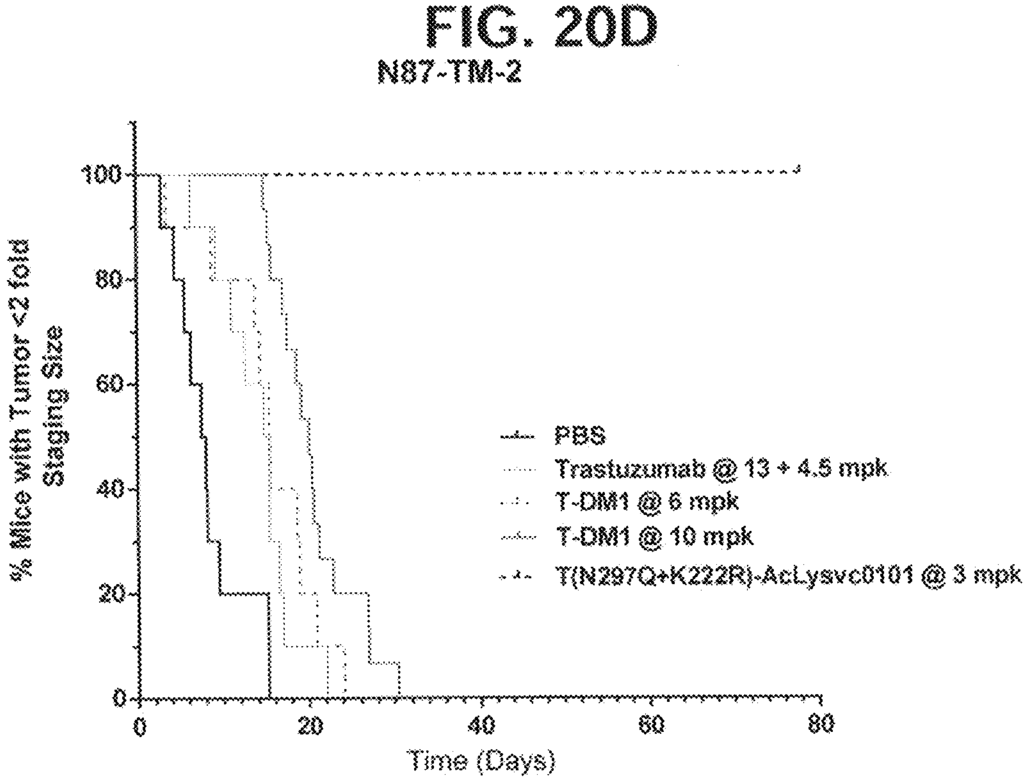

Mice were treated with the following agents: (1) vehicle control PBS, (2) trastuzumab antibody at 13 mg/kg, followed by 4.5 mg/kg; (3) T-DM1 at 6 mg/kg; (4) T-DM1 at 10 mg/kg; (5) T-DM1 at 10 mg/kg, then T(N297Q+K222R)-AcLysvc0101 at 3 mg/kg; (6) T(N297Q+K222R)-AcLysvc0101 at 3 mg/kg. Tumor sizes were monitored and results are indicated in FIG. 20. The N87 (FIG. 19 and FIG. 20A) and N87-TM-2 (FIG. 19 and FIG. 20B) tumors showed an ADC efficacy profile similar to that seen in the in vitro cytotoxicity assays (FIGS. 19 and 20B), wherein the N87-TM drug resistant cells were refractory to T-DM1 but still responded to trastuzumab derived ADCs with cleavable linkers. In fact, tumors that were refractory to T-DM1 and grew to about 1 gram were switched to therapy with T(N297Q+K222R)-AcLysvc0101 and effectively regressed (FIG. 20B). In a time-to-event analysis of this study, T-DM1 at 6 and 10 mg/kg prevented tumor doubling in >50% of mice for at least 60 days in the N87 model, but T-DM1 failed to do so in the N87-TM-2 model (FIGS. 20C and 20D). T(N297Q+K222R)-AcLysvc0101 dosed at 3 mg/kg prevented any tumor doubling of both N87 and N87-TM tumors in the mice for the duration of the study (~80 days) (FIGS. 20C and 20D).

Figure 20E:
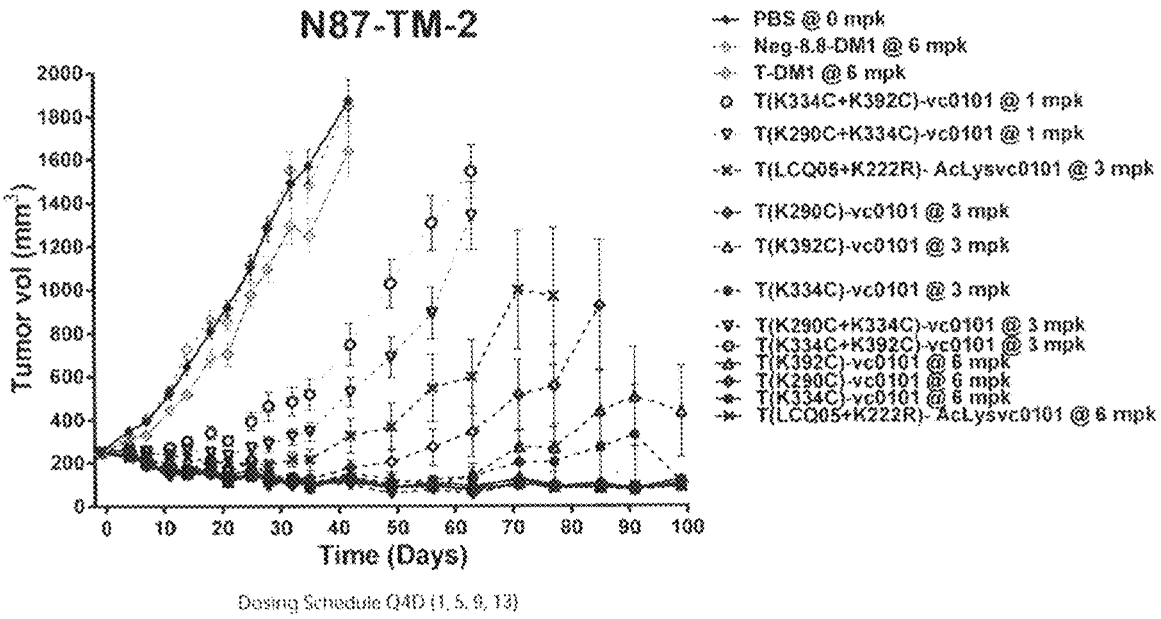

In another study, all cleavable linked ADCs that overcame T-DM1 resistance in vitro remained effective in this N87-TM2 tumor model that was non-responsive to T-DM1 (FIG. 19 and FIG. 20E).

Figure 20F:
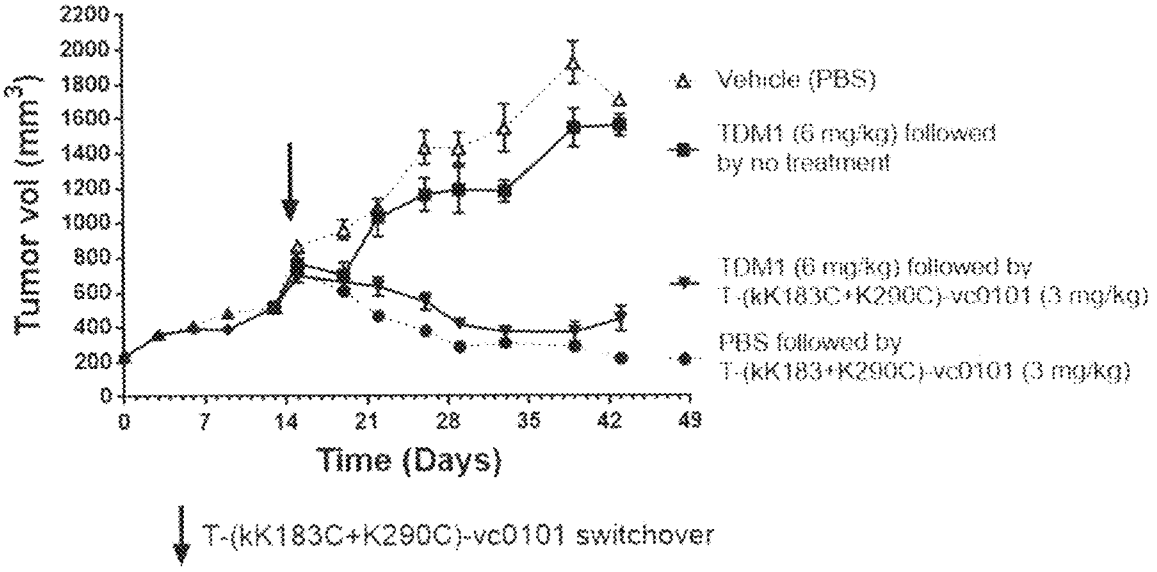

It was then assessed whether T(kK183+K290C)-vc0101 ADC could inhibit the growth of tumors which were refractory to TDM1. N87-TM tumors treated with either vehicle or T-DM1 grew through these treatments, however tumors switched to T(kK183C+K290C)-vc0101 therapy at day 14 immediately regressed (FIG. 20F).

Example 15: In Vivo T-DM1 Resistant Models

A. Generation of T-DM1 Resistant Cells In Vivo

All animal studies were approved by the Pfizer Pearl River Institutional Animal Care and Use Committee according to established guidelines. To generate xenografts, nude (Nu/Nu) female mice were implanted subcutaneously with $7.5\times10^6$ N87 cells in 50% Matrigel (BD Biosciences). The animals were randomized when average tumor volume reach ~300 $mm^3$ into two groups: 1) vehicle control (n=10) and 2) T-DM1 treated (n=20). T-DM1 ADC (6.5 mg/kg) or vehicle (PBS) were administered intravenously in saline on day 0 and then the animals were dosed weekly with 6.5 mg/kg for up to 30 weeks. Tumors were measured twice per week or weekly and mass calculated as volume=(width×width×length)/2. No weight loss was observed in mice in all treatment groups in these studies.

Figure 21A:
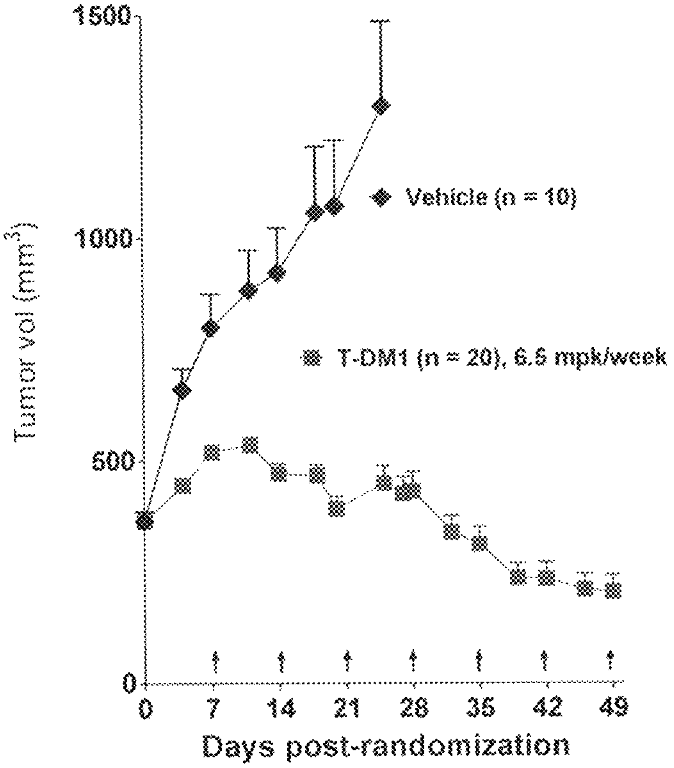
FIGS. 21A-21E depict generation and characterization of T-DM1 resistant cells generated in vivo. (A) N87 gastric cancer cells were initially sensitive to T-DM1 when implanted in vivo. (B) Over time, the implanted N87 cells became resistant to T-DM1 but remained sensitive to (C) T-vc0101, (D) T(N297Q+K222R)-AcLysvc0101 and (E) T(kK183+K290C)-vc0101.
Figure 21B:
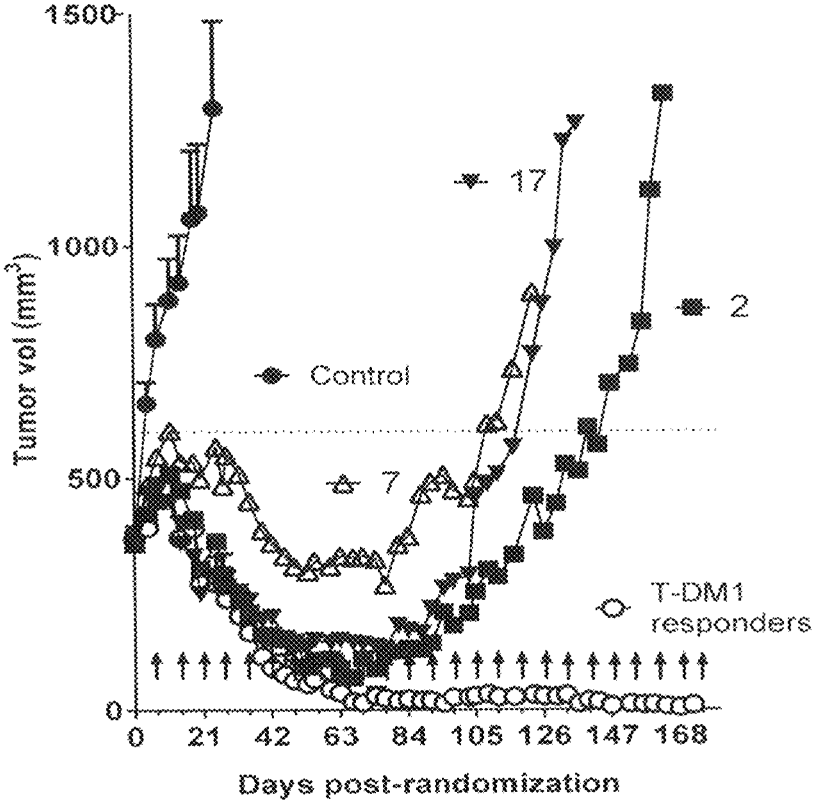
Figure 21C:
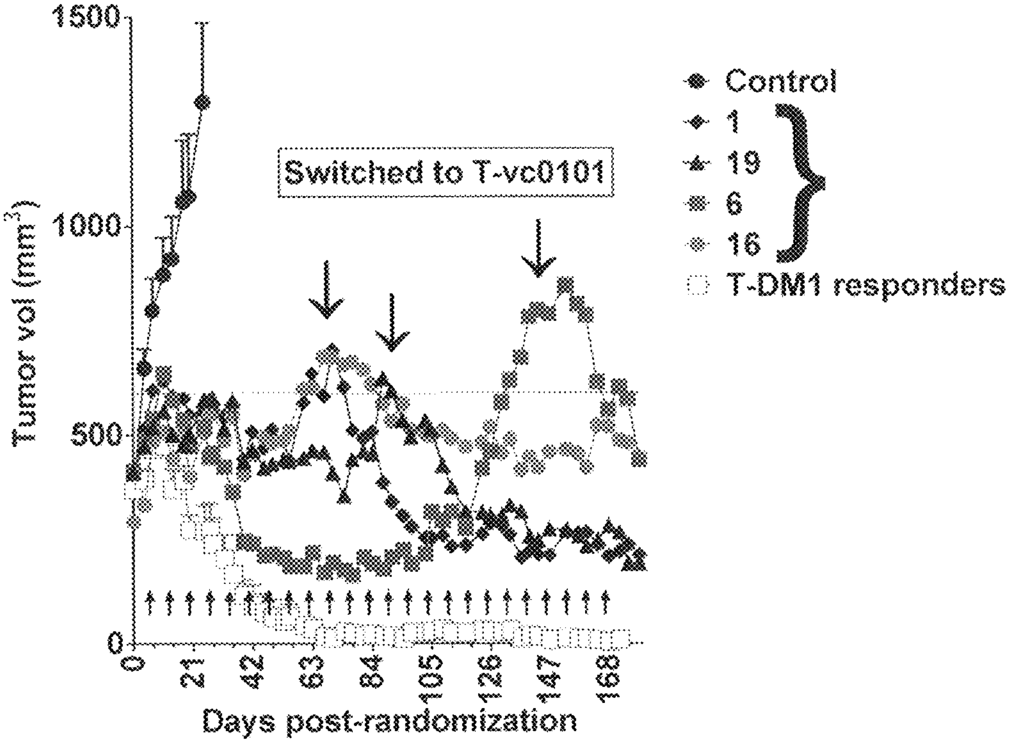

Animals were considered refractory or relapsed under T-DM1 treatment when the individual tumor volume reached ~600 $mm^3$ (doubled original size of tumor at randomization). Compared to control group, most tumors initially responded to T-DM1 treatment as shown in FIG. 21A. More specifically, 17 out of 20 mice responded to initial T-DM1 treatment but significant number of tumors (13 out of 20) relapsed under T-DM1 treatment. Over time the implanted N87 tumor cells became resistant to T-DM1 (FIG. 21B). Three tumors that did not initially responded to T-DM1 treatment were harvested for Her2 expression determination by IHC indicating no HER2 expression changes. The remaining 10 relapsed tumors are described below.

Four tumors which initially responded to T-DM1 treatment and then relapsed were switched to T-vc0101 treatment weekly at 2.6 mg/kg on day 77 (mice 1 and 16), 91 (mouse 19), 140 (mouse 6). As shown in FIG. 19C, T-DM1 resistant tumors generated in vivo responded to T-vc0101 indicating acquired T-DM1 resistant tumors are sensitive to vc0101 ADC treatment.

Figure 21D:
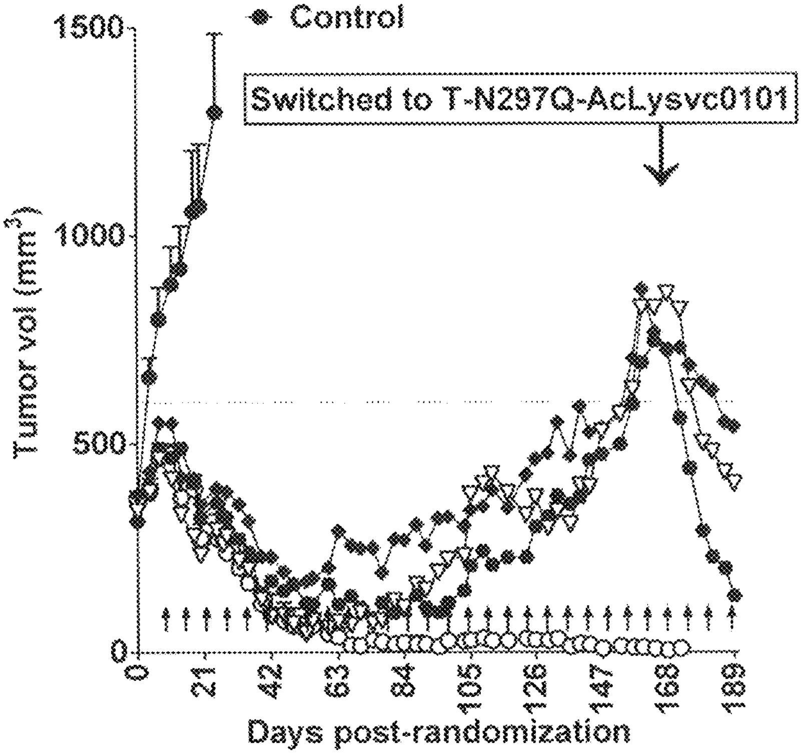
Figure 21E:
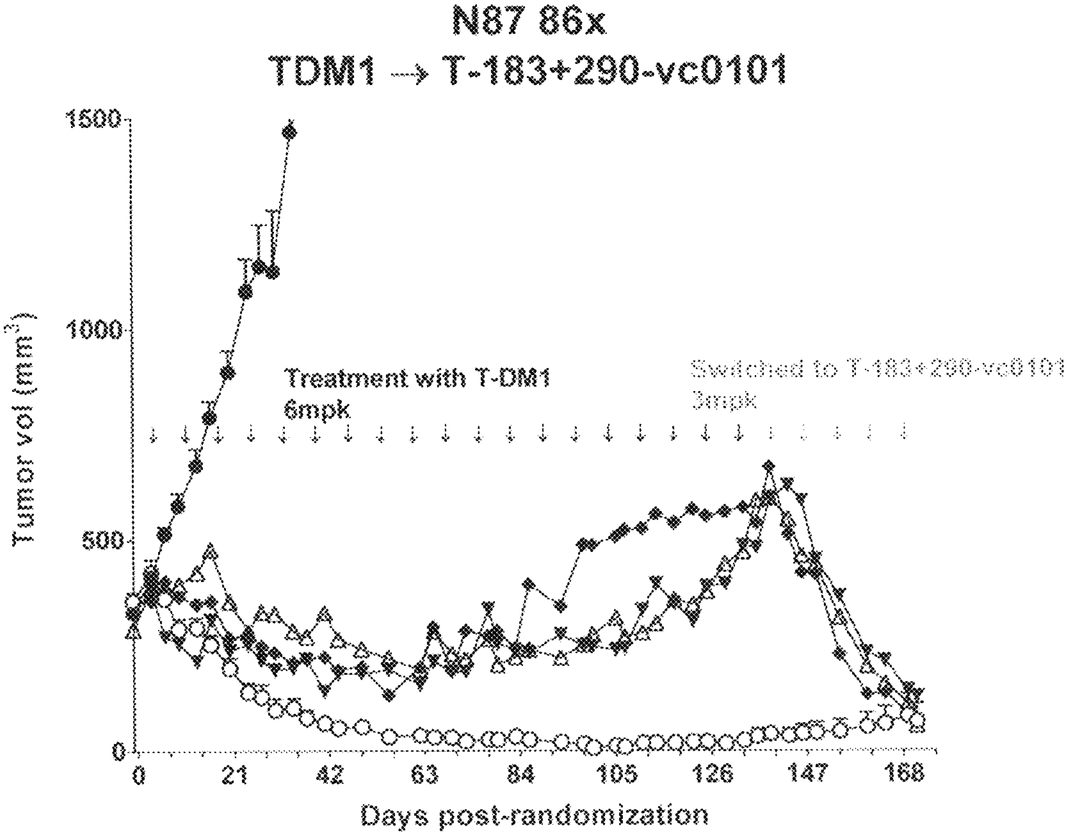

Another three tumors initially responded to T-DM1 treatment and then relapsed were switched to T(N297Q+K222R)-AcLysvc0101 treatment weekly at 2.6 mg/kg on day 110 (mice 4, 13, and 18). As shown in FIG. 21D, T-DM1 resistant tumors generated in vivo also responded to T(N297Q+K222R)-AcLysvc0101. A follow-on experiment was performed to evaluate T(kK183C+K290C)-vc0101, similar results were obtained indicating that T-DM1 resistant tumors generated in vivo were sensitive to T(kK183C+K290C)-vc0101 treatment as shown in FIG. 21E.

In summary, all T-DM1 refractory tumors having follow-on treatment were sensitive to the vc0101 ADC treatment (7 of 7) indicating that in vivo resistant T-DM1 tumors can be treated with cleavable vc0101 conjugates.

Additional three tumors (mouse 7, 17 and 2 as shown in FIG. 21B) initially responded to T-DM1 and then relapsed were excised for in vitro characterization. After 2-5 months of culturing the excised tumors in vitro these cells were evaluated for resistance to T-DM1 and characterized in vitro (see Sections B and C of this Example below).

B. Cytotoxicity Studies

Cells relapsed from T-DM1 treatment and cultured in vitro (as described in Section A of this Example) were seeded in 96-well plates and dosed the following day with 4-fold serial dilutions of the ADCs or unconjugated payloads. Cells were incubated for 96 hours in a humidified 37° C./5% $CO_2$ incubator. CellTiter Glo Solution (Promega, Madison, Wis.) was added to the plates and absorbance measured on a Victor plate reader (Perkin-Elmer, Waltham, Mass.) at wavelength 490 nm. $IC_{50}$ values were calculated using a four-parameter logistic model with XLfit (IDBS, Bridgewater, N.J.).

Figure 22A:
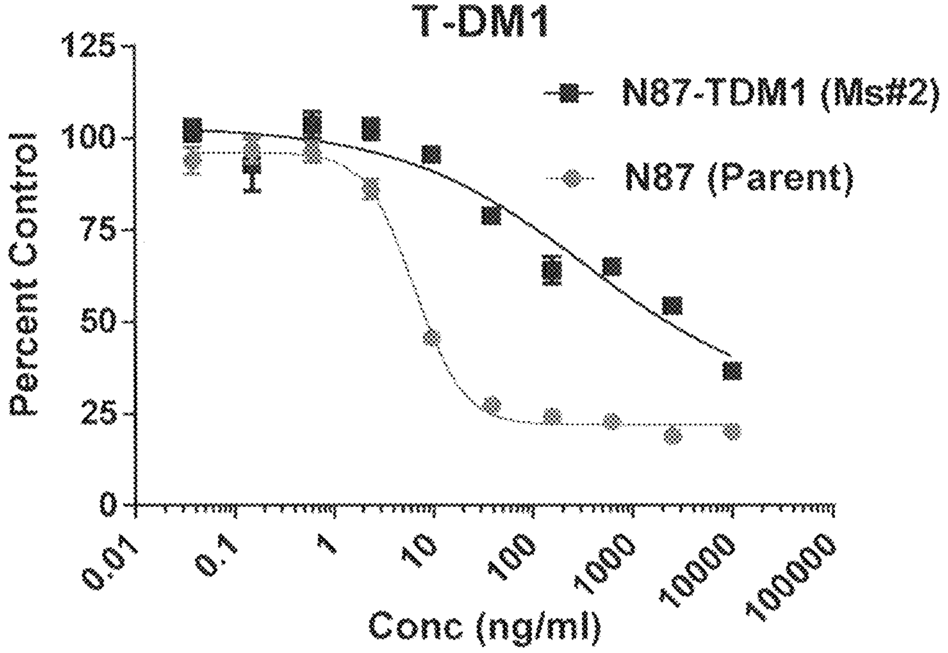
FIGS. 22A-22D depict in vitro cytotoxicity of four trastuzumab derived ADCs on T-DM1 resistant cells (N87-TDM) generated in vivo compared to T-DM1 sensitive parental N87 cells with tumor volume plotted over time. (A) T-DM1; (B) T(kK183+K290C)-vc0101; (C) T(LCQ05+K222R)-AcLysvc0101; (D) T(N297Q+K222R)-AcLysvc0101.
Figure 22B:
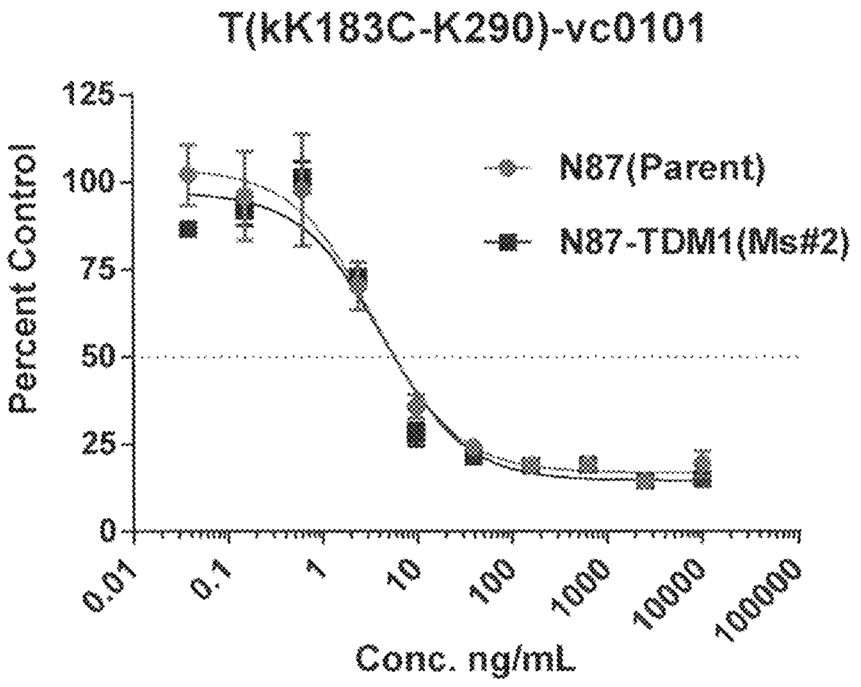
Figure 22C:
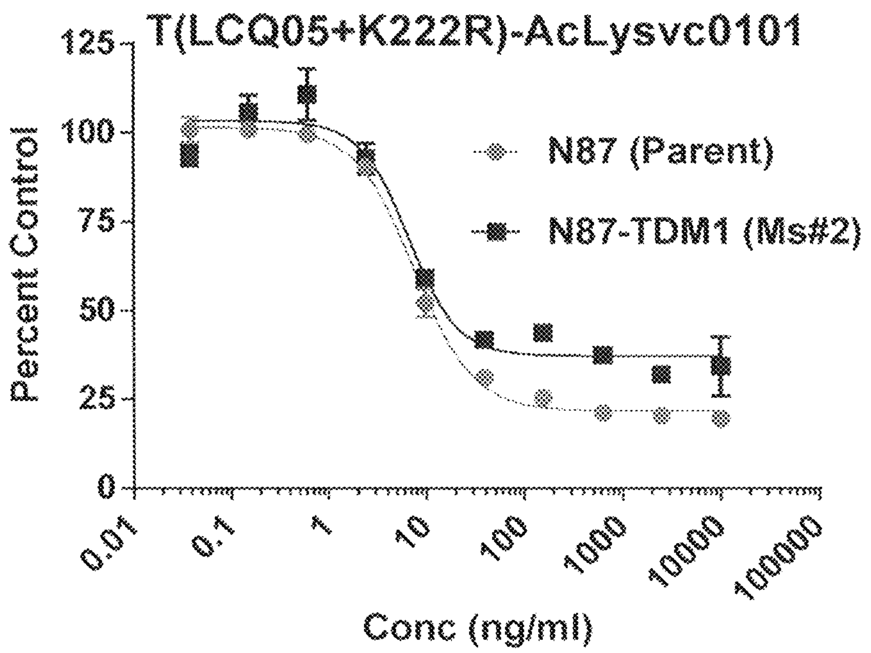
Figure 22D:
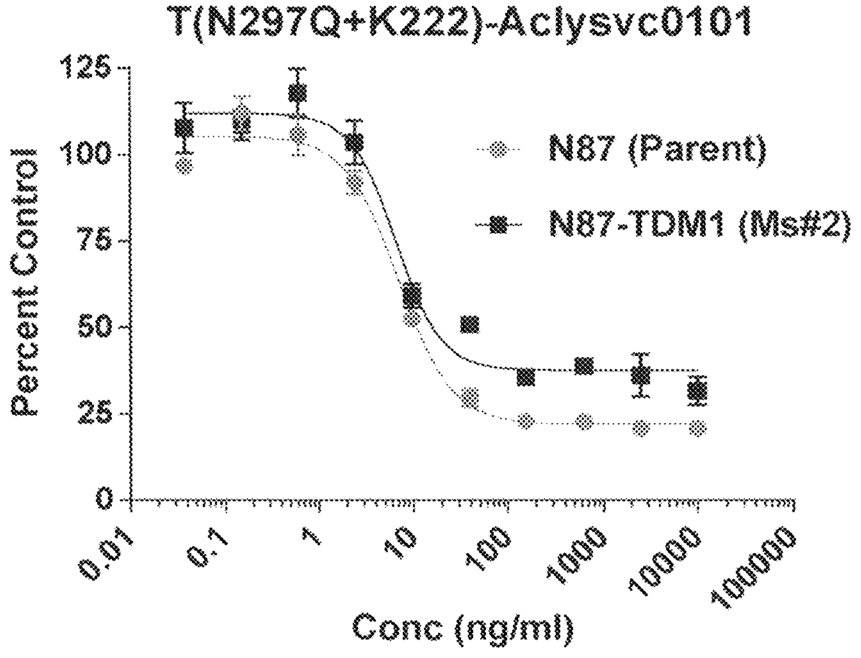

Cytotoxicity screening results are summarized in Tables 19 and 20. The cells were resistant to T-DM1 (FIG. 22A) when compared to the parental but sensitive to cleavable vc0101 conjugates T-vc0101 (data not shown), T(kK183C+K290C)-vc0101 (FIG. 22B), T(LCQ05+K222R)-AcLysvc0101 (FIG. 22C) and T(N297Q+K222R)-AcLysvc0101 (FIG. 22D) (Table 19). The T-DM1 resistant cells were surprisingly sensitive to the parent payload DM1 as well as the 0101 payload (Table 20).

TABLE 19

| Resistant Cell Sensitivity to ADCs | | | | | |
|---|---|---|---|---|---|
| ADC | N87 parental | N87-T-DM1 Mouse #7 | N87-T-DM1 Mouse #17 | N87-T-DM1 Mouse #2 | Fold Resistance |
| T-DM1 | 16 | 1388 | 944 | 3700 | ~60-230 |
| T(kK183C+K290C)-vc0101 | 5 | — | — | 5 | 1 |
| T(LCQ05+K222R)-AcLysvc0101 | 25 | 9 | 10 | 18 | ~1 |
| T(N297Q+K222R)-AcLysvc0101 | 9 | 7 | 13 | 16 | ~1 |
| T(K334C+K392C)-vc0101 | 6 | — | 11 | 4 | ~1 |
| T(K290C+K334C)-vc0101 | 6 | — | 16 | 4 | ~1-2 |

$IC_{50}$ values are shown for each of the cell lines

TABLE 20

| Resistant Cell Line Sensitivity to Free Payload | | | |
|---|---|---|---|
| Cell Line | DM1-Sme | Aur-0101 | Doxorubicin |
| N87 | 10 | 0.5 | 48 |
| N87-T-DM1_Ms2 | 23 | 0.40 | 46 |
| N87-T-DM1_Ms7 | 20 | 0.60 | 79 |
| N87-T-DM1_Ms17 | 27 | 0.28 | 34 |

C. Her2 Expression by FACS and Western Blot

Her2 expression was characterized on cells relapsed from T-DM1 treatment and cultured in vitro (as described in Section A of this Example). For FACS analysis, cells were trypsinized, spun down and resuspended in fresh media. The cells were then incubated for one hour at 4° C. with 5 μg/mL of Trastuzumab-PE (custom synthesized 1:1 PE labeled Trastuzumab by eBiosciences (San Diego, Calif.)). The cells were then washed twice and then resuspended in PBS. The mean fluorescence intensity was read using Accuri flow cytometer (BD Biosciences San Jose, Calif.).

For western blot analysis, the cells were lysed using RIPA lysis buffer (with protease inhibitors and phosphatase inhibitor) on ice for 15 minutes then vortexed and spun down at maximum speed in a microcentrifuge at 4° C. The supernatant was collected and 4× sample buffer and reducing agent were added to the samples normalizing for total protein in each sample. The samples were run on a 4-12% Bis tris gel and transferred on to nitrocellulose membrane. The membranes were blocked for an hour and incubated with HER2 antibody (Cell Signalling, 1:1000) over night at 4° C. The membranes were then washed 3 times in 1×TBST and incubated with an anti-mouse HRP antibody (Cell Signalling, 1:5000) for 1 hour washed 3 times and probed.

Figure 23A:
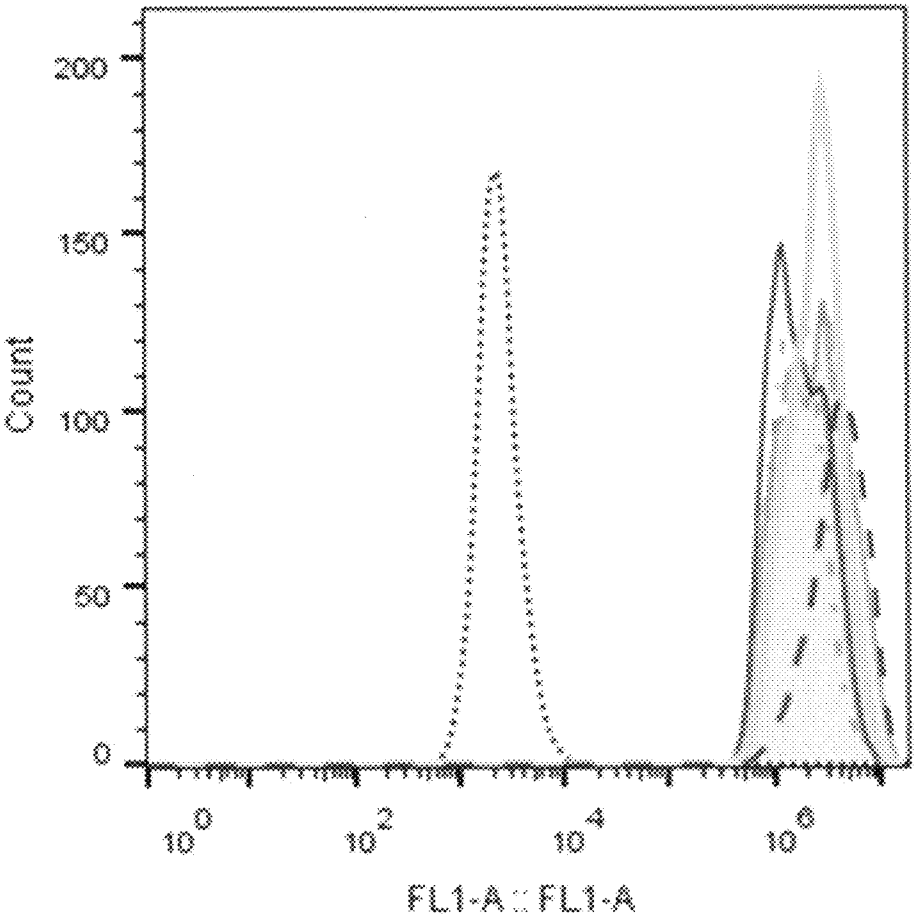
FIGS. 23A-23B depict HER2 protein expression levels on T-DM1 resistant cells (N87-TDM1, from mice 2, 17 and 18) generated in vivo compared to T-DM1 sensitive parental N87 cells. (A) FACS analysis and (B) western blot analysis. No significant difference in HER2 protein expression was observed.
Figure 23B:
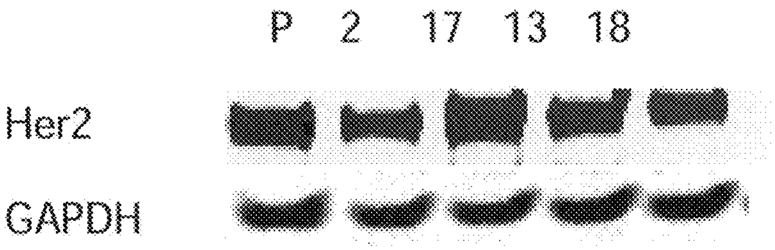

The HER2 expression levels of the T-DM1 relapsed tumors were similar to the control tumors (without T-DM1 treatment) as evaluated by FACS (FIG. 23A) and western blot (FIG. 23B).

D. T-DM1 Resistance is not Due to Expression of Drug Efflux Pumps

Figure 24A:
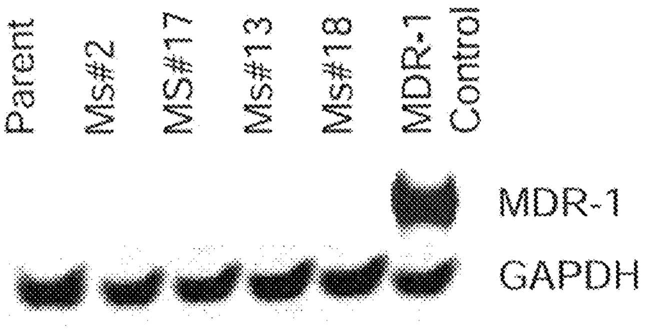
FIGS. 24A-24D depict that T-DM1 resistance in N87-TDM1 (mice 2, 7 and 17) is not due to drug efflux pumps. (A) a western blot showing MDR1 protein expression. In vitro cytotoxicity of T-DM1 resistant cells (N87-TDM1) and T-DM1 sensitive N87 parental cells in the presence of free drug (B) 0101; (C) doxorubicin; (D) T-DM1.
Figure 24B:
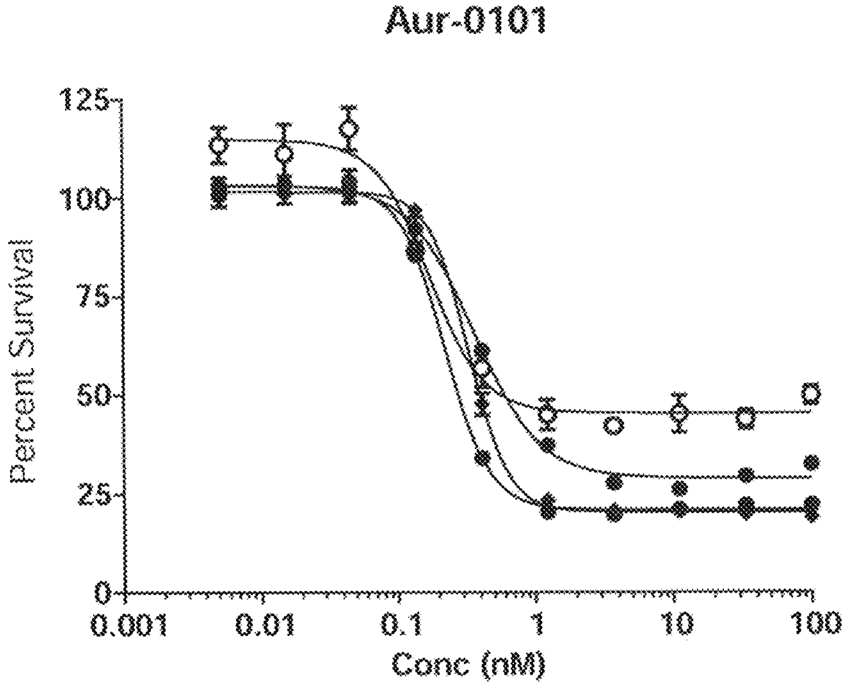
Figure 24C:
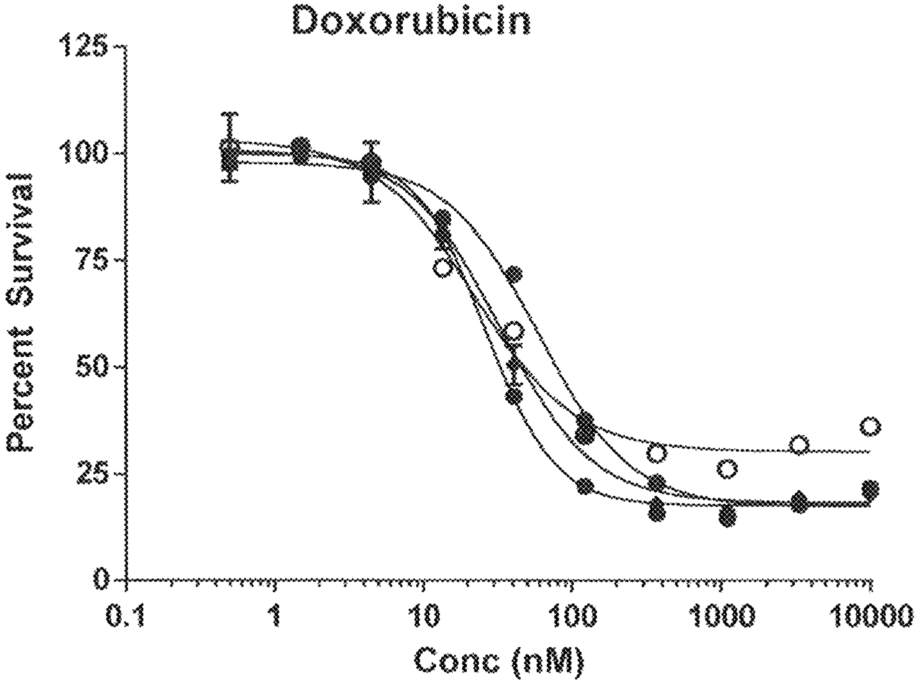
Figure 24D:
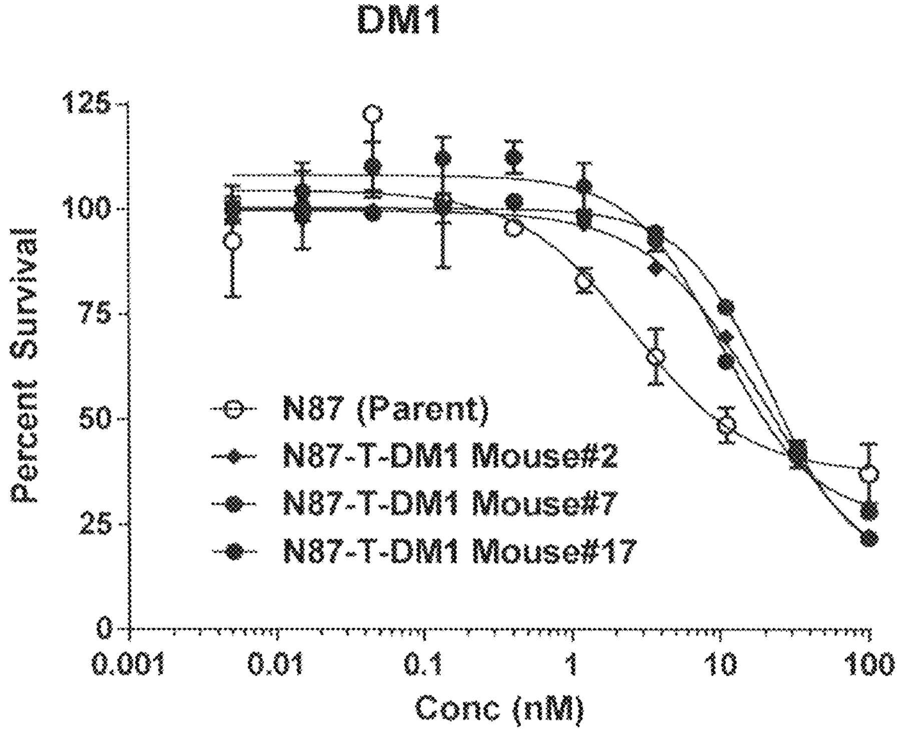

The cell lines do not express MDR1 by western blot (FIG. 24A) and cells are not resistant to MDR-1 substrate free drug 0101 (FIG. 24B). No resistance to doxorubicin (FIG. 24C) was observed indicating that resistant mechanism is not through MRP1. However, the cells are still resistant to free DM1 (FIG. 24D).

Example 16: Pharmacokinetics (PK)

Exposure of conventional or site specific vc0101 antibody drug conjugates were determined after an IV bolus dose administration of either 5 or 6 mg/kg to cynomolgus monkeys. Concentrations of total antibody (total Ab; measurement of both conjugated mAb and unconjugated mAb) and ADC (mAb that is conjugated to at least one drug molecule) was measured using ligand binding assays (LBA). The ADC in was made using vc0101 in all cases except for T(LCQ05) were AcLysvc0101 was used. Conventional conjugation (not site specific conjugation) was used to make the ADC from trastuzumab.

Figure 25A:
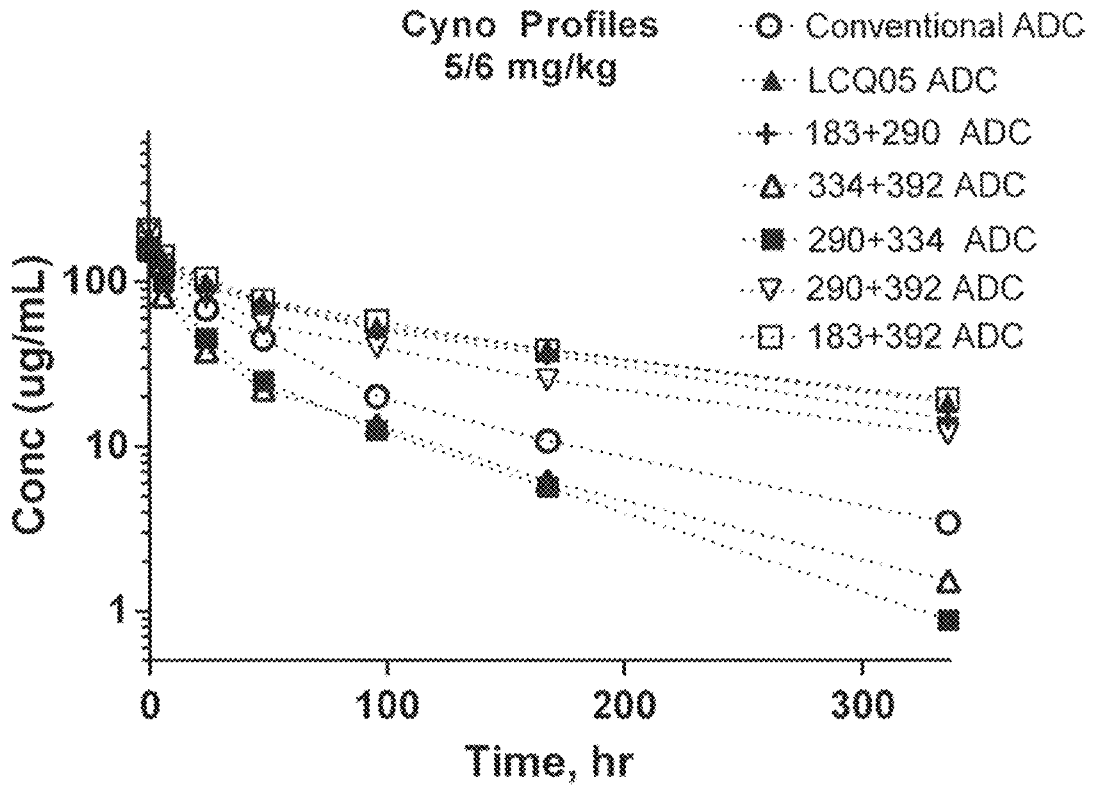
FIGS. 25A-25B depict concentration vs time profiles and pharmacokinetics/toxicokinetics of (A) both total Ab and trastuzumab ADC (T-vc0101) or T(kK183C+K290C) site specific ADC after dose administration to cynomolgus monkeys and (B) the ADC analyte of trastuzumab (T-vc0101) or various site specific ADCs after dose administration to cynomolgus monkeys.

Concentration vs time profiles and pharmacokinetics/toxicokinetics of both total Ab and trastuzumab ADC (T-vc0101) (5 mg/kg) or T(kK183C+K290C) site specific ADC (6 mg/kg) after dose administration to cynomolgus monkeys (FIG. 25A and Table 21). Exposure of the T(kK183C+K290C) site specific ADC has both increased exposure and stability when compared to the conventional conjugate.

Figure 25B:
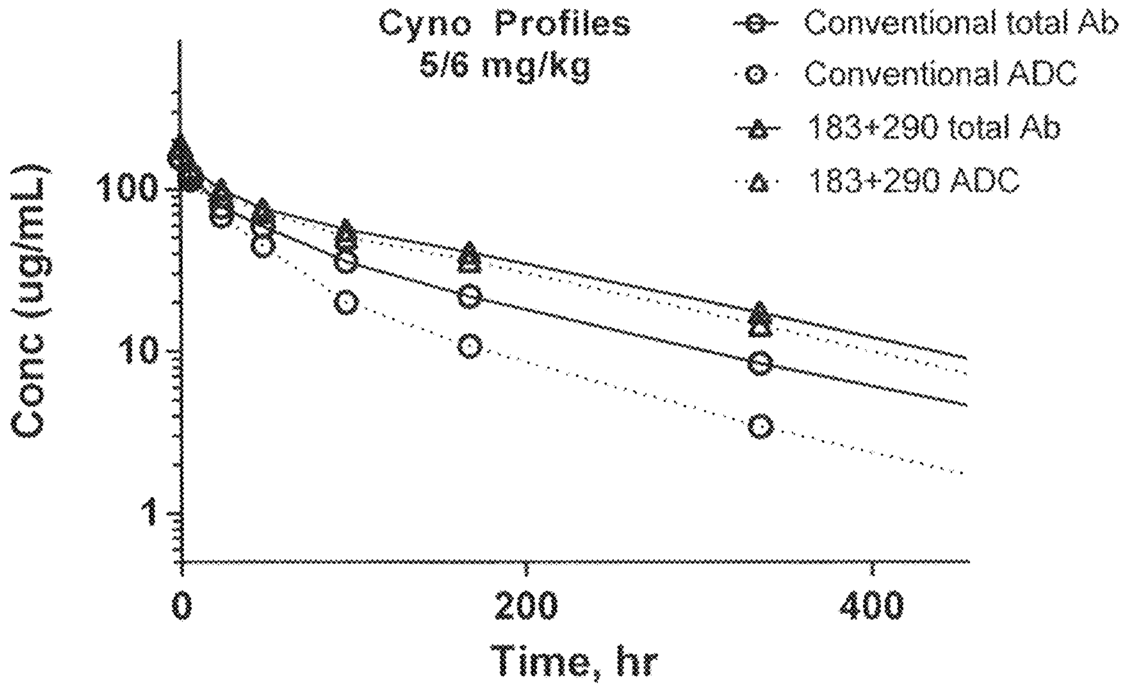

Concentration vs time profiles and pharmacokinetics/toxicokinetics of the ADC analyte of trastuzumab (T-vc0101) (5 mg/kg) or T(kK183C+K290C), T(LCQ05), T(K334C+K392C), T(K290C+K334C), T(K290C+K392C) and T(kK183C+K392C) site specific ADC (6 mg/kg) after dose administration to cynomolgus monkeys (FIG. 25B and Table 21). Exposure several site specific ADC (T(LCQ05), T(kK183C+K290C), T(K290C+K392C) and T(kK183C+K392C)) are higher compared to that of the trastuzumab ADC using conventional conjugation. However, exposure of two other site specific ADC (T(K290C+K334C) and T(K334C+K392C)) do not have higher exposure than the trastuzumab ADC indicating that not all site specific ADCs will have pharmacokinetic properties better than the trastuzumab ADC made using conventional conjugation.

TABLE 21

| Pharmacokinetics | | | | |
|---|---|---|---|---|
| mAb/ADC | Dose (mg/kg) | Analyte | Cmax (μg/mL) | AUC (0-336 h) (μg · h/mL) |
| trastuzumab | 5 | Total Ab | 157 | 11100 |
| | | ADC | 154 | 7660 |
| T(K290C+K334C) | 6 | Total Ab | 165 | 5770 |
| | | ADC | 163 | 5060 |
| T(K334C+K392C) | 6 | Total Ab | 159 | 5320 |
| | | ADC | 157 | 4770 |
| T(LCQ05) | 5 | Total Ab | 165 ± 19 | 16400 ± 1020 |
| | | ADC | 164 ± 22 | 16300 ± 989 |
| T(kK183C+K290C) | 6 | Total Ab | 187 | 16800 |
| | | ADC | 181 | 15300 |
| T(K183C+K392C) | 6 | Total Ab | 195 | 18500 |
| | | ADC | 196 | 16900 |
| T(K290C+K392C) | 6 | Total Ab | 205 | 13300 |
| | | ADC | 208 | 12300 |

Figure 26:
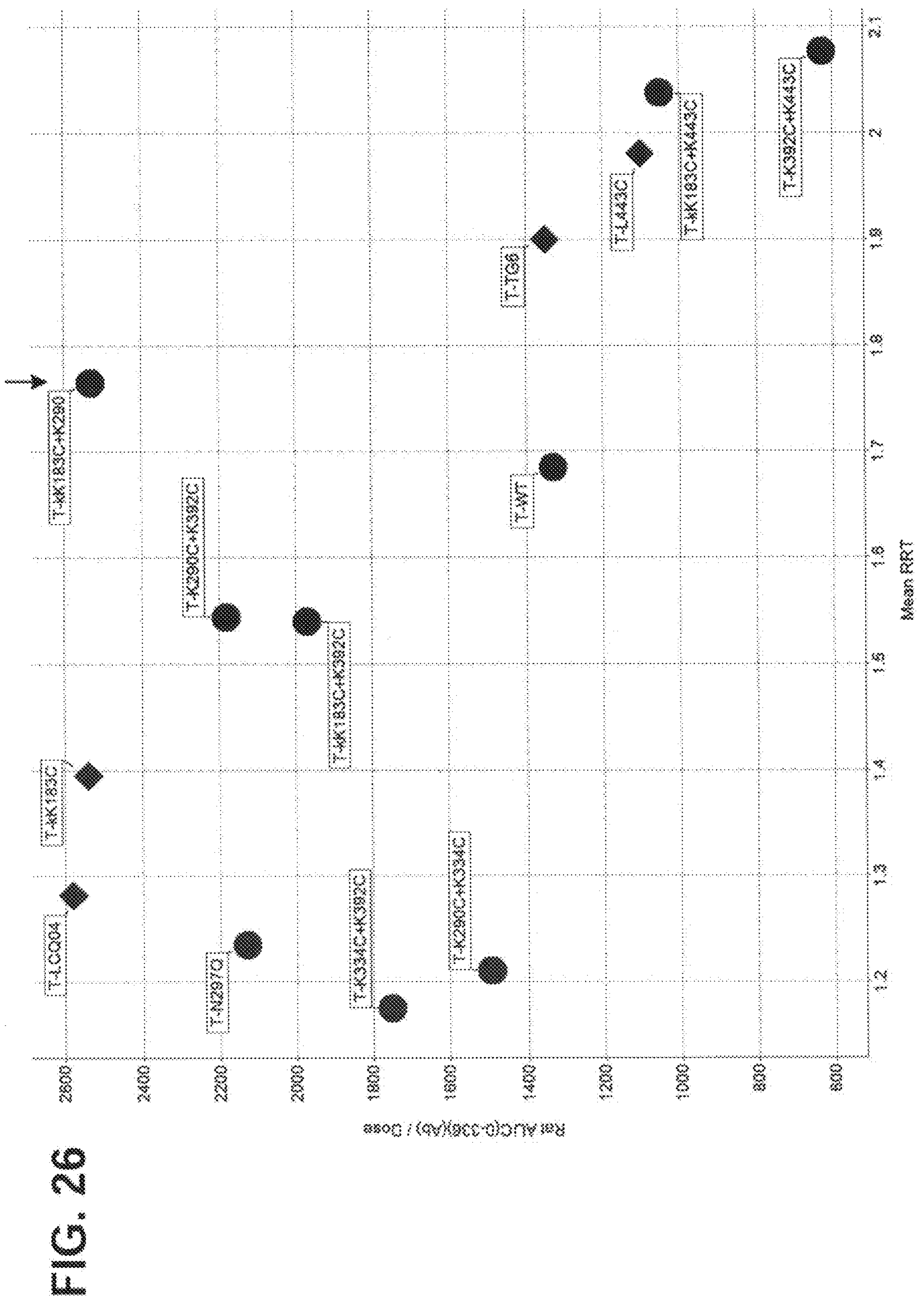
FIG. 26 depicts relative retention values by hydrophobic interaction chromatography (HIC) vs exposure (AUC) in rats. The X-axis represents Relative Retention Time by HIV; while the Y-axis represents pharmacokinetic dose-normalized exposure in rats ("area under curve", AUC for antibody, from 0 to 336 hours, divided by drug dose of 10 mg/kg). Symbol shape denotes approximate drug loading (DAR): diamond=DAR 2; circle=DAR 4. Arrow indicates T(kK183C+K290C)-vc0101.

Example 17: Relative Retention Values by Hydrophobic Interaction Chromatography Vs. Exposure (AUC) in Rats Hydrophobicity is a physical property of a protein that can be assessed by hydrophobicity interaction chromatography (HIC), and the retention times of protein samples differ based on their relative hydrophobicity. ADCs can be compared with their respective antibody by calculating a relative retention time (RRT), which is the ratio of the HIC retention time of the ADC divided by the HIC retention time of the respective antibody. Highly hydrophobic ADCs have higher RRT, and it is possible that these ADCs may also have more pharmacokinetic liability, specifically lower area-under-the-curve (AUC, or exposure). When the HIC values of ADCs with various site mutations were compared with their measured AUC in rats, the distribution in FIG. 26 was observed.

ADCs with RRT≥1.9 showed lower AUC values, while ADCs with lower RRT tended to have higher AUC, although the relationship was not direct. The ADC T(kK183C+K290C)-vc0101 was observed to have a relatively higher RRT (mean value of 1.77) and therefore was expected to have a relatively lower AUC. Surprisingly, the observed AUC was relatively high, hence it was not obvious to predict the exposure of this ADC from the hydrophobicity data.

Example 18: Toxicity Studies

In two independent exploratory toxicity studies, a total of ten male and female cynomolgus monkeys were divided into 5 dosage groups (1/gender/dosage) and dosed IV once every 3 weeks (study days 1, 22 and 43). On study day 46 (3 days after the $3^{rd}$ dose administration) animals were euthanized and protocol specified blood and tissue samples were collected. Clinical observations, clinical pathology, macroscopic and microscopic pathology evaluations were conducted in life and post necropsy. For anatomic pathology evaluation, severity of histopathology findings was recorded on a subjective, relative, study specific basis.

Figure 27:
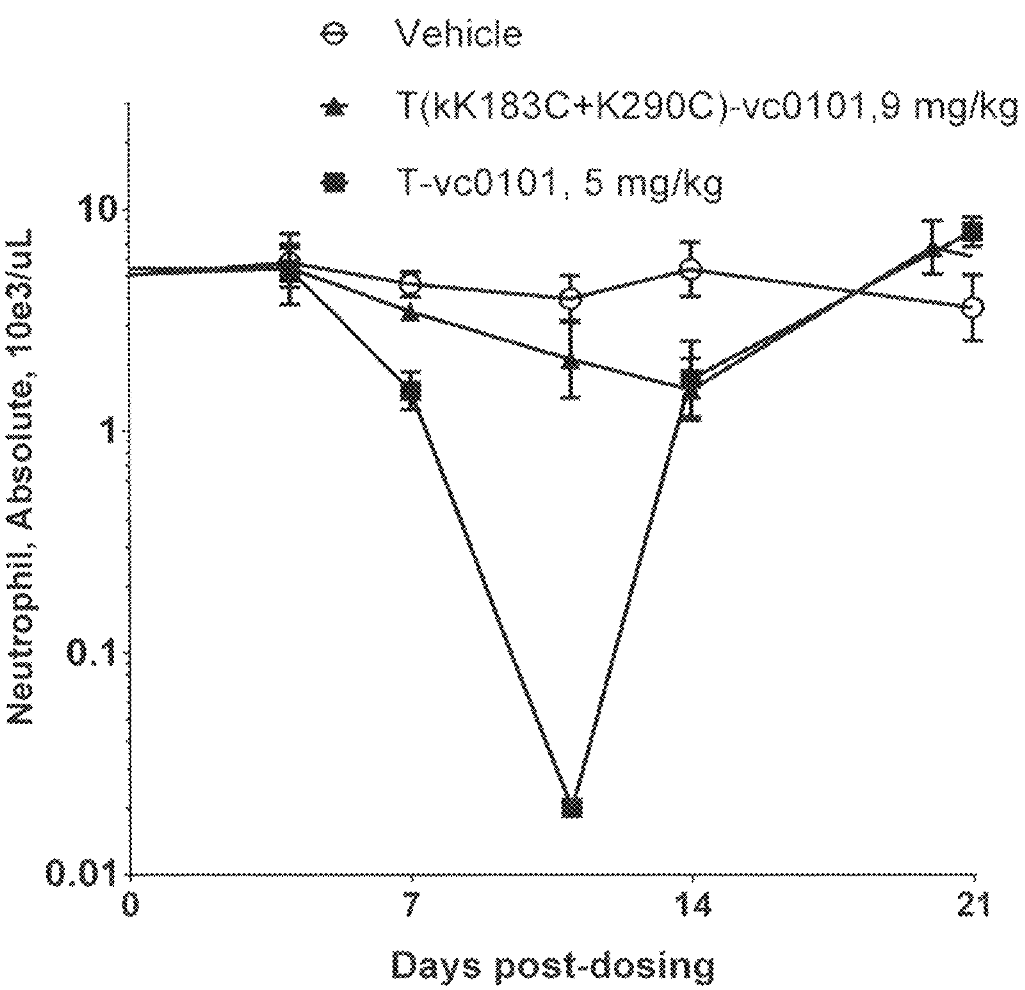
FIG. 27 depicts a toxicity study using T-vc0101 conventional conjugate ADC and T(kK183C+K290C)-vc0101 site specific ADC. T-vc0101 induced severe neutropenia at 5 mg/kg while the T(kK183C+K290C)-vc0101 caused a minimal drop in neutrophil counts at 9 mg/kg.

In cynomolgus monkey exploratory toxicity studies at 3 and 5 mg/kg, T-vc0101 caused transient but marked (390/μl) to severe (40/μl to non-detectable) neutropenia at Day 11 post the first dose. In contrast at 9 mg/kg, all cynomolgus monkeys dosed with T(kK183C+K290C)-vc0101 had none to minimal neutropenia with neutrophil counts well above 500/μl at any time-points tested (FIG. 27). In fact, T(kK183C+K290C)-vc0101 dosed animals showed average neutrophil counts (>1000 μL) at day 11 and 14 as compared to vehicle controls.

Microscopically in the bone marrow at 3 and 5 mg/kg, the cynomolgus monkey dosed with T-vc0101 had compound-related increased M/E ratio. Increased myeloid/erythroid (M/E) ratio consisted of decreased erythroid precursors combined with an increase of primarily mature granulocytes. In contrast, at 6 and 9 mg/kg, only the male dosed with T(kK183C+K290C)-vc0101 at 6 mg/kg/dose had minimal to mild increased cellularity of mature granulocytes (data not shown).

Therefore, the hematologic and microscopic data clearly indicated that the ADC conjugate based on site-specific-mutation technology, T(kK183C+K290C)-vc010 clearly improved the T-vc010 induced bone marrow toxicity and neutropenia.

Example 19: ADC Crystal Structure

The crystal structures were obtained for T(K290C+K334C)-vc0101, T(K290C+K392C)-vc0101 and T(K334C+K392C)-vc0101. These particular ADCs were chosen for crystallography since conjugation to the K290C+K334C and K334C+K392C double cysteine-variants, but not the K290C+K392C, abolished ADCC activity.

The conjugated Fc regions were prepared for crystallography using papain cleavage of the ADCs. Crystals of the same morphology were obtained for the three conjugated IgG1-Fc regions using the same conditions: 100 mM NaCitrate pH 5.0+100 mM $MgCl_2$+15% PEG 4K.

Wild type human IgG1-Fc structures deposited in the PDB are relatively similar showing that the CH2-CH2 domains contact each other through Asn297-linked glycans (carbohydrate or glycan antennas) and that the CH3-CH3 domains form a stable interface that is relatively constant between structures. Fc structures exist in either a “closed” or “open” confirmation and the deglycosylated Fc structure adopts the “open” structure conformation thus demonstrating that the glycan antennas hold the CH2 regions together. Additionally, a published structure of an unconjugated Phe241Ala-IgG1 Fc mutant (Yu et al. “Engineering Hydrophobic Protein-Carbohydrate interactions to fine-tune monoclonal antibodies”. JACS 2013) shows one partially disordered CH2 domain since this mutation leads to destabilization of CH2-glycan interface and CH2-CH2 interface since aromatic Phe residue cannot stabilize the carbohydrate.

The “CH2 domain” of a human IgG Fc region (also referred to as “Cγ2” domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton et al., 1985, Molec. Immunol. 22: 161-206).

The “CH3 domain” comprises the stretch of residues C-terminal to a CH2 domain in an Fc region (i.e. from about amino acid residue 341 to about amino acid residue 447 of an IgG).

Figure 28A:
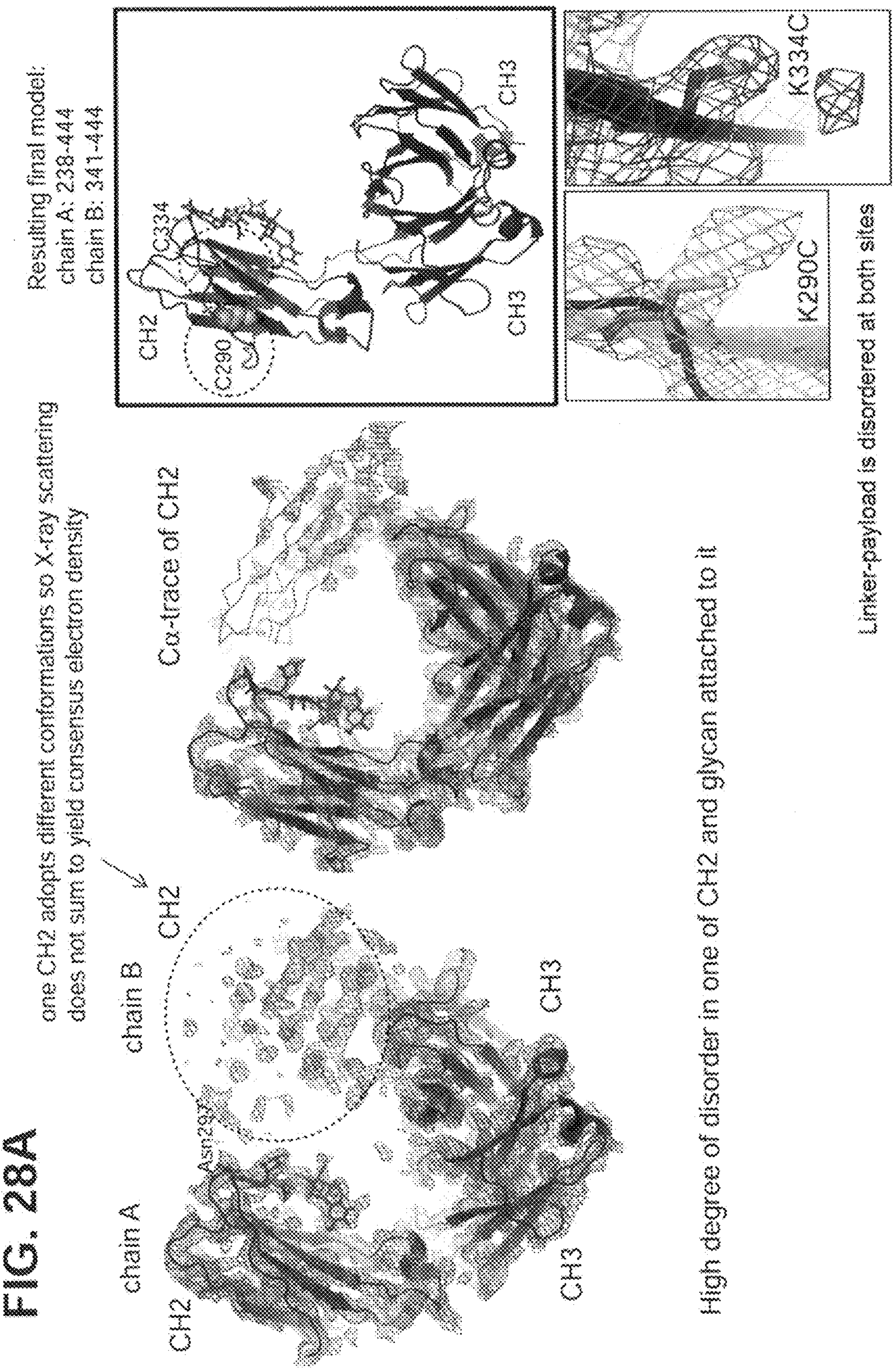
FIGS. 28A-28C depict the crystal structure of (A) T(K290C+K334C)-vc0101; (B) T(K290C+K392C)-vc0101; and (C) T(K334C+K392C)-vc0101.
Figure 28B:
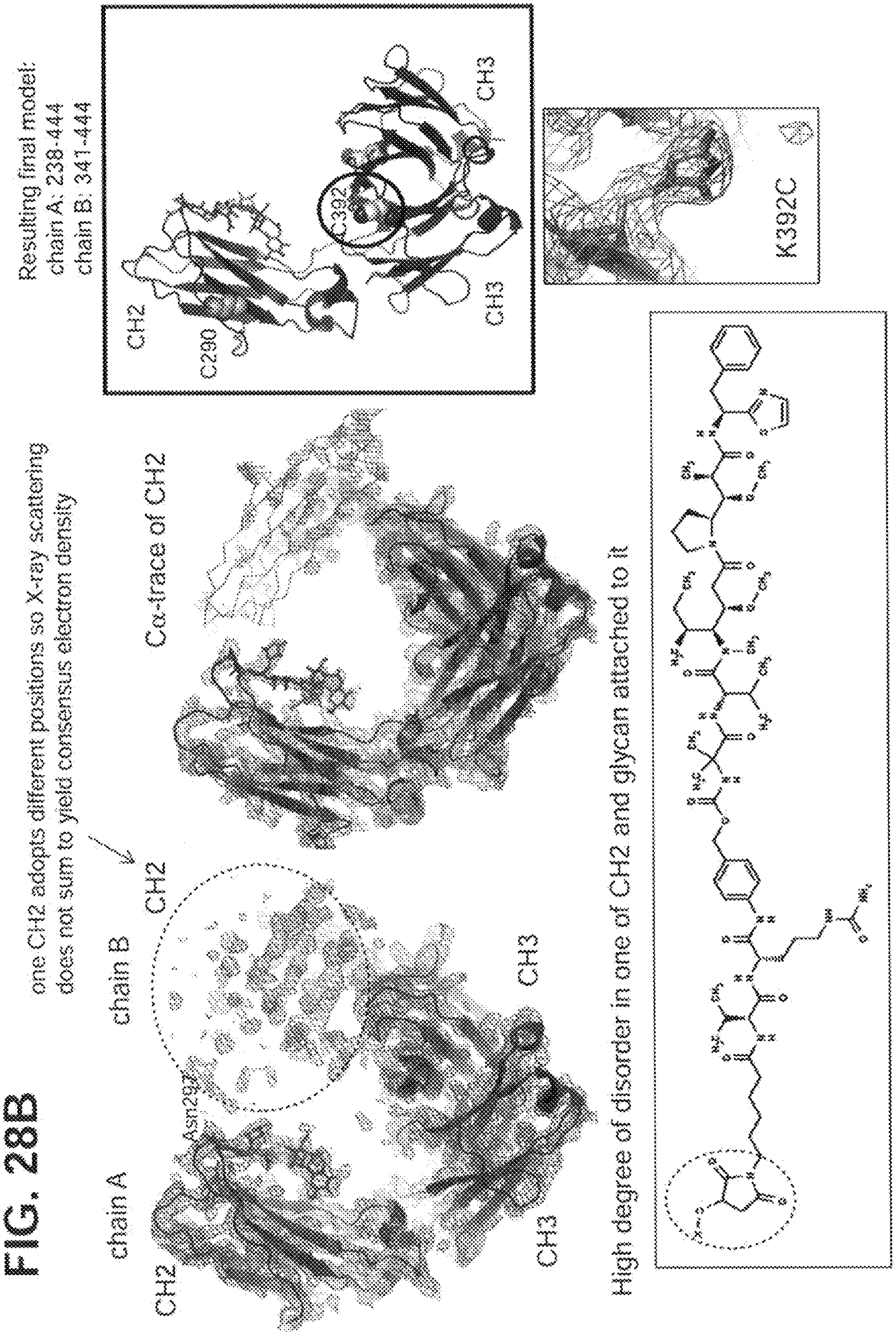
Figure 28C:
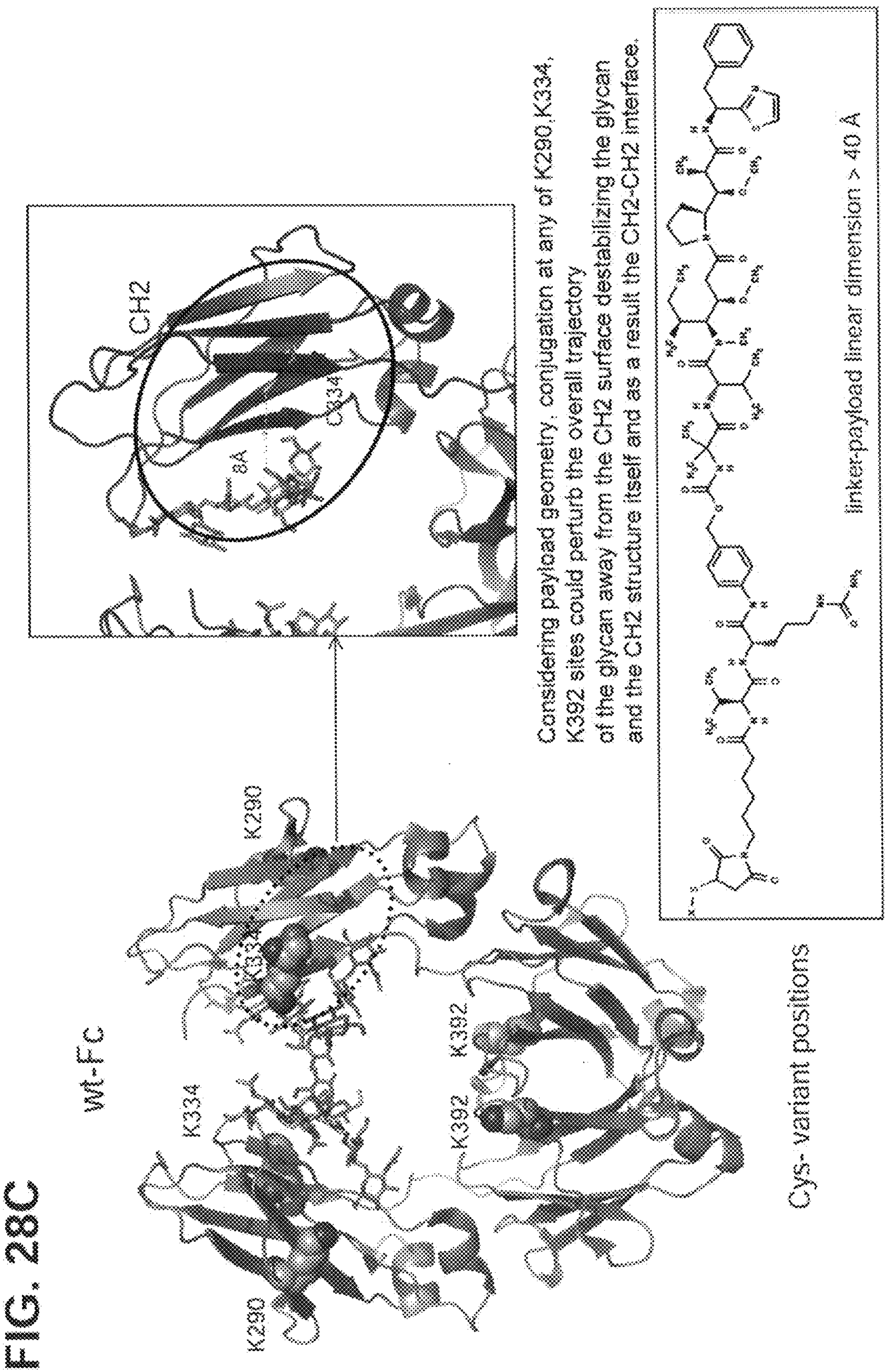

The solved structures for both T(K290C+K334C)-vc0101 and T(K290C+K392C)-vc0101 Fc regions were similar showing that the Fc dimer contained one CH2 and both CH3s that were highly ordered (like wild type Fc). However, they also contain a disordered CH2 with glycan attached (FIG. 28A and FIG. 28B). The higher degree of destabilization of one CH2 domain was attributed to the close proximity of conjugation sites to glycan antennas. Considering 0101 payload geometry, conjugation at any of K290, K334, K392 sites could perturb the overall trajectory of the glycan away from the CH2 surface destabilizing the glycan and the CH2 structure itself and as a result the CH2-CH2 interface (FIG. 28C). A higher degree of heterogeneity is available to these 0101 site-specifically conjugated double cysteine-Fc-variants relative to WT-Fc, Phe241Ala-Fc or deglycosylated-Fc. When engineered cysteine-variant positions were mapped on the structure of WT-Fc in complex with FcYR type IIb, it showed that conjugation at C334 could directly interfere with binding to FcYRIIb (FIG. 28C). This heterogeneity in CH2 positioning caused by mutation or conjugation could result in significant decrease in FcRIIb binding. Therefore these results suggested that either conformation heterogeneity or conjugation of 0101 to certain combinations of engineered cysteines within the IgG1-Fc could affect ADCC activity for the double cysteine variants containing the K334C site, or perhaps both.

Example 20: Different Conjugation Sites Results in Different ADC Properties

A. General Procedure for the Synthesis of Cys-Mutant ADCs

A solution of trastuzumab incorporating one or more engineered cyststeine residues (as shown in the Table 22) was prepared in 50 mM phosphate buffer, pH 7.4. PBS, EDTA (0.5 M stock), and TCEP (0.5 M stock) were added such that the final protein concentration was 10 mg/mL, the final EDTA concentration was 20 mM, and the final TCEP concentration was approximately 6.6 mM (100 molar eq.). The reaction was allowed to stand at rt for 48 h then buffer exchanged into PBS using GE PD-10 Sephadex G25 columns per the manufacturer's instructions. The resulting solution was treated with approximately 50 equivalents of dehydroascorbate (50 mM stock in 1:1 EtOH/water). The antibody was allowed to stand at 4° C. overnight and subsequently buffer exchanged into PBS using GE PD-10 Sephadex G25 columns per the manufacturer's instructions. Slight variations of the above procedure were employed on some mutants.

The antibody thus prepared was diluted to ~2.5 mg/mL in PBS containing 10% DMA (vol/vol) and treated with vc0101 (10 molar eq.) as a 10 mM stock solution in DMA. After 2 h at rt, the mixture was buffer exchanged into PBS (per above) and purified by size-exclusion chromatography on a Superdex200 column. The monomeric fractions were concentrated and filter sterilized to give the final ADC. See Table 22 below for product characterization.

TABLE 22

Summary of ADC properties

| ADC | LCMS DAR (mol/mol) | HIC DAR (mol/mol) | LCMS Observed Mass Shift | LCMS Expected Mass Shift | % monomer | HIC RT Main Peak (min) | HIC relative retention time (RRT) |
|---|---|---|---|---|---|---|---|
| T(A114C)-vc0101 | 1.9 | 1.74 | 1342 | 1341 | 94% | 7.15 | 1.40 |
| T(kK183C)-vc0101 | 2 | 2 | 1341 | 1341 | 99% | 7.05 | 1.38 |
| T(K290C)-vc0101 | 2.1 | 2.1 | 1341 | 1341 | 99% | 7.85 | 1.53 |
| T(K334C)-vc0101 | 2.1 | 2.1 | 1341 | 1341 | 99% | 5.90 | 1.15 |
| T(Q347C)-vc0101 | 1.9 | NA | 1341 | 1341 | 99% | 8.41 | 1.64 |
| T(S375C)-vc0101 | 2 | NA | 1340 | 1341 | 99% | 6.23 | 1.22 |
| T(E380C)-vc0101 | 2 | 1.9 | 1341 | 1341 | 99% | 7.93 | 1.55 |
| T(K388C)-vc0101 | 1.9 | NA | 1340 | 1341 | 97% | 8.75 | 1.71 |
| T(K392C)-vc0101 | 2.1 | 2.1 | 1341 | 1341 | 98% | 6.60 | 1.29 |
| T(N421C)-vc0101 | 1.9 | NA | 1342 | 1341 | 93% | 8.20 | 1.60 |
| T(L443C)-vc0101 | 2 | 2 | 1344 | 1341 | 90% | 9.10 | 1.78 |
| T(kK183C + K334C)-vc0101 | 3.7 | NA | 1341 | 1341 | 95% | 7.00 | 1.37 |
| T(kK183C + K392C)-vc0101 | 4 | 4 | 1342 | 1341 | 97% | 7.70 | 1.50 |
| T(K290C + K334C)-vc0101 | 4 | 4 | 1342 | 1341 | 97% | 6.03 | 1.18 |
| T(K334C + K392C)-vc0101 | 4 | 4 | 1343 | 1341 | 97% | 5.91 | 1.15 |
| T(K392C + L443C)-vc0101 | 3.2 | NA | 1340 | 1341.68 | 97% | 10.85 | 2.12 |
| Trastuzumab mAb | | | | | | 5.12 | 1.00 |

B. General Analytical Methods for Conjugation Examples

LCMS: Column=Waters BEH300-C4, 2.1×100 mm (P/N=186004496); Instrument=Acquity UPLC with an SQD2 mass spec detector; Flow rate=0.7 mL/min; Temperature=80° C.; Buffer A=water+0.1% formic acid; Buffer B=acetonitrile+0.1% formic acid. The gradient ran from 3% B to 95% B over 2 minutes, holds at 95% B for 0.75 min, and then re-equilibrates at 3% B. The sample was reduced with TCEP or DTT immediately prior to injection. The eluate was monitored by LCMS (400-2000 daltons) and the protein peak was deconvoluted using MaxEnt1. DAR was reported as a weight average loading.

SEC: Column: Superdex200 (5/150 GL); Mobile phase: Phosphate buffered saline containing 2% acetonitrile, pH 7.4; Flow rate=0.25 mL/min; Temperature=ambient; Instrument: Agilent 1100 HPLC.

HIC: Column: TSKGel Butyl NPR, 4.6 mm×3.5 cm (P/N=S0557-835); Buffer A=1.5 M ammonium sulfate containing 10 mM phosphate, pH 7; Buffer B=10 mM phosphate, pH 7+20% isopropyl alcohol; Flow rate=0.8 mL/min; Temperature=ambient; Gradient=0% B to 100% B over 12 minutes, hold at 100% B for 2 minutes, then re-equilibrate at 100% A; Instrument: Agilent 1100 HPLC.

C. Determination of Hydrophobicity of Site Specific Vc0101 Conjugates

ADCs of Table 22 were evaluated by hydrophobic interaction chromatography (method above) in order to determine the relative hydrophobicity of the various conjugates. ADC hydrophobicity has been reported to correlate with total antibody exposure.

Conjugates to sites 334, 375, and 392 exhibited to smallest shift in retention time as compared to the unmodified antibody while conjugates to sites 421, 443, and 347 showed the largest shift in retention time. The relative hydrophobicity of each ADC was calculated by dividing the retention time of the ADC by the retention time of the unmodified antibody, thus resulting in a "relative retention time" or "RRT". An RRT of ~1 indicates that the ADC has approximately the same hydrophobicity as the unmodified antibody. The RRT for each ADC is shown in Table 22.

D. ADC Plasma Stability of Site Specific Vc0101 Conjugates

ADC samples (~1.5 mg/mL) were diluted into mouse, rat or human plasma to yield a final solution of 50 μg/mL ADC in plasma. Samples were incubated at 37° C. under 5% $CO_2$, and aliquots were taken at three time points (0, 24 h, and 72 h). Each time point of ADC samples from the plasma incubation (25 μL) was deglycosylated with IgG0 at 37° C. for 1 h. Following the deglycosylation, a capture antibody (biotinylated goat anti-human IgG1 Fcγ fragment specific at 1 mg/mL for mouse and rat plasma, or biotinylated anti-trastuzumab antibody at 1 mg/mL for human plasma) was added and the mixture was heated at 37° C. for 1 h followed by gentle shaking at room temperature for a second hour. Dynabead MyOne Streptavidin T1 magnetic beads were added to the samples and incubated at room temperature for 1 h with gentle shaking. The sample plate was then washed with 200 μL PBS+0.05% Tween-20, 200 μL PBS and HPLC grade water. The bound ADC was eluted with 55 μL of 2% of formic acid (FA) (v/v). 50 μL aliquot of each sample were transferred into a new plate followed by an additional 5 μL of 200 mM TCEP.

The intact protein analysis was carried out with Xevo G2 Q-TOF mass spectrometer coupled with nanoAcquity UPLC (Waters) using BEH300 C4, 1.7 μm, 0.3×100 mm iKey column. The mobile phase A (MPA) consisted of 0.1% FA in water (v/v) and the mobile phase B (MPB) consisted of 0.1% FA in acetonitrile (v/v). The chromatographic separation was achieved at a flow rate of 0.3 μL/min using a linear gradient of MPB from 5% to 90% over 7 min. The LC column temperature was set at 85° C. Data acquisition was conducted with MassLynx software version 4.1. The mass acquisition range was from 700 Da to 2400 Da. Data analysis including deconvolution was performed using Biopharmalynx version 1.33.

Loading and succinimide ring opening (a +18 dalton peak) was monitored over time. The loading data is reported as % DAR loss compared to 0 h DAR. The ring-opening data is reported as the % of ring-opened species as compared to total species present at 72 h. Several site mutants resulted in very stable ADCs (334C, 421C, and 443C) while some sites lost significant amounts of linker-payload (380C and 114C). The rate of ring-opening varied considerably between the sites. Several sites such as 392C, 183C, and 334C resulted in very little ring opening while other sites such as 421C, 388C, and 347C resulted in rapid and spontaneous ring opening.

Sites that result in rapid and spontaneous ring opening may be useful for the generation of conjugates that have reduced hydrophobicity and/or increased PK exposure. This finding runs counter to the prevailing understanding that ring stability correlates with plasma stability. In some aspects therefore, conjugation at one or more of sites 421C, 388C, and 347C can be particularly advantageous when using a linker-payload with a high hydrophobicity. In some aspects, high hydrophobicity is a relative retention time (RRT) value (as measured by HIC) of 1.5 or more. In some aspects, high hydrophobicity is a RRT value of 1.7 or more. In some aspects, high hydrophobicity is a RRT value of 1.8 or more. In some aspects, high hydrophobicity is a RRT value of 1.9 or more. In some aspects, high hydrophobicity is a RRT value of 2.0 or more.

TABLE 23

Plasma stability of various ADCs

| ADC | % DAR Loss @ 72-h | % Succinamide hydrolysis @ 72-h |
|---|---|---|
| T(K334C)-vc0101 | 0% | 18% |
| T(N421C)-vc0101 | 0% | 100 |
| T(L443C)-vc0101 | 0% | 40% |
| T(K388C)-vc0101 | −1.3% | 100% |
| T(K392C)-vc0101 | 3.0% | 0% |
| T(K290C)-vc0101 | 9.5% | 21% |
| T(Q347C)-vc0101 | 10% | 66% |
| T(kK183C)-vc0101 | 11% | 29% |
| T(S375C)-vc0101 | 12% | 46% |
| T(A114C)-vc0101 | 20% | 33% |
| T(E380C)-vc0101 | 49% | 29% |

E. Glutathione Stability of Site Specific Vc0101 Conjugates

The ADC samples were diluted into aqueous glutathione to yield a final GSH concentration of 0.5 mM and final protein concentration of ~0.1 mg/mL in a phosphate buffer, pH 7.4. The samples were then incubated at 37° C. and aliquots were removed at three time points to determine the DAR (T−0, T−3 day, T−6 day). The aliquot from each time point was treated with TCEP and analyzed by LC-MS per the method described in Example 20.A.

Loading and succinimide ring opening (a +18 dalton peak) was monitored over time. The loading data is reported as % DAR loss compared to 0 h DAR. (Table 24) The ring-opening data is reported as the % of ring-opened species as compared to total species present at 72 h. Several site mutants resulted in very stable ADCs (334C, 421C, and 443C) while some sites lost significant amounts of linker-payload (380C and 114C). The rate of ring-opening varied considerably between the sites. Several sites such as 392C, 183C, and 334C resulted in very little ring opening while other sites such as 421C, 388C, and 347C resulted in considerable ring-opening. The results of this assay correlates quite well with the plasma stability results (Example 20.D) suggesting that thiol-mediated deconjugation is the major pathway of payload loss in plasma. Combined, these results suggest that particular sites such as 334, 443, 290, and 392 may be especially useful for the conjugation of payload-linkers that are readily lost through a thiol-mediated deconjugation. Such payload-linkers include those that utilize the common mc and vc linkages (e.g. vc-101, vc-MMAE, mc-MMAF etc).

TABLE 24

Glutathione stability of various vc0101 site specific conjugates

| ADC | % DAR Loss @ 72-h | % Succinamide hydrolysis @ 72-h |
|---|---|---|
| T(A114C)-vc0101 | 12% | 41% |
| T(kK183C)-vc0101 | 7% | 17% |
| T(K334C)-vc0101 | 4% | 26% |
| T(Q347C)-vc0101 | 10% | 71% |
| T(S375C)-vc0101 | 18% | 47% |
| T(E380C)-vc0101 | 79% | 50% |
| T(K388C)-vc0101 | 19% | 100% |
| T(K392C)-vc0101 | 0% | 17% |

TABLE 24-continued

| Glutathione stability of various vc0101 site specific conjugates | | |
|---|---|---|
| ADC | % DAR Loss @ 72-h | % Succinamide hydrolysis @ 72-h |
| T(N421C)-vc0101 | 0% | 80% |
| T(L443C)-vc0101 | 12% | 41% |
| T(K290C)-vc0101 | 17% | 33% |

F. Pharmacokinetic Evaluation of Select Site Specific Vc0101 Conjugates in Mice

Non-tumor bearing athymic female nu/nu (nude) mice (6-8 weeks of age) were obtained from Charles River Laboratories. All procedures using mice were approved by the Institutional Animal Care and Use Committee according to established guidelines. Mice (n=3 or 4) were administered a single intravenous dose of an ADC at 3 mg/kg based on the antibody component. Blood samples were collected from each mouse via the tail vein at 0.083, 6, 24, 48, 96, 168 and 336 hours post-dose. The total antibody ($T_{ab}$) and ADC concentrations were determined by a LBA where a sheep anti-human IgG antibody was used for capture, a goat anti-human IgG antibody was used for detection of $T_{ab}$ or an anti-payload antibody was used for detection of ADC. Plasma concentration data for each animal was analyzed using Watson LIMS version 7.4 (Thermo). Exposure varied based on site. The ADCs made from the 290C and 443C mutants exhibited the lowest exposure, while ADCs made from the 183C and 392C sites exhibited the highest exposure. For many applications, sites with a high exposure may be preferred, as this will lead to increased duration of therapeutic agent. However, for certain applications, it may be preferable to use a conjugate with a lower exposure (such as 290C and 443C). In particular, applications where a lower exposure (i.e. lower PK) may include, but are not limited to, use in the brain, the CNS, and the eye. Indications include cancer, especially of the brain, CNS and/or eye.

TABLE 25

| PK exposure of various site-specific vc0101 ADCs | | |
|---|---|---|
| ADC | tAb AUC (0-last) (mg*h/mL) | ADC AUC (0-last) (mg*h/mL) |
| T(kK183C)-vc0101 | 7150 | 5980 |
| T(K290C)-vc0101 | 4240 | 3480 |
| T(K334C)-vc0101 | 5130 | 4500 |
| T(Q347C)-vc0101 | 5080 | 4070 |
| T(K388C)-vc0101 | 6100 | 3680 |
| T(K392C)-vc0101 | 6400 | 6010 |
| T(L443C)-vc0101 | 4430 | 4500 |

G. Cathepsin Cleavage of Site Specific Vc0101 Conjugates

Cathepsin B was activated using 6 mM dithiothreitol (DTT) in 150 mM sodium acetate, pH 5.2 for 15 min at 37° C. 50 ng of the activated cathepsin-B was then mixed with 20 uL of 1 mg/mL of ADC at a final concentration of 2 mM DTT, 50 mM sodium acetate, pH 5.2. Reactions were quenched using 10 uM E-64 cysteine protease inhibitor in 250 mM borate buffer, pH 8.5 following incubation at 37° C. for 20 min, 1 h, 2 h and 4 h. After the assay, the samples were reduced using TCEP and analyzed by LC/MS using the conditions described in Example 21.A. The data showed that the rate of linker cleavage depends heavily on the site of conjugation. Particular sites are cleaved very quickly, such as 443C, 388C, and 290C while other sites are cleaved very slowly, such as 334C, 375C, and 392C. In some aspects, it may be advantageous to conjugate to sites that lend themselves to slow cleavage. In other aspects, quick cleavage is preferred. For example, it may be preferable to release the payload quickly to reduce time spent in the endosome. In further aspects rapid payload cleavage can be advantageously permit penetration of the payload where the conjugated molecule may not be able to do so, such as certain solid tumors. In further aspects, rapid cleavage can permit the payload to be delivered to adjacent cells that do not express the antibody's antigen, thus permitting treatment of a heterogenous tumor, for example.

TABLE 26

| Linker cleavage kinetics of various site-specific vc0101 ADCs | | | | |
|---|---|---|---|---|
| ADC | % Linker cleavage @ 20 min | % Linker cleavage @ 1 h | % Linker cleavage @ 2 h | % Linker cleavage @ 4 h |
| T(A114C)-vc0101 | 29% | 71% | 100% | 100% |
| T(kK183C)-vc0101 | 31% | 95% | 100% | 100% |
| T(K290C)-vc0101 | 54% | 100% | 100% | 100% |
| T(K334C)-vc0101 | 0% | 0% | 0% | 13% |
| T(Q347C)-vc0101 | 42% | 89% | 100% | 100% |
| T(S375C)-vc0101 | 0% | 0% | 0% | 5% |
| T(E380C)-vc0101 | 15% | 48% | 83% | 92% |
| T(K388C)-vc0101 | 82% | 100% | 100% | 100% |
| T(K392C)-vc0101 | 0% | 0% | 0% | 0% |
| T(N421C)-vc0101 | 31% | 61% | 73% | 100% |
| T(L443C)-vc0101 | 100% | 100% | 100% | 100% |

H. Thermal Stability of Site Specific Vc0101 Conjugates

The ADC was diluted to 0.2 mg/mL in PBS (pH 7.4) containing 10 mM EDTA. The ADCs were placed in a sealed vial and heated to 45° C. An aliquot (10 μL) was removed at 1-week increments to evaluate the level of high molecular weight species (HMWS) and low molecular weight species (LMWS) that formed over time by size exclusion chromatography (SEC). The SEC conditions are outlined in Example 21.A. Under these conditions, the monomer eluted at approximately 3.6 minutes. Any protein material eluting to the left of the monomer peak was counted as HMWS and any protein material eluting to the right of the monomer peak was counted as LMWS. Results are shown in Table 27 below. Select ADCs showed excellent thermal stability, such as 183C, 375C, and 334C, while other ADCs showed significant decomposition, such as 443C and 392C+443C.

TABLE 27

| Thermal stability of various site-specific vc0101 ADCs | | | | | | |
|---|---|---|---|---|---|---|
| ADC | Day 1 (HMWS) | Day 1 (LMWS) | Day 1 (Monomer) | Day 21 (HMWS) | Day 21 (LMWS) | Day 21 (Monomer) |
| T(A114C)-vc0101 | 3.31% | 3.00% | 93.60% | 1.70% | 5.30% | 93.80% |
| T(kK183C)-vc0101 | 0.40% | 0.60% | 99.00% | 0.40% | 1.30% | 98.30% |
| T(K290C)-vc0101 | 0.90% | 0.30% | 98.70% | 2.00% | 2.80% | 95.20% |

TABLE 27-continued

Thermal stability of various site-specific vc0101 ADCs

| ADC | Day 1 (HMWS) | Day 1 (LMWS) | Day 1 (Monomer) | Day 21 (HMWS) | Day 21 (LMWS) | Day 21 (Monomer) |
|---|---|---|---|---|---|---|
| T(K334C)-vc0101 | 0.80% | 0.40% | 98.80% | 1.10% | 2.60% | 96.30% |
| T(Q347C)-vc0101 | 1.10% | 0.40% | 98.50% | 1.20% | 1.50% | 97.30% |
| T(S375C)-vc0101 | 0.70% | 0.60% | 98.70% | 0.80% | 2.10% | 97.20% |
| T(E380C)-vc0101 | 0.90% | 0.30% | 98.80% | 1.60% | 1.70% | 96.60% |
| T(K388C)-vc0101 | 1.90% | 0.70% | 97.40% | 1.20% | 2.10% | 96.70% |
| T(K392C)-vc0101 | 1.20% | 0.50% | 98.30% | 1.40% | 2.40% | 96.10% |
| T(N421C)-vc0101 | 2.60% | 4.30% | 93.00% | 2.60% | 6.10% | 91.30% |
| T(L443C)-vc0101 | 5.20% | 4.60% | 90.10% | 5.80% | 6.30% | 87.40% |
| T(kK183C + K334C)-vc0101 | 4.60% | 0.50% | 94.90% | 5.70% | 1.90% | 92.40% |
| T(kK183C + K392C)-vc0101 | 2.10% | 0.70% | 97.10% | 2.10% | 1.60% | 96.30% |
| T(K290C + K334C)-vc0101 | 2.80% | 0.60% | 96.60% | 4.30% | 1.90% | 93.70% |
| T(K334C + K392C)-vc0101 | 1.90% | 0.70% | 97.40% | 2.70% | 2.40% | 94.90% |
| T(K392C + L443C)-vc0101 | 2.80% | 0.60% | 96.60% | 8.80% | 2.90% | 88.30% |

I. Efficacy of Various Vc0101 Site-Mutants

Figure 29:
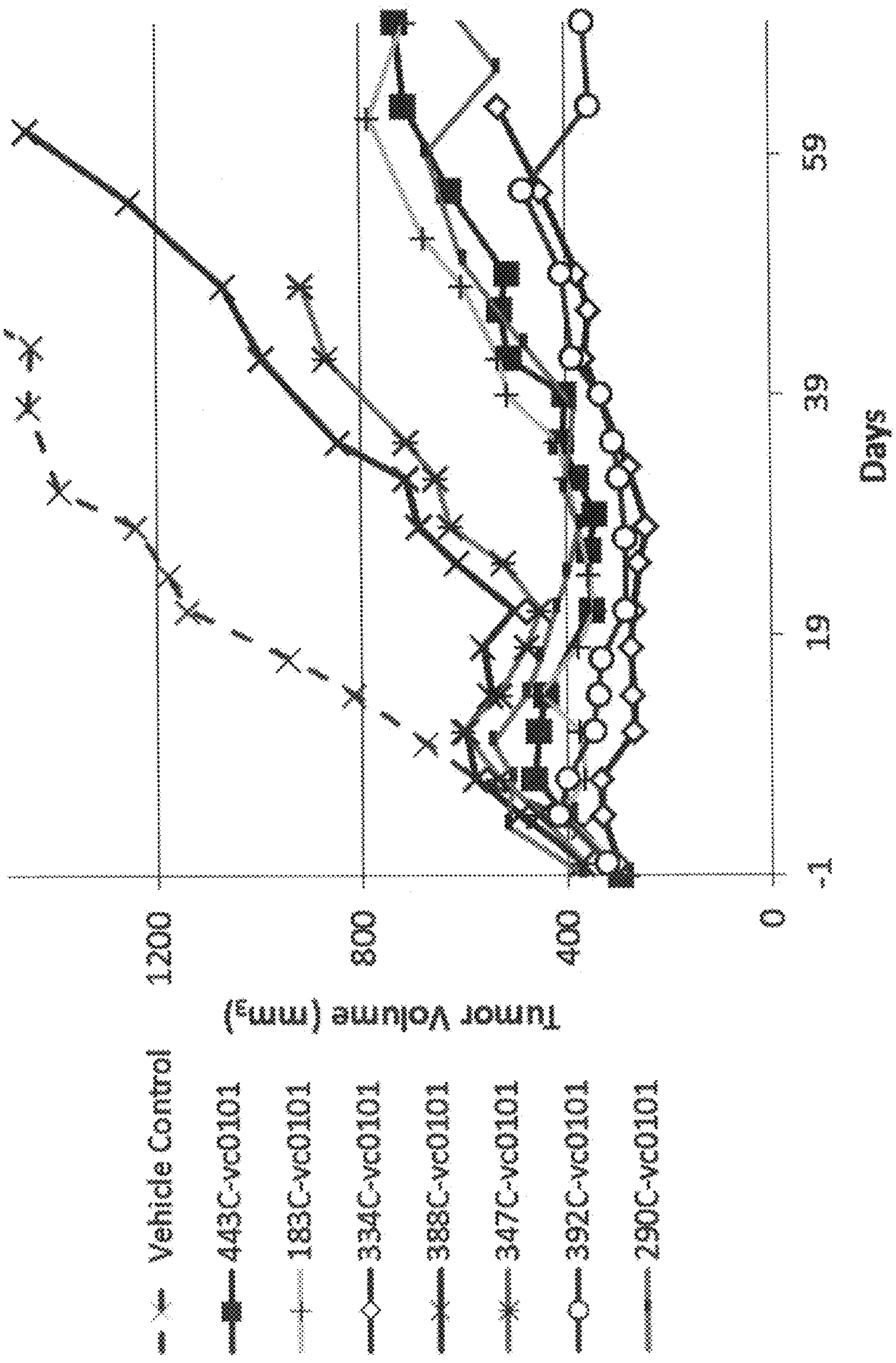
FIG. 29 depicts in vivo efficacy on a xenograft model using the N87 cell line. All ADCs tested showed efficacy at 3 mpk.

In vivo efficacy studies of antibody-drug conjugates were performed in a target-expressing xenograft model using the N87 cell line. Approximately 7.5 million tumor cells in 50% matrigel were implanted subcutaneously into 6-8 weeks old nude mice until the tumor sizes reach between 250 and 350 $mm^3$. The drug was dosed through bolus tail vein injection. Animals were injected with 10, 3, or 1 mg/kg of antibody drug conjugate a total of four times, once every 4 days (on days 1, 5, 9, and 13). All experimental animals are monitored for body weight changes weekly. Tumor volume is measured twice a week for the first 50 days and once weekly thereafter by a Caliper device and calculated with the following formula: Tumor volume=(length×width$^2$)/2. Animals are humanely sacrificed before their tumor volumes reach 2500 $mm^3$. The tumor size is generally observed to decrease after the first week of treatment. Animals were monitored continuously for tumor re-growth after the treatment has discontinued (up to 100 days post-treatment). Data from the 3 mpk dosing group is shown in FIG. 29. ADCs generated from the 388C and 347C mutants exhibited slightly lower potency than ADCs from the 334C, 183C, 392C and 443C mutants.

What is claimed is:

1. An antibody drug conjugate of the formula: Ab-(L-D), wherein:

(a) Ab is an antibody that binds to HER2 and comprises a heavy chain comprising SEQ ID NO:18 and a light chain comprising SEQ ID NO:42; and (b) L-D is a linker-drug moiety, wherein L is maleimido-caproyl-valine-citrulline-p-aminobenzyloxycarbonyl (vc) and D is 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide or a pharmaceutically acceptable salt or solvate thereof.

2. A pharmaceutical composition comprising the antibody drug conjugate of claim 1 and a pharmaceutically acceptable carrier.

3. A composition comprising a plurality of an antibody drug conjugates of claim 1, and optionally a pharmaceutical carrier, wherein the composition has a DAR of 4.

4. An antibody drug conjugate of the formula: Ab-(L-D), wherein:

a) Ab is an antibody that binds to HER2 and comprises a heavy chain polypeptide encoded by the nucleic acid set forth in ATCC Accession No. PTA-122673 and a light chain polypeptide encoded by the nucleic acid set forth in ATCC Accession Nos. PTA-122672; and b) L-D is a linker-drug moiety, wherein L is maleimido-caproyl-valine-citrulline-p-aminobenzyloxycarbonyl (vc) and D is 2-methylalanyl-N-[(3R,4S,5S)-3-methoxy-1-{(2S)-2-[(1R,2R)-1-methoxy-2-methyl-3-oxo-3-{[(1 S)-2-phenyl-1-(1,3-thiazol-2-yl)ethyl]amino}propyl]pyrrolidin-1-yl}-5-methyl-1-oxoheptan-4-yl]-N-methyl-L-valinamide or a pharmaceutically acceptable salt or solvate thereof.

5. A pharmaceutical composition comprising the antibody drug conjugate of claim 4 and a pharmaceutically acceptable carrier.

6. A composition comprising a plurality of an antibody drug conjugates of claim 4, and optionally a pharmaceutical carrier, wherein the composition has a DAR of 4.

* * * * *

UNITED STATES PATENT AND TRADEMARK OFFICE

CERTIFICATE OF CORRECTION

PATENT NO. : 10,689,458 B2
APPLICATION NO. : 15/356750
DATED : June 23, 2020
INVENTOR(S) : Dangshe Ma et al.

It is certified that error appears in the above-identified patent and that said Letters Patent is hereby corrected as shown below:

Column 230
Line 63 Claim 4 "PTA-122673" should be --PTA-122672--
Line 65 Claim 4 "PTA-122672" should be --PTA-122673--

Signed and Sealed this
Eighth Day of September, 2020

Andrei Iancu
*Director of the United States Patent and Trademark Office*

SEQUENCE LISTING

```
<160> NUMBER OF SEQ ID NOS: 95

<210> SEQ ID NO 1
<211> LENGTH: 120
<212> TYPE: PRT
<213> ORGANISM: Artificial Sequence
<220> FEATURE:
<223> OTHER INFORMATION: Synthetic peptide sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 2

```
Asp Thr Tyr Ile His
1               5
```

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 3

```
Arg Ile Tyr Pro Thr Asn Gly Tyr Thr Arg Tyr Ala Asp Ser Val Lys
1               5                   10                  15

Gly
```

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 4

```
Trp Gly Gly Asp Gly Phe Tyr Ala Met Asp Tyr
1               5                   10
```

<210> SEQ ID NO 5
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 5

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 6
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

-continued

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 7
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
```

```
                85                  90                  95

Thr Phe Gly Gln Gly Thr Lys Val Glu Ile Lys
            100                 105

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 8

Arg Ala Ser Gln Asp Val Asn Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 9

Ser Ala Ser Phe Leu Tyr Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 10

Gln Gln His Tyr Thr Thr Pro Pro Thr
1               5

<210> SEQ ID NO 11
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 214
<212> TYPE: PRT
```

<213> ORGANISM: Artificial Sequence
<220> FEATURE:
<223> OTHER INFORMATION: Synthetic peptide sequence

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 13
<211> LENGTH: 330
<212> TYPE: PRT
<213> ORGANISM: Artificial Sequence
<220> FEATURE:
<223> OTHER INFORMATION: Synthetic peptide sequence

<400> SEQUENCE: 13

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Arg Thr His Thr Cys Pro Pro Cys
            100                 105                 110
```

-continued

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 450
<212> TYPE: PRT
<213> ORGANISM: Artificial Sequence
<220> FEATURE:
<223> OTHER INFORMATION: Synthetic peptide sequence

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 15
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 15

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

-continued

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Cys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 16
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

-continued

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Cys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 17
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 17

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Cys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 18
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
```

```
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Cys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly

<210> SEQ ID NO 19
<211> LENGTH: 330
<212> TYPE: PRT
<213> ORGANISM: Artificial Sequence
<220> FEATURE:
<223> OTHER INFORMATION: Synthetic peptide sequence

<400> SEQUENCE: 19

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 20
<211> LENGTH: 450

-continued

<212> TYPE: PRT
<213> ORGANISM: Artificial Sequence
<220> FEATURE:
<223> OTHER INFORMATION: Synthetic peptide sequence

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 21
<211> LENGTH: 330
<212> TYPE: PRT
<213> ORGANISM: Artificial Sequence
<220> FEATURE:
<223> OTHER INFORMATION: Synthetic peptide sequence

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
<211> LENGTH: 450
<212> TYPE: PRT
<213> ORGANISM: Artificial Sequence
<220> FEATURE:
<223> OTHER INFORMATION: Synthetic peptide sequence

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 23
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Cys Thr Ile Ser Lys Ala Lys Gly
    210                 215                 220
```

-continued

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 24
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Cys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 25
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Cys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 26
<211> LENGTH: 449
<212> TYPE: PRT
<213> ORGANISM: Artificial Sequence
<220> FEATURE:
<223> OTHER INFORMATION: Synthetic peptide sequence
<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

-continued

```
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Cys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 27
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Cys Ser Pro Gly
                325
```

<210> SEQ ID NO 28
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Cys Ser Pro
        435                 440                 445

Gly
```

<210> SEQ ID NO 29
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 29

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

-continued

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Cys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Cys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 30
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

-continued

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Cys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Cys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 31
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 31

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Cys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Cys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 32
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 32

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr

-continued

```
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Cys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Cys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly

<210> SEQ ID NO 33
<211> LENGTH: 330
<212> TYPE: PRT
<213> ORGANISM: Artificial Sequence
<220> FEATURE:
<223> OTHER INFORMATION: Synthetic peptide sequence

<400> SEQUENCE: 33

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Arg Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 34
<211> LENGTH: 450

-continued

<212> TYPE: PRT
<213> ORGANISM: Artificial Sequence
<220> FEATURE:
<223> OTHER INFORMATION: Synthetic peptide sequence

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 35
<211> LENGTH: 330
<212> TYPE: PRT
<213> ORGANISM: Artificial Sequence
<220> FEATURE:
<223> OTHER INFORMATION: Synthetic peptide sequence

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Arg Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 450
<212> TYPE: PRT
<213> ORGANISM: Artificial Sequence
<220> FEATURE:
<223> OTHER INFORMATION: Synthetic peptide sequence

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 37
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Cys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Cys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 38
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Cys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Cys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 39
<211> LENGTH: 329
<212> TYPE: PRT
<213> ORGANISM: Artificial Sequence
<220> FEATURE:
<223> OTHER INFORMATION: Synthetic peptide sequence

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Cys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Cys Ser Pro Gly
                325

<210> SEQ ID NO 40
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Cys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Cys Ser Pro
        435                 440                 445

Gly

<210> SEQ ID NO 41
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Cys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 42
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Cys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 43
<211> LENGTH: 115
<212> TYPE: PRT
<213> ORGANISM: Artificial Sequence
<220> FEATURE:
<223> OTHER INFORMATION: Synthetic peptide sequence

<400> SEQUENCE: 43

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
```

```
                85                  90                  95

Pro Val Thr Lys Ser Phe Asn Arg Gly Glu Cys Gly Gly Leu Leu Gln
            100                 105                 110

Gly Pro Pro
        115

<210> SEQ ID NO 44
<211> LENGTH: 222
<212> TYPE: PRT
<213> ORGANISM: Artificial Sequence
<220> FEATURE:
<223> OTHER INFORMATION: Synthetic peptide sequence

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Leu Leu Gln Gly Pro Pro
    210                 215                 220

<210> SEQ ID NO 45
<211> LENGTH: 360
<212> TYPE: DNA
<213> ORGANISM: Artificial Sequence
<220> FEATURE:
<223> OTHER INFORMATION: Synthetic nucleotide sequence

<400> SEQUENCE: 45
gaggtgcagc tggtggaatc cggcggaggc ctggtccagc ctggcggatc tctgcggctg      60
tcttgcgccg cctccggctt caacatcaag gacacctaca tccactgggt ccgacaggca     120
cctggcaagg gactggaatg ggtggcccgg atctacccca ccaacggcta caccagatac     180
gccgactccg tgaagggccg gttcaccatc tccgccgaca cctccaagaa caccgcctac     240
ctgcagatga actccctgcg ggccgaggac accgccgtgt actactgctc cagatgggga     300
```
ggcgacggct tctacgccat ggactactgg ggccagggca ccctggtcac cgtgtctagc 360

<210> SEQ ID NO 46
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 46
gaggtgcagc tggtggaatc cggcggaggc ctggtccagc ctggcggatc tctgcggctg 60
tcttgcgccg cctccggctt caacatcaag gacacctaca tccactgggt ccgacaggca 120
cctggcaagg gactggaatg ggtggcccgg atctacccca ccaacggcta caccagatac 180
gccgactccg tgaagggccg gttcaccatc tccgccgaca cctccaagaa caccgcctac 240
ctgcagatga actccctgcg ggccgaggac accgccgtgt actactgctc cagatgggga 300
ggcgacggct tctacgccat ggactactgg ggccagggca ccctggtcac cgtgtctagc 360
gcgtcgacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc cccgggt 1347

<210> SEQ ID NO 47
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 47
gacatccaga tgacccagtc cccctccagc ctgtccgcct ctgtgggcga cagagtgacc 60
atcacctgtc gggcctccca ggacgtgaac accgccgtgg cctggtatca gcagaagccc 120
ggcaaggccc ccaagctgct gatctactcc gcctccttcc tgtactccgg cgtgccctcc 180
cggttctccg gctccagatc tggcaccgac tttaccctga ccatctccag cctgcagccc 240
gaggacttcg ccacctacta ctgccagcag cactacacca cccccccac ctttggccag 300

-continued ggcaccaagg tggaaatcaa g 321

<210> SEQ ID NO 48
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 48
gacatccaga tgacccagtc cccctccagc ctgtccgcct ctgtgggcga cagagtgacc 60
atcacctgtc gggcctccca ggacgtgaac accgccgtgg cctggtatca gcagaagccc 120
ggcaaggccc ccaagctgct gatctactcc gcctccttcc tgtactccgg cgtgccctcc 180
cggttctccg gctccagatc tggcaccgac tttaccctga ccatctccag cctgcagccc 240
gaggacttcg ccacctacta ctgccagcag cactacacca cccccccac ctttggccag 300 ggcaccaagg tggaaatcaa gcggaccgtg gccgctccct ccgtgttcat cttcccaccc 360
tccgacgagc agctgaagtc cggcaccgcc tccgtcgtgt gcctgctgaa caacttctac 420
ccccgcgagg ccaaggtgca gtggaaggtg gacaacgccc tgcagtccgg caactcccag 480
gaatccgtca ccgagcagga ctccaaggac agcacctact ccctgtcctc caccctgacc 540
ctgtccaagg ccgactacga gaagcacaag gtgtacgcct gcgaagtgac ccaccagggc 600
ctgtccagcc ccgtgaccaa gtccttcaac cggggcgagt gc 642

<210> SEQ ID NO 49
<211> LENGTH: 990
<212> TYPE: DNA
<213> ORGANISM: Artificial Sequence
<220> FEATURE:
<223> OTHER INFORMATION: Synthetic nucleotide sequence

<400> SEQUENCE: 49
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtagtgacc gtgccctcca gcagcttggg cacccagacc 240
tacatctgca acgtgaatca caagcccagc aacaccaagg tggacaagaa agttgagccc 300
aaatcttgtg accgtactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc tccgggaaaa 990

<210> SEQ ID NO 50
<211> LENGTH: 1350
<212> TYPE: DNA
<213> ORGANISM: Artificial Sequence
<220> FEATURE:
<223> OTHER INFORMATION: Synthetic nucleotide sequence

<400> SEQUENCE: 50
gaggtgcagc tggtggagtc cggcggcggc ctggttcagc ccggcggatc actgaggctc 60
tcctgtgccg ccagcggctt caacatcaag gacacataca tccactgggt tcgccaggct 120
cctggcaagg gactggagtg ggtcgctagg atctacccca ccaatgggta caccaggtac 180
gccgactccg tgaaggggcg gttcacaatc tcagccgata ctagcaaaaa tacagcctac 240
ttgcagatga actccctgag agcagaggat accgccgtgt actattgctc tcgctggggc 300
ggcgacggct tctacgctat ggattattgg ggccagggaa ccttggtcac cgtctcctca 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtagtgacc gtgccctcca gcagcttggg cacccagacc 600
tacatctgca acgtgaatca caagcccagc aacaccaagg tggacaagaa agttgagccc 660
aaatcttgtg accgtactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc tccgggaaaa 1350

<210> SEQ ID NO 51
<211> LENGTH: 987
<212> TYPE: DNA
<213> ORGANISM: Artificial Sequence
<220> FEATURE:
<223> OTHER INFORMATION: Synthetic nucleotide sequence

<400> SEQUENCE: 51
gcgtcgacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccatgcccc aaggacaccc tcatgatctc ccggacccct 420

-continued

```
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggt                                        987

<210> SEQ ID NO 52
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 52
gaggtgcagc tggtggaatc cggcggaggc ctggtccagc ctggcggatc tctgcggctg     60
tcttgcgccg cctccggctt caacatcaag gacacctaca tccactgggt ccgacaggca    120
cctggcaagg gactggaatg ggtggcccgg atctacccca ccaacggcta caccagatac    180
gccgactccg tgaagggccg gttcaccatc tccgccgaca cctccaagaa caccgcctac    240
ctgcagatga actccctgcg ggccgaggac accgccgtgt actactgctc cagatgggga    300
ggcgacggct tctacgccat ggactactgg ggccagggca ccctggtcac cgtgtctagc    360
gcgtcgacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccatgcccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc cccgggt                                       1347

<210> SEQ ID NO 53
<211> LENGTH: 987
```

-continued

<212> TYPE: DNA
<213> ORGANISM: Artificial Sequence
<220> FEATURE:
<223> OTHER INFORMATION: Synthetic nucleotide sequence

<400> SEQUENCE: 53
gcgtcgacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacatgcc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc cccgggt 987

<210> SEQ ID NO 54
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 54
gaggtgcagc tggtggaatc cggcggaggc ctggtccagc ctggcggatc tctgcggctg 60
tcttgcgccg cctccggctt caacatcaag gacacctaca tccactgggt ccgacaggca 120
cctggcaagg gactggaatg ggtggcccgg atctacccca ccaacggcta caccagatac 180
gccgactccg tgaagggccg gttcaccatc tccgccgaca cctccaagaa caccgcctac 240
ctgcagatga actccctgcg ggccgaggac accgccgtgt actactgctc cagatgggga 300
ggcgacggct tctacgccat ggactactgg ggccagggca ccctggtcac cgtgtctagc 360
gcgtcgacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840

```
tacgtggacg gcgtggaggt gcataatgcc aagacatgcc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc cccgggt                                       1347
```

<210> SEQ ID NO 55
<211> LENGTH: 990
<212> TYPE: DNA
<213> ORGANISM: Artificial Sequence
<220> FEATURE:
<223> OTHER INFORMATION: Synthetic nucleotide sequence

<400> SEQUENCE: 55

```
gcctccacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtagtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacgcc    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc tccgggaaaa                                     990
```

<210> SEQ ID NO 56
<211> LENGTH: 1350
<212> TYPE: DNA
<213> ORGANISM: Artificial Sequence
<220> FEATURE:
<223> OTHER INFORMATION: Synthetic nucleotide sequence

<400> SEQUENCE: 56

```
gaggtgcagc tggtggagtc cggcggcggc ctggttcagc ccggcggatc actgaggctc     60
tcctgtgccg ccagcggctt caacatcaag gacacataca tccactgggt tcgccaggct    120
cctggcaagg gactggagtg ggtcgctagg atctacccca ccaatgggta caccaggtac    180
gccgactccg tgaaggggcg gttcacaatc tcagccgata ctagcaaaaa tacagcctac    240
```

```
ttgcagatga actccctgag agcagaggat accgccgtgt actattgctc tcgctggggc    300
ggcgacggct tctacgctat ggattattgg ggccagggaa ccttggtcac cgtctcctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtagtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacgcc    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggaaaa                                    1350
```

<210> SEQ ID NO 57
<211> LENGTH: 1055
<212> TYPE: DNA
<213> ORGANISM: Artificial Sequence
<220> FEATURE:
<223> OTHER INFORMATION: Synthetic nucleotide sequence

<400> SEQUENCE: 57

```
gcctccacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtagtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtaccaa    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
```
cagcagggga acgtcttctc atgctccgtg atgcatgagg ctctgcacaa ccactacacg 960
cagaagagcc tctccctgtc tccgggaaaa gccgccagcg gcttcaacat caaggacaca 1020
tacatccact gggttcgcca ggctcctggc aaggg 1055

<210> SEQ ID NO 58
<211> LENGTH: 1415
<212> TYPE: DNA
<213> ORGANISM: Artificial Sequence
<220> FEATURE:
<223> OTHER INFORMATION: Synthetic nucleotide sequence

<400> SEQUENCE: 58
gaggtgcagc tggtggagtc cggcggcggc ctggttcagc ccggcggatc actgaggctc 60
tcctgtgccg ccagcggctt caacatcaag gacacataca tccactgggt tcgccaggct 120
cctggcaagg gactggagtg ggtcgctagg atctacccca ccaatgggta caccaggtac 180
gccgactccg tgaaggggcg gttcacaatc tcagccgata ctagcaaaaa tacagcctac 240
ttgcagatga actccctgag agcagaggat accgccgtgt actattgctc tcgctggggc 300
ggcgacggct tctacgctat ggattattgg ggccagggaa ccttggtcac cgtctcctca 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtagtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtaccaa 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc tccgggaaaa gccgccagcg gcttcaacat caaggacaca 1380
tacatccact gggttcgcca ggctcctggc aaggg 1415

<210> SEQ ID NO 59
<211> LENGTH: 987
<212> TYPE: DNA
<213> ORGANISM: Artificial Sequence
<220> FEATURE:
<223> OTHER INFORMATION: Synthetic nucleotide sequence

<400> SEQUENCE: 59
gcgtcgacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180

```
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagtg caccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggt                                         987
```

<210> SEQ ID NO 60
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 60

```
gaggtgcagc tggtggaatc cggcggaggc ctggtccagc ctggcggatc tctgcggctg     60
tcttgcgccg cctccggctt caacatcaag gacacctaca tccactgggt ccgacaggca    120
cctggcaagg gactggaatg ggtggcccgg atctacccca ccaacggcta caccagatac    180
gccgactccg tgaagggccg gttcaccatc tccgccgaca cctccaagaa caccgcctac    240
ctgcagatga actccctgcg ggccgaggac accgccgtgt actactgctc cagatgggga    300
ggcgacggct tctacgccat ggactactgg ggccagggca ccctggtcac cgtgtctagc    360
gcgtcgacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagtg caccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
```
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc cccgggt 1347

<210> SEQ ID NO 61
<211> LENGTH: 987
<212> TYPE: DNA
<213> ORGANISM: Artificial Sequence
<220> FEATURE:
<223> OTHER INFORMATION: Synthetic nucleotide sequence

<400> SEQUENCE: 61
gcgtcgacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact actgcaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc cccgggt 987

<210> SEQ ID NO 62
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 62
gaggtgcagc tggtggaatc cggcggaggc ctggtccagc ctggcggatc tctgcggctg 60
tcttgcgccg cctccggctt caacatcaag gacacctaca tccactgggt ccgacaggca 120
cctggcaagg gactggaatg ggtggcccgg atctacccca ccaacggcta caccagatac 180
gccgactccg tgaagggccg gttcaccatc tccgccgaca cctccaagaa caccgcctac 240
ctgcagatga actccctgcg ggccgaggac accgccgtgt actactgctc cagatgggga 300
ggcgacggct tctacgccat ggactactgg ggccagggca ccttggtcac cgtgtctagc 360
gcgtcgacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact actgcaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc cccgggt 1347

<210> SEQ ID NO 63
<211> LENGTH: 987
<212> TYPE: DNA
<213> ORGANISM: Artificial Sequence
<220> FEATURE:
<223> OTHER INFORMATION: Synthetic nucleotide sequence

<400> SEQUENCE: 63
gcgtcgacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctcctgctc cccgggt 987

<210> SEQ ID NO 64
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 64
gaggtgcagc tggtggaatc cggcggaggc ctggtccagc ctggcggatc tctgcggctg 60
tcttgcgccg cctccggctt caacatcaag gacacctaca tccactgggt ccgacaggca 120
cctggcaagg gactggaatg ggtggcccgg atctacccca ccaacggcta caccagatac 180
gccgactccg tgaagggccg gttcaccatc tccgccgaca cctccaagaa caccgcctac 240
ctgcagatga actccctgcg ggccgaggac accgccgtgt actactgctc cagatgggga 300
ggcgacggct tctacgccat ggactactgg ggccagggca ccctggtcac cgtgtctagc 360
gcgtcgacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctcctgctc cccgggt 1347

<210> SEQ ID NO 65
<211> LENGTH: 987
<212> TYPE: DNA
<213> ORGANISM: Artificial Sequence
<220> FEATURE:
<223> OTHER INFORMATION: Synthetic nucleotide sequence

<400> SEQUENCE: 65
gcgtcgacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacatgcc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagtg caccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc cccgggt 987

<210> SEQ ID NO 66
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 66
gaggtgcagc tggtggaatc cggcggaggc ctggtccagc ctggcggatc tctgcggctg 60
tcttgcgccg cctccggctt caacatcaag gacacctaca tccactgggt ccgacaggca 120
cctggcaagg gactggaatg ggtggcccgg atctacccca ccaacggcta caccagatac 180
gccgactccg tgaagggccg gttcaccatc tccgccgaca cctccaagaa caccgcctac 240
ctgcagatga actccctgcg ggccgaggac accgccgtgt actactgctc cagatgggga 300
ggcgacggct tctacgccat ggactactgg ggccagggca ccctggtcac cgtgtctagc 360
gcgtcgacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacatgcc cgcgggagga gcagtacaac 900
agcacgtacc gtgtggtcag cgtcctcacc gtcctgcacc aggactggct gaatggcaag 960
gagtacaagt gcaaggtctc caacaaagcc ctcccagccc ccatcgagtg caccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc cccgggt 1347

<210> SEQ ID NO 67
<211> LENGTH: 987
<212> TYPE: DNA
<213> ORGANISM: Artificial Sequence
<220> FEATURE:
<223> OTHER INFORMATION: Synthetic nucleotide sequence

<400> SEQUENCE: 67

```
gcgtcgacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacatgcc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact actgcaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggt                                         987
```

<210> SEQ ID NO 68
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 68

```
gaggtgcagc tggtggaatc cggcggaggc ctggtccagc ctggcggatc tctgcggctg     60
tcttgcgccg cctccggctt caacatcaag gacacctaca tccactgggt ccgacaggca    120
cctggcaagg gactggaatg ggtggcccgg atctacccca ccaacggcta caccagatac    180
gccgactccg tgaagggccg gttcaccatc tccgccgaca cctccaagaa caccgcctac    240
ctgcagatga actccctgcg ggccgaggac accgccgtgt actactgctc cagatgggga    300
ggcgacggct tctacgccat ggactactgg ggccagggca ccctggtcac cgtgtctagc    360
gcgtcgacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacatgcc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
```
atgaccaaga accaggtcag cctgacctgc ctggtcaaag gcttctatcc cagcgacatc 1140
gccgtggagt gggagagcaa tgggcagccg gagaacaact actgcaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc cccgggt 1347

<210> SEQ ID NO 69
<211> LENGTH: 990
<212> TYPE: DNA
<213> ORGANISM: Artificial Sequence
<220> FEATURE:
<223> OTHER INFORMATION: Synthetic nucleotide sequence

<400> SEQUENCE: 69
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtagtgacc gtgccctcca gcagcttggg cacccagacc 240
tacatctgca acgtgaatca caagcccagc aacaccaagg tggacaagaa agttgagccc 300
aaatcttgtg accgtactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc tccgggaaaa 990

<210> SEQ ID NO 70
<211> LENGTH: 1350
<212> TYPE: DNA
<213> ORGANISM: Artificial Sequence
<220> FEATURE:
<223> OTHER INFORMATION: Synthetic nucleotide sequence

<400> SEQUENCE: 70
gaggtgcagc tggtggagtc cggcggcggc ctggttcagc ccggcggatc actgaggctc 60
tcctgtgccg ccagcggctt caacatcaag gacacataca tccactgggt tcgccaggct 120
cctggcaagg gactggagtg ggtcgctagg atctacccca ccaatgggta caccaggtac 180
gccgactccg tgaaggggcg gttcacaatc tcagccgata ctagcaaaaa tacagcctac 240
ttgcagatga actccctgag agcagaggat accgccgtgt actattgctc tcgctggggc 300
ggcgacggct tctacgctat ggattattgg ggccagggaa ccttggtcac cgtctcctca 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtagtgacc gtgccctcca gcagcttggg cacccagacc 600
tacatctgca acgtgaatca caagcccagc aacaccaagg tggacaagaa agttgagccc 660
aaatcttgtg accgtactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacgcc 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc tccgggaaaa 1350

<210> SEQ ID NO 71
<211> LENGTH: 1055
<212> TYPE: DNA
<213> ORGANISM: Artificial Sequence
<220> FEATURE:
<223> OTHER INFORMATION: Synthetic nucleotide sequence

<400> SEQUENCE: 71
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtagtgacc gtgccctcca gcagcttggg cacccagacc 240
tacatctgca acgtgaatca caagcccagc aacaccaagg tggacaagaa agttgagccc 300
aaatcttgtg accgtactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtaccaa 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc tccgggaaaa gccgccagcg gcttcaacat caaggacaca 1020
tacatccact gggttcgcca ggctcctggc aaggg 1055

<210> SEQ ID NO 72
<211> LENGTH: 1415
<212> TYPE: DNA
<213> ORGANISM: Artificial Sequence
<220> FEATURE:
<223> OTHER INFORMATION: Synthetic nucleotide sequence

<400> SEQUENCE: 72
gaggtgcagc tggtggagtc cggcggcggc ctggttcagc ccggcggatc actgaggctc 60
tcctgtgccg ccagcggctt caacatcaag gacacataca tccactgggt tcgccaggct 120
cctggcaagg gactggagtg ggtcgctagg atctacccca ccaatgggta caccaggtac 180
gccgactccg tgaaggggcg gttcacaatc tcagccgata ctagcaaaaa tacagcctac 240
ttgcagatga actccctgag agcagaggat accgccgtgt actattgctc tcgctggggc 300
ggcgacggct tctacgctat ggattattgg ggccagggaa ccttggtcac cgtctcctca 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtagtgacc gtgccctcca gcagcttggg cacccagacc 600
tacatctgca acgtgaatca caagcccagc aacaccaagg tggacaagaa agttgagccc 660
aaatcttgtg accgtactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtaccaa 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc tccgggaaaa gccgccagcg gcttcaacat caaggacaca 1380
tacatccact gggttcgcca ggctcctggc aaggg 1415

<210> SEQ ID NO 73
<211> LENGTH: 987
<212> TYPE: DNA
<213> ORGANISM: Artificial Sequence
<220> FEATURE:
<223> OTHER INFORMATION: Synthetic nucleotide sequence

<400> SEQUENCE: 73
gcgtcgacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360

-continued

```
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagtg caccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact actgcaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggt                                        987

<210> SEQ ID NO 74
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 74
gaggtgcagc tggtggaatc cggcggaggc ctggtccagc ctggcggatc tctgcggctg     60
tcttgcgccg cctccggctt caacatcaag gacacctaca tccactgggt ccgacaggca    120
cctggcaagg gactggaatg ggtggcccgg atctacccca ccaacggcta caccagatac    180
gccgactccg tgaagggccg gttcaccatc tccgccgaca cctccaagaa caccgcctac    240
ctgcagatga actccctgcg ggccgaggac accgccgtgt actactgctc cagatgggga    300
ggcgacggct tctacgccat ggactactgg ggccagggca ccctggtcac cgtgtctagc    360
gcgtcgacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagtg caccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact actgcaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc cccgggt                                       1347
```

-continued

<210> SEQ ID NO 75
<211> LENGTH: 987
<212> TYPE: DNA
<213> ORGANISM: Artificial Sequence
<220> FEATURE:
<223> OTHER INFORMATION: Synthetic nucleotide sequence

<400> SEQUENCE: 75
gcgtcgacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact actgcaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctcctgctc cccgggt 987

<210> SEQ ID NO 76
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 76
gaggtgcagc tggtggaatc cggcggaggc ctggtccagc ctggcggatc tctgcggctg 60
tcttgcgccg cctccggctt caacatcaag gacacctaca tccactgggt ccgacaggca 120
cctggcaagg gactggaatg ggtggcccgg atctacccca ccaacggcta caccagatac 180
gccgactccg tgaagggccg gttcaccatc tccgccgaca cctccaagaa caccgcctac 240
ctgcagatga actccctgcg ggccgaggac accgccgtgt actactgctc cagatgggga 300
ggcgacggct tctacgccat ggactactgg ggccagggca ccctggtcac cgtgtctagc 360
gcgtcgacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780

-continued

```
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact actgcaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctcctgctc cccgggt                                       1347
```

```
<210> SEQ ID NO 77
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 77
cggaccgtgg ccgctccctc cgtgttcatc ttcccaccct ccgacgagca gctgaagtcc     60
ggcaccgcct ccgtcgtgtg cctgctgaac aacttctacc cccgcgaggc caaggtgcag    120
tggaaggtgg acaacgccct gcagtccggc aactcccagg aatccgtcac cgagcaggac    180
tccaaggaca gcacctactc cctgtcctcc accctgaccc tgtcctgcgc cgactacgag    240
aagcacaagg tgtacgcctg cgaagtgacc caccagggcc tgtccagccc cgtgaccaag    300
tccttcaacc ggggcgagtg c                                              321
```

```
<210> SEQ ID NO 78
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 78
gacatccaga tgacccagtc cccctccagc ctgtccgcct ctgtgggcga cagagtgacc     60
atcacctgtc gggcctccca ggacgtgaac accgccgtgg cctggtatca gcagaagccc    120
ggcaaggccc ccaagctgct gatctactcc gcctccttcc tgtactccgg cgtgccctcc    180
cggttctccg gctccagatc tggcaccgac tttaccctga ccatctccag cctgcagccc    240
gaggacttcg ccacctacta ctgccagcag cactacacca cccccccac ctttggccag     300 ggcaccaagg tggaaatcaa gcggaccgtg gccgctccct ccgtgttcat cttcccaccc    360
tccgacgagc agctgaagtc cggcaccgcc tccgtcgtgt gcctgctgaa caacttctac    420 cccgcgagg ccaaggtgca gtggaaggtg gacaacgccc tgcagtccgg caactcccag     480
gaatccgtca ccgagcagga ctccaaggac agcacctact ccctgtcctc caccctgacc    540
ctgtcctgcg ccgactacga gaagcacaag gtgtacgcct gcgaagtgac ccaccagggc    600
ctgtccagcc ccgtgaccaa gtccttcaac cggggcgagt gc                       642
```

```
<210> SEQ ID NO 79
<211> LENGTH: 321
<212> TYPE: DNA
<213> ORGANISM: Artificial Sequence
```

<220> FEATURE:
<223> OTHER INFORMATION: Synthetic nucleotide sequence

<400> SEQUENCE: 79
cgtacggtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg t 321

<210> SEQ ID NO 80
<211> LENGTH: 666
<212> TYPE: DNA
<213> ORGANISM: Artificial Sequence
<220> FEATURE:
<223> OTHER INFORMATION: Synthetic nucleotide sequence

<400> SEQUENCE: 80
gatatccaga tgacacagtc cccctccagc ctctccgcta gtgtcggaga tagagtgaca 60
attacatgtc gggcaagcca ggacgtcaat accgccgtgg cctggtatca gcagaagcca 120
ggaaaggccc caaaactcct gatctactcc gcctccttcc tgtactcagg ggtcccttca 180
cgcttctccg gttcccggag cggcaccgac ttcactctga ctatctcaag cttgcagccc 240
gaggacttcg ccacatacta ttgccagcag cactatacca cccccctac cttcggtcag 300 ggaactaagg tggaaattaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gtggtggcct gcttcagggc 660
ccacca 666

<210> SEQ ID NO 81
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 81

Gly Gly Leu Leu Gln Gly Pro Pro
1 5

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 82

Gly Gly Leu Leu Gln Gly Gly
1 5

<210> SEQ ID NO 83

-continued

<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 83

Leu Leu Gln Gly Ala
1 5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 84

Gly Gly Leu Leu Gln Gly Ala
1 5

<210> SEQ ID NO 85
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 85

Leu Leu Gln Gly
1

<210> SEQ ID NO 86
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 86

Leu Leu Gln Gly Pro Gly
1 5

<210> SEQ ID NO 87
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 87

Leu Leu Gln Gly Pro Ala
1 5

<210> SEQ ID NO 88
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 88

Leu Leu Gln Gly Pro
1 5

<210> SEQ ID NO 89
<211> LENGTH: 4

<212> TYPE: PRT
<213> ORGANISM: Artificial Sequence
<220> FEATURE:
<223> OTHER INFORMATION: Synthetic peptide sequence

<400> SEQUENCE: 89

Leu Leu Gln Pro
1

<210> SEQ ID NO 90
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 90

Leu Leu Gln Pro Gly Lys
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 91

Leu Leu Gln Gly Ala Pro Gly Lys
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 92

Leu Leu Gln Gly Ala Pro Gly
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 93

Leu Leu Gln Gly Ala Pro
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (4)..(4)

-continued

```
<223> OTHER INFORMATION: Xaa is G or P
<220> FEATURE:
<221> NAME/KEY: MISC_FEATURE
<222> LOCATION: (5)..(5)
<223> OTHER INFORMATION: Xaa is A, G, P, or absent
<220> FEATURE:
<221> NAME/KEY: MISC_FEATURE
<222> LOCATION: (6)..(6)
<223> OTHER INFORMATION: Xaa is A, G, K, P, or absent
<220> FEATURE:
<221> NAME/KEY: MISC_FEATURE
<222> LOCATION: (7)..(7)
<223> OTHER INFORMATION: Xaa is G, K or absent
<220> FEATURE:
<221> NAME/KEY: MISC_FEATURE
<222> LOCATION: (8)..(8)
<223> OTHER INFORMATION: Xaa is K or absent

<400> SEQUENCE: 94

Leu Leu Gln Xaa Xaa Xaa Xaa Xaa
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (4)..(4)
<223> OTHER INFORMATION: Xaa is any naturally occurring amino acid
<220> FEATURE:
<221> NAME/KEY: MISC_FEATURE
<222> LOCATION: (5)..(5)
<223> OTHER INFORMATION: Xaa is any naturally occurring amino acid or
      absent
<220> FEATURE:
<221> NAME/KEY: MISC_FEATURE
<222> LOCATION: (6)..(6)
<223> OTHER INFORMATION: Xaa is any naturally occurring amino acid or
      absent
<220> FEATURE:
<221> NAME/KEY: MISC_FEATURE
<222> LOCATION: (7)..(7)
<223> OTHER INFORMATION: Xaa is any naturally occurring amino acid or
      absent
<220> FEATURE:
<221> NAME/KEY: MISC_FEATURE
<222> LOCATION: (8)..(8)
<223> OTHER INFORMATION: Xaa is any naturally occurring amino acid or
      absent

<400> SEQUENCE: 95

Leu Leu Gln Xaa Xaa Xaa Xaa Xaa
1               5
```